United States Patent
Keyt et al.

(10) Patent No.: US 11,639,389 B2
(45) Date of Patent: *May 2, 2023

(54) BINDING MOLECULES WITH MODIFIED J-CHAIN

(71) Applicant: IGM Biosciences, Inc., Mountain View, CA (US)

(72) Inventors: Bruce A. Keyt, Hillsborough, CA (US); Leonard G. Presta, San Francisco, CA (US); Ramesh Baliga, Redwood City, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,870

(22) PCT Filed: Sep. 30, 2016

(86) PCT No.: PCT/US2016/055053
§ 371 (c)(1),
(2) Date: Mar. 29, 2018

(87) PCT Pub. No.: WO2017/059387
PCT Pub. Date: Apr. 6, 2017

(65) Prior Publication Data
US 2019/0185570 A1    Jun. 20, 2019

Related U.S. Application Data

(60) Provisional application No. 62/235,486, filed on Sep. 30, 2015.

(51) Int. Cl.
| | | |
|---|---|---|
| C07K 16/28 | (2006.01) | |
| C07K 16/30 | (2006.01) | |
| C07K 16/46 | (2006.01) | |
| C07K 16/18 | (2006.01) | |

(52) U.S. Cl.
CPC .......... *C07K 16/2827* (2013.01); *C07K 16/18* (2013.01); *C07K 16/2809* (2013.01); *C07K 16/2818* (2013.01); *C07K 16/2878* (2013.01); *C07K 16/2887* (2013.01); *C07K 16/30* (2013.01); *C07K 16/468* (2013.01); *C07K 2317/21* (2013.01); *C07K 2317/31* (2013.01); *C07K 2317/622* (2013.01); *C07K 2317/73* (2013.01); *C07K 2317/732* (2013.01); *C07K 2317/94* (2013.01); *C07K 2319/33* (2013.01); *C07K 2319/735* (2013.01); *C07K 2319/74* (2013.01)

(58) Field of Classification Search
CPC .................................................. C07K 16/468
See application file for complete search history.

(56) References Cited

U.S. PATENT DOCUMENTS

| | | | |
|---|---|---|---|
| 5,434,340 A | 7/1995 | Krimpenfort | |
| 5,798,229 A | 8/1998 | Strittmatter | |
| 5,831,034 A | 11/1998 | Katinger | |
| 5,911,989 A | 6/1999 | Katinger | |
| 6,165,463 A * | 12/2000 | Platz ................... | A61K 9/0075 424/130.1 |
| 6,284,536 B1 | 9/2001 | Morrison | |
| 6,476,198 B1 | 11/2002 | Kang | |
| 6,676,924 B2 | 1/2004 | Hansen | |
| 7,074,403 B1 | 7/2006 | Goldenberg | |
| 7,109,304 B2 | 9/2006 | Hansen | |
| 7,138,496 B2 | 11/2006 | Hua | |
| 7,151,164 B2 | 12/2006 | Hansen | |
| 7,238,785 B2 | 7/2007 | Govindan | |
| 7,251,164 B2 | 7/2007 | Okhonin | |
| 7,282,567 B2 | 10/2007 | Goldenberg | |
| 7,300,655 B2 | 11/2007 | Hansen | |
| 7,311,912 B1 * | 12/2007 | Hein ................... | A61K 39/395 424/134.1 |
| 7,312,318 B2 | 12/2007 | Hansen | |
| 7,387,773 B2 | 6/2008 | Murray | |
| 7,402,312 B2 | 7/2008 | Rosen | |
| 7,541,440 B2 | 6/2009 | Goldenberg | |
| 7,601,351 B1 | 10/2009 | Rosen | |
| 7,612,180 B2 | 11/2009 | Goldenberg | |
| 7,709,615 B2 | 5/2010 | Irie | |
| 7,932,360 B2 | 4/2011 | Van Berkel | |
| 7,951,378 B2 | 5/2011 | Larrick | |
| 8,066,994 B2 | 11/2011 | Gillies | |
| 8,114,965 B2 | 2/2012 | Maddon | |
| 8,153,125 B2 | 4/2012 | Watkins | |
| 8,257,703 B2 | 9/2012 | Irie | |

(Continued)

FOREIGN PATENT DOCUMENTS

| | | |
|---|---|---|
| AU | 697387 B | 3/1996 |
| AU | 708301 B2 | 5/1996 |

(Continued)

OTHER PUBLICATIONS

Cregger (Arch Pathol Lab Med, vol. 130, p. 1026-1030, 2006) (Year: 2006).*
Rudikoff et al. (Proceedings of the National Academy of Sciences USA, vol. 79, p. 1979-1983, 1982) (Year: 1982).*
Wang, Y., et al., (2007), "The design, construction and function of a new chimeric anti-CD20 antibody", Journal of Biotechnology, 129: 726-731.
Ammann, J., et al. (2014), "Development and use of IgM/J-Chain Fusion Proteins for Chacterization of Immunoglobulin Superfamily Ligand-Receptor Interactions", Current Protocols in Protein Science, 19.24.1-19.24.11, Supplement 75.

(Continued)

*Primary Examiner* — Laura B Goddard
*Assistant Examiner* — Sarah A Alsomairy

(57) ABSTRACT

The present invention provides binding molecules that include an IgM, IgA, IgG/IgM or IgG/IgA antibody with a modified J-chain that includes a binding moiety that antagonizes a T-cell inhibitory signaling pathway, and their uses.

14 Claims, 19 Drawing Sheets

Specification includes a Sequence Listing.

(56) References Cited

U.S. PATENT DOCUMENTS

| | | |
|---|---|---|
| 8,333,971 B2 | 12/2012 | Goldenberg |
| 8,337,844 B2 | 12/2012 | Carr |
| 8,377,435 B2 | 2/2013 | Bhat |
| 8,871,216 B2 | 10/2014 | Chang |
| 9,173,961 B2 | 11/2015 | Deckert |
| 9,409,976 B2 | 8/2016 | Teng |
| 9,458,241 B2 | 10/2016 | Bhat |
| 9,938,347 B2 | 4/2018 | Wang |
| 9,951,134 B2* | 4/2018 | Keyt .................. C07K 16/283 |
| 10,351,631 B2 | 7/2019 | Keyt |
| 10,400,038 B2 | 9/2019 | Keyt |
| 10,604,559 B2 | 3/2020 | Carroll |
| 10,618,978 B2 | 4/2020 | Keyt |
| 10,689,449 B2 | 6/2020 | Wang |
| 10,899,835 B2 | 1/2021 | Baliga |
| 10,954,302 B2 | 3/2021 | Keyt |
| 10,975,147 B2 | 4/2021 | Keyt |
| 11,401,337 B2 | 8/2022 | Baliga |
| 11,535,664 B2 | 12/2022 | Carroll |
| 11,542,342 B2 | 1/2023 | Keyt |
| 2002/0006630 A1* | 1/2002 | Sirbasku ............. A61K 31/138 435/7.23 |
| 2002/0168367 A1 | 11/2002 | Larrick |
| 2004/0005318 A1* | 1/2004 | Davis ................ A61K 39/0011 424/144.1 |
| 2004/0137001 A1 | 7/2004 | Schreiber |
| 2004/0156826 A1 | 8/2004 | Dangond |
| 2005/0003431 A1 | 1/2005 | Wucherpfennig |
| 2005/0129616 A1* | 6/2005 | Salcedo ............... A61K 39/395 424/1.49 |
| 2005/0202026 A1* | 9/2005 | Hiatt .................... C07K 14/705 424/178.1 |
| 2005/0287153 A1 | 12/2005 | Dennis |
| 2006/0063234 A1 | 3/2006 | Jones |
| 2006/0153854 A1 | 7/2006 | Bhat |
| 2007/0014720 A1 | 1/2007 | Gazit-Bornstein |
| 2007/0154469 A1 | 7/2007 | Irie |
| 2007/0248601 A1 | 10/2007 | Cogne |
| 2007/0249812 A1 | 10/2007 | Hayasaka |
| 2008/0044413 A1* | 2/2008 | Hammond ......... C07K 16/2809 424/135.1 |
| 2008/0145420 A1 | 6/2008 | Simon |
| 2009/0022738 A1* | 1/2009 | Hofmeister ....... C07K 16/2809 424/173.1 |
| 2009/0130089 A9 | 5/2009 | Smith |
| 2009/0291899 A1 | 11/2009 | Ferrante |
| 2010/0093979 A1 | 4/2010 | Lazar |
| 2010/0172899 A1 | 7/2010 | Irie |
| 2010/0184959 A1 | 7/2010 | Guler-Gane |
| 2010/0279932 A1 | 11/2010 | Ledbetter |
| 2010/0279939 A1 | 11/2010 | Fries |
| 2011/0110852 A1 | 5/2011 | Miller |
| 2011/0129412 A1 | 6/2011 | Gazit-Bornstein |
| 2011/0318339 A1 | 12/2011 | Smider |
| 2012/0039870 A9 | 2/2012 | Dolk |
| 2012/0045432 A9 | 2/2012 | Yu |
| 2012/0258126 A1 | 10/2012 | Schoeller |
| 2012/0269830 A1 | 10/2012 | Horowitz |
| 2013/0095097 A1 | 4/2013 | Blankenship |
| 2013/0164283 A1 | 6/2013 | Bhat |
| 2013/0189258 A1* | 7/2013 | Rother ............. A61K 39/39541 424/135.1 |
| 2013/0280167 A1 | 10/2013 | Rodriguez |
| 2014/0010809 A1 | 1/2014 | Ledbetter |
| 2014/0044739 A1 | 2/2014 | Teng |
| 2014/0088295 A1 | 3/2014 | Smith et al. |
| 2014/0154252 A1 | 6/2014 | Thompson |
| 2014/0249044 A1 | 9/2014 | Braz Gonçalves |
| 2015/0004167 A1 | 1/2015 | Wu |
| 2015/0038682 A1 | 2/2015 | Tsurushita |
| 2015/0259420 A1* | 9/2015 | Triebel ............. A61K 39/39558 424/130.1 |
| 2016/0222132 A1 | 8/2016 | Keyt |
| 2016/0326233 A1 | 11/2016 | Mondelli |
| 2016/0368971 A1 | 12/2016 | Keyt |
| 2017/0183409 A1 | 6/2017 | Keyt |
| 2017/0283510 A1 | 10/2017 | Keyt |
| 2017/0320955 A1 | 11/2017 | Wang |
| 2018/0009897 A1 | 1/2018 | Wang |
| 2018/0118814 A1 | 5/2018 | Carroll |
| 2018/0118816 A1 | 5/2018 | Keyt |
| 2018/0265596 A1 | 9/2018 | Keyt |
| 2019/0002566 A1 | 1/2019 | Keyt |
| 2019/0100597 A1 | 4/2019 | Keyt |
| 2019/0330360 A1 | 10/2019 | Wang |
| 2019/0330374 A1 | 10/2019 | Wang |
| 2019/0338031 A1 | 11/2019 | Keyt |
| 2019/0338040 A1 | 11/2019 | Keyt |
| 2019/0338041 A1 | 11/2019 | Baliga |
| 2020/0190190 A1 | 6/2020 | Keyt |
| 2020/0239572 A1 | 7/2020 | Baliga |
| 2020/0255546 A1 | 8/2020 | Keyt |
| 2020/0377577 A1 | 12/2020 | Keyt |
| 2021/0002353 A1 | 1/2021 | Carroll |
| 2021/0032357 A1 | 2/2021 | Keyt |
| 2021/0087273 A1 | 3/2021 | Baliga |
| 2021/0147567 A1 | 5/2021 | Baliga |
| 2021/0163600 A1 | 6/2021 | Keyt |
| 2021/0380701 A1 | 12/2021 | Baliga |
| 2021/0388098 A1 | 12/2021 | Keyt |
| 2022/0106398 A1 | 4/2022 | Baliga |
| 2022/0106399 A1 | 4/2022 | Baliga |
| 2022/0169751 A1 | 6/2022 | Wang |
| 2022/0267415 A1 | 8/2022 | Ku |
| 2022/0289856 A1 | 9/2022 | Amoury |
| 2022/0306760 A1 | 9/2022 | Keyt |
| 2022/0340676 A1 | 10/2022 | Baliga |
| 2022/0372142 A1 | 11/2022 | Baliga |

FOREIGN PATENT DOCUMENTS

| | | |
|---|---|---|
| AU | 2004297218 B2 | 6/2005 |
| CA | 2358520 C | 7/2000 |
| CA | 2662701 C | 10/2008 |
| EP | 642585 B1 | 3/1995 |
| EP | 1169352 A | 1/2002 |
| EP | 1301541 A2 | 4/2003 |
| EP | 1617870 A | 1/2006 |
| EP | 1833848 A2 | 9/2007 |
| EP | 2219458 A1 | 8/2010 |
| EP | 2254592 A2 | 12/2010 |
| EP | 2264163 B1 | 12/2010 |
| EP | 2300498 A2 | 3/2011 |
| EP | 2465871 B1 | 6/2012 |
| EP | 2649184 B1 | 10/2013 |
| EP | 2655415 A2 | 10/2013 |
| EP | 2771361 A1 | 9/2014 |
| EP | 2962103 A2 | 1/2016 |
| JP | 2004525630 | 8/2004 |
| JP | 2005522998 | 8/2005 |
| WO | 1989001975 | 3/1989 |
| WO | 1998030591 | 7/1998 |
| WO | 2001012820 | 2/2001 |
| WO | 2001014424 | 3/2001 |
| WO | 2004110143 | 12/2004 |
| WO | 2004110143 A2 | 12/2004 |
| WO | 2005103081 | 11/2005 |
| WO | 2006052641 | 5/2006 |
| WO | 2006130458 | 12/2006 |
| WO | 2008140477 A9 | 11/2008 |
| WO | 2009013620 | 1/2009 |
| WO | 2009130575 | 10/2009 |
| WO | 2010105256 | 9/2010 |
| WO | 2013061098 | 5/2013 |
| WO | 2013087913 | 6/2013 |
| WO | 2013/120012 A2 | 8/2013 |
| WO | 2013120012 | 8/2013 |
| WO | 2013150138 | 10/2013 |
| WO | 2013188870 | 12/2013 |
| WO | 2014022592 | 2/2014 |
| WO | 2014/124457 | 8/2014 |
| WO | 2014124457 | 8/2014 |
| WO | 2014165093 | 10/2014 |

(56) References Cited

FOREIGN PATENT DOCUMENTS

| WO | 2014/207064 | 12/2014 |
|---|---|---|
| WO | 2014207064 | 12/2014 |
| WO | 2015037000 A1 | 3/2015 |
| WO | 2015053887 | 4/2015 |
| WO | 2015103072 | 7/2015 |
| WO | 2015120474 | 8/2015 |
| WO | 2015/153912 A1 | 10/2015 |
| WO | 2015151081 | 10/2015 |
| WO | 2015153912 | 10/2015 |
| WO | 2016/118641 A1 | 7/2016 |
| WO | 2016118641 | 7/2016 |
| WO | 2016/141303 A2 | 9/2016 |
| WO | 2016/154593 A1 | 9/2016 |
| WO | 2016141303 | 9/2016 |
| WO | 2016154593 | 9/2016 |
| WO | 2016/168758 | 10/2016 |
| WO | 2016168758 | 10/2016 |
| WO | 2017/059387 A1 | 4/2017 |
| WO | 2017059380 | 4/2017 |
| WO | 2017059387 | 4/2017 |
| WO | 2017196867 | 11/2017 |
| WO | 2018/017761 | 1/2018 |
| WO | 2018/017763 | 1/2018 |
| WO | 2018/017888 | 1/2018 |
| WO | 2018/017889 | 1/2018 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |
| WO | 2021030688 | 2/2021 |
| WO | 2021034646 | 2/2021 |
| WO | 2021041250 | 3/2021 |
| WO | 2021055765 | 3/2021 |
| WO | 2021141902 | 7/2021 |
| WO | 2021216756 | 10/2021 |
| WO | 2021231639 | 11/2021 |
| WO | 2022026475 | 2/2022 |
| WO | 2022109023 | 5/2022 |
| WO | 2022178047 | 8/2022 |

OTHER PUBLICATIONS

Aggarwal, B., et al., "Historical perspectives on tumor necrosis factor and its superfamily: 25 years later, a golden journey", 2012, Blood, vol. 119 (No. 3), pp. 651-665.

Ammann, J., et al., (2012), "Detection of weak receptor-ligand interactions using IgM and J-chain-based fusion proteins", European Journal of Immunology, 42:1354-1356.

Andersen, J., et al., "Extending Serum Half-life of Albumin by Engineering Neonatal Fc Receptor (FcRn) Binding", 2014, Journal of Biological Chemistry, vol. 289, No. 19, pp. 13492-13502.

Azuma, Y., et al., "Recombinant Human Hexamer-Dominant IgM Monoclonal Antibody to Ganglioside GM3 for Treatment of Melanoma", 2007, Clin Cancer Res, vol. 13 (No. 9), pp. 2745-2750 with correction on article.

Bakema et al, "Immunoglobulin A, A next generation of therapeutic antibodies?", mAbs, Aug. 2011, vol. 3, No. 4, 352-361.

Braathen, R., et al. (2002), "The Carboxyl-terminal Domanins of IgA and IgM Direct Isotype-specific Polymerication and Interaction with the Polymeric Immunoglobulin Receptor", The Journal of Biological Chemistry, vol. 277, No. 45, pp. 42755-42762.

Brodska et al., "Correlation of PD-L1 Surface Expression on Leukemia Cells with the Ratio of PD-L1 mRNA Variants and with Electrophoretic Mobility", Cancer Immunology Research, Aug. 2016, pp. 815-819, vol. 4, No. 10.

Cao, Y., et al. , (2011), "Targeting cell surface Beta2-microglobulin by pentameric IgM antibodies", British Journal of Haematology, 154:111-121.

Chintalacharuvu, K., et al., "Hybrid IgA2/IgG1 antibodies with tailor-made effector functions", 2001, Clin. Immunol., vol. 101 (No. 1), pp. 21-31.

Ćirić B., et al. (2009), "Effect of Valency on Binding Properties of the Antihuman IgM Monoclonal Antibody 202", Hybridoma, vol. 14. No. 6, pp. 537-544.

Czajkowsky, D.M., Shao, Z., 2009. The human IgM pentamer is a mushroom-shaped molecule with a flexural bias. PNAS, vol. 106, pp. 14960-14965.

Davis, A., (1989), "IgM—Molecular requirements for its assembly and function", Immunology Today, vol. 10, No. 4, 7 pages.

Dennis, M., et al. "Albumin Binding as a General Strategy for Improving the Pharmacokinetics of Proteins", 2002, J. Biol. Chem. 277, 35035-35043.

Dennis, M., et al., (2012), "Transferrin Antibodies into the Brain", Neuropsychopharmacology Reviews, 37: 302-303.

Ducry, L., et al., "Antibody-drug conjugates: linking cytotoxic payloads to monoclonal antibodies", 2010, Bioconjug. Chem. 21, 5-13.

Frutiger, S., et al., 1992, "Disulfide Bond Assignment in Human J Chain and its Covalent Pairing with Immunoglobulin M", Biochemistry, vol. 31, pp. 12643-12647.

Fukushima, N., et al., (2002), "Chacterization of Recombinant Monoclonal IgA Anti-PDC-E2 Autoantibodies Derived From patients with PBC", Hepatology: 35: 1383-1392.

Garcia-Pardo, A., Lamm, M.E., Plaut, A.G., Frangione, B., 1981. J chain is covalently bound to both monomer subunits in human secretory IgA. J. Biol. Chem. 256, 11734-11738.

Gibson Josefine, "Anti-PD-L1 for metastatic triple-negative breast cancer.", The Lancet. Oncology Jun. 2015, (Jun. 2015), vol. 16, No. 6, ISSN 1474-5488, p. e264, XP002765988.

Gilmour, J.E.M., et al. (2008), "Effet of the presence or absence of J Chain on expresion of recombinant anti-kell immunoglobulin", Transfusion Medicine, 18: 167-174.

Hopp, J., et al., (2010), "The effects of affinity and valency of an albumin-binding domain (ABD) on the half-life of a single-chain diabody-ABD fusion protein", vol. 23(11): 827-834.

Houghton, J., et al., (2015), "Site-specifically labeled CA19.9-targeted immunoconjugates for the PET, NIRF, and multimodal PET/NIRF imaging of pancreatic cancer", PNAS, vol. 112, No. 52: 15850-15855.

Johansen, F., et al., (2000), "Role of J Cahin in Secretory Immunoglobulin Formation", Scand. J. Immunol., 52: 240-248.

Johansen, F., et al., (2001), "The J Chain Is Essential for Polymeric Ig Receptor-Mediated Epithelial Transport of IgA", The Journal of Immunology, 167: 5185-5192.

Jones, A., et al., (2007), "Blood-Brain Barrier Transport of Therapeutics via Receptor-Mediation", Pharm Res., 24(9): 1759-1771.

Joos, B., et al., 2006, "Long-Term Multiple-Dose Pharmacokinetics of Human Monoclonal Antibodies (MAbs) against Human Immunodeficiency Virus Type 1 Envelope gp120 (MAb 2G12) and gp41 (MAbs 4E10 and 2F5)", Antimicrob Agents Chemother 50, 1773-1779.

Klein, J., et al., (2014,) "Design and characterization of structured protein linkers with differing flexibilities" Protein Eng Des Sel 27, 325-330.

Kragten, E., et al., (1995), "Site-specific analysis of the N-Glycans on Murine Polymeric Immunoglobulin A. Using Liquid Chromatography/Electrospray Mass Spectrometry", vol. 30, 1679-1686.

Krugmann, S., et al. (1997), "Structural Requirements for Assembly of Dimeric IgA Probed by Site-Directed Mutagenesis of J Chain and a Cysteine Residue of the α-chain CH2 Domain", The Journal of Immunology, 159: 244-249.

Ksiezak-Reding, H., et al., 1988, "Alz 50, a monoclonal antibody to Alzheimer's disease antigen, cross-reacts with tau proteins from bovine and normal human brain", J. Biol. Chem. 263, 7943-7947.

Lewis, A.K., et al., 2014, "Open and Closed Conformations of the Isolated Transmembrane Domain of Death Receptor 5 Support a New Model of Activation" Biophys J 106, L21-L24.

Liedtke, M., et al., 2012. "Phase I trial of a novel human monoclonal antibody mAb216 in patients with relapsed or refractory B-cell acute lymphoblastic leukemia" Haematologica 97, 30-37.

(56) References Cited

OTHER PUBLICATIONS

Lines, J.L., Pantazi, E., Mak, J., Sempere, L.F., Wang, L., O'Connell, S., Ceeraz, S., Suriawinata, A.A., Yan, S., Ernstoff, M.S., Noelle, R., 2014. VISTA Is an Immune Checkpoint Molecule for Human T Cells. Cancer Res 74, 1924-1932. https://doi.org/10.1158/0008-5472.CAN-13-1504.

Liu, X., et al., (2005), "Preliminary study on recombination of J-HNP-1 and its antibacterial effect in vitro" Shijie Huaren Xiaohua Zazhi, 13(22), 2640-2644, English Abstract Only Available.

Liu, X., et al., (2005), "Recombinant of J chain-HNP-1 cDNA and the construction of expression vector",Di-San Junyi Daxue Xuebao, 27(8), 697-699. English Abstract Only Available.

Mestecky, J., et al., (1973), "J-chain of polymeric IgA myeloma proteins", Protides of the Biological Fluids, vol. 20: 279-283 , Abstract Only Available.

Meyer et al., "Improved In Vivo Anti-Tumor Effects of IgA-Her2 Antibodies Through Half-Life Extension and Serum Exposure Enhancement by FcRn Targeting", mAbs, Jan. 2016, pp. 87-98, vol. 8, Issue 1.

Mongini, P., et al., (1995), "Human B Cell Activation, Effect of T Cell Cytokines on the Physicochemical Binding Requirements for Achieving Cell cycle Progression Via the Membrane IgM Signaling Pathway", The Journal of Immunology, 155: 3385-3400.

Mordenti, J., et al. (1999), "Intraocular Pharmacokinetics and Safety of a Humanized Monoclonal Antibody in Rabbits after Intravitreal Administration of a Solution or a PLGA Microsphere Formulation", Toxicological Sciences, 52: 101-106.

Mordenti, J., et al., (1999), "Comparisons of the Intraocular Tissue Distribution, Pharmacokinetics, and Safety of 125I-Labeled Full-Length and Fab Antibodies in Rhesus Monkeys Following Intravitreal Administration", Investigative Pathology, vol. 27, No. 5, pp. 536-544.

Mosmann, T.R., et al. (1978), "Modification and Fate of J. Chain in myeloma cells in the presence and absence of polymeric immunoglobulin secretion", Eur. J Immunol. 8: 84-101.

Müller, M. et al., (2012), "Improving the pharmacokinetic properties of biologies by fusion to an anti-HSA shark VNAR domain" MAbs 4, 673-685.

Niwa, H., Yamamura, K., Miyazaki, J., 1991. Efficient selection for high-expression transfectants with a novel eukaryotic vector. Gene 108, 193-199.

Nocentini, G., et al., (1997), "A new member of the tumor necrosis factor/nerve growth factor receptor family inhibits T cell receptor-induced apoptosis", Proc. Natl. Acad. Sci. U.S.A. 94, 6216-6221.

Ofei, F., Hurel, S., Newkirk, J., Sopwith, M., Taylor, R., 1996. Effects of an engineered human anti-TNF-alpha antibody (CDP571) on insulin sensitivity and glycemic control in patients with NIDDM. Diabetes 45, 881-885.

Palanichamy Arumugam et al, "Rituximab efficiently depletes increased CD20-expressing T cells in multiple sclerosis patients.", Journal of Immunology (Baltimore, MD.: 1950) Jul. 15, 2014, (Jul. 15, 2014), vol. 193, No. 2, pp. 580-586.

Pardoll, D.M., (2012). "The blockade of immune checkpoints in cancer immunotherapy" Nat. Rev. Cancer 12, 252-264.

Paterson, J., et al., (2006), "The differential expression of LCK and BAFF-receptor and their role in apoptosis in human lymphomas", Haematologica 91: 772-780.

Tavolaro, S., (2013), "IgD cross-linking induces gene expression profiling changes and enhances apoptosis in chronic lymphocytic leukemia cells", Leukemia Research, 37: 455-462.

Tussiwand, R., et al., (2012), "BAFF-R expression correlates with positive selection of immature B cells", European Journal of Immunology, 42: 206-216.

Ponders and Richards, "Tertiary templates for proteins. Use of packing criteria in the enumeration of allowed sequences for different structural classes," J. Mol. Biol. 1987, vol. 193, pp. 775-791.

Presta, "Antibody engineering," Curr. Op. Struct. Biol. 1992, vol. 2, pp. 593-596.

Rabbitts et al. "Human immunoglobulin heavy chain genes: evolutionary comparisons of C mu, C delta and C gamma genes and associated switch sequences," GenBank Accession No. CAB37838, Nucleic Acids Research 1981 vol. 9, No. 18, pp. 4509-4524.

Raju et al., "Potential therapeutic roles for antibody mixtures," Exp. Op. Biol. Ther. 2013, vol. 13, No. 10, pp. 1347-1352.

Symersky, J., et al., (2000), "Expression of the recombinant human immunoglobulin J Chain in *Escherichia coli*", Molecular Immunology, 37: 133-140.

Riechmann et al., "Reshaping human antibodies for therapy," Nature 1988, vol. 332, pp. 323-329.

Roopenian, D., et al. (2007), "FcRn: the neonatal Fc receptor comes of age", Nature Immunology, vol. 7, 715-725.

Seifert, O., et al., (2012), "The IgM CH2 domain as covalently linked homodimerization module for the generation of fusion proteins with dual specificty", Protein engineering, Design & Selection, vol. 25, No. 10, 603-612.

Tabrizi, M., et al. (2010), "Biodistribution Mechanisms of Therapeutic Monoclonal Antibodies in Health and Disease", The AAPS Journal, vol. 12, No. 1, pp. 33-43.

Jeon, H., et al., (2014), "Structure and Cancer Immunotherapy of the B7 Family Member B7x", Cell Rep., vol. 9(3): 1089-1098.

Maekawa, N., et al., (2014), "Expression of PD-L1 on Canine Tumor Cells and Enhancement of IFN-γ Production from Tumor-Infiltrating Cells by PD-L1 Blockade", PLOS One, vol. 9(6), e98415.

Müller, M.R., Saunders, K., Grace, C., Jin, M., Piche-Nicholas, N., Steven, J., O'Dwyer, R., Wu, L., Khetemenee, L., Vugmeyster, Y., Hickling, T.P., Tchistiakova, L., Olland, S., Gill, D., Jensen, A., Barelle, C.J., 2012. Improving the pharmacokinetic properties of biologies by fusion to an anti-HSA shark VNAR domain. MAbs 4, 673-685. https://doi.org/10.4161/mabs.22242.

Nocentini, G., Giunchi, L., Ronchetti, S., Krausz, L.T., Bartoli, A., Moraca, R., Migliorati, G., Riccardi, C., 1997. A new member of the tumor necrosis factor/nerve growth factor receptor family inhibits T cell receptor-induced apoptosis. Proc. Natl. Acad. Sci. U.S.A. 94, 6216-6221.

Pardoll, D.M, 2012. The blockade of immune checkpoints in cancer immunotherapy. Nat. Rev. Cancer 12, 252-264. https://doi.org/10.1038/nrc3239.

Paulik, M., Grieco, P., Kim, C., Maxeiner, H.G., Grunert, H.P., Zeichhardt, H., Morré, D.M., Morré, D.J., 1999. Drug-antibody conjugates with anti-HIV activity. Biochem. Pharmacol. 58, 1781-1790.

Postow, M.A., Callahan, M.K., Wolchok, J.D., 2015. Immune Checkpoint Blockade in Cancer Therapy. J. Clin. Oncol. 33, 1974-1982. https://doi.org/10.1200/JCO.2014.59.4358.

Redwan, E.-R.M., Matar, S.M., Serour, I.A., 2006. Recombinant human J-chain: fix the protein aggregations and yield maximize. Hum Antibodies 15, 95-102.

Smith, R.I., Coloma, M.J., Morrison, S.L., 1995. Addition of a mu-tailpiece to IgG results in polymeric antibodies with enhanced effector functions including complement-mediated cytolysis by IgG4. The Journal of Immunology 154, 2226-2236.

Sørensen, V., Rasmussen, I.B., Sundvold, V., Michaelsen, T.E., Sandlie, I., 2000. Structural requirements for incorporation of J chain into human IgM and IgA. Int. Immunol. 12, 19-27.

Tchoudakova, A., et al., 2009, "High level expression of functional human IgMs in human PER.C6 cells", MAbs 1, 163-171.

Vcelar, B., et al., 2007, "Reassessment of autoreactivity of the broadly neutralizing HIV antibodies 4E10 and 2F5 and retrospective analysis of clinical safety data" AIDS 21, 2161-2170.

Wood, C.R., et al., 1990, "High level synthesis of immunoglobulins in Chinese hamster ovary cells". J. Immunol. 145, 3011-3016.

Yu, X., et al., 2009, "The surface protein TIGIT suppresses T cell activation by promoting the generation of mature immunoregulatory dendritic cells," Nat. Immunol. 10, 48-57.

Yoo, E., et al., 1999, "Structural Requirements for Polymeric Immunoglobulin Assembly and Association with J Chain" vol. 274, No. 47, pp. 33771-33777.

(56) References Cited

OTHER PUBLICATIONS

Baliga, R., et al., (2016) "High Avidity Anti-CD20 IgM Antibody for enhanced Complement-Dependent Cell Killing of Low CD20 Expressing Tumor Cells", Poster Presented at the PEGS Boston Meeting Apr. 25-29, 2016.
Cao, Y., et al., (2011), "Targeting cell surface ß2-microglobulin by pentameric IgM antibodies", Br J Haematol, 154(1): 111-121.
Casset, F., et al., (2003), "A peptide mimetic of an anti-CD4 monoclonal antibody by rational design", Biochemical and biophysical Research Communications, 307: 198-205.
Chen, Y., et al., (1999), Selection and Analysis of an Optimized Anti-VEGF Antibody: Crystal Structure of an Affinity-matured Fab in Complex with Antigen, 293: 865-881.
De Pascalis, R., et al., (2002), "Grafting of "Abbreviated" Complementarity-Determining Regions Containing specificity-Determining Residues Essential for Ligand Contact to Engineer a Less Immunogenic Humanized Monoclonal Antibody", The Journal of Immunology, 169: 3076-3084.
Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.
Gaetano, N., et al., (2003), "Complement Activation Determines the Therapeutic Activity of Rituximab in Vivo", The Journal of Immunology, 171: 1581-1587.
Johnson, R., et al. (2012) "Biological Activity of Anti-CD20 Multivalent HPMA Copolymer-Fab' Conjugates", Biomacromolecules, vol. 13, pp. 727-735.
Lamminmaki, U., et al., (2001), "Crystal Structure of a Recombinant Anti-estradiol Fab Fragment in Complex with 17ß Estradiol", The Journal of Biological Chemistry, vol. 276(39): 36687-36694.
MacCallum R., et al. (1996), "Antibody-antigen Interactions: Contact Analysis and binding Site Topography", J. Mol. Bio. 262: 732-745.
Padlan, E., et al., (1989), "Structure of an antibody-antigen complex: crystal structure of the HyHel-10 Fab-lysozyme complex;", Proc. Natl. Acad. Sci. USA, vol. 86: 5938-5942.
Pascal, V., et al. (2012) "Anti-CD20 IgA can protect mice against lymphoma development: evaluation of the direct impact of IgA and cytotoxic effector recruitment on CD20 Target cells", Haematologica, the Hematology Journal, vol. 97(11), pp. 1686-1694.
Randall, T., et al., (1992), "Direct Evidence That J Chain Regulates the Polymeric Structure of IgM in Antibody-secreting B Cells", The Journal of Biological Chemistry, vol. 267(25), 18002-18007.
Rossi, E., et al. (2008) "Novel Designs of Multivalent Anti-CD20 Humanized Antibodies as Improved Lymphoma Therapeutics", Cancer Res, vol. 68(20), pp. 8384-8392.
Rudikoff, S., et al., (1982), "Single amino acid substitution altering antigen-binding specificity", Proc. Natl. Acad. Sci. USA, 79: 1979-1983.
Vajdos, F., et al., (2002), "Comprehensive Functional Maps of the Antigen-binding Site of an Anti-ErbB2 Antibody Obtained with Shotgun Scanning Mutagenesis", J. Mol. Biol. 320: 415-428.
Weiskopf, K., et al. (2013) "Engineered SIRPa Variants as Immunotherapeutic Adjuvants to Anticancer Antibodies", Science Express, vol. 341, pp. 89-91 with supplemental materials, 36 pages.
Woof et al., "Structure and Function Relationships in IgA", Mucosal Immunology, Nov. 2011, pp. 590-597, vol. 4 No. 6.
Wu, H., et al. (1999), "Humanization of a Murine Monoclonal Antibody by simultaneous Optimization of Framework and CDR Residues", J. Mol. Biol. 294: 151-162.
Gibson, "Anti-PD-L1 for metastatic triple-negative breast cancer", Lancet Oncol., May 2015, pp. e264, vol. 16, No. 6.
Harao et al., "Abstract LB-263: Enhancing of CD8+ tumor-infiltrating lymphocyte expansion from triple-negative breast cancer patients using of 41 BB costimulation", American Association for Cancer Research, Oct. 2014, 2 pages.
Ipalanichamy et al., "Rituximab Efficiently Depletes Increased CD20-Expressing T Cells in multiple Sclerosis Patients", Journal of Immunology, Jul. 15, 2014, pp. 580-586, vol. 193, No. 2.
Albrecht, H., et al. (2006), "Recombinant Antibodies: From the Laboratory to the Clinic", Cancer Biotherapy & Radiopharmaceuticals, vol. 21: 285-304.
Mariuzza, R. A., (1987), "The Structural Basis of Antigen-Antibody Recognition", vol. 16: 139-159.
Singer, M., et al., "Genes and Genomes", Moscow, "Mir", 1998, vol. 1: 63-64, no translation available, reference is believed to be a standard textbook reference on antibody structure.
Ammann, J., et al. (2014), "Development and use of IgM/J-Chain Fusion Proteins for Chacterization of Immunoglobulin Superfamily Ligand-Receptor Interactions", Current Protocols in Protein Science, Supplement 75.
Arnold, J., et al., (2005), "Human serum IgM glycosylation: identification of glycoforms that can bind to mannan-binding lectin", The Journal of Biological Chemistry, vol. 280(32): 29080-29087.
Bacac, M., et al., (2018), "CD20-TCB with Obinutuzumab Pretreatment as Next-Generation Treatment of Hematologic Malignancies, Clinical Cancer Research, 24(19): 4785-4797, includes supplementary methods," Binding to CD20- and CD3-expressing cells, 24 additional pages.
Baliga, R., et al., (2019), "IGM-2323: High Avidity IgM-based CD20 x CD3 Bispecific Antibody for Enhanced T-Cell Dependent Killing with Minimal Cytokine Release", Abstract 1574 at American Society of Hematology Annual Meeting, Dec. 7-10, 2019, Orlando, FL.
Beers, S., et al., (2010), "Antigenic modulation limits the efficacy of anti-CD20 antibodies: implications for antibody selection", Blood, 115(25): 5191-5201.
Bornstein, G., et al., (2010), "Development of a new fully human anti-CD20 monoclonal antibody for the treatment of B-cell malignancies", Invest New Drugs, 28:561-574.
Bortoletto, N., et al., (2002), "Optimizing anti-CD3 affinity for effective T cell targeting against tumor cells", Eur. J. Immunol, 32: 3102-3107.
Bowles, J., et al., (2006), "Anti-CD20 monoclonal antibody with enhanced affinity for CD16 activates NK cells at lower concentrations and more effectively than rituximab", Blood, 108(8): 2648-2654.
Brüggemann, M., et al., (1987), "Comparison of the effector functions of human immunoglobulins using a matched set of chimeric antibodies", J. Exp. Med, 166: 1351-1361.
Castro, C., et al., (2014), "Putting J chain back on the map: how might its expression define plasma cell development?", The Journal of Immunology, 193: 3248-3255.
Chu, S., et al., (2014), "Immunotherapy with Long-Lived Anti-CD20 x Anti-CD3 Bispecific Antibodies Stimulates Potent T Cell-mediated Killing of Human B Cell lines and Circulating and Lymphoid B Cells in Monkeys: A Potential Therapy tor B Cell Lymphomas and Leukemias", Xencor, Inc., Monrovia, California 91016 USA, Poster.
Czuczman, M., et al., (2008), "Acquirement of rituximab resistance in lymphoma cell lines is associated with both global CD20 gene and protein down-regulation regulated at the pretranscriptional and posttranscriptional levels", Clin Cancer Res, 14(5): 1561-1570.
Davis, T., et al., (1999), "Single-agent monoclonal antibody efficacy in bulky non-Hodgkin's lymphoma: results of a phase II trial of rituximab", J. Clin Oncol. 17: 1851-1857.
Davis, T., et al., (2000), "Rituximab anti-CD20 monoclonal antibody therapy in non-Hodgkin's lymphoma: safety and efficacy of re-treatment", Journal of Clinical Oncology, 18(17): 3135-3143.
Ghielmini, M., (2004), "Prolonged treatment with rituximab in patients with follicular lymphoma significantly increases event-free survival and response duration compared with the standard weekly x 4 schedule", Blood, 103(12): 4416-4423.
Hagenbeek, A., et al., (2009), "Evaluation of Ofatumumab, a Novel Human CD20 Monoclonal Antibody, as Single Agent Therapy in Rituximab-Refractory Follicular Lymphoma", Blood, 114(22): 935, 6 pages.
Haidar, JH., et al., (2003), "Loss of CD20 expression in relapsed lymphomas after rituximab therapy", Eur J. Haematol, 70: 330-332.

(56) References Cited

OTHER PUBLICATIONS

Harao M., et al., (2014), "Abstract LB-263: Enhancing of CD8+ tumor-infiltrating lymphocyte expansion from triple-negative breast cancer patients using of 41BB costimulation", American Associaton for Cancer Research, URL: http://cancerres.aacrjournals.org/content/74/19_Supplement/LB-263, XP002765987.
Hensel, F., et al., (2013), "Early development of PAT-SM6 for the treatment of melanoma", Melanoma Research, 23: 264-275.
Hsu, D., et al., (1999), "A humanized anti-CD3 antibody, HuM291, with low mitogenic activity, mediates complete and reversible T-cell depletion in chimpanzees", Transplantation, 68(4): 545-554.
Klimovich, V. B., (2011), "IgM and Its Receptors: Structural and Functional Aspects", Biochemistry, 76(5): 534-549.
Maloney, D., et al., (1997), "IDEC-C2B8 (Rituximab) anti-CD20 monoclonal antibody therapy in patients with relapsed low-grade non-Hodgkin's lymphoma", Blood, 90(6): 2188-2195.
Mandikian, D., et al., (2018), "Relative Target Affinities of T Cell-Dependent Bispecific Antibodies Determine Biodistribution in a Solid Tumor Mouse Model", Mol Cancer Ther., 17(4): 776-785, doi: 10.1158/1535-7163. MCT-17-0657.
Marcus, R., et al., (2017), "Obinutuzumab for the First-Line Treatment of Follicular Lymphoma", N Engl. J. Med. 377(14): 1331-44.
Mølhøj, M., et al., (2007), "CD19-/CD3-bispecific antibody of the BiTE class is far superior to tandem diabody with respect to redirected tumor cell lysis", Molecular Immunology 44: 1935-1943.
NCBI Reference Sequence (2018): NP_653247.1,Apr. 17, 2013, Immunoglobulin J chain precursor [*Homo sapiens*].
Miles, M., et al., (1995), "Polymer IgM assembly and secretion in lymphoid and nonlymphoid cell lines: evidence that J chain is required for pentamer IgM synthesis", Proc. Natl. Acad. Sci. USA, 92:2884-2888.
Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.
Rezvani, A., et al., (2011), "Rituximab Resistance", Best Pract Res Clin Haematol, 24(2): 203-216.
Saber, H., et al., (2017), "An FDA oncology analysis of CD3 bispecific constructs and first-in-human dose selection", Regulatory Toxicology and Pharmacology, 90: 144-152.
Smith, E., et al., (2015), "A novel, native-format bispecific antibody triggering T-cell killing of B-cells is robustly active in mouse tumor models and cynomolgus monkeys", Scientific Reports, 5:17943, 12 pages.
Strohl, W., et al., (2015), "Fusion Proteins for Half-Life Extension of Biologies as a Strategy to Make Biobetters", BioDrugs, 29: 215-239.
Sun, L., et al., (2015), "Anti-CD20/CD3 T cell-dependent bispecific antibody for the treatment of B cell malignancies", Immunotherapy, vol. 7(287), 287ra70, 11 pages.

Teachey, D., et al., (2013), "Cytokine release syndrome after blinatumomab treatment related to abnormal macrophage activation and ameliorated with cytokine directed therapy", Blood Journal, DOI 10.1182/blood-2013-02-485623.
Valley, C., et al., (2014), "Tumor Necrosis Factor-related Apoptosis-inducing Ligand (TRAIL) Induces Death Receptor 5 Networks That Are Highly Organized", The Journal of Biological chemistry, vol. 287, No. 25, pp. 21265-21278.
Van Imhoff, G., et al., (2017), "Ofatumumab Versus Rituximab Salvage Chemoimmunotherapy in Relapsed or Refractory Diffuse Large B-Cell Lymphoma: The ORCHARRD Study", Journal of Clinical Oncology, 35(5): 544-551.
Vitolo, U., et al., (2017), "Obinutuzumab or Rituximab Plus Cyclophosphamide, Doxorubicin, Vincristine, and Prednisone in Previously Untreated Diffuse Large B-Cell Lymphoma", Journal of Clinical Oncology, 35(31): 3529-3537.
Wing, M., (2008), "Monoclonal Antibody First Dose Cytokine Release Syndromes—Mechanisms and Prediction", Journal of Immunotoxicology, 5: 11-18.
Wu, J., et al., (2015), "Blinatumomab: a bispecific T cell engager (BiTE) antibody against CD19/CD3 for refractory acute lymphoid leukemia", Journal of Hematology & Oncology, 8:104, DOI 10.1186/s13045-015-0195-4, 7 pages.
Request for Supplement Examination as filed on Jun. 18, 2021 with USPTO re U.S. Pat. No. 9,951,134, dated Apr. 24, 2018.
Supplemental Examination Certificate dated Aug. 16, 2021 with USPTO re U.S. Pat. No. 9,951,134.
U.S. Appl. No. 17/386,397, Specification, Claims, Abstract and Drawings as filed Jul. 27, 2021 with U.S. Patent Office.
U.S. Appl. No. 17/635,078, Specification, Claims, Abstract and Drawings as filed Feb. 14, 2022 with U.S. Patent Office.
U.S. Appl. No. 17/758,207, Specification, Claims, Abstract and Drawings as filed Jun. 29, 2022 with U.S. Patent Office.
U.S. Appl. No. 17/761,428, Specification, Claims, Abstract and Drawings as filed Mar. 17, 2022 with U.S. Patent Office.
U.S. Appl. No. 17/806,339, Specification, Claims, Abstract and Drawings as filed Jun. 10, 2022 with U.S. Patent Office.
U.S. Appl. No. 17/812,614, Specification, Claims, Abstract and Drawings as filed Jul. 14, 2022 with U.S. Patent Office.
U.S. Appl. No. 17/996,760, Specification, Claims, Abstract and Drawings as filed Oct. 20, 2022 with U.S. Patent Office.
U.S. Appl. No. 18/052,388, Specification, Claims, Abstract and Drawings as filed Nov. 3, 2022 with U.S. Patent Office.
U.S. Appl. No. 17/998,307, Specification, Claims, Abstract and Drawings as filed Nov. 9, 2022 with U.S. Patent Office.
U.S. Appl. No. 18/054,776, Specification, Claims, Abstract and Drawings as filed Nov. 11, 2022 with U.S. Patent Office.
U.S. Appl. No. 18/055,340, Specification, Claims, Abstract and Drawings as filed Nov. 14, 2022 with U.S. Patent Office.

\* cited by examiner

Mature Human J Chain

- QEDERIVLVDNKCKCARITSRIIRSSEDPNEDIVERNI
  RIIVPLNNRENISDPTSPLRTRFVYHLSDLCKKCDPT
  EVELDNQIVTATQSNICDEDSATETCYTYDRNKCYT
  AVVPLVYGGETKMVETALTPDACYPD (SEQ ID NO: 1)
- Number of amino acids: 137
- Molecular weight: 15594.4
- Theoretical pI: 4.59

FIG. 3

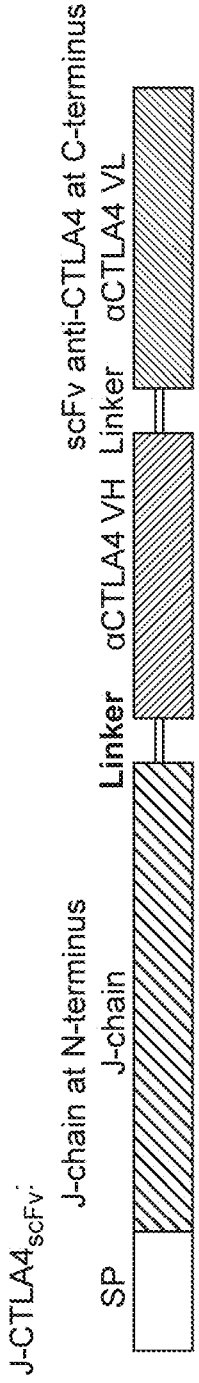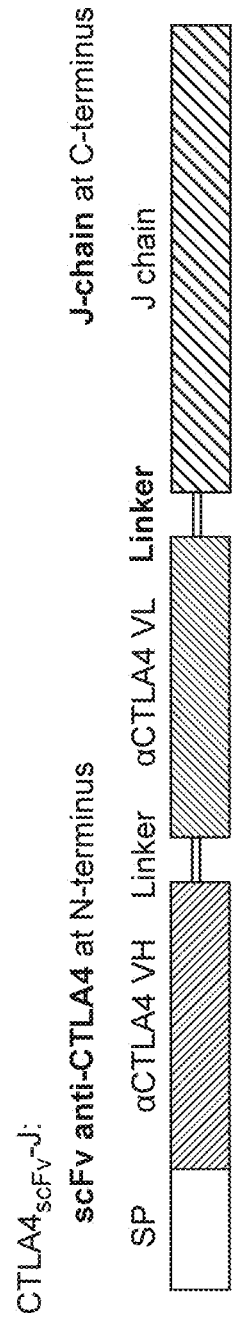
FIG. 5

Menu driven approach to binding molecules:
Antibody target X J-chain binding moiety target

| Antibody Target | J-chain binding moiety target |
|---|---|
| Super agonist targets:<br>CD137 (4-1BB), OX40, CD40, GITR, CD27, HVEM<br><br>Low expression level targets:<br>EGFR, HER2, HER3, EpCAM, CEACAM, Gp100, MAGE1, PD-L1<br><br>Low affinity targets:<br>NY-ESO-1, Sialyl Lewis X antigen, Tn antigen<br><br>Hematologic cancer targets:<br>CD19, CD20, CD22, CD33, CD38, CD52, CD70 | Antagonists of T-cell inhibitory signaling pathways:<br><br>CTLA4<br>PD-1<br>TIM3<br>LAG3<br>BTLA<br>VISTA<br>TIGIT<br>CD3 |

FIG. 7

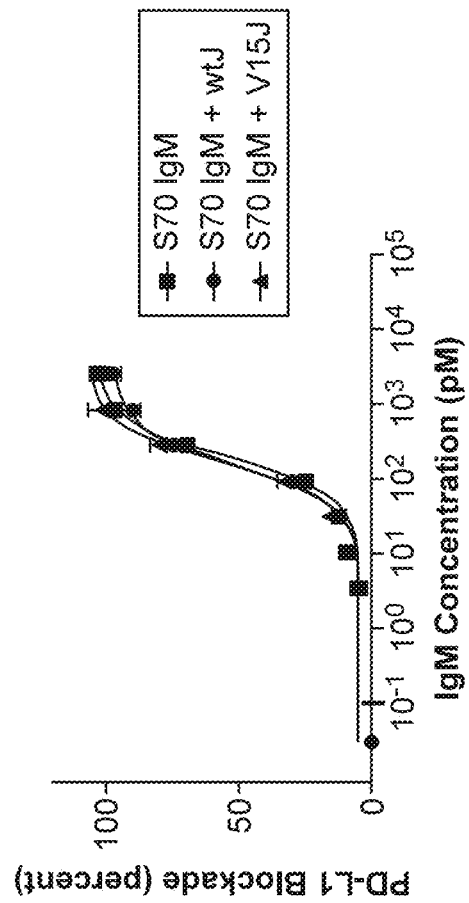
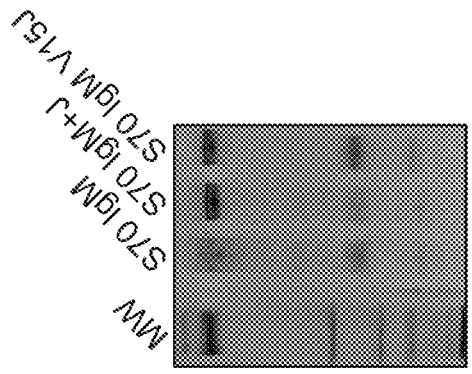
FIG. 12B
FIG. 12A

SEQUENCE LISTING

```
<160> NUMBER OF SEQ ID NOS: 152

<210> SEQ ID NO 1
<211> LENGTH: 137
<212> TYPE: PRT
<213> ORGANISM: Homo sapiens

<400> SEQUENCE: 1

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135

<210> SEQ ID NO 2
<211> LENGTH: 393
<212> TYPE: PRT
<213> ORGANISM: Artificial Sequence
<220> FEATURE:
<223> OTHER INFORMATION: CTLA4 scFv-15 aa Linker-J

<400> SEQUENCE: 2

Gln Val Gln Leu Val Glu Ser Gly Gly Gly Val Val Gln Pro Gly Arg
```

```
1               5                   10                  15
Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
                100                 105                 110

Leu Val Thr Val Ser Ser Gly Gly Gly Ser Gly Gly Gly Gly Ser
            115                 120                 125

Gly Gly Gly Gly Ser Glu Ile Val Leu Thr Gln Ser Pro Gly Thr Leu
130                 135                 140

Ser Leu Ser Pro Gly Glu Arg Ala Thr Leu Ser Cys Arg Ala Ser Gln
145                 150                 155                 160

Ser Val Gly Ser Ser Tyr Leu Ala Trp Tyr Gln Gln Lys Pro Gly Gln
                165                 170                 175

Ala Pro Arg Leu Leu Ile Tyr Gly Ala Phe Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
210                 215                 220

Tyr Gly Ser Ser Pro Trp Thr Phe Gly Gln Gly Thr Lys Val Glu Ile
225                 230                 235                 240

Lys Gly Gly Gly Gly Ser Gly Gly Gly Gly Ser Gly Gly Gly Gly Ser
                245                 250                 255

Gln Glu Asp Glu Arg Ile Val Leu Val Asp Asn Lys Cys Lys Cys Ala
                260                 265                 270

Arg Ile Thr Ser Arg Ile Ile Arg Ser Ser Glu Asp Pro Asn Glu Asp
            275                 280                 285

Ile Val Glu Arg Asn Ile Arg Ile Ile Val Pro Leu Asn Asn Arg Glu
            290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
                340                 345                 350

Ala Thr Glu Thr Cys Tyr Thr Tyr Asp Arg Asn Lys Cys Tyr Thr Ala
                355                 360                 365

Val Val Pro Leu Val Tyr Gly Gly Glu Thr Lys Met Val Glu Thr Ala
            370                 375                 380

Leu Thr Pro Asp Ala Cys Tyr Pro Asp
385                 390

<210> SEQ ID NO 3
<211> LENGTH: 393
<212> TYPE: PRT
<213> ORGANISM: Artificial Sequence
```

<220> FEATURE:
<223> OTHER INFORMATION: J-15 aa Linker-CTLA4 scFv

<400> SEQUENCE: 3

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Glu Asp Ser
                85                  90                  95

Ala Thr Glu Thr Cys Tyr Thr Tyr Asp Arg Asn Lys Cys Tyr Thr Ala
                100                 105                 110

Val Val Pro Leu Val Tyr Gly Glu Thr Lys Met Val Glu Thr Ala
            115                 120                 125

Leu Thr Pro Asp Ala Cys Tyr Pro Asp Gly Gly Gly Ser Gly Gly
        130                 135                 140

Gly Gly Ser Gly Gly Gly Ser Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Ser Tyr Thr Met His Trp Val Arg Gln Ala
            180                 185                 190

Pro Gly Lys Gly Leu Glu Trp Val Thr Phe Ile Ser Tyr Asp Gly Asn
        195                 200                 205

Asn Lys Tyr Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Ile Tyr Tyr Cys Ala Arg Thr Gly Trp Leu Gly Pro
                245                 250                 255

Phe Asp Tyr Trp Gly Gln Gly Thr Leu Val Thr Val Ser Ser Gly Gly
            260                 265                 270

Gly Gly Ser Gly Gly Gly Gly Ser Gly Gly Gly Gly Ser Glu Ile Val
        275                 280                 285

Leu Thr Gln Ser Pro Gly Thr Leu Ser Leu Ser Pro Gly Glu Arg Ala
290                 295                 300

Thr Leu Ser Cys Arg Ala Ser Gln Ser Val Gly Ser Ser Tyr Leu Ala
305                 310                 315                 320

Trp Tyr Gln Gln Lys Pro Gly Gln Ala Pro Arg Leu Leu Ile Tyr Gly
                325                 330                 335

Ala Phe Ser Arg Ala Thr Gly Ile Pro Asp Arg Phe Ser Gly Ser Gly
            340                 345                 350

Ser Gly Thr Asp Phe Thr Leu Thr Ile Ser Arg Leu Glu Pro Glu Asp
        355                 360                 365

Phe Ala Val Tyr Tyr Cys Gln Gln Tyr Gly Ser Ser Pro Trp Thr Phe
370                 375                 380

Gly Gln Gly Thr Lys Val Glu Ile Lys
385                 390
```

<210> SEQ ID NO 4
<211> LENGTH: 595
<212> TYPE: PRT
<213> ORGANISM: Artificial Sequence
<220> FEATURE:
<223> OTHER INFORMATION: IgM heavy chain with a Vh region derived from an anti-PD-L1 antibody

<400> SEQUENCE: 4

```
Met Asp Pro Lys Gly Ser Leu Ser Trp Arg Ile Leu Phe Leu Ser
 1               5                  10                  15

Leu Ala Phe Glu Leu Ser Tyr Gly Glu Val Gln Leu Val Glu Ser Gly
                20                  25                  30

Gly Gly Leu Val Gln Pro Gly Gly Ser Leu Arg Leu Ser Cys Ala Ala
            35                  40                  45

Ser Gly Phe Thr Phe Ser Asp Ser Trp Ile His Trp Val Arg Gln Ala
        50                  55                  60

Pro Gly Lys Gly Leu Glu Trp Val Ala Trp Ile Ser Pro Tyr Gly Gly
 65                  70                  75                  80

Ser Thr Tyr Tyr Ala Asp Ser Val Lys Gly Arg Phe Thr Ile Ser Ala
                85                  90                  95

Asp Thr Ser Lys Asn Thr Ala Tyr Leu Gln Met Asn Ser Leu Arg Ala
            100                 105                 110

Glu Asp Thr Ala Val Tyr Tyr Cys Ala Arg Arg His Trp Pro Gly Gly
        115                 120                 125

Phe Asp Tyr Trp Gly Gln Gly Thr Leu Val Thr Val Ser Ala Gly Ser
130                 135                 140

Ala Ser Ala Pro Thr Leu Phe Pro Leu Val Ser Cys Glu Asn Ser Pro
145                 150                 155                 160

Ser Asp Thr Ser Ser Val Ala Val Gly Cys Leu Ala Gln Asp Phe Leu
                165                 170                 175

Pro Asp Ser Ile Thr Phe Ser Trp Lys Tyr Lys Asn Asn Ser Asp Ile
            180                 185                 190

Ser Ser Thr Arg Gly Phe Pro Ser Val Leu Arg Gly Gly Lys Tyr Ala
        195                 200                 205

Ala Thr Ser Gln Val Leu Leu Pro Ser Lys Asp Val Met Gln Gly Thr
    210                 215                 220

Asp Glu His Val Val Cys Lys Val Gln His Pro Asn Gly Asn Lys Glu
225                 230                 235                 240

Lys Asn Val Pro Leu Pro Val Ile Ala Glu Leu Pro Pro Lys Val Ser
                245                 250                 255

Val Phe Val Pro Pro Arg Asp Gly Phe Phe Gly Asn Pro Arg Lys Ser
            260                 265                 270

Lys Leu Ile Cys Gln Ala Thr Gly Phe Ser Pro Arg Gln Ile Gln Val
        275                 280                 285

Ser Trp Leu Arg Glu Gly Lys Gln Val Gly Ser Gly Val Thr Thr Asp
    290                 295                 300

Gln Val Gln Ala Glu Ala Lys Glu Ser Gly Pro Thr Thr Tyr Lys Val
305                 310                 315                 320

Thr Ser Thr Leu Thr Ile Lys Glu Ser Asp Trp Leu Ser Gln Ser Met
                325                 330                 335

Phe Thr Cys Arg Val Asp His Arg Gly Leu Thr Phe Gln Gln Asn Ala
            340                 345                 350

Ser Ser Met Cys Val Pro Asp Gln Asp Thr Ala Ile Arg Val Phe Ala
```

```
                    355                 360                 365
Ile Pro Pro Ser Phe Ala Ser Ile Phe Leu Thr Lys Ser Thr Lys Leu
370                 375                 380

Thr Cys Leu Val Thr Asp Leu Thr Thr Tyr Asp Ser Val Thr Ile Ser
385                 390                 395                 400

Trp Thr Arg Gln Asn Gly Glu Ala Val Lys Thr His Thr Asn Ile Ser
                405                 410                 415

Glu Ser His Pro Asn Ala Thr Phe Ser Ala Val Gly Glu Ala Ser Ile
            420                 425                 430

Cys Glu Asp Asp Trp Asn Ser Gly Glu Arg Phe Thr Cys Thr Val Thr
        435                 440                 445

His Thr Asp Leu Pro Ser Pro Leu Lys Gln Thr Ile Ser Arg Pro Lys
    450                 455                 460

Gly Val Ala Leu His Arg Pro Asp Val Tyr Leu Leu Pro Pro Ala Arg
465                 470                 475                 480

Glu Gln Leu Asn Leu Arg Glu Ser Ala Thr Ile Thr Cys Leu Val Thr
                485                 490                 495

Gly Phe Ser Pro Ala Asp Val Phe Val Gln Trp Met Gln Arg Gly Gln
            500                 505                 510

Pro Leu Ser Pro Glu Lys Tyr Val Thr Ser Ala Pro Met Pro Glu Pro
        515                 520                 525

Gln Ala Pro Gly Arg Tyr Phe Ala His Ser Ile Leu Thr Val Ser Glu
    530                 535                 540

Glu Glu Trp Asn Thr Gly Glu Thr Tyr Thr Cys Val Val Ala His Glu
545                 550                 555                 560

Ala Leu Pro Asn Arg Val Thr Glu Arg Thr Val Asp Lys Ser Thr Gly
                565                 570                 575

Lys Pro Thr Leu Tyr Asn Val Ser Leu Val Met Ser Asp Thr Ala Gly
            580                 585                 590

Thr Cys Tyr
        595

<210> SEQ ID NO 5
<211> LENGTH: 214
<212> TYPE: PRT
<213> ORGANISM: Artificial Sequence
<220> FEATURE:
<223> OTHER INFORMATION: Light chain for bispecific anti-PDL1 IgM

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 235
<212> TYPE: PRT
<213> ORGANISM: Artificial Sequence
<220> FEATURE:
<223> OTHER INFORMATION: IgM Light chain sequence of an anti-CD20
      antibody

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 7
<211> LENGTH: 593
```

<212> TYPE: PRT
<213> ORGANISM: Artificial Sequence
<220> FEATURE:
<223> OTHER INFORMATION: IgM Heavy chain sequence of an anti-CD20 antibody

<400> SEQUENCE: 7

```
Met Gly Trp Ser Tyr Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ser Gly Ser Ala Ser
130                 135                 140

Ala Pro Thr Leu Phe Pro Leu Val Ser Cys Glu Asn Ser Pro Ser Asp
145                 150                 155                 160

Thr Ser Ser Val Ala Val Gly Cys Leu Ala Gln Asp Phe Leu Pro Asp
                165                 170                 175

Ser Ile Thr Phe Ser Trp Lys Tyr Lys Asn Asn Ser Asp Ile Ser Ser
            180                 185                 190

Thr Arg Gly Phe Pro Ser Val Leu Arg Gly Gly Lys Tyr Ala Ala Thr
        195                 200                 205

Ser Gln Val Leu Leu Pro Ser Lys Asp Val Met Gln Gly Thr Asp Glu
    210                 215                 220

His Val Val Cys Lys Val Gln His Pro Asn Gly Asn Lys Glu Lys Asn
225                 230                 235                 240

Val Pro Leu Pro Val Ile Ala Glu Leu Pro Pro Lys Val Ser Val Phe
                245                 250                 255

Val Pro Pro Arg Asp Gly Phe Phe Gly Asn Pro Arg Lys Ser Lys Leu
            260                 265                 270

Ile Cys Gln Ala Thr Gly Phe Ser Pro Arg Gln Ile Gln Val Ser Trp
        275                 280                 285

Leu Arg Glu Gly Lys Gln Val Gly Ser Gly Val Thr Thr Asp Gln Val
    290                 295                 300

Gln Ala Glu Ala Lys Glu Ser Gly Pro Thr Thr Tyr Lys Val Thr Ser
305                 310                 315                 320

Thr Leu Thr Ile Lys Glu Ser Asp Trp Leu Ser Gln Ser Met Phe Thr
                325                 330                 335

Cys Arg Val Asp His Arg Gly Leu Thr Phe Gln Gln Asn Ala Ser Ser
            340                 345                 350

Met Cys Val Pro Asp Gln Asp Thr Ala Ile Arg Val Phe Ala Ile Pro
        355                 360                 365

Pro Ser Phe Ala Ser Ile Phe Leu Thr Lys Ser Thr Lys Leu Thr Cys
    370                 375                 380
```

```
Leu Val Thr Asp Leu Thr Thr Tyr Asp Ser Val Thr Ile Ser Trp Thr
385                 390                 395                 400

Arg Gln Asn Gly Glu Ala Val Lys Thr His Thr Asn Ile Ser Glu Ser
                405                 410                 415

His Pro Asn Ala Thr Phe Ser Ala Val Gly Glu Ala Ser Ile Cys Glu
            420                 425                 430

Asp Asp Trp Asn Ser Gly Glu Arg Phe Thr Cys Thr Val Thr His Thr
        435                 440                 445

Asp Leu Pro Ser Pro Leu Lys Gln Thr Ile Ser Arg Pro Lys Gly Val
    450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
            500                 505                 510

Ser Pro Glu Lys Tyr Val Thr Ser Ala Pro Met Pro Glu Pro Gln Ala
        515                 520                 525

Pro Gly Arg Tyr Phe Ala His Ser Ile Leu Thr Val Ser Glu Glu Glu
    530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
            580                 585                 590

Tyr

<210> SEQ ID NO 8
<211> LENGTH: 412
<212> TYPE: PRT
<213> ORGANISM: Artificial Sequence
<220> FEATURE:
<223> OTHER INFORMATION: J chain sequence for V15J

<400> SEQUENCE: 8

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Ser Tyr Thr Met His Trp Val Arg Gln Ala Pro Gly Gln Gly Leu
    50                  55                  60

Glu Trp Met Gly Tyr Ile Asn Pro Arg Ser Gly Tyr Thr His Tyr Asn
65                  70                  75                  80

Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
        115                 120                 125

Trp Gly Gln Gly Thr Leu Val Thr Val Ser Ser Gly Gly Gly Gly Ser
    130                 135                 140
```

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
                180                 185                 190

Pro Gly Lys Ala Pro Lys Arg Leu Ile Tyr Asp Thr Ser Lys Leu Ala
                195                 200                 205

Ser Gly Val Pro Ser Arg Phe Ser Gly Ser Gly Ser Gly Thr Asp Phe
210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Leu Glu Ile Lys Gly Gly Gly Gly Ser Gly Gly Gly Gly Ser Gly Gly
                260                 265                 270

Gly Gly Ser Gln Glu Asp Glu Arg Ile Val Leu Val Asp Asn Lys Cys
                275                 280                 285

Lys Cys Ala Arg Ile Thr Ser Arg Ile Ile Arg Ser Ser Glu Asp Pro
290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
                340                 345                 350

Glu Leu Asp Asn Gln Ile Val Thr Ala Thr Gln Ser Asn Ile Cys Asp
                355                 360                 365

Glu Asp Ser Ala Thr Glu Thr Cys Tyr Thr Tyr Asp Arg Asn Lys Cys
                370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp
                405                 410

<210> SEQ ID NO 9
<211> LENGTH: 415
<212> TYPE: PRT
<213> ORGANISM: Artificial Sequence
<220> FEATURE:
<223> OTHER INFORMATION: J-chain sequence for J15V

<400> SEQUENCE: 9

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
                35                  40                  45

Glu Asp Pro Asn Glu Asp Ile Val Glu Arg Asn Ile Arg Ile Ile Val
50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

```
Thr Glu Val Glu Leu Asp Asn Gln Ile Val Thr Ala Thr Gln Ser Asn
                100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
        130                 135                 140

Lys Met Val Glu Thr Ala Leu Thr Pro Asp Ala Cys Tyr Pro Asp Gly
145                 150                 155                 160

Gly Gly Gly Ser Gly Gly Gly Gly Ser Gly Gly Gly Ser Gln Val
                165                 170                 175

Gln Leu Val Gln Ser Gly Ala Glu Val Lys Lys Pro Gly Ala Ser Val
                180                 185                 190

Lys Val Ser Cys Lys Ala Ser Gly Tyr Thr Phe Ile Ser Tyr Thr Met
                195                 200                 205

His Trp Val Arg Gln Ala Pro Gly Gln Gly Leu Glu Trp Met Gly Tyr
            210                 215                 220

Ile Asn Pro Arg Ser Gly Tyr Thr His Tyr Asn Gln Lys Leu Lys Asp
225                 230                 235                 240

Lys Ala Thr Leu Thr Ala Asp Lys Ser Ala Ser Thr Ala Tyr Met Glu
                245                 250                 255

Leu Ser Ser Leu Arg Ser Glu Asp Thr Ala Val Tyr Tyr Cys Ala Arg
                260                 265                 270

Ser Ala Tyr Tyr Asp Tyr Asp Gly Phe Ala Tyr Trp Gly Gln Gly Thr
            275                 280                 285

Leu Val Thr Val Ser Ser Gly Gly Gly Ser Gly Gly Gly Gly Ser
                290                 295                 300

Gly Gly Gly Gly Ser Asp Ile Gln Met Thr Gln Ser Pro Ser Ser Leu
305                 310                 315                 320

Ser Ala Ser Val Gly Asp Arg Val Thr Ile Thr Cys Ser Ala Ser Ser
                325                 330                 335

Ser Val Ser Tyr Met Asn Trp Tyr Gln Gln Lys Pro Gly Lys Ala Pro
            340                 345                 350

Lys Arg Leu Ile Tyr Asp Thr Ser Lys Leu Ala Ser Gly Val Pro Ser
            355                 360                 365

Arg Phe Ser Gly Ser Gly Ser Gly Thr Asp Phe Thr Leu Thr Ile Ser
    370                 375                 380

Ser Leu Gln Pro Glu Asp Phe Ala Thr Tyr Tyr Cys Gln Gln Trp Ser
385                 390                 395                 400

Ser Asn Pro Pro Thr Phe Gly Gly Gly Thr Lys Leu Glu Ile Lys
                405                 410                 415

<210> SEQ ID NO 10
<211> LENGTH: 417
<212> TYPE: PRT
<213> ORGANISM: Artificial Sequence
<220> FEATURE:
<223> OTHER INFORMATION: J-chain sequence for O15J

<400> SEQUENCE: 10

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45
```

-continued

Gly Tyr Ile Asn Pro Ser Arg Gly Tyr Thr Asn Tyr Asn Gln Lys Phe
         50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Ser Leu Asp Tyr Trp Gly Gln Gly
             100                 105                 110

Thr Thr Leu Thr Val Ser Ser Gly Gly Gly Gly Ser Gly Gly Gly Gly
         115                 120                 125

Ser Gly Gly Gly Gly Ser Gln Ile Val Leu Thr Gln Ser Pro Ala Ile
130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                 165                 170                 175

Pro Lys Arg Trp Ile Tyr Asp Thr Ser Lys Leu Ala Ser Gly Val Pro
             180                 185                 190

Ala His Phe Arg Gly Ser Gly Ser Gly Thr Ser Tyr Ser Leu Thr Ile
         195                 200                 205

Ser Gly Met Glu Ala Glu Asp Ala Ala Thr Tyr Tyr Cys Gln Gln Trp
210                 215                 220

Ser Ser Asn Pro Phe Thr Phe Gly Ser Gly Thr Lys Leu Glu Ile Lys
225                 230                 235                 240

Gly Gly Gly Gly Ser Gly Gly Gly Gly Ser Gly Gly Gly Gly Ser Gln
                 245                 250                 255

Glu Asp Glu Arg Ile Val Leu Val Asp Asn Lys Cys Lys Cys Ala Arg
             260                 265                 270

Ile Thr Ser Arg Ile Ile Arg Ser Ser Glu Asp Pro Asn Glu Asp Ile
         275                 280                 285

Val Glu Arg Asn Ile Arg Ile Ile Val Pro Leu Asn Asn Arg Glu Asn
         290                 295                 300

Ile Ser Asp Pro Thr Ser Pro Leu Arg Thr Arg Phe Val Tyr His Leu
305                 310                 315                 320

Ser Asp Leu Cys Lys Lys Cys Asp Pro Thr Glu Val Glu Leu Asp Asn
                 325                 330                 335

Gln Ile Val Thr Ala Thr Gln Ser Asn Ile Cys Asp Glu Asp Ser Ala
             340                 345                 350

Thr Glu Thr Cys Tyr Thr Tyr Asp Arg Asn Lys Cys Tyr Thr Ala Val
         355                 360                 365

Val Pro Leu Val Tyr Gly Gly Glu Thr Lys Met Val Glu Thr Ala Leu
370                 375                 380

Thr Pro Asp Ala Cys Tyr Pro Asp Gly Gly Ser Glu Gln Lys Leu
385                 390                 395                 400

Ile Ser Glu Glu Asp Leu Asn Ser Ala Val Asp His His His His
             405                 410                 415

His

<210> SEQ ID NO 11
<211> LENGTH: 413
<212> TYPE: PRT
<213> ORGANISM: Artificial Sequence
<220> FEATURE:
<223> OTHER INFORMATION: J-chain sequence for J150

<400> SEQUENCE: 11

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
    130                 135                 140

Gly Gly Ser Gly Gly Gly Gly Ser Gln Val Gln Leu Gln Gln Ser Gly
145                 150                 155                 160

Ala Glu Leu Ala Arg Pro Gly Ala Ser Val Lys Met Ser Cys Lys Ala
                165                 170                 175

Ser Gly Tyr Thr Phe Thr Arg Tyr Thr Met His Trp Val Lys Gln Arg
            180                 185                 190

Pro Gly Gln Gly Leu Glu Trp Ile Gly Tyr Ile Asn Pro Ser Arg Gly
        195                 200                 205

Tyr Thr Asn Tyr Asn Gln Lys Phe Lys Asp Lys Ala Thr Leu Thr Thr
    210                 215                 220

Asp Lys Ser Ser Ser Thr Ala Tyr Met Gln Leu Ser Ser Leu Thr Ser
225                 230                 235                 240

Glu Asp Ser Ala Val Tyr Tyr Cys Ala Arg Tyr Tyr Asp Asp His Tyr
                245                 250                 255

Ser Leu Asp Tyr Trp Gly Gln Gly Thr Thr Leu Thr Val Ser Ser Gly
            260                 265                 270

Gly Gly Gly Ser Gly Gly Gly Gly Ser Gly Gly Gly Gly Ser Gln Ile
        275                 280                 285

Val Leu Thr Gln Ser Pro Ala Ile Met Ser Ala Ser Pro Gly Glu Lys
    290                 295                 300

Val Thr Met Thr Cys Ser Ala Ser Ser Ser Val Ser Tyr Met Asn Trp
305                 310                 315                 320

Tyr Gln Gln Lys Ser Gly Thr Ser Pro Lys Arg Trp Ile Tyr Asp Thr
                325                 330                 335

Ser Lys Leu Ala Ser Gly Val Pro Ala His Phe Arg Gly Ser Gly Ser
            340                 345                 350

Gly Thr Ser Tyr Ser Leu Thr Ile Ser Gly Met Glu Ala Glu Asp Ala
        355                 360                 365

Ala Thr Tyr Tyr Cys Gln Gln Trp Ser Ser Asn Pro Phe Thr Phe Gly
    370                 375                 380

Ser Gly Thr Lys Leu Glu Ile Lys Glu Gln Lys Leu Ile Ser Glu Glu
385                 390                 395                 400

Asp Leu Asn Ser Ala Val Asp His His His His His
                405                 410
```

<210> SEQ ID NO 12
<211> LENGTH: 451
<212> TYPE: PRT
<213> ORGANISM: Artificial Sequence
<220> FEATURE:
<223> OTHER INFORMATION: IgM Heavy chain sequence of an anti-DR5 antibody

<400> SEQUENCE: 12

```
Glu Val Gln Leu Val Gln Ser Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
```

```
              355                 360                 365
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: IgM Light chain sequence of the anti-DR5
      antibody

<400> SEQUENCE: 13

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 14
<211> LENGTH: 574
<212> TYPE: PRT
<213> ORGANISM: Artificial Sequence
<220> FEATURE:
```

<223> OTHER INFORMATION: IGM-55.5 heavy chain

<400> SEQUENCE: 14

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Met Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
    370                 375                 380

Gly Glu Ala Val Lys Thr His Thr Asn Ile Ser Glu Ser His Pro Asn
385                 390                 395                 400
```

```
Ala Thr Phe Ser Ala Val Gly Glu Ala Ser Ile Cys Glu Asp Asp Trp
                405                 410                 415
Asn Ser Gly Glu Arg Phe Thr Cys Thr Val Thr His Thr Asp Leu Pro
            420                 425                 430
Ser Pro Leu Lys Gln Thr Ile Ser Arg Pro Lys Gly Val Ala Leu His
            435                 440                 445
Arg Pro Asp Val Tyr Leu Leu Pro Pro Ala Arg Glu Gln Leu Asn Leu
        450                 455                 460
Arg Glu Ser Ala Thr Ile Thr Cys Leu Val Thr Gly Phe Ser Pro Ala
465                 470                 475                 480
Asp Val Phe Val Gln Trp Met Gln Arg Gly Gln Pro Leu Ser Pro Glu
                485                 490                 495
Lys Tyr Val Thr Ser Ala Pro Met Pro Glu Pro Gln Ala Pro Gly Arg
            500                 505                 510
Tyr Phe Ala His Ser Ile Leu Thr Val Ser Glu Glu Glu Trp Asn Thr
            515                 520                 525
Gly Glu Thr Tyr Thr Cys Val Val Ala His Glu Ala Leu Pro Asn Arg
        530                 535                 540
Val Thr Glu Arg Thr Val Asp Lys Ser Thr Gly Lys Pro Thr Leu Tyr
545                 550                 555                 560
Asn Val Ser Leu Val Met Ser Asp Thr Ala Gly Thr Cys Tyr
                565                 570

<210> SEQ ID NO 15
<211> LENGTH: 214
<212> TYPE: PRT
<213> ORGANISM: Artificial Sequence
<220> FEATURE:
<223> OTHER INFORMATION: Light chain for IGM-55.5

<400> SEQUENCE: 15

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Ile
                85                  90                  95
Thr Phe Gly Gln Gly Thr Arg Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 16
<211> LENGTH: 223
<212> TYPE: PRT
<213> ORGANISM: Homo sapiens
<400> SEQUENCE: 16

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 17
<211> LENGTH: 288
<212> TYPE: PRT
<213> ORGANISM: Homo sapiens
<400> SEQUENCE: 17

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80
```

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 18
<211> LENGTH: 301
<212> TYPE: PRT
<213> ORGANISM: Homo sapiens

<400> SEQUENCE: 18

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
            50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
            85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
            130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
            165                 170                 175

```
Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 19
<211> LENGTH: 360
<212> TYPE: PRT
<213> ORGANISM: Homo sapiens

<400> SEQUENCE: 19

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
```

-continued

```
                245                 250                 255
Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Gly Gln Pro Gln Val Gly Lys Glu
                355                 360

<210> SEQ ID NO 20
<211> LENGTH: 241
<212> TYPE: PRT
<213> ORGANISM: Homo sapiens

<400> SEQUENCE: 20

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Gly Lys Gln Asn Glu Leu Ser Asp Thr Ala
130                 135                 140

Gly Arg Glu Ile Asn Leu Val Asp Ala His Leu Lys Ser Glu Gln Thr
145                 150                 155                 160

Glu Ala Ser Thr Arg Gln Asn Ser Gln Val Leu Leu Ser Glu Thr Gly
                165                 170                 175

Ile Tyr Asp Asn Asp Pro Asp Leu Cys Phe Arg Met Gln Glu Gly Ser
                180                 185                 190

Glu Val Tyr Ser Asn Pro Cys Leu Glu Glu Asn Lys Pro Gly Ile Val
            195                 200                 205

Tyr Ala Ser Leu Asn His Ser Val Ile Gly Leu Asn Ser Arg Leu Ala
        210                 215                 220

Arg Asn Val Lys Glu Ala Pro Thr Glu Tyr Ala Ser Ile Cys Val Arg
225                 230                 235                 240

Ser
```

```
<210> SEQ ID NO 21
<211> LENGTH: 311
<212> TYPE: PRT
<213> ORGANISM: Homo sapiens

<400> SEQUENCE: 21

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 22
<211> LENGTH: 244
<212> TYPE: PRT
<213> ORGANISM: Homo sapiens

<400> SEQUENCE: 22

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
```

```
                 20                  25                  30
Ile Ser Ala Glu Lys Gly Gly Ser Ile Ile Leu Gln Cys His Leu Ser
             35                  40                  45

Ser Thr Thr Ala Gln Val Thr Gln Val Asn Trp Glu Gln Gln Asp Gln
 50                  55                  60

Leu Leu Ala Ile Cys Asn Ala Asp Leu Gly Trp His Ile Ser Pro Ser
 65                  70                  75                  80

Phe Lys Asp Arg Val Ala Pro Gly Pro Gly Leu Gly Leu Thr Leu Gln
                 85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
            130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
            210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 23
<211> LENGTH: 288
<212> TYPE: PRT
<213> ORGANISM: Homo sapiens

<400> SEQUENCE: 23

Met Gln Ile Pro Gln Ala Pro Trp Pro Val Val Trp Ala Val Leu Gln
1               5                  10                  15

Leu Gly Trp Arg Pro Gly Trp Phe Leu Asp Ser Pro Asp Arg Pro Trp
                20                  25                  30

Asn Pro Pro Thr Phe Phe Pro Ala Leu Leu Val Val Thr Glu Gly Asp
             35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
```

```
                145                 150                 155                 160
Arg Pro Ala Gly Gln Phe Gln Thr Leu Val Val Gly Val Val Gly
                    165                 170                 175
Leu Leu Gly Ser Leu Val Leu Leu Val Trp Val Leu Ala Val Ile Cys
                    180                 185                 190
Ser Arg Ala Ala Arg Gly Thr Ile Gly Ala Arg Arg Thr Gly Gln Pro
                    195                 200                 205
Leu Lys Glu Asp Pro Ser Ala Val Pro Val Phe Ser Val Asp Tyr Gly
                    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                    245                 250                 255
Met Gly Thr Ser Ser Pro Ala Arg Arg Gly Ser Ala Asp Gly Pro Arg
                    260                 265                 270
Ser Ala Gln Pro Leu Arg Pro Glu Asp Gly His Cys Ser Trp Pro Leu
                    275                 280                 285

<210> SEQ ID NO 24
<211> LENGTH: 290
<212> TYPE: PRT
<213> ORGANISM: Homo sapiens

<400> SEQUENCE: 24

Met Arg Ile Phe Ala Val Phe Ile Phe Met Thr Tyr Trp His Leu Leu
1                   5                   10                  15
Asn Ala Phe Thr Val Thr Val Pro Lys Asp Leu Tyr Val Val Glu Tyr
                    20                  25                  30
Gly Ser Asn Met Thr Ile Glu Cys Lys Phe Pro Val Glu Lys Gln Leu
                    35                  40                  45
Asp Leu Ala Ala Leu Ile Val Tyr Trp Glu Met Glu Asp Lys Asn Ile
                    50                  55                  60
Ile Gln Phe Val His Gly Glu Glu Asp Leu Lys Val Gln His Ser Ser
65                  70                  75                  80
Tyr Arg Gln Arg Ala Arg Leu Leu Lys Asp Gln Leu Ser Leu Gly Asn
                    85                  90                  95
Ala Ala Leu Gln Ile Thr Asp Val Lys Leu Gln Asp Ala Gly Val Tyr
                    100                 105                 110
Arg Cys Met Ile Ser Tyr Gly Gly Ala Asp Tyr Lys Arg Ile Thr Val
                    115                 120                 125
Lys Val Asn Ala Pro Tyr Asn Lys Ile Asn Gln Arg Ile Leu Val Val
                    130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                    165                 170                 175
Gly Lys Thr Thr Thr Thr Asn Ser Lys Arg Glu Glu Lys Leu Phe Asn
                    180                 185                 190
Val Thr Ser Thr Leu Arg Ile Asn Thr Thr Thr Asn Glu Ile Phe Tyr
                    195                 200                 205
Cys Thr Phe Arg Arg Leu Asp Pro Glu Glu Asn His Thr Ala Glu Leu
                    210                 215                 220
Val Ile Pro Glu Leu Pro Leu Ala His Pro Pro Asn Glu Arg Thr His
225                 230                 235                 240
```

```
Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 25
<211> LENGTH: 301
<212> TYPE: PRT
<213> ORGANISM: Homo sapiens

<400> SEQUENCE: 25

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
            165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 26
```

```
<211> LENGTH: 360
<212> TYPE: PRT
<213> ORGANISM: Homo sapiens

<400> SEQUENCE: 26

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                    85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
        210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Gly Gln Pro Gln Val Gly Lys Glu
            355                 360

<210> SEQ ID NO 27
<211> LENGTH: 121
<212> TYPE: PRT
```

<213> ORGANISM: Artificial Sequence
<220> FEATURE:
<223> OTHER INFORMATION: Rituximab VH

<400> SEQUENCE: 27

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120
```

<210> SEQ ID NO 28
<211> LENGTH: 5
<212> TYPE: PRT
<213> ORGANISM: Artificial Sequence
<220> FEATURE:
<223> OTHER INFORMATION: Rituximab HCDR1

<400> SEQUENCE: 28

```
Ser Tyr Asn Met His
1               5
```

<210> SEQ ID NO 29
<211> LENGTH: 17
<212> TYPE: PRT
<213> ORGANISM: Artificial Sequence
<220> FEATURE:
<223> OTHER INFORMATION: Rituximab HCDR2

<400> SEQUENCE: 29

```
Ala Ile Tyr Pro Gly Asn Gly Asp Thr Ser Tyr Asn Gln Lys Phe Lys
1               5                   10                  15

Gly
```

<210> SEQ ID NO 30
<211> LENGTH: 12
<212> TYPE: PRT
<213> ORGANISM: Artificial Sequence
<220> FEATURE:
<223> OTHER INFORMATION: Rituximab HCDR3

<400> SEQUENCE: 30

```
Ser Thr Tyr Tyr Gly Gly Asp Trp Tyr Phe Asn Val
1               5                   10
```

<210> SEQ ID NO 31
<211> LENGTH: 107
<212> TYPE: PRT
<213> ORGANISM: Artificial Sequence
<220> FEATURE:
<223> OTHER INFORMATION: Rituximab VL

```
<400> SEQUENCE: 31

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 32
<211> LENGTH: 10
<212> TYPE: PRT
<213> ORGANISM: Artificial Sequence
<220> FEATURE:
<223> OTHER INFORMATION: Rituximab LCDR1

<400> SEQUENCE: 32

Arg Ala Ser Ser Ser Val Ser Tyr Ile His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Rituximab LCDR2

<400> SEQUENCE: 33

Ala Thr Ser Asn Leu Ala Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Rituximab LCDR3

<400> SEQUENCE: 34

Gln Gln Trp Thr Ser Asn Pro Pro Thr
1               5

<210> SEQ ID NO 35
<211> LENGTH: 200
<212> TYPE: PRT
<213> ORGANISM: Artificial Sequence
<220> FEATURE:
<223> OTHER INFORMATION: 900 VH

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
```

```
                35                  40                  45
Gly Ala Ile Tyr Pro Gly Asn Gly Asp Thr Ser Tyr Asn Gln Lys Phe
            50                  55                  60

Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr
            195                 200

<210> SEQ ID NO 36
<211> LENGTH: 13
<212> TYPE: PRT
<213> ORGANISM: Artificial Sequence
<220> FEATURE:
<223> OTHER INFORMATION: 900HCDR3

<400> SEQUENCE: 36

Val Val Tyr Tyr Ser Asn Ser Tyr Trp Tyr Phe Asp Val
 1               5                  10

<210> SEQ ID NO 37
<211> LENGTH: 200
<212> TYPE: PRT
<213> ORGANISM: Artificial Sequence
<220> FEATURE:
<223> OTHER INFORMATION: 900 VL

<400> SEQUENCE: 37

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu
        195                 200

<210> SEQ ID NO 38
<211> LENGTH: 10
<212> TYPE: PRT
<213> ORGANISM: Artificial Sequence
<220> FEATURE:
<223> OTHER INFORMATION: 900LCDR1

<400> SEQUENCE: 38

Arg Ala Ser Ser Ser Val Ser Tyr Met His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: 900LCDR2

<400> SEQUENCE: 39

Ala Pro Ser Asn Leu Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: 900LCDR3

<400> SEQUENCE: 40

Gln Gln Trp Ser Phe Asn Pro Pro Thr
1               5

<210> SEQ ID NO 41
<211> LENGTH: 121
<212> TYPE: PRT
<213> ORGANISM: Artificial Sequence
<220> FEATURE:
<223> OTHER INFORMATION: 125 VH

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Tyr Asn Gln Lys Ser
    50                  55                  60

Lys Leu Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser
        115                 120
```

```
<210> SEQ ID NO 42
<211> LENGTH: 17
<212> TYPE: PRT
<213> ORGANISM: Artificial Sequence
<220> FEATURE:
<223> OTHER INFORMATION: 125HCDR2

<400> SEQUENCE: 42

Ala Ile Tyr Pro Leu Thr Gly Asp Thr Ser Tyr Asn Gln Lys Ser Lys
1               5                   10                  15

Leu
```

```
<210> SEQ ID NO 43
<211> LENGTH: 12
<212> TYPE: PRT
<213> ORGANISM: Artificial Sequence
<220> FEATURE:
<223> OTHER INFORMATION: 125HCDR3

<400> SEQUENCE: 43

Ser Thr Tyr Val Gly Gly Asp Trp Gln Phe Asp Val
1               5                   10
```

```
<210> SEQ ID NO 44
<211> LENGTH: 106
<212> TYPE: PRT
<213> ORGANISM: Artificial Sequence
<220> FEATURE:
<223> OTHER INFORMATION: 125 VL

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys
            100                 105
```

```
<210> SEQ ID NO 45
<211> LENGTH: 10
<212> TYPE: PRT
<213> ORGANISM: Artificial Sequence
<220> FEATURE:
<223> OTHER INFORMATION: 125LCDR1

<400> SEQUENCE: 45

Arg Ala Ser Ser Ser Val Pro Tyr Ile His
```

<210> SEQ ID NO 46
<211> LENGTH: 7
<212> TYPE: PRT
<213> ORGANISM: Artificial Sequence
<220> FEATURE:
<223> OTHER INFORMATION: 125LCDR2

<400> SEQUENCE: 46

Ala Thr Ser Ala Leu Ala Ser
1               5

<210> SEQ ID NO 47
<211> LENGTH: 9
<212> TYPE: PRT
<213> ORGANISM: Artificial Sequence
<220> FEATURE:
<223> OTHER INFORMATION: 125LCDR3

<400> SEQUENCE: 47

Gln Gln Trp Leu Ser Asn Pro Pro Thr
1               5

<210> SEQ ID NO 48
<211> LENGTH: 121
<212> TYPE: PRT
<213> ORGANISM: Artificial Sequence
<220> FEATURE:
<223> OTHER INFORMATION: 844 VH #2

<400> SEQUENCE: 48

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Thr
        35                  40                  45

Gly Ala Ile Tyr Pro Gly Asn Gly Asp Thr Ser Tyr Asn Gln Lys Phe
    50                  55                  60

Lys Gly Lys Thr Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 49
<211> LENGTH: 121
<212> TYPE: PRT
<213> ORGANISM: Artificial Sequence
<220> FEATURE:
<223> OTHER INFORMATION: 844 VH #3

<400> SEQUENCE: 49

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile 35                  40                  45

Gly Ala Ile Tyr Pro Gly Asn Gly Asp Thr Ser Tyr Asn Gln Lys Phe
         50                  55                  60

Lys Gly Lys Thr Thr Leu Thr Ala Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Thr Tyr Tyr Gly Asp Trp Tyr Phe Asn Val Trp Gly
             100                 105                 110

Ala Gly Thr Thr Val Thr Val Ser Ala
             115                 120

<210> SEQ ID NO 50
<211> LENGTH: 106
<212> TYPE: PRT
<213> ORGANISM: Artificial Sequence
<220> FEATURE:
<223> OTHER INFORMATION: 844 VL #5

<400> SEQUENCE: 50

Gln Ile Val Leu Ser Gln Ser Pro Ala Ile Ile Thr Ala Ser Pro Gly
 1               5                  10                  15

Glu Lys Val Thr Met Thr Cys Arg Ala Ser Thr Ser Ala Ser Tyr Ile
                 20                  25                  30

His Trp Phe Gln Gln Lys Pro Thr Ser Pro Lys Pro Trp Ile Tyr
             35                  40                  45

Ala Thr Ser Asn Leu Ala Ser Gly Val Pro Ser Arg Phe Ser Gly Ser
         50                  55                  60

Gly Ser Gly Thr Thr Tyr Ser Met Thr Ile Ser Ser Leu Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
             100                 105

<210> SEQ ID NO 51
<211> LENGTH: 10
<212> TYPE: PRT
<213> ORGANISM: Artificial Sequence
<220> FEATURE:
<223> OTHER INFORMATION: 844 VL #5 LCDR1

<400> SEQUENCE: 51

Arg Ala Ser Thr Ser Ala Ser Tyr Ile His
 1               5                  10

<210> SEQ ID NO 52
<211> LENGTH: 106
<212> TYPE: PRT
<213> ORGANISM: Artificial Sequence
<220> FEATURE:
<223> OTHER INFORMATION: 844 VL #6

<400> SEQUENCE: 52

Gln Ile Val Leu Ser Gln Ser Pro Ala Ile Ile Thr Ala Ser Pro Gly
 1               5                  10                  15

Glu Lys Val Thr Met Thr Cys Arg Ala Ser Thr Ser Val Ser Tyr Ile
                 20                  25                  30

His Trp Phe Gln Gln Lys Pro Thr Ser Pro Lys Pro Trp Ile Tyr
             35                  40                  45

```
Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105
```

<210> SEQ ID NO 53
<211> LENGTH: 10
<212> TYPE: PRT
<213> ORGANISM: Artificial Sequence
<220> FEATURE:
<223> OTHER INFORMATION: 844 VL #6, #7 LCDR1

<400> SEQUENCE: 53

```
Arg Ala Ser Thr Ser Val Ser Tyr Ile His
1               5                   10
```

<210> SEQ ID NO 54
<211> LENGTH: 106
<212> TYPE: PRT
<213> ORGANISM: Artificial Sequence
<220> FEATURE:
<223> OTHER INFORMATION: 844 VL #7

<400> SEQUENCE: 54

```
Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105
```

<210> SEQ ID NO 55
<211> LENGTH: 106
<212> TYPE: PRT
<213> ORGANISM: Artificial Sequence
<220> FEATURE:
<223> OTHER INFORMATION: 844 VL #8

<400> SEQUENCE: 55

```
Gln Ile Val Leu Ser Gln Ser Pro Ala Ile Ile Thr Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
    50                  55                  60
```

```
Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 56
<211> LENGTH: 122
<212> TYPE: PRT
<213> ORGANISM: Artificial Sequence
<220> FEATURE:
<223> OTHER INFORMATION: 844 VH #10

<400> SEQUENCE: 56

Glu Val Gln Leu Gln Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Thr Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Tyr Tyr Gly Ser Ser Tyr Trp Phe Phe Asp Val Trp
                100                 105                 110

Gly Thr Gly Thr Thr Val Thr Val Ser Ser
            115                 120

<210> SEQ ID NO 57
<211> LENGTH: 13
<212> TYPE: PRT
<213> ORGANISM: Artificial Sequence
<220> FEATURE:
<223> OTHER INFORMATION: 844 VH #10 HCDR3

<400> SEQUENCE: 57

Ser Asn Tyr Tyr Gly Ser Ser Tyr Trp Phe Phe Asp Val
1               5                   10

<210> SEQ ID NO 58
<211> LENGTH: 106
<212> TYPE: PRT
<213> ORGANISM: Artificial Sequence
<220> FEATURE:
<223> OTHER INFORMATION: 844 VL #12

<400> SEQUENCE: 58

Asp Ile Val Leu Thr Gln Ser Pro Ala Ile Thr Ala Ser Pro Gly
1               5                   10                  15

Glu Lys Val Thr Met Thr Cys Arg Ala Ser Ser Ser Val Asn Tyr Met
                20                  25                  30

Asp Trp Tyr Gln Lys Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
```

```
                65                  70                  75                  80
Asp Ala Ala Thr Tyr Tyr Cys Gln Gln Trp Ser Phe Asn Pro Pro Thr
                        85                  90                  95

Phe Gly Gly Gly Thr Lys Leu Glu Ile Lys
                100                 105
```

<210> SEQ ID NO 59
<211> LENGTH: 10
<212> TYPE: PRT
<213> ORGANISM: Artificial Sequence
<220> FEATURE:
<223> OTHER INFORMATION: 844 VL #12 LCDR1

<400> SEQUENCE: 59

```
Arg Ala Ser Ser Ser Val Asn Tyr Met Asp
1               5                   10
```

<210> SEQ ID NO 60
<211> LENGTH: 9
<212> TYPE: PRT
<213> ORGANISM: Artificial Sequence
<220> FEATURE:
<223> OTHER INFORMATION: 844 VL #12 LCDR3

<400> SEQUENCE: 60

```
Gln Gln Trp Ser Phe Asn Pro Pro Thr
1               5
```

<210> SEQ ID NO 61
<211> LENGTH: 121
<212> TYPE: PRT
<213> ORGANISM: Artificial Sequence
<220> FEATURE:
<223> OTHER INFORMATION: 164 VH

<400> SEQUENCE: 61

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Lys Gln Ala Pro Gly Gln Gly Leu Glu Trp Ile
                35                  40                  45

Gly Ala Ile Tyr Pro Gly Asn Gly Asp Thr Ser Tyr Asn Gln Lys Phe
            50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
                100                 105                 110

Gln Gly Thr Thr Val Thr Val Ser Ser
        115                 120
```

<210> SEQ ID NO 62
<211> LENGTH: 12
<212> TYPE: PRT
<213> ORGANISM: Artificial Sequence
<220> FEATURE:
<223> OTHER INFORMATION: 164 VH HCDR3

<400> SEQUENCE: 62

Ser Thr Tyr Tyr Gly Gly Asp Trp Tyr Phe Asp Val

-continued

<210> SEQ ID NO 63
<211> LENGTH: 125
<212> TYPE: PRT
<213> ORGANISM: Artificial Sequence
<220> FEATURE:
<223> OTHER INFORMATION: 164 VL

<400> SEQUENCE: 63

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Met Thr Cys Arg Ala Ser Ser Ser Val
        35                  40                  45

Ser Tyr Ile His Trp Phe Gln Gln Lys Pro Gly Lys Ala Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Asp Tyr Thr Phe Thr Ile Ser Ser Leu
                85                  90                  95

Gln Pro Glu Asp Ile Ala Thr Tyr Tyr Cys Gln Gln Trp Thr Ser Asn
            100                 105                 110

Pro Pro Thr Phe Gly Gly Gly Thr Lys Leu Glu Ile Lys
        115                 120                 125

<210> SEQ ID NO 64
<211> LENGTH: 122
<212> TYPE: PRT
<213> ORGANISM: Artificial Sequence
<220> FEATURE:
<223> OTHER INFORMATION: 1.5.3 VH

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Ser Gly Ser Pro Asn Phe Asp Tyr Trp
            100                 105                 110

Gly Gln Gly Thr Leu Val Thr Val Ser Ser
        115                 120

<210> SEQ ID NO 65
<211> LENGTH: 10
<212> TYPE: PRT
<213> ORGANISM: Artificial Sequence
<220> FEATURE:
<223> OTHER INFORMATION: 1.5.3 HCDR1

<400> SEQUENCE: 65

```
Gly Tyr Ser Phe Thr Ser Tyr Trp Ile Gly
1               5                   10

<210> SEQ ID NO 66
<211> LENGTH: 17
<212> TYPE: PRT
<213> ORGANISM: Artificial Sequence
<220> FEATURE:
<223> OTHER INFORMATION: 1.5.3 HCDR2

<400> SEQUENCE: 66

Ile Ile Tyr Pro Gly Asp Ser Asp Thr Arg Tyr Ser Pro Ser Phe Gln
1               5                   10                  15

Gly

<210> SEQ ID NO 67
<211> LENGTH: 13
<212> TYPE: PRT
<213> ORGANISM: Artificial Sequence
<220> FEATURE:
<223> OTHER INFORMATION: 1.5.3 HCDR3

<400> SEQUENCE: 67

His Pro Ser Tyr Gly Ser Gly Ser Pro Asn Phe Asp Tyr
1               5                   10

<210> SEQ ID NO 68
<211> LENGTH: 112
<212> TYPE: PRT
<213> ORGANISM: Artificial Sequence
<220> FEATURE:
<223> OTHER INFORMATION: 1.5.3 VL

<400> SEQUENCE: 68

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

<210> SEQ ID NO 69
<211> LENGTH: 16
<212> TYPE: PRT
<213> ORGANISM: Artificial Sequence
<220> FEATURE:
<223> OTHER INFORMATION: 1.5.3 LCDR1

<400> SEQUENCE: 69

Arg Ser Ser Gln Ser Leu Val Tyr Ser Asp Gly Asn Thr Tyr Leu Ser
1               5                   10                  15

<210> SEQ ID NO 70
<211> LENGTH: 7
```

<212> TYPE: PRT
<213> ORGANISM: Artificial Sequence
<220> FEATURE:
<223> OTHER INFORMATION: 1.5.3 LCDR2

<400> SEQUENCE: 70

Lys Ile Ser Asn Arg Phe Ser
1               5

<210> SEQ ID NO 71
<211> LENGTH: 9
<212> TYPE: PRT
<213> ORGANISM: Artificial Sequence
<220> FEATURE:
<223> OTHER INFORMATION: 1.5.3 LCDR3

<400> SEQUENCE: 71

Val Gln Ala Thr Gln Phe Pro Leu Thr
1               5

<210> SEQ ID NO 72
<211> LENGTH: 1347
<212> TYPE: DNA
<213> ORGANISM: Homo sapiens

<400> SEQUENCE: 72

```
gccccaaccc tttcccccct cgtctcctgt gagaattccc cgtcggatac gagcagcgtg    60
gccgttggct gcctcgcaca ggacttcctt cccgactcca tcactttctc ctggaaatac   120
aagaacaact ctgacatcag cagcacccgg ggcttcccat cagtcctgag aggggggcaag   180 cacgcagcca cctcacaggt gctgctgcct tccaaggacg tcatgcaggg cacagacgaa   240
cacgtggtgt gcaaagtcca gcaccccaac ggcaacaaag aaaagaacgt gcctcttcca   300
gtgattgctg agctgcctcc caaagtgagc gtcttcgtcc caccccgcga cggcttcttc   360
ggcaaccccc gcaagtccaa gctcatctgc caggccacgg gtttcagtcc ccggcagatt   420
caggtgtcct ggctgcgcga ggggaagcag gtggggtctg gcgtcaccac ggaccaggtg   480
caggctgagg caaaggagtc tgggaccacg acctacaagg tgaccagcac actgaccatc   540
aaagagagcg actggctcag ccagagcatg ttcacctgcc gcgtggatca gggggcctg   600 accttccagc agaatgcgtc ctccatgtgt ggccccgatc aagacacagc catccgggtc   660
ttctccatcc ccccatcctt tgccagcatc ttcctcacca gtccaccaa gttgacctgc   720 ctggtcacag acctgaccac ctatgacagc gtgaccatct cctggaccg ccagaatggc   780 gaagctgtga aacccacac caacatctcc gagagccacc ccaatgccac tttcagcgcc   840
gtgggtgagg ccagcatctg cgaggatgac tggaattccg gggagaggtt cacgtgcacc   900
gtgacccaca cagacctgcc ctcgccactg aagcagacca tctcccggcc caaggggtgg   960
gccctgcaca ggcccgatgt ctacttgctg ccaccagccc gggagcagct gaacctgcgg  1020
gagtcggcca ccatcacgtg cctggtgacg ggcttctctc ccgcggacgt cttcgtgcag  1080
tggatgcaga gggggcagcc cttgtccccg gagaagtatg tgaccagcgc cccaatgcct  1140
gagccccagg ccccaggccg gtacttcgcc cacagcatcc tgaccgtgtc cgaagaggaa  1200
tggaacacgg gggagaccta cacctgcgtg gtggcccatg aggccctgcc caacagggtc  1260
accgagagga ccgtggacaa gtccaccggt aaacccaccc tgtacaacgt gtccctggtc  1320
atgtccgaca gctggcac ctgctac                                         1347
```

<210> SEQ ID NO 73

<211> LENGTH: 453
<212> TYPE: PRT
<213> ORGANISM: Homo sapiens

<400> SEQUENCE: 73

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
```

```
385                 390                 395                 400
Ser Glu Glu Trp Asn Thr Gly Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
                435                 440                 445

Ala Gly Thr Cys Tyr
        450

<210> SEQ ID NO 74
<211> LENGTH: 480
<212> TYPE: DNA
<213> ORGANISM: Artificial Sequence
<220> FEATURE:
<223> OTHER INFORMATION: J Chain DNA

<400> SEQUENCE: 74
atgaagaacc atttgctttt ctggggagtc ctggcggttt ttattaaggc tgttcatgtg      60
aaagcccaag aagatgaaag gattgttctt gttgacaaca atgtaagtg tgcccggatt     120 acttccagga tcatccgttc ttccgaagat cctaatgagg acattgtgga gagaaacatc    180
cgaattattg ttcctctgaa caacagggag aatatctctg atcccacctc accattgaga    240
accagatttg tgtaccattt gtctgacctc tgtaaaaaat gtgatcctac agaagtggag    300
ctggataatc agatagttac tgctacccag agcaatatct gtgatgaaga cagtgctaca    360
gagacctgct acactatga cagaaacaag tgctacacag ctgtggtccc actcgtatat    420
ggtggtgaga ccaaaatggt ggaaacagcc ttaacccag atgcctgcta tcctgactaa    480
```

```
<210> SEQ ID NO 75
<211> LENGTH: 158
<212> TYPE: PRT
<213> ORGANISM: Artificial Sequence
<220> FEATURE:
<223> OTHER INFORMATION: J Chain AA

<400> SEQUENCE: 75

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Ile Val Pro
    50                  55                  60

Leu Asn Asn Arg Glu Asn Ile Ser Asp Pro Thr Ser Pro Leu Arg Thr
65                  70                  75                  80

Arg Phe Val Tyr His Leu Ser Asp Leu Cys Lys Lys Cys Asp Pro Thr
                85                  90                  95

Glu Val Glu Leu Asp Asn Gln Ile Val Thr Ala Thr Gln Ser Asn Ile
                100                 105                 110

Cys Asp Glu Asp Ser Ala Thr Glu Thr Cys Tyr Thr Tyr Asp Arg Asn
            115                 120                 125

Lys Cys Tyr Thr Ala Val Val Pro Leu Val Tyr Gly Gly Glu Thr Lys
        130                 135                 140

Met Val Glu Thr Ala Leu Thr Pro Asp Ala Cys Tyr Pro Asp
145                 150                 155
```

<210> SEQ ID NO 76
<211> LENGTH: 297
<212> TYPE: PRT
<213> ORGANISM: Homo sapiens

<400> SEQUENCE: 76

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 77
<211> LENGTH: 1725
<212> TYPE: DNA
<213> ORGANISM: Artificial Sequence
<220> FEATURE:
<223> OTHER INFORMATION: Ritux-IgM heavy chain DNA

<400> SEQUENCE: 77
caggttcagc tgcagcagcc cggagccgag ctggtcaaac tggcgctag tgtgaaaatg      60 tcatgcaagg catccggata cacattcact agctataaca tgcactgggt gaagcagacc     120

```
cccggcaggg gtctggagtg gatcggagct atctacccg gcaacggaga cacatcttat    180
aatcagaagt ttaaaggcaa ggccaccctg acagctgata agtccagctc taccgcatac    240
atgcagctga gttcactgac aagcgaggac tccgccgtgt actattgcgc ccggtccact    300
tactatggcg gagattggta tttcaatgtg tggggagcag gcaccacagt caccgtctcg    360
agcggcagtg ctagcgcccc aacccttttc cccctcgtct cctgtgagaa ttccccgtcg    420
gatacgagca gcgtggccgt tggctgcctc gcacaggact ccttcccga ctccatcact    480 ttctcctgga atacaagaa caactctgac atcagcagca cccggggctt cccatcagtc    540
ctgagagggg gcaagtacgc agccacctca caggtgctgc tgccttccaa ggacgtcatg    600
cagggcacag acgaacacgt ggtgtgcaaa gtccagcacc ccaacggcaa caaagaaaag    660
aacgtgcctc ttccagtgat tgctgagctg cctcccaaag tgagcgtctt cgtcccaccc    720
cgcgacggct tcttcggcaa ccccgcaag tccaagctca tctgccaggc cacgggtttc    780
agtccccggc agattcaggt gtcctggctg cgcgagggga agcaggtggg gtctggcgtc    840
accacggacc aggtgcaggc tgaggccaaa gagtctgggc ccacgaccta caaggtgacc    900
agcacactga ccatcaaaga gagcgactgg ctcagccaga gcatgttcac ctgccgcgtg    960
gatcacaggg gcctgacctt ccagcagaat gcgtcctcca tgtgtgtccc cgatcaagac   1020
acagccatcc gggtcttcgc catcccccca tcctttgcca gcatcttcct caccaagtcc   1080
accaagttga cctgcctggt cacagacctg accacctatg acagcgtgac catctcctgg   1140
acccgccaga tggcgaagc tgtgaaaacc cacaccaaca tctccgagag ccaccccaat   1200
gccactttca gcgccgtggg tgaggccagc atctgcgagg atgactggaa ttccggggag   1260
aggttcacgt gcaccgtgac ccacacagac ctgccctcgc cactgaagca gaccatctcc   1320
cggcccaagg gggtggccct gcacaggccc gatgtctact gctgccacc agcccgggag   1380 cagctgaacc tgcgggagtc ggccaccatc acgtgcctgg tgacgggctt ctctcccgcg   1440
gacgtcttcg tgcagtggat gcagaggggg cagcccttgt ccccggagaa gtatgtgacc   1500
agcgccccaa tgcctgagcc ccaggcccca ggccggtact cgccacag catcctgacc   1560 gtgtccgaag aggaatggaa cacggggag acctacacct gcgtggtggc ccatgaggcc   1620
ctgcccaaca gggtcaccga gaggaccgtg acaagtcca ccggtaaacc cacccctgtac   1680 aacgtgtccc tggtcatgtc cgacacagct ggcacctgct actga              1725
```

<210> SEQ ID NO 78  
<211> LENGTH: 574  
<212> TYPE: PRT  
<213> ORGANISM: Artificial Sequence  
<220> FEATURE:  
<223> OTHER INFORMATION: Ritux-IgM heavy chain AA

<400> SEQUENCE: 78

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80
```

-continued

```
Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ser Gly Ser Ala Ser Ala Pro Thr
            115                 120                 125

Leu Phe Pro Leu Val Ser Cys Glu Asn Ser Pro Ser Asp Thr Ser Ser
        130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
                180                 185                 190

Leu Leu Pro Ser Lys Asp Val Met Gln Gly Thr Asp Glu His Val Val
            195                 200                 205

Cys Lys Val Gln His Pro Asn Gly Asn Lys Glu Lys Asn Val Pro Leu
        210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
            275                 280                 285

Ala Lys Glu Ser Gly Pro Thr Thr Tyr Lys Val Thr Ser Thr Leu Thr
        290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
                340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
        370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
                420                 425                 430

Ser Pro Leu Lys Gln Thr Ile Ser Arg Pro Lys Gly Val Ala Leu His
            435                 440                 445

Arg Pro Asp Val Tyr Leu Leu Pro Pro Ala Arg Glu Gln Leu Asn Leu
        450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495
```

```
Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
        530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570
```

<210> SEQ ID NO 79
<211> LENGTH: 642
<212> TYPE: DNA
<213> ORGANISM: Artificial Sequence
<220> FEATURE:
<223> OTHER INFORMATION: Ritux-light chain DNA

<400> SEQUENCE: 79

```
caaattgtgc tgtctcagag tccagctatc ctgagcgcat ctcccggaga gaaggtgacc      60
atgacatgca gagcctccag ctctgtctcc tacatccact ggttccagca gaagcccggc     120
tcctccccaa accctggat ctacgccacc tctaacctgg ctagtggtgt gcctgtcagg     180
tttagtggat cagggtccgg caccagctac tctctgacaa tcagccgggt ggaggctgaa     240
gacgccgcta catactattg ccagcagtgg acttctaatc ccctaccctt cggcggaggg     300
acaaagctgg agatcaagcg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                       642
```

<210> SEQ ID NO 80
<211> LENGTH: 213
<212> TYPE: PRT
<213> ORGANISM: Artificial Sequence
<220> FEATURE:
<223> OTHER INFORMATION: Ritux-light chain AA

<400> SEQUENCE: 80

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
```

|  |  | 115 |  |  |  | 120 |  |  |  | 125 |  |
|--|--|--|--|--|--|--|--|--|--|--|--|
| Ala | Ser | Val | Cys | Leu | Leu | Asn | Asn | Phe | Tyr | Pro | Arg | Glu | Ala | Lys |
|  |  | 130 |  |  |  | 135 |  |  |  | 140 |  |

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210

<210> SEQ ID NO 81
<211> LENGTH: 1728
<212> TYPE: DNA
<213> ORGANISM: Artificial Sequence
<220> FEATURE:
<223> OTHER INFORMATION: 1.5.3 - IgM heavy chain DNA

<400> SEQUENCE: 81

```
gaggtgcagc tggtgcagtc cggcgccgag gtgaagaagc ccggcgagtc cctgaagatc    60
tcctgcaagg gctccggcta ctccttcacc tcctactgga tcggctgggt gaggcagatg   120
cccggcaagg gcctggagtg gatgggcatc atctaccccg gcgactccga caccaggtac   180
tccccctcct ccagggccca ggtgaccatc tccgccgaca gtccatcac caccgcctac   240
ctgcagtggt cctccctgaa ggcctccgac accgccatgt actactgcgc caggcacccc   300
tcctacggct ccggctcccc caacttcgac tactggggcc agggcaccct ggtgaccgtg   360
tcctccggca gtgctagcgc cccaaccctt ttccccctcg tctcctgtga gaattccccg   420
tcggatacga gcagcgtggc cgttggctgc ctcgcacagg acttccttcc cgactccatc   480
actttctcct ggaaatacaa gaacaactct gacatcagca gcacccgggg cttcccatca   540
gtcctgagag gggcaagta cgcagccacc tcacaggtgc tgctgccttc aaggacgtc    600
atgcagggca cagacgaaca cgtggtgtgc aaagtccagc accccaacgg caacaaagaa   660
aagaacgtgc ctcttccagt gattgctgag ctgcctccca agtgagcgt cttcgtccca   720
ccccgcgacg gcttcttcgg caaccccgc aagtccaagc tcatctgcca ggccacgggt   780
ttcagtcccc ggcagattca ggtgtcctgg ctgcgcgagg ggaagcaggt ggggtctggc   840
gtcaccacgg accaggtgca ggctgaggcc aaagagtctg gcccacgac ctacaaggtg    900
accagcacac tgaccatcaa agagagcgac tggctcagcc agagcatgtt cacctgccgc   960
gtggatcaca ggggcctgac cttccagcag aatgcgtcct ccatgtgtgt ccccgatcaa  1020
gacacagcca tccgggtctt cgccatcccc ccatcctttg ccagcatctt cctcaccaag  1080
tccaccaagt tgacctgcct ggtcacagac ctgaccacct atgacagcgt gaccatctcc  1140
tggacccgcc agaatggcga agctgtgaaa acccacacca catctccga gagccaccccc  1200
aatgccactt tcagcgccgt gggtgaggcc agcatctgcg aggatgactg gaattccggg  1260
gagaggttca cgtgcaccgt gacccacaca gacctgccct cgccactgaa gcagaccatc  1320
tcccggccca gggggtggc cctgcacagg cccgatgtct acttgctgcc accagcccgg  1380
gagcagctga acctgcggga gtcggccacc atcacgtgcc tggtgacggg cttctctccc  1440
gcggacgtct tcgtgcagtg gatgcagagg gggcagccct gtccccgga gaagtatgtg  1500
```

-continued

```
accagcgccc caatgcctga gccccaggcc ccaggccggt acttcgccca cagcatcctg    1560
accgtgtccg aagaggaatg gaacacgggg gagacctaca cctgcgtggt ggcccatgag    1620
gccctgccca cagggtcac cgagaggacc gtggacaagt ccaccggtaa acccaccctg    1680
tacaacgtgt ccctggtcat gtccgacaca gctggcacct gctactga               1728
```

<210> SEQ ID NO 82
<211> LENGTH: 575
<212> TYPE: PRT
<213> ORGANISM: Artificial Sequence
<220> FEATURE:
<223> OTHER INFORMATION: 1.5.3 -IgM heavy chain AA

<400> SEQUENCE: 82

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Ser Gly Ser Pro Asn Phe Asp Tyr Trp
            100                 105                 110

Gly Gln Gly Thr Leu Val Thr Val Ser Ser Gly Ser Ala Ser Ala Pro
        115                 120                 125

Thr Leu Phe Pro Leu Val Ser Cys Glu Asn Ser Pro Ser Asp Thr Ser
    130                 135                 140

Ser Val Ala Val Gly Cys Leu Ala Gln Asp Phe Leu Pro Asp Ser Ile
145                 150                 155                 160

Thr Phe Ser Trp Lys Tyr Lys Asn Asn Ser Asp Ile Ser Ser Thr Arg
                165                 170                 175

Gly Phe Pro Ser Val Leu Arg Gly Gly Lys Tyr Ala Ala Thr Ser Gln
            180                 185                 190

Val Leu Leu Pro Ser Lys Asp Val Met Gln Gly Thr Asp Glu His Val
        195                 200                 205

Val Cys Lys Val Gln His Pro Asn Gly Asn Lys Glu Lys Asn Val Pro
    210                 215                 220

Leu Pro Val Ile Ala Glu Leu Pro Pro Lys Val Ser Val Phe Val Pro
225                 230                 235                 240

Pro Arg Asp Gly Phe Phe Gly Asn Pro Arg Lys Ser Lys Leu Ile Cys
                245                 250                 255

Gln Ala Thr Gly Phe Ser Pro Arg Gln Ile Gln Val Ser Trp Leu Arg
            260                 265                 270

Glu Gly Lys Gln Val Gly Ser Gly Val Thr Thr Asp Gln Val Gln Ala
        275                 280                 285

Glu Ala Lys Glu Ser Gly Pro Thr Thr Tyr Lys Val Thr Ser Thr Leu
    290                 295                 300

Thr Ile Lys Glu Ser Asp Trp Leu Ser Gln Ser Met Phe Thr Cys Arg
305                 310                 315                 320
```

```
Val Asp His Arg Gly Leu Thr Phe Gln Gln Asn Ala Ser Ser Met Cys
            325                 330                 335

Val Pro Asp Gln Asp Thr Ala Ile Arg Val Phe Ala Ile Pro Pro Ser
        340                 345                 350

Phe Ala Ser Ile Phe Leu Thr Lys Ser Thr Lys Leu Thr Cys Leu Val
            355                 360                 365

Thr Asp Leu Thr Thr Tyr Asp Ser Val Thr Ile Ser Trp Thr Arg Gln
        370                 375                 380

Asn Gly Glu Ala Val Lys Thr His Thr Asn Ile Ser Glu Ser His Pro
385                 390                 395                 400

Asn Ala Thr Phe Ser Ala Val Gly Glu Ala Ser Ile Cys Glu Asp Asp
            405                 410                 415

Trp Asn Ser Gly Glu Arg Phe Thr Cys Thr Val Thr His Thr Asp Leu
        420                 425                 430

Pro Ser Pro Leu Lys Gln Thr Ile Ser Arg Pro Lys Gly Val Ala Leu
            435                 440                 445

His Arg Pro Asp Val Tyr Leu Leu Pro Pro Ala Arg Glu Gln Leu Asn
    450                 455                 460

Leu Arg Glu Ser Ala Thr Ile Thr Cys Leu Val Thr Gly Phe Ser Pro
465                 470                 475                 480

Ala Asp Val Phe Val Gln Trp Met Gln Arg Gly Gln Pro Leu Ser Pro
            485                 490                 495

Glu Lys Tyr Val Thr Ser Ala Pro Met Pro Glu Pro Gln Ala Pro Gly
        500                 505                 510

Arg Tyr Phe Ala His Ser Ile Leu Thr Val Ser Glu Glu Glu Trp Asn
    515                 520                 525

Thr Gly Glu Thr Tyr Thr Cys Val Val Ala His Glu Ala Leu Pro Asn
        530                 535                 540

Arg Val Thr Glu Arg Thr Val Asp Lys Ser Thr Gly Lys Pro Thr Leu
545                 550                 555                 560

Tyr Asn Val Ser Leu Val Met Ser Asp Thr Ala Gly Thr Cys Tyr
            565                 570                 575
```

<210> SEQ ID NO 83
<211> LENGTH: 660
<212> TYPE: DNA
<213> ORGANISM: Artificial Sequence
<220> FEATURE:
<223> OTHER INFORMATION: 1.5.3 light chain DNA

<400> SEQUENCE: 83

```
gacatcgtga tgacccagac cccctgtcc tccccgtga ccctgggcca gcccgcctcc      60
atctcctgca ggtcctccca gtccctggtg tactccgacg gcaacaccta cctgtcctgg    120
ctgcagcaga ggcccggcca gccccccagg ctgctgatct acaagatctc caacaggttc    180
tccggcgtgc ccgacaggtt ctccggctcc ggcgccggca ccgacttcac cctgaagatc    240
tccagggtgg aggccgagga cgtgggcgtg tactactgcg tgcaggccac ccagttcccc    300
ctgaccttcg gcggcggcac caaggtggag atcaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 84
<211> LENGTH: 219
<212> TYPE: PRT
<213> ORGANISM: Artificial Sequence
<220> FEATURE:
<223> OTHER INFORMATION: 1.5.3 light chain AA

<400> SEQUENCE: 84

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 85
<211> LENGTH: 353
<212> TYPE: PRT
<213> ORGANISM: Homo sapiens

<400> SEQUENCE: 85

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95
```

```
Val Thr Val Pro Cys Pro Val Pro Ser Thr Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
        130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
                180                 185                 190

Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
        210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
        260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 86
<211> LENGTH: 340
<212> TYPE: PRT
<213> ORGANISM: Homo sapiens

<400> SEQUENCE: 86

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
                100                 105                 110
```

```
Arg Leu Ser Leu His Arg Pro Ala Leu Glu Asp Leu Leu Gly Ser
            115                 120                 125
Glu Ala Asn Leu Thr Cys Thr Leu Thr Gly Leu Arg Asp Ala Ser Gly
130                 135                 140
Ala Thr Phe Thr Trp Thr Pro Ser Ser Gly Lys Ser Ala Val Gln Gly
145                 150                 155                 160
Pro Pro Glu Arg Asp Leu Cys Gly Cys Tyr Ser Val Ser Ser Val Leu
                165                 170                 175
Pro Gly Cys Ala Gln Pro Trp Asn His Gly Thr Phe Thr Cys Thr
            180                 185                 190
Ala Ala His Pro Glu Leu Lys Thr Pro Leu Thr Ala Asn Ile Thr Lys
            195                 200                 205
Ser Gly Asn Thr Phe Arg Pro Glu Val His Leu Leu Pro Pro Ser
210                 215                 220
Glu Glu Leu Ala Leu Asn Glu Leu Val Thr Leu Thr Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
            260                 265                 270
Ser Gln Gly Thr Thr Thr Phe Ala Val Thr Ser Ile Leu Arg Val Ala
            275                 280                 285
Ala Glu Asp Trp Lys Lys Gly Asp Thr Phe Ser Cys Met Val Gly His
290                 295                 300
Glu Ala Leu Pro Leu Ala Phe Thr Gln Lys Thr Ile Asp Arg Met Ala
305                 310                 315                 320
Gly Lys Pro Thr His Val Asn Val Ser Val Val Met Ala Glu Val Asp
                325                 330                 335
Gly Thr Cys Tyr
            340

<210> SEQ ID NO 87
<211> LENGTH: 764
<212> TYPE: PRT
<213> ORGANISM: Homo sapiens

<400> SEQUENCE: 87

Met Leu Leu Phe Val Leu Thr Cys Leu Leu Ala Val Phe Pro Ala Ile
1               5                   10                  15
Ser Thr Lys Ser Pro Ile Phe Gly Pro Glu Glu Val Asn Ser Val Glu
            20                  25                  30
Gly Asn Ser Val Ser Ile Thr Cys Tyr Tyr Pro Pro Thr Ser Val Asn
        35                  40                  45
Arg His Thr Arg Lys Tyr Trp Cys Arg Gln Gly Ala Arg Gly Gly Cys
    50                  55                  60
Ile Thr Leu Ile Ser Ser Glu Gly Tyr Val Ser Ser Lys Tyr Ala Gly
65                  70                  75                  80
Arg Ala Asn Leu Thr Asn Phe Pro Glu Asn Gly Thr Phe Val Val Asn
                85                  90                  95
Ile Ala Gln Leu Ser Gln Asp Asp Ser Gly Arg Tyr Lys Cys Gly Leu
            100                 105                 110
Gly Ile Asn Ser Arg Gly Leu Ser Phe Asp Val Ser Leu Glu Val Ser
        115                 120                 125
Gln Gly Pro Gly Leu Leu Asn Asp Thr Lys Val Tyr Thr Val Asp Leu
    130                 135                 140
```

```
Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
            195                 200                 205

Gln Leu Arg Leu Ser Asp Ala Gly Gln Tyr Leu Cys Gln Ala Gly Asp
210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
                260                 265                 270

Gln Ser Ser Gly Glu Asn Cys Asp Val Val Asn Thr Leu Gly Lys
                275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
                340                 345                 350

Pro Arg Ser Pro Thr Val Val Lys Gly Val Ala Gly Gly Ser Val Ala
                355                 360                 365

Val Leu Cys Pro Tyr Asn Arg Lys Glu Ser Lys Ser Ile Lys Tyr Trp
370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
                420                 425                 430

Ser Arg Asp Ala Gly Phe Tyr Trp Cys Leu Thr Asn Gly Asp Thr Leu
                435                 440                 445

Trp Arg Thr Thr Val Glu Ile Lys Ile Ile Glu Gly Glu Pro Asn Leu
                450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
                500                 505                 510

Pro Ser Lys Ala Phe Val Asn Cys Asp Glu Asn Ser Arg Leu Val Ser
                515                 520                 525

Leu Thr Leu Asn Leu Val Thr Arg Ala Asp Glu Gly Trp Tyr Trp Cys
                530                 535                 540

Gly Val Lys Gln Gly His Phe Tyr Gly Glu Thr Ala Ala Val Tyr Val
545                 550                 555                 560
```

-continued

```
Ala Val Glu Glu Arg Lys Ala Gly Ser Arg Asp Val Ser Leu Ala
                565                 570                 575
Lys Ala Asp Ala Ala Pro Asp Glu Lys Val Leu Asp Ser Gly Phe Arg
            580                 585                 590
Glu Ile Glu Asn Lys Ala Ile Gln Asp Pro Arg Leu Phe Ala Glu Glu
        595                 600                 605
Lys Ala Val Ala Asp Thr Arg Asp Gln Ala Asp Gly Ser Arg Ala Ser
    610                 615                 620
Val Asp Ser Gly Ser Ser Glu Gln Gly Ser Ser Arg Ala Leu
625                 630                 635                 640
Val Ser Thr Leu Val Pro Leu Gly Leu Val Leu Ala Val Gly Ala Val
                645                 650                 655
Ala Val Gly Val Ala Arg Ala Arg His Arg Lys Asn Val Asp Arg Val
            660                 665                 670
Ser Ile Arg Ser Tyr Arg Thr Asp Ile Ser Met Ser Asp Phe Glu Asn
        675                 680                 685
Ser Arg Glu Phe Gly Ala Asn Asp Asn Met Gly Ala Ser Ser Ile Thr
    690                 695                 700
Gln Glu Thr Ser Leu Gly Gly Lys Glu Phe Val Ala Thr Glu
705                 710                 715                 720
Ser Thr Thr Glu Thr Lys Glu Pro Lys Lys Ala Lys Arg Ser Ser Lys
                725                 730                 735
Glu Glu Ala Glu Met Ala Tyr Lys Asp Phe Leu Leu Gln Ser Ser Thr
            740                 745                 750
Val Ala Ala Glu Ala Gln Asp Gly Pro Gln Glu Ala
        755                 760
```

<210> SEQ ID NO 88
<211> LENGTH: 585
<212> TYPE: PRT
<213> ORGANISM: Homo sapiens

<400> SEQUENCE: 88

```
Lys Ser Pro Ile Phe Gly Pro Glu Val Asn Ser Val Glu Gly Asn
1               5                   10                  15
Ser Val Ser Ile Thr Cys Tyr Tyr Pro Pro Thr Ser Val Asn Arg His
                20                  25                  30
Thr Arg Lys Tyr Trp Cys Arg Gln Gly Ala Arg Gly Gly Cys Ile Thr
            35                  40                  45
Leu Ile Ser Ser Glu Gly Tyr Val Ser Lys Tyr Ala Gly Arg Ala
    50                  55                  60
Asn Leu Thr Asn Phe Pro Glu Asn Gly Thr Phe Val Val Asn Ile Ala
65                  70                  75                  80
Gln Leu Ser Gln Asp Asp Ser Gly Arg Tyr Lys Cys Gly Leu Gly Ile
                85                  90                  95
Asn Ser Arg Gly Leu Ser Phe Asp Val Ser Leu Glu Val Ser Gln Gly
            100                 105                 110
Pro Gly Leu Leu Asn Asp Thr Lys Val Tyr Thr Val Asp Leu Gly Arg
        115                 120                 125
Thr Val Thr Ile Asn Cys Pro Phe Lys Thr Glu Asn Ala Gln Lys Arg
    130                 135                 140
Lys Ser Leu Tyr Lys Gln Ile Gly Leu Tyr Pro Val Leu Val Ile Asp
145                 150                 155                 160
Ser Ser Gly Tyr Val Asn Pro Asn Tyr Thr Gly Arg Ile Arg Leu Asp
                165                 170                 175
```

```
Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
            195                 200                 205

Asn Ser Asn Lys Lys Asn Ala Asp Leu Gln Val Leu Lys Pro Glu Pro
210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
            275                 280                 285

Ser Phe Ser Val Val Ile Thr Gly Leu Arg Lys Glu Asp Ala Gly Arg
            290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
                325                 330                 335

Ser Pro Thr Val Val Lys Gly Val Ala Gly Ser Val Ala Val Leu
            340                 345                 350

Cys Pro Tyr Asn Arg Lys Glu Ser Lys Ser Ile Lys Tyr Trp Cys Leu
            355                 360                 365

Trp Glu Gly Ala Gln Asn Gly Arg Cys Pro Leu Leu Val Asp Ser Glu
            370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
            405                 410                 415

Asp Ala Gly Phe Tyr Trp Cys Leu Thr Asn Gly Asp Thr Leu Trp Arg
            420                 425                 430

Thr Thr Val Glu Ile Lys Ile Ile Glu Gly Pro Asn Leu Lys Val
            435                 440                 445

Pro Gly Asn Val Thr Ala Val Leu Gly Glu Thr Leu Lys Val Pro Cys
            450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
            485                 490                 495

Lys Ala Phe Val Asn Cys Asp Glu Asn Ser Arg Leu Val Ser Leu Thr
            500                 505                 510

Leu Asn Leu Val Thr Arg Ala Asp Glu Gly Trp Tyr Trp Cys Gly Val
            515                 520                 525

Lys Gln Gly His Phe Tyr Gly Glu Thr Ala Ala Val Tyr Val Ala Val
            530                 535                 540

Glu Glu Arg Lys Ala Ala Gly Ser Arg Asp Val Ser Leu Ala Lys Ala
545                 550                 555                 560

Asp Ala Ala Pro Asp Glu Lys Val Leu Asp Ser Gly Phe Arg Glu Ile
            565                 570                 575

Glu Asn Lys Ala Ile Gln Asp Pro Arg
            580                 585
```

<210> SEQ ID NO 89
<211> LENGTH: 684
<212> TYPE: DNA
<213> ORGANISM: Artificial Sequence
<220> FEATURE:
<223> OTHER INFORMATION: J15ABD DNA

<400> SEQUENCE: 89

```
atggaatgga gctgggtctt tctcttcttc ctgtcagtaa cgactggtgt ccactcccag      60
gaagatgagc ggatcgtgct ggtggacaac aagtgcaagt gcgcccggat cacctcccgg     120
atcatccggt cctccgagga tcccaacgag gacatcgtgg aacggaacat cagaatcatc     180
gtgcccctga caaccgcga gaacatctcc gaccccacca gccctctgcg gaccagattc     240
gtgtaccacc tgtccgacct gtgcaagaag tgcgaccca ccgaggtgga actggacaac     300
cagatcgtga ccgccaccca gtccaacatc tgcgacgag actccgccac cgagacatgc     360
tacacctacg accggaacaa gtgctacacc gccgtggtgc ctctggtgta cggcggcgag     420
acaaagatgg tggaaaccgc cctgacccc gacgcctgct atcctgatgg aggcggagga     480
tctggtggcg gtggttctgg cggagggggc tctcagcacg atgaggccgt ggacgccaat     540
tctctggccg aggctaaggt gctggccaac agagagctgg ataagtacgg cgtgtccgac     600
tactacaaga acctgatcaa caacgccaag accgtggaag gcgtgaaggc cctgatcgac     660
gagatcctgg ctgccctgcc ttga                                            684
```

<210> SEQ ID NO 90
<211> LENGTH: 227
<212> TYPE: PRT
<213> ORGANISM: Artificial Sequence
<220> FEATURE:
<223> OTHER INFORMATION: J15ABD AA

<400> SEQUENCE: 90

```
Met Glu Trp Ser Trp Val Phe Leu Phe Leu Ser Val Thr Thr Gly
1               5                   10                  15
Val His Ser Gln Glu Asp Glu Arg Ile Val Leu Val Asp Asn Lys Cys
            20                  25                  30
Lys Cys Ala Arg Ile Thr Ser Arg Ile Ile Arg Ser Ser Glu Asp Pro
        35                  40                  45
Asn Glu Asp Ile Val Glu Arg Asn Ile Arg Ile Val Pro Leu Asn
    50                  55                  60
Asn Arg Glu Asn Ile Ser Asp Pro Thr Ser Pro Leu Arg Thr Arg Phe
65                  70                  75                  80
Val Tyr His Leu Ser Asp Leu Cys Lys Lys Cys Asp Pro Thr Glu Val
                85                  90                  95
Glu Leu Asp Asn Gln Ile Val Thr Ala Thr Gln Ser Asn Ile Cys Asp
            100                 105                 110
Glu Asp Ser Ala Thr Glu Thr Cys Tyr Thr Tyr Asp Arg Asn Lys Cys
        115                 120                 125
Tyr Thr Ala Val Val Pro Leu Val Tyr Gly Gly Glu Thr Lys Met Val
    130                 135                 140
Glu Thr Ala Leu Thr Pro Asp Ala Cys Tyr Pro Asp Gly Gly Gly Gly
145                 150                 155                 160
Ser Gly Gly Gly Gly Ser Gly Gly Gly Ser Gln His Asp Glu Ala
                165                 170                 175
Val Asp Ala Asn Ser Leu Ala Glu Ala Lys Val Leu Ala Asn Arg Glu
            180                 185                 190
```

Leu Asp Lys Tyr Gly Val Ser Asp Tyr Tyr Lys Asn Leu Ile Asn Asn
        195                 200                 205

Ala Lys Thr Val Glu Gly Val Lys Ala Leu Ile Asp Glu Ile Leu Ala
    210                 215                 220

Ala Leu Pro
225

<210> SEQ ID NO 91
<211> LENGTH: 684
<212> TYPE: DNA
<213> ORGANISM: Artificial Sequence
<220> FEATURE:
<223> OTHER INFORMATION: ABD15J DNA

<400> SEQUENCE: 91

```
atggaatgga gctgggtctt tctcttcttc ctgtcagtaa cgactggtgt ccactcccag      60
cacgatgagg ccgtggacgc caattctctg gccgaggcta aggtgctggc caacagagag     120
ctggataagt acggcgtgtc cgactactac aagaaccTga tcaacaacgc caagaccgtg     180
gaaggcgtga aggccctgat cgacgagatc ctggctgccc tgcctggagg cggaggatct     240
ggtggcggtg gttctggcgg aggggGCtct caggaagatg agcggatcgt gctggtggac     300
aacaagtgca gtgcgcccg atcacctcc cggatcatcc ggtcctccga ggatcccaac      360
gaggacatcg tggaacggaa catcagaatc atcgtgcccc tgaacaaccg cgagaacatc     420
tccgaccccc ccagccctct gcggaccaga ttcgtgtacc acctgtccga cctgtgcaag     480
aagtgcgacc ctaccgaggt ggaactggac aaccagatcg tgaccgccac ccagtccaac     540
atctgcgacg aggactccgc caccgagaca tgctacacct acgaccggaa caagtgctac     600
accgccgtgg tgcctctggt gtacggcggc gagacaaaga tggtggaaac cgccctgacc     660
cccgacgcct gctatcctga ttga                                           684
```

<210> SEQ ID NO 92
<211> LENGTH: 227
<212> TYPE: PRT
<213> ORGANISM: Artificial Sequence
<220> FEATURE:
<223> OTHER INFORMATION: ABD15J AA

<400> SEQUENCE: 92

Met Glu Trp Ser Trp Val Phe Leu Phe Phe Leu Ser Val Thr Thr Gly
1               5                   10                  15

Val His Ser Gln His Asp Glu Ala Val Asp Ala Asn Ser Leu Ala Glu
            20                  25                  30

Ala Lys Val Leu Ala Asn Arg Glu Leu Asp Lys Tyr Gly Val Ser Asp
        35                  40                  45

Tyr Tyr Lys Asn Leu Ile Asn Asn Ala Lys Thr Val Glu Gly Val Lys
    50                  55                  60

Ala Leu Ile Asp Glu Ile Leu Ala Ala Leu Pro Gly Gly Gly Gly Ser
65                  70                  75                  80

Gly Gly Gly Gly Ser Gly Gly Gly Ser Gln Glu Asp Glu Arg Ile
            85                  90                  95

Val Leu Val Asp Asn Lys Cys Lys Cys Ala Arg Ile Thr Ser Arg Ile
            100                 105                 110

Ile Arg Ser Ser Glu Asp Pro Asn Glu Asp Ile Val Glu Arg Asn Ile
            115                 120                 125

Arg Ile Ile Val Pro Leu Asn Asn Arg Glu Asn Ile Ser Asp Pro Thr

```
                130             135              140
Ser Pro Leu Arg Thr Arg Phe Val Tyr His Leu Ser Asp Leu Cys Lys
145                 150                 155                 160

Lys Cys Asp Pro Thr Glu Val Glu Leu Asp Asn Gln Ile Val Thr Ala
                165                 170                 175

Thr Gln Ser Asn Ile Cys Asp Glu Asp Ser Ala Thr Glu Thr Cys Tyr
                180                 185                 190

Thr Tyr Asp Arg Asn Lys Cys Tyr Thr Ala Val Val Pro Leu Val Tyr
                195                 200                 205

Gly Gly Glu Thr Lys Met Val Glu Thr Ala Leu Thr Pro Asp Ala Cys
                210                 215                 220

Tyr Pro Asp
225

<210> SEQ ID NO 93
<211> LENGTH: 2286
<212> TYPE: DNA
<213> ORGANISM: Artificial Sequence
<220> FEATURE:
<223> OTHER INFORMATION: HSA15J DNA

<400> SEQUENCE: 93
atgaaatggg tcacctttat ctccctgctg ttcctgttct cctccgccta ctctcggggc      60
gtgttcagaa gagacgccca caatcggag gtagcgcacc ggttcaaaga cttgggagaa      120
gaaaacttta aggcccttgt actcattgcg tttgcgcagt atttgcagca gtgcccattc     180
gaggaccatg tcaaacttgt caacgaagtg acagagtttg cgaaaacttg cgtcgccgac     240
gaatccgcgg agaactgtga caagtcgctg catacgttgt tcgggataa gctctgtacc     300 gtagcgacct tgagggaaac ttacggggaa atggcggact gttgcgctaa gcaggagccg     360
gaacggaacg agtgtttcct tcagcataag gatgacaacc ccaacctccc tagattggtc     420
agacccgaag tggatgtgat gtgcacagca ttccatgaca atgaggaaac ctttctcaaa     480
aagtatttgt acgagattgc ccgacgacac ccctatttct acgctcccga gttgctcttc     540
ttcgcgaaac ggtataaagc tgcctttact gaatgctgtc aagcagcgga caaggccgca     600
tgcctccttc ccaaattgga tgaactccgc gatgaaggga aggcgtcatc ggccaaacag     660
cggcttaagt gcgcatcgct tcagaaattc ggagagaggg cgttcaaagc gtgggccgtc     720
gcgagactgt cgcagagatt ccctaaggcg aatttgcag aggtatcgaa gctcgtgaca     780
gacctcacaa aggtccacac cgaatgttgc catggagacc tgcttgagtg cgccgatgat     840
agggcagacc tcgcaaagta catttgtgag aatcaggaca gcattagctc caagctgaaa     900
gagtgctgtg agaagccttt gctggaaaaa tcccactgta tcgccgaggt agaaaacgat     960
gaaatgcccg ctgatcttcc ctcgctggcg gcagacttcg tcgagtcgaa ggacgtctgc    1020
aagaattacg cagaggcaaa agatgtgttt cttggaatgt tcctttatga gtatgcgaga    1080
aggcacccgg attattccgt ggtactgctc ttgcgattgg cgaaaacgta cgaaacaacg    1140
cttgagaagt gttgtgcggc tgccgacccg catgagtgct acgccaaggt atttgatgag    1200 tttaaaccte ttgtcgagga accccagaat cttatcaagc agaactgcga gcttttcaag    1260
cagttgggtg aatacaaatt ccagaacgcg cttctggtga ggtataccaa gaaagtacct    1320
caagtctcaa cacccacact cgtcgaggtg tcacggaacc tcgggaaagt agggtcgaag    1380
tgctgtaaac acccagaggc caagcgcatg ccctgtgcgg aggactacct ctcggtagtg    1440
ttgaatcaac tgtgtgtcct ccacgaaaag acgccggtgt cagaccgcgt cacaaagtgc    1500
```

-continued

```
tgcacggaga gcctggtcaa tagacgcccc tgcttctcag cgctggaggt ggatgagaca    1560
tacgtcccga aagagtttaa cgccgaaacg tttacttttc atgctgatat ctgtacgttg    1620
tcagagaagg aaaggcaaat caagaaacaa actgcgcttg tggaactggt gaagcacaaa    1680
ccgaaggcga ctaaggaaca gctgaaggcg gtgatggatg actttgccgc gttcgtagag    1740
aaatgctgta aagcagacga taaggagact tgttttgcgg aagagggacc taaacttgtt    1800
gctgcaagtc aagctgcctt aggcttagga ggcggaggat ctggtggcgg tggttctggc    1860
ggagggggct ctcaggaaga tgagcggatc gtgctggtgg acaacaagtg caagtgcgcc    1920
cggatcacct cccggatcat ccggtcctcc gaggatccca acgaggacat cgtggaacgg    1980
aacatcagaa tcatcgtgcc cctgaacaac cgcgagaaca tctccgaccc caccagccct    2040
ctgcggacca gattcgtgta ccacctgtcc gacctgtgca agaagtgcga ccctaccgag    2100
gtggaactgg acaaccagat cgtgaccgcc acccagtcca acatctgcga cgaggactcc    2160
gccaccgaga catgctacac ctacgaccgg aacaagtgct acaccgccgt ggtgcctctg    2220
gtgtacggcg gcgagacaaa gatggtggaa accgccctga ccccgacgc ctgctatcct    2280 gattag                                                              2286
```

<210> SEQ ID NO 94
<211> LENGTH: 761
<212> TYPE: PRT
<213> ORGANISM: Artificial Sequence
<220> FEATURE:
<223> OTHER INFORMATION: HSA15J AA

<400> SEQUENCE: 94

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
```

```
            210                 215                 220
Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Lys Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Pro Lys Leu Val Ala Ala Ser Gln Ala Ala Leu Gly
        595                 600                 605

Leu Gly Gly Gly Gly Ser Gly Gly Gly Gly Ser Gly Gly Gly Gly Ser
    610                 615                 620

Gln Glu Asp Glu Arg Ile Val Leu Val Asp Asn Lys Cys Lys Cys Ala
625                 630                 635                 640
```

```
Arg Ile Thr Ser Arg Ile Ile Arg Ser Ser Glu Asp Pro Asn Glu Asp
                645                 650                 655

Ile Val Glu Arg Asn Ile Arg Ile Ile Val Pro Leu Asn Asn Arg Glu
            660                 665                 670

Asn Ile Ser Asp Pro Thr Ser Pro Leu Arg Thr Arg Phe Val Tyr His
        675                 680                 685

Leu Ser Asp Leu Cys Lys Lys Cys Asp Pro Thr Glu Val Glu Leu Asp
    690                 695                 700

Asn Gln Ile Val Thr Ala Thr Gln Ser Asn Ile Cys Asp Glu Asp Ser
705                 710                 715                 720

Ala Thr Glu Thr Cys Tyr Thr Tyr Asp Arg Asn Lys Cys Tyr Thr Ala
                725                 730                 735

Val Val Pro Leu Val Tyr Gly Gly Glu Thr Lys Met Val Glu Thr Ala
            740                 745                 750

Leu Thr Pro Asp Ala Cys Tyr Pro Asp
        755                 760

<210> SEQ ID NO 95
<211> LENGTH: 2280
<212> TYPE: DNA
<213> ORGANISM: Artificial Sequence
<220> FEATURE:
<223> OTHER INFORMATION: J15HSA DNA

<400> SEQUENCE: 95
atgaagaacc atctgctgtt ctggggcgtg ctggccgtgt tcatcaaggc cgtgcacgtg      60
aaggcccagg aagatgagcg gatcgtgctg gtggacaaca agtgcaagtg cgcccggatc     120
acctcccgga tcatccggtc ctccgaggat cccaacgagg acatcgtgga acggaacatc     180
agaatcatcg tgcccctgaa caaccgcgag aacatctccg accccaccag ccctctgcgg     240
accagattcg tgtaccacct gtccgacctg tgcaagaagt gcgaccctac cgaggtggaa     300
ctggacaacc agatcgtgac cgccacccag tccaacatct gcgacgagga ctccgccacc     360
gagacatgct acacctacga ccggaacaag tgctacaccg ccgtggtgcc tctggtgtac     420
ggcggcgaga caaagatggt ggaaaccgcc ctgacccccg acgcctgcta tcctgatgga     480
ggcggaggat ctggtggcgg tggttctggc ggagggggct ctgacgccca caatcggag      540 gtagcgcacc ggttcaaaga cttgggagaa gaaaacttta aggcccttgt actcattgcg     600
tttgcgcagt atttgcagca gtgcccattc gaggaccatg tcaaacttgt caacgaagtg     660
acagagtttg cgaaaacttg cgtcgccgac gaatccgcgg agaactgtga caagtcgctg     720
catacgttgt tcggggataa gctctgtacc gtagcgacct tgaggggaaac ttacggggaa     780 atggcggact gttgcgctaa gcaggagccg gaacggaacg agtgtttcct tcagcataag     840
gatgacaacc ccaacctccc tagattggtc agacccgaag tggatgtgat gtgcacagca     900
ttccatgaca atgaggaaac ctttctcaaa aagtatttgt acgagattgc ccgacgacac     960
ccctatttct acgctcccga gttgctcttc ttcgcgaaac ggtataaagc tgcctttact    1020
gaatgctgtc aagcagcgga caaggccgca tgcctccttc ccaaattgga tgaactccgc    1080
gatgaaggga aggcgtcatc ggccaaacag cggcttaagt gcgcatcgct tcagaaattc    1140
ggagagaggg cgttcaaagc gtgggccgtc gcgagactgt cgcagagatt ccctaaggcg    1200
gaatttgcag aggtatcgaa gctcgtgaca gacctcacaa aggtccacac cgaatgttgc    1260
catggagacc tgcttgagtg cgccgatgat agggcagacc tcgcaaagta catttgtgag    1320
```

```
aatcaggaca gcattagctc caagctgaaa gagtgctgtg agaagccttt gctggaaaaa   1380
tcccactgta tcgccgaggt agaaaacgat gaaatgcccg ctgatcttcc ctcgctggcg   1440
gcagacttcg tcgagtcgaa ggacgtctgc aagaattacg cagaggcaaa agatgtgttt   1500
cttggaatgt tcctttatga gtatgcgaga aggcacccgg attattccgt ggtactgctc   1560
ttgcgattgg cgaaaacgta cgaaacaacg cttgagaagt gttgtgcggc tgccgacccg   1620
catgagtgct acgccaaggt atttgatgag tttaaacctc ttgtcgagga accccagaat   1680
cttatcaagc agaactgcga gcttttcaag cagttgggtg aatacaaatt ccagaacgcg   1740
cttctggtga ggtataccaa gaaagtacct caagtctcaa cacccacact cgtcgaggtg   1800
tcacggaacc tcgggaaagt agggtcgaag tgctgtaaac acccagaggc caagcgcatg   1860
ccctgtgcgg aggactacct ctcggtagtg ttgaatcaac tgtgtgtcct ccacgaaaag   1920
acgccggtgt cagaccgcgt cacaaagtgc tgcacggaga gcctggtcaa tagacgcccc   1980
tgcttctcag cgctggaggt ggatgagaca tacgtcccga agagtttaa cgccgaaacg   2040 tttactttc atgctgatat ctgtacgttg tcagagaagg aaaggcaaat caagaaacaa   2100
actgcgcttg tggaactggt gaagcacaaa ccgaaggcga ctaaggaaca gctgaaggcg   2160
gtgatggatg actttgccgc gttcgtagag aaatgctgta aagcagacga taaggagact   2220
tgttttgcgg aagagggacc taaacttgtt gctgcaagtc aagctgcctt aggcttatag   2280
```

<210> SEQ ID NO 96
<211> LENGTH: 759
<212> TYPE: PRT
<213> ORGANISM: Artificial Sequence
<220> FEATURE:
<223> OTHER INFORMATION: J15HSA AA

<400> SEQUENCE: 96

```
Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
        50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Gly Ser Gly Gly Gly Gly Ser Asp Ala
                165                 170                 175

His Lys Ser Glu Val Ala His Arg Phe Lys Asp Leu Gly Glu Glu Asn
            180                 185                 190

Phe Lys Ala Leu Val Leu Ile Ala Phe Ala Gln Tyr Leu Gln Gln Cys
```

```
            195                 200                 205
Pro Phe Glu Asp His Val Lys Leu Val Asn Glu Val Thr Glu Phe Ala
210                 215                 220

Lys Thr Cys Val Ala Asp Glu Ser Ala Glu Asn Cys Asp Lys Ser Leu
225                 230                 235                 240

His Thr Leu Phe Gly Asp Lys Leu Cys Thr Val Ala Thr Leu Arg Glu
                245                 250                 255

Thr Tyr Gly Glu Met Ala Asp Cys Cys Ala Lys Gln Glu Pro Glu Arg
            260                 265                 270

Asn Glu Cys Phe Leu Gln His Lys Asp Asp Asn Pro Asn Leu Pro Arg
            275                 280                 285

Leu Val Arg Pro Glu Val Asp Val Met Cys Thr Ala Phe His Asp Asn
290                 295                 300

Glu Glu Thr Phe Leu Lys Lys Tyr Leu Tyr Glu Ile Ala Arg Arg His
305                 310                 315                 320

Pro Tyr Phe Tyr Ala Pro Glu Leu Leu Phe Phe Ala Lys Arg Tyr Lys
                325                 330                 335

Ala Ala Phe Thr Glu Cys Cys Gln Ala Ala Asp Lys Ala Ala Cys Leu
            340                 345                 350

Leu Pro Lys Leu Asp Glu Leu Arg Asp Glu Gly Lys Ala Ser Ser Ala
            355                 360                 365

Lys Gln Arg Leu Lys Cys Ala Ser Leu Gln Lys Phe Gly Glu Arg Ala
370                 375                 380

Phe Lys Ala Trp Ala Val Ala Arg Leu Ser Gln Arg Phe Pro Lys Ala
385                 390                 395                 400

Glu Phe Ala Glu Val Ser Lys Leu Val Thr Asp Leu Thr Lys Val His
                405                 410                 415

Thr Glu Cys Cys His Gly Asp Leu Leu Glu Cys Ala Asp Asp Arg Ala
            420                 425                 430

Asp Leu Ala Lys Tyr Ile Cys Glu Asn Gln Asp Ser Ile Ser Ser Lys
            435                 440                 445

Leu Lys Glu Cys Cys Glu Lys Pro Leu Leu Glu Lys Ser His Cys Ile
450                 455                 460

Ala Glu Val Glu Asn Asp Glu Met Pro Ala Asp Leu Pro Ser Leu Ala
465                 470                 475                 480

Ala Asp Phe Val Glu Ser Lys Asp Val Cys Lys Asn Tyr Ala Glu Ala
                485                 490                 495

Lys Asp Val Phe Leu Gly Met Phe Leu Tyr Glu Tyr Ala Arg Arg His
            500                 505                 510

Pro Asp Tyr Ser Val Val Leu Leu Leu Arg Leu Ala Lys Thr Tyr Glu
            515                 520                 525

Thr Thr Leu Glu Lys Cys Cys Ala Ala Ala Asp Pro His Glu Cys Tyr
530                 535                 540

Ala Lys Val Phe Asp Glu Phe Lys Pro Leu Val Glu Glu Pro Gln Asn
545                 550                 555                 560

Leu Ile Lys Gln Asn Cys Glu Leu Phe Lys Gln Leu Gly Glu Tyr Lys
                565                 570                 575

Phe Gln Asn Ala Leu Leu Val Arg Tyr Thr Lys Lys Val Pro Gln Val
            580                 585                 590

Ser Thr Pro Thr Leu Val Glu Val Ser Arg Asn Leu Gly Lys Val Gly
            595                 600                 605

Ser Lys Cys Cys Lys His Pro Glu Ala Lys Arg Met Pro Cys Ala Glu
610                 615                 620
```

```
Asp Tyr Leu Ser Val Val Leu Asn Gln Leu Cys Val Leu His Glu Lys
625                 630                 635                 640

Thr Pro Val Ser Asp Arg Val Thr Lys Cys Cys Thr Glu Ser Leu Val
            645                 650                 655

Asn Arg Arg Pro Cys Phe Ser Ala Leu Glu Val Asp Glu Thr Tyr Val
                660                 665                 670

Pro Lys Glu Phe Asn Ala Glu Thr Phe Thr Phe His Ala Asp Ile Cys
            675                 680                 685

Thr Leu Ser Glu Lys Glu Arg Gln Ile Lys Lys Gln Thr Ala Leu Val
        690                 695                 700

Glu Leu Val Lys His Lys Pro Lys Ala Thr Lys Glu Gln Leu Lys Ala
705                 710                 715                 720

Val Met Asp Asp Phe Ala Ala Phe Val Glu Lys Cys Cys Lys Ala Asp
                725                 730                 735

Asp Lys Glu Thr Cys Phe Ala Glu Glu Gly Pro Lys Leu Val Ala Ala
            740                 745                 750

Ser Gln Ala Ala Leu Gly Leu
        755
```

<210> SEQ ID NO 97
<211> LENGTH: 1452
<212> TYPE: DNA
<213> ORGANISM: Artificial Sequence
<220> FEATURE:
<223> OTHER INFORMATION: V15J15ABD DNA

<400> SEQUENCE: 97

```
atgggtggt cctacattat cctgttcctc gtggccaccg ccactggcgt gcactcacag      60
gtgcagctgg tgcagtctgg cgccgaagtg aagaaacctg gcgcctccgt gaaggtgtcc    120
tgcaaggcct ccggctacac cttcatcagc tacaccatgc actgggtgcg acaggcccct    180
ggacagggcc tggaatggat gggctacatc aaccctagat ctggctacac ccactacaac    240
cagaagctga aggacaaggc caccctgacc gccgacaagt ctgcctccac cgcctacatg    300
gaactgtcct ccctgcggag cgaggacacc gccgtgtact actgtgccag atccgcctac    360
tacgactacg acggcttcgc ctattggggc cagggcaccc tcgtgacagt gtctagcggt    420
ggcggaggat ctggcggagg cggtagtggc ggtggcggat ctgatatcca gatgacccag    480
tccccctcca gcctgtctgc ctctgtgggc gacagagtga caattacctg ctccgccagc    540
tcctccgtgt cttacatgaa ctggtatcag cagaagcccg gcaaggcccc caagcggctg    600
atctacgaca cctccaagct ggcctctggc gtgccctcca gattctccgg ctctggctct    660
ggcaccgact taccctgac catcagctcc ctgcagcccg aggacttcgc cacctactac    720
tgccagcagt ggtcctccaa ccctcccacc tttggcggag gcaccaaggt ggaaatcaaa    780
ggcggcggag aagcggggg aggcggttct gggggtggtg gatctcagga agatgagcgg    840
atcgtgctgg tggacaacaa gtgcaagtgc cccggatca cctcccggat catccggtcc    900
tccgaggatc ccaacgagga catcgtggaa cggaacatca gaatcatcgt gcccctgaac    960
aaccgcgaga acatctccga ccccaccagc cctctgcgga ccagattcgt gtaccacctg   1020
tccgacctgt gcaagaagtg cgaccctacc gaggtggaac tggacaacca gatcgtgacc   1080
gccacccagt ccaacatctg cgacgaggac tccgccaccg agacatgcta cacctacgac   1140
cggaacaagt gctacaccgc cgtggtgcct ctggtgtacg cggcgagac aaagatggtg   1200
gaaaccgccc tgacccccga cgcctgctat cctgatgag gcggaggatc tggtggcggt   1260
```

```
ggttctggcg gagggggctc tcagcacgat gaggccgtgg acgccaattc tctggccgag    1320
gctaaggtgc tggccaacag agagctggat aagtacggcg tgtccgacta ctacaagaac    1380
ctgatcaaca acgccaagac cgtggaaggc gtgaaggccc tgatcgacga gatcctggct    1440
gccctgcctt ga                                                         1452
```

<210> SEQ ID NO 98
<211> LENGTH: 483
<212> TYPE: PRT
<213> ORGANISM: Artificial Sequence
<220> FEATURE:
<223> OTHER INFORMATION: V15J15ABD AA

<400> SEQUENCE: 98

```
Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Ile Ser Tyr Thr Met His Trp Val Arg Gln Ala Pro Gly Gln Gly Leu
        50                  55                  60

Glu Trp Met Gly Tyr Ile Asn Pro Arg Ser Gly Tyr Thr His Tyr Asn
65                  70                  75                  80

Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Val Glu Ile Lys Gly Gly Gly Gly Ser Gly Gly Gly Gly Ser Gly Gly
            260                 265                 270

Gly Gly Ser Gln Glu Asp Glu Arg Ile Val Leu Val Asp Asn Lys Cys
        275                 280                 285

Lys Cys Ala Arg Ile Thr Ser Arg Ile Ile Arg Ser Ser Glu Asp Pro
    290                 295                 300

Asn Glu Asp Ile Val Glu Arg Asn Ile Arg Ile Ile Val Pro Leu Asn
305                 310                 315                 320
```

Asn Arg Glu Asn Ile Ser Asp Pro Thr Ser Pro Leu Arg Thr Arg Phe
                    325                 330                 335

Val Tyr His Leu Ser Asp Leu Cys Lys Lys Cys Asp Pro Thr Glu Val
            340                 345                 350

Glu Leu Asp Asn Gln Ile Val Thr Ala Thr Gln Ser Asn Ile Cys Asp
        355                 360                 365

Glu Asp Ser Ala Thr Glu Thr Cys Tyr Thr Tyr Asp Arg Asn Lys Cys
    370                 375                 380

Tyr Thr Ala Val Val Pro Leu Val Tyr Gly Glu Thr Lys Met Val
385                 390                 395                 400

Glu Thr Ala Leu Thr Pro Asp Ala Cys Tyr Pro Asp Gly Gly Gly
                405                 410                 415

Ser Gly Gly Gly Gly Ser Gly Gly Gly Ser Gln His Asp Glu Ala
                420                 425                 430

Val Asp Ala Asn Ser Leu Ala Glu Ala Lys Val Leu Ala Asn Arg Glu
            435                 440                 445

Leu Asp Lys Tyr Gly Val Ser Asp Tyr Tyr Lys Asn Leu Ile Asn Asn
        450                 455                 460

Ala Lys Thr Val Glu Gly Val Lys Ala Leu Ile Asp Glu Ile Leu Ala
465                 470                 475                 480

Ala Leu Pro

<210> SEQ ID NO 99
<211> LENGTH: 3039
<212> TYPE: DNA
<213> ORGANISM: Artificial Sequence
<220> FEATURE:
<223> OTHER INFORMATION: V15J15HSA(K573P) DNA

<400> SEQUENCE: 99

```
atgggggtggt cctacattat cctgttcctc gtggccaccg ccactggcgt gcactcacag      60
gtgcagctgg tgcagtctgg cgccgaagtg aagaaacctg gcgcctccgt gaaggtgtcc     120
tgcaaggcct ccggctacac cttcatcagc tacaccatgc actgggtgcg acaggcccct     180
ggacagggcc tggaatggat gggctacatc aaccctagat ctggctacac ccactacaac     240
cagaagctga aggacaaggc caccctgacc gccgacaagt ctgcctccac cgcctacatg     300
gaactgtcct ccctgcggag cgaggacacc gccgtgtact actgtgccag atccgcctac     360
tacgactacg acggcttcgc ctattggggc cagggcaccc tcgtgacagt gtctagcggt     420
ggcggaggat ctggcggagg cggtagtggc ggtggcggat ctgatatcca gatgacccag     480
tccccctcca gcctgtctgc ctctgtgggc gacagagtga caattacctg ctccgccagc     540
tcctccgtgt cttacatgaa ctggtatcag cagaagcccg gcaaggcccc caagcggctg     600
atctacgaca cctccaagct ggcctctggc gtgccctcca gattctccgg ctctggctct     660
ggcaccgact ttaccctgac catcagctcc ctgcagcccg aggacttcgc cacctactac     720
tgccagcagt ggtcctccaa ccctcccacc tttggcggag caccaaggt ggaaatcaaa      780
ggcggcggag aagcggggg aggcggttct ggggggtggtg atctcagga agatgagcgg     840
atcgtgctgg tggacaacaa gtgcaagtgc gcccggatca cctcccggat catccggtcc     900
tccgaggatc ccaacgagga catcgtggaa cggaacatca gaatcatcgt gcccctgaac     960
aaccgcgaga acatctccga ccccaccagc cctctgcgga ccagattcgt gtaccacctg    1020
tccgacctgt gcaagaagtg cgaccctacc gaggtggaac tggacaacca gatcgtgacc    1080
gccacccagt ccaacatctg cgacgaggac tccgccaccg agacatgcta cacctacgac    1140
```

```
cggaacaagt gctacaccgc cgtggtgcct ctggtgtacg gcggcgagac aaagatggtg    1200
gaaaccgccc tgaccccga cgcctgctat cctgatggag cggaggatc tggtggcggt     1260 ggttctggcg aggggggctc tgacgcccac aaatcggagg tagcgcaccg gttcaaagac   1320
ttgggagaag aaaactttaa ggcccttgta ctcattgcgt ttgcgcagta tttgcagcag   1380
tgcccattcg aggaccatgt caaacttgtc aacgaagtga cagagtttgc gaaaacttgc   1440
gtcgccgacg aatccgcgga gaactgtgac aagtcgctgc atacgttgtt cggggataag   1500
ctctgtaccg tagcgacctt gagggaaact tacggggaaa tggcggactg ttgcgctaag   1560
caggagccgg aacggaacga gtgtttcctt cagcataagg atgacaaccc caacctccct   1620
agattggtca gacccgaagt ggatgtgatg tgcacagcat ccatgacaa tgaggaaacc    1680 tttctcaaaa agtatttgta cgagattgcc cgacgcacac cctattccta cgctcccgag   1740
ttgctcttct cgcgaaacg gtataaagct gcctttactg aatgctgtca agcagcggac    1800
aaggccgcat gcctccttcc caaattggat gaactccgcg atgaagggaa ggcgtcatcg   1860
gccaaacagc ggcttaagtg cgcatcgctt cagaaattcg agagagggc gttcaaagcg    1920 tgggccgtcg cgagactgtc gcagagattc cctaaggcgg aatttgcaga ggtatcgaag   1980
ctcgtgacag acctcacaaa ggtccacacc gaatgttgcc atggagacct gcttgagtgc   2040
gccgatgata gggcagacct cgcaaagtac atttgtgaga atcaggacag cattagctcc   2100
aagctgaaag agtgctgtga aagcctttg ctggaaaaat cccactgtat cgccgaggta    2160
gaaaacgatg aaatgcccgc tgatcttccc tcgctggcgg cagacttcgt cgagtcgaag   2220
gacgtctgca gaattacgc agaggcaaaa gatgtgtttc ttggaatgtt ccttatgag    2280 tatgcgagaa ggcaccccga ttattccgtg gtactgctct tgcgattggc gaaaacgtac   2340
gaaacaacgc ttgagaagtg ttgtgcggct gccgacccgc atgagtgcta cgccaaggta   2400
tttgatgagt ttaaacctct tgtcgaggaa ccccagaatc ttatcaagca gaactgcgag   2460
cttttcaagc agttgggtga atacaaattc cagaacgcgc ttctggtgag gtataccaag   2520
aaagtacctc aagtctcaac acccacactc gtcgaggtgt cacgaacct cgggaaagta    2580 gggtcgaagt gctgtaaaca cccagaggcc aagcgcatgc cctgtgcgga ggactacctc   2640
tcggtagtgt tgaatcaact gtgtgtcctc cacgaaaaga cgccggtgtc agaccgcgtc   2700
acaaagtgct gcacggagag cctggtcaat agacgcccct gcttctcagc gctgaggtg    2760 gatgagacat acgtcccgaa agagtttaac gccgaaacgt ttacttttca tgctgatatc   2820
tgtacgttgt cagagaagga aaggcaaatc aagaaacaaa ctgcgcttgt ggaactggtg   2880
aagcacaaac cgaaggcgac taaggaacag ctgaaggcgg tgatggatga cttttgccgcg   2940 ttcgtagaga aatgctgtaa agcagacgat aaggagactt gttttgcgga agagggacct   3000
aaacttgttg ctgcaagtca agctgcctta ggcttatag                          3039
```

<210> SEQ ID NO 100
<211> LENGTH: 1012
<212> TYPE: PRT
<213> ORGANISM: Artificial Sequence
<220> FEATURE:
<223> OTHER INFORMATION: V15J15HSA(K573P) AA

<400> SEQUENCE: 100

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys

```
                20                  25                  30
Pro Gly Ala Ser Val Lys Val Ser Cys Lys Ala Ser Gly Tyr Thr Phe
            35                  40                  45
Ile Ser Tyr Thr Met His Trp Val Arg Gln Ala Pro Gly Gln Gly Leu
50                  55                  60
Glu Trp Met Gly Tyr Ile Asn Pro Arg Ser Gly Tyr Thr His Tyr Asn
65                  70                  75                  80
Gln Lys Leu Lys Asp Lys Ala Thr Leu Thr Ala Asp Lys Ser Ala Ser
            85                  90                  95
Thr Ala Tyr Met Glu Leu Ser Ser Leu Arg Ser Glu Asp Thr Ala Val
            100                 105                 110
Tyr Tyr Cys Ala Arg Ser Ala Tyr Tyr Asp Tyr Asp Gly Phe Ala Tyr
            115                 120                 125
Trp Gly Gln Gly Thr Leu Val Thr Val Ser Ser Gly Gly Gly Gly Ser
            130                 135                 140
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
                165                 170                 175
Cys Ser Ala Ser Ser Val Ser Tyr Met Asn Trp Tyr Gln Gln Lys
                180                 185                 190
Pro Gly Lys Ala Pro Lys Arg Leu Ile Tyr Asp Thr Ser Lys Leu Ala
            195                 200                 205
Ser Gly Val Pro Ser Arg Phe Ser Gly Ser Gly Ser Gly Thr Asp Phe
            210                 215                 220
Thr Leu Thr Ile Ser Ser Leu Gln Pro Glu Asp Phe Ala Thr Tyr Tyr
225                 230                 235                 240
Cys Gln Gln Trp Ser Ser Asn Pro Pro Thr Phe Gly Gly Gly Thr Lys
                245                 250                 255
Val Glu Ile Lys Gly Gly Gly Gly Ser Gly Gly Gly Gly Ser Gly Gly
                260                 265                 270
Gly Gly Ser Gln Glu Asp Glu Arg Ile Val Leu Val Asp Asn Lys Cys
            275                 280                 285
Lys Cys Ala Arg Ile Thr Ser Arg Ile Ile Arg Ser Ser Glu Asp Pro
            290                 295                 300
Asn Glu Asp Ile Val Glu Arg Asn Ile Arg Ile Ile Val Pro Leu Asn
305                 310                 315                 320
Asn Arg Glu Asn Ile Ser Asp Pro Thr Ser Pro Leu Arg Thr Arg Phe
                325                 330                 335
Val Tyr His Leu Ser Asp Leu Cys Lys Lys Cys Asp Pro Thr Glu Val
            340                 345                 350
Glu Leu Asp Asn Gln Ile Val Thr Ala Thr Gln Ser Asn Ile Cys Asp
            355                 360                 365
Glu Asp Ser Ala Thr Glu Thr Cys Tyr Thr Tyr Asp Arg Asn Lys Cys
            370                 375                 380
Tyr Thr Ala Val Val Pro Leu Val Tyr Gly Gly Glu Thr Lys Met Val
385                 390                 395                 400
Glu Thr Ala Leu Thr Pro Asp Ala Cys Tyr Pro Asp Gly Gly Gly Gly
                405                 410                 415
Ser Gly Gly Gly Gly Ser Gly Gly Gly Ser Asp Ala His Lys Ser
            420                 425                 430
Glu Val Ala His Arg Phe Lys Asp Leu Gly Glu Glu Asn Phe Lys Ala
            435                 440                 445
```

```
Leu Val Leu Ile Ala Phe Ala Gln Tyr Leu Gln Gln Cys Pro Phe Glu
    450                 455                 460

Asp His Val Lys Leu Val Asn Glu Val Thr Glu Phe Ala Lys Thr Cys
465                 470                 475                 480

Val Ala Asp Glu Ser Ala Glu Asn Cys Asp Lys Ser Leu His Thr Leu
                485                 490                 495

Phe Gly Asp Lys Leu Cys Thr Val Ala Thr Leu Arg Glu Thr Tyr Gly
            500                 505                 510

Glu Met Ala Asp Cys Cys Ala Lys Gln Glu Pro Glu Arg Asn Glu Cys
        515                 520                 525

Phe Leu Gln His Lys Asp Asp Asn Pro Asn Leu Pro Arg Leu Val Arg
    530                 535                 540

Pro Glu Val Asp Val Met Cys Thr Ala Phe His Asp Asn Glu Glu Thr
545                 550                 555                 560

Phe Leu Lys Lys Tyr Leu Tyr Glu Ile Ala Arg Arg His Pro Tyr Phe
                565                 570                 575

Tyr Ala Pro Glu Leu Leu Phe Phe Ala Lys Arg Tyr Lys Ala Ala Phe
            580                 585                 590

Thr Glu Cys Cys Gln Ala Ala Asp Lys Ala Ala Cys Leu Leu Pro Lys
        595                 600                 605

Leu Asp Glu Leu Arg Asp Glu Gly Lys Ala Ser Ser Ala Lys Gln Arg
    610                 615                 620

Leu Lys Cys Ala Ser Leu Gln Lys Phe Gly Glu Arg Ala Phe Lys Ala
625                 630                 635                 640

Trp Ala Val Ala Arg Leu Ser Gln Arg Phe Pro Lys Ala Glu Phe Ala
                645                 650                 655

Glu Val Ser Lys Leu Val Thr Asp Leu Thr Lys Val His Thr Glu Cys
            660                 665                 670

Cys His Gly Asp Leu Leu Glu Cys Ala Asp Asp Arg Ala Asp Leu Ala
        675                 680                 685

Lys Tyr Ile Cys Glu Asn Gln Asp Ser Ile Ser Ser Lys Leu Lys Glu
    690                 695                 700

Cys Cys Glu Lys Pro Leu Leu Glu Lys Ser His Cys Ile Ala Glu Val
705                 710                 715                 720

Glu Asn Asp Glu Met Pro Ala Asp Leu Pro Ser Leu Ala Ala Asp Phe
                725                 730                 735

Val Glu Ser Lys Asp Val Cys Lys Asn Tyr Ala Glu Ala Lys Asp Val
            740                 745                 750

Phe Leu Gly Met Phe Leu Tyr Glu Tyr Ala Arg Arg His Pro Asp Tyr
        755                 760                 765

Ser Val Val Leu Leu Leu Arg Leu Ala Lys Thr Tyr Glu Thr Thr Leu
    770                 775                 780

Glu Lys Cys Cys Ala Ala Ala Asp Pro His Glu Cys Tyr Ala Lys Val
785                 790                 795                 800

Phe Asp Glu Phe Lys Pro Leu Val Glu Glu Pro Gln Asn Leu Ile Lys
                805                 810                 815

Gln Asn Cys Glu Leu Phe Lys Gln Leu Gly Glu Tyr Lys Phe Gln Asn
            820                 825                 830

Ala Leu Leu Val Arg Tyr Thr Lys Lys Val Pro Gln Val Ser Thr Pro
        835                 840                 845

Thr Leu Val Glu Val Ser Arg Asn Leu Gly Lys Val Gly Ser Lys Cys
    850                 855                 860
```

Cys Lys His Pro Glu Ala Lys Arg Met Pro Cys Ala Glu Asp Tyr Leu
865                 870                 875                 880

Ser Val Val Leu Asn Gln Leu Cys Val Leu His Glu Lys Thr Pro Val
                885                 890                 895

Ser Asp Arg Val Thr Lys Cys Cys Thr Glu Ser Leu Val Asn Arg Arg
            900                 905                 910

Pro Cys Phe Ser Ala Leu Glu Val Asp Glu Thr Tyr Val Pro Lys Glu
        915                 920                 925

Phe Asn Ala Glu Thr Phe Thr Phe His Ala Asp Ile Cys Thr Leu Ser
    930                 935                 940

Glu Lys Glu Arg Gln Ile Lys Lys Gln Thr Ala Leu Val Glu Leu Val
945                 950                 955                 960

Lys His Lys Pro Lys Ala Thr Lys Glu Gln Leu Lys Ala Val Met Asp
                965                 970                 975

Asp Phe Ala Ala Phe Val Glu Lys Cys Cys Lys Ala Asp Asp Lys Glu
            980                 985                 990

Thr Cys Phe Ala Glu Glu Gly Pro  Lys Leu Val Ala Ala  Ser Gln Ala
        995                 1000                 1005

Ala Leu  Gly Leu
    1010

<210> SEQ ID NO 101
<211> LENGTH: 3039
<212> TYPE: DNA
<213> ORGANISM: Artificial Sequence
<220> FEATURE:
<223> OTHER INFORMATION: V151JHSA(wt) DNA

<400> SEQUENCE: 101

```
atggggtggt cctacattat cctgttcctc gtggccaccg ccactggcgt gcactcacag      60
gtgcagctgg tgcagtctgg cgccgaagtg aagaaacctg gcgcctccgt gaaggtgtcc     120
tgcaaggcct ccggctacac cttcatcagc tacaccatgc actgggtgcg acaggccoct     180 ggacagggcc tggaatggat gggctacatc aaccctagat ctggctacac ccactacaac     240
cagaagctga aggacaaggc cacccctgac cgccgacaag ctgcctccac cgcctacatg     300
gaactgtcct ccctgcggag cgaggacacc gccgtgtact actgtgccag atccgcctac     360
tacgactacg acgccttcgc ctattgggc cagggcaccc tcgtgacagt gtctagcggt     420
ggcggaggat ctggcggagg cggtagtggc ggtggcggat ctgatatcca gatgacccag     480
tccccctcca gcctgtctgc ctctgtgggc gacagagtga caattacctg ctccgccagc     540
tcctccgtgt cttacatgaa ctggtatcag cagaagcccg gcaaggcccc caagcggctg     600
atctacgaca cctccaagct ggcctctggc gtgccctcca gattctccgg ctctggctct     660
ggcaccgact ttaccctgac catcagctcc ctgcagcccg aggacttcgc cacctactac     720
tgccagcagt ggtcctccaa ccctcccacc tttggcggag caccaaggt ggaaatcaaa     780 ggcggcggag aagcgggggg aggcggttct ggggggtggtg gatctcagga agatgagcgg     840
atcgtgctgg tggacaacaa gtgcaagtgc gcccggatca cctcccggat catccggtcc     900
tccgaggatc ccaacgagga catcgtggaa cggaacatca gaatcatcgt gccctgaac     960 aaccgcgaga catctccga ccccaccagc cctctgcgga ccagattcgt gtaccacctg    1020
tccgacctgt gcaagaagtg cgaccctacc gaggtggaac tggacaacca gatcgtgacc    1080
gccacccagt ccaacatctg cgacgaggac tccgccaccg agacatgcta cacctacgac    1140
cggaacaagt gctacaccgc cgtggtgcct ctggtgtacg gcggcgagac aaagatggtg    1200
```

```
gaaaccgccc tgacccccga cgcctgctat cctgatggag gcggaggatc tggtggcggt    1260
ggttctggcg gagggggctc tgacgccac aaatcggagg tagcgcaccg gttcaaagac    1320
ttgggagaag aaaactttaa ggcccttgta ctcattgcgt ttgcgcagta tttgcagcag    1380
tgcccattcg aggaccatgt caaacttgtc aacgaagtga cagagtttgc gaaaacttgc    1440
gtcgccgacg aatccgcgga gaactgtgac aagtcgctgc atacgttgtt cggggataag    1500
ctctgtaccg tagcgacctt gagggaaact tacggggaaa tggcggactg ttgcgctaag    1560
caggagccgg aacggaacga gtgtttcctt cagcataagg atgacaaccc caacctccct    1620
agattggtca gacccgaagt ggatgtgatg tgcacagcat ccatgacaa tgaggaaacc    1680 tttctcaaaa agtatttgta cgagattgcc cgacgacacc cctatttcta cgctcccgag    1740
ttgctcttct tcgcgaaacg gtataaagct gcctttactg aatgctgtca agcagcggac    1800
aaggccgcat gcctccttcc caaattggat gaactccgcg atgaagggaa ggcgtcatcg    1860
gccaaacagc ggcttaagtg cgcatcgctt cagaaattcg agagagggc gttcaaagcg    1920 tgggccgtcg cgagactgtc gcagagattc cctaaggcgg aatttgcaga ggtatcgaag    1980
ctcgtgacag acctcacaaa ggtccacacc gaatgttgcc atggagacct gcttgagtgc    2040
gccgatgata gggcagacct cgcaaagtac atttgtgaga atcaggacag cattagctcc    2100
aagctgaaag agtgctgtga aagcctttg ctggaaaaat cccactgtat cgccgaggta    2160
gaaaacgatg aaatgcccgc tgatcttccc tcgctggcgg cagacttcgt cgagtcgaag    2220
gacgtctgca agaattacgc agaggcaaaa gatgtgtttc ttggaatgtt cctttatgag    2280
tatgcgagaa ggcacccgga ttattccgtg gtactgctct tgcgattggc gaaaacgtac    2340
gaaacaacgc ttgagaagtg ttgtgcggct gccgacccgc atgagtgcta cgccaaggta    2400
tttgatgagt ttaaacctct tgtcgaggaa ccccagaatc ttatcaagca gaactgcgag    2460
cttttcaagc agttgggtga atacaaattc cagaacgcgc ttctggtgag gtataccaag    2520
aaagtacctc aagtctcaac acccacactc gtcgaggtgt cacggaacct cgggaaagta    2580
gggtcgaagt gctgtaaaca cccagaggcc aagcgcatgc cctgtgcgga ggactacctc    2640
tcggtagtgt tgaatcaact gtgtgtcctc cacgaaaaga cgccggtgtc agaccgcgtc    2700
acaaagtgct gcacggagag cctggtcaat agacgcccct gcttctcagc gctggaggtg    2760
gatgagacat acgtcccgaa agagtttaac gccgaaacgt ttacttttca tgctgatatc    2820
tgtacgttgt cagagaagga aaggcaaatc aagaaacaaa ctgcgcttgt ggaactggtg    2880
aagcacaaac cgaaggcgac taaggaacag ctgaaggcgg tgatggatga ctttgccgcg    2940
ttcgtagaga aatgctgtaa agcagacgat aaggagactt gttttgcgga agagggaaag    3000
aaacttgttg ctgcaagtca agctgcctta ggcttatag                          3039
```

<210> SEQ ID NO 102
<211> LENGTH: 1012
<212> TYPE: PRT
<213> ORGANISM: Artificial Sequence
<220> FEATURE:
<223> OTHER INFORMATION: V15J15HSA(wt) AA

<400> SEQUENCE: 102

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

-continued

Pro Gly Ala Ser Val Lys Val Ser Cys Lys Ala Ser Gly Tyr Thr Phe
             35                  40                  45

Ile Ser Tyr Thr Met His Trp Val Arg Gln Ala Pro Gly Gln Gly Leu
 50                  55                  60

Glu Trp Met Gly Tyr Ile Asn Pro Arg Ser Gly Tyr Thr His Tyr Asn
 65                  70                  75                  80

Gln Lys Leu Lys Asp Lys Ala Thr Leu Thr Ala Asp Lys Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
            115                 120                 125

Trp Gly Gln Gly Thr Leu Val Thr Val Ser Ser Gly Gly Gly Gly Ser
            130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
            195                 200                 205

Ser Gly Val Pro Ser Arg Phe Ser Gly Ser Gly Ser Gly Thr Asp Phe
210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
            245                 250                 255

Val Glu Ile Lys Gly Gly Gly Gly Ser Gly Gly Gly Gly Ser Gly Gly
            260                 265                 270

Gly Gly Ser Gln Glu Asp Glu Arg Ile Val Leu Val Asp Asn Lys Cys
            275                 280                 285

Lys Cys Ala Arg Ile Thr Ser Arg Ile Ile Arg Ser Ser Glu Asp Pro
290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
            340                 345                 350

Glu Leu Asp Asn Gln Ile Val Thr Ala Thr Gln Ser Asn Ile Cys Asp
            355                 360                 365

Glu Asp Ser Ala Thr Glu Thr Cys Tyr Thr Tyr Asp Arg Asn Lys Cys
370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp Gly Gly Gly Gly
            405                 410                 415

Ser Gly Gly Gly Gly Ser Gly Gly Gly Gly Ser Asp Ala His Lys Ser
            420                 425                 430

Glu Val Ala His Arg Phe Lys Asp Leu Gly Glu Glu Asn Phe Lys Ala
            435                 440                 445

Leu Val Leu Ile Ala Phe Ala Gln Tyr Leu Gln Gln Cys Pro Phe Glu

```
                450             455             460
Asp His Val Lys Leu Val Asn Glu Val Thr Glu Phe Ala Lys Thr Cys
465                 470                 475                 480

Val Ala Asp Glu Ser Ala Glu Asn Cys Asp Lys Ser Leu His Thr Leu
                485                 490                 495

Phe Gly Asp Lys Leu Cys Thr Val Ala Thr Leu Arg Glu Thr Tyr Gly
                500                 505                 510

Glu Met Ala Asp Cys Cys Ala Lys Gln Glu Pro Glu Arg Asn Glu Cys
                515                 520                 525

Phe Leu Gln His Lys Asp Asp Asn Pro Asn Leu Pro Arg Leu Val Arg
530                 535                 540

Pro Glu Val Asp Val Met Cys Thr Ala Phe His Asp Asn Glu Glu Thr
545                 550                 555                 560

Phe Leu Lys Lys Tyr Leu Tyr Glu Ile Ala Arg Arg His Pro Tyr Phe
                565                 570                 575

Tyr Ala Pro Glu Leu Leu Phe Phe Ala Lys Arg Tyr Lys Ala Ala Phe
                580                 585                 590

Thr Glu Cys Cys Gln Ala Ala Asp Lys Ala Ala Cys Leu Leu Pro Lys
                595                 600                 605

Leu Asp Glu Leu Arg Asp Glu Gly Lys Ala Ser Ser Ala Lys Gln Arg
610                 615                 620

Leu Lys Cys Ala Ser Leu Gln Lys Phe Gly Glu Arg Ala Phe Lys Ala
625                 630                 635                 640

Trp Ala Val Ala Arg Leu Ser Gln Arg Phe Pro Lys Ala Glu Phe Ala
                645                 650                 655

Glu Val Ser Lys Leu Val Thr Asp Leu Thr Lys Val His Thr Glu Cys
                660                 665                 670

Cys His Gly Asp Leu Leu Glu Cys Ala Asp Asp Arg Ala Asp Leu Ala
                675                 680                 685

Lys Tyr Ile Cys Glu Asn Gln Asp Ser Ile Ser Ser Lys Leu Lys Glu
                690                 695                 700

Cys Cys Glu Lys Pro Leu Leu Glu Lys Ser His Cys Ile Ala Glu Val
705                 710                 715                 720

Glu Asn Asp Glu Met Pro Ala Asp Leu Pro Ser Leu Ala Ala Asp Phe
                725                 730                 735

Val Glu Ser Lys Asp Val Cys Lys Asn Tyr Ala Glu Ala Lys Asp Val
                740                 745                 750

Phe Leu Gly Met Phe Leu Tyr Glu Tyr Ala Arg Arg His Pro Asp Tyr
                755                 760                 765

Ser Val Val Leu Leu Leu Arg Leu Ala Lys Thr Tyr Glu Thr Thr Leu
770                 775                 780

Glu Lys Cys Cys Ala Ala Ala Asp Pro His Glu Cys Tyr Ala Lys Val
785                 790                 795                 800

Phe Asp Glu Phe Lys Pro Leu Val Glu Glu Pro Gln Asn Leu Ile Lys
                805                 810                 815

Gln Asn Cys Glu Leu Phe Lys Gln Leu Gly Glu Tyr Lys Phe Gln Asn
                820                 825                 830

Ala Leu Leu Val Arg Tyr Thr Lys Lys Val Pro Gln Val Ser Thr Pro
                835                 840                 845

Thr Leu Val Glu Val Ser Arg Asn Leu Gly Lys Val Gly Ser Lys Cys
                850                 855                 860

Cys Lys His Pro Glu Ala Lys Arg Met Pro Cys Ala Glu Asp Tyr Leu
865                 870                 875                 880
```

Ser Val Val Leu Asn Gln Leu Cys Val Leu His Glu Lys Thr Pro Val
            885                 890                 895

Ser Asp Arg Val Thr Lys Cys Cys Thr Glu Ser Leu Val Asn Arg Arg
            900                 905                 910

Pro Cys Phe Ser Ala Leu Glu Val Asp Glu Thr Tyr Val Pro Lys Glu
            915                 920                 925

Phe Asn Ala Glu Thr Phe Thr Phe His Ala Asp Ile Cys Thr Leu Ser
            930                 935                 940

Glu Lys Glu Arg Gln Ile Lys Lys Gln Thr Ala Leu Val Glu Leu Val
945                 950                 955                 960

Lys His Lys Pro Lys Ala Thr Lys Glu Gln Leu Lys Ala Val Met Asp
            965                 970                 975

Asp Phe Ala Ala Phe Val Glu Lys Cys Cys Lys Ala Asp Asp Lys Glu
            980                 985                 990

Thr Cys Phe Ala Glu Glu Gly Lys  Lys Leu Val Ala Ala  Ser Gln Ala
            995                 1000                1005

Ala Leu  Gly Leu
    1010

<210> SEQ ID NO 103
<211> LENGTH: 1791
<212> TYPE: DNA
<213> ORGANISM: Artificial Sequence
<220> FEATURE:
<223> OTHER INFORMATION: S70 IgM HC DNA

<400> SEQUENCE: 103
atggacccca agggcagcct gagctggaga atcctgctgt tcctgagcct ggccttcgag      60
ctgagctacg gcgaagtgca gctggtggaa tctggcggcg gactggtgca gcctggcgga    120
tctctgagac tgtcttgtgc cgcctccggc tttaccttct ccgactcctg gatccactgg    180
gtgcgacagg ccctggcaa gggactgaa tgggtggcct ggatctctcc ctacggcggc    240
tctacctact acgccgactc cgtgaagggc cggttcacca tctctgccga cacctccaag    300
aacaccgcct acctgcagat gaactccctg cgggccgagg acaccgccgt gtactactgt    360
gctcggagac attggcctgg cggcttcgac tattgggccc agggcacact cgtgaccgtg    420
tctgctggaa gtgctagcgc cccaaccctt ttcccctcg tctcctgtga aattccccg    480 tcggatacga gcagcgtggc cgttggctgc ctcgcacagg acttccttcc cgactccatc    540
actttctcct ggaaatacaa gaacaactct gacatcagca gcaccccggg cttcccatca    600
gtcctgagag ggggcaagta cgcagccacc tcacaggtgc tgctgccttc caaggacgtc    660
atgcagggca cagacgaaca cgtggtgtgc aaagtccagc accccaacgg caacaaagaa    720
aagaacgtgc ctcttccagt gattgctgag ctgcctccca agtgagcgt cttcgtccca    780 ccccgcgacg gcttcttcgg caaccccgc aagtccaagc tcatctgcca ggccacgggt    840
ttcagtcccc ggcagattca ggtgtcctgg ctgcgcgagg ggaagcaggt ggggtctggc    900
gtcaccacgg accaggtgca ggctgaggcc aaagagtctg gcccacgac ctacaaggtg    960 accagcacac tgaccatcaa agagagcgac tggctcagcc agagcatgtt cacctgccgc   1020
gtggatcaca ggggcctgac cttccagcag aatgcgtcct ccatgtgtgt ccccgatcaa   1080
gacacagcca tccgggtctt cgccatcccc ccatcctttg ccagcatctt cctcaccaag   1140
tccaccaagt tgacctgcct ggtcacagac ctgaccacct atgacagcgt gaccatctcc   1200
tggacccgcc agaatggcga agctgtgaaa acccacacca catctccga gagccacccc   1260

```
aatgccactt tcagcgccgt gggtgaggcc agcatctgcg aggatgactg gaattccggg    1320
gagaggttca cgtgcaccgt gacccacaca gacctgccct cgccactgaa gcagaccatc    1380
tcccggccca aggggtggc cctgcacagg cccgatgtct acttgctgcc accagcccgg     1440
gagcagctga acctgcggga gtcggccacc atcacgtgcc tggtgacggg cttctctccc    1500
gcggacgtct tcgtgcagtg gatgcagagg gggcagccct gtccccgga gaagtatgtg     1560 accagcgccc caatgcctga gccccaggcc ccaggccggt acttcgccca gcatcctg      1620 accgtgtccg aagaggaatg gaacacgggg gagacctaca cctgcgtggt ggcccatgag    1680
gccctgccca cagggtcac cgagaggacc gtggacaagt ccaccggtaa acccaccctg     1740
tacaacgtgt ccctggtcat gtccgacaca gctggcacct gctactagta a             1791
```

<210> SEQ ID NO 104
<211> LENGTH: 595
<212> TYPE: PRT
<213> ORGANISM: Artificial Sequence
<220> FEATURE:
<223> OTHER INFORMATION: S70 IgM HC AA

<400> SEQUENCE: 104

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Asp Ser Trp Ile His Trp Val Arg Gln Ala
    50                  55                  60

Pro Gly Lys Gly Leu Glu Trp Val Ala Trp Ile Ser Pro Tyr Gly Gly
65                  70                  75                  80

Ser Thr Tyr Tyr Ala Asp Ser Val Lys Gly Arg Phe Thr Ile Ser Ala
                85                  90                  95

Asp Thr Ser Lys Asn Thr Ala Tyr Leu Gln Met Asn Ser Leu Arg Ala
            100                 105                 110

Glu Asp Thr Ala Val Tyr Tyr Cys Ala Arg Arg His Trp Pro Gly Gly
        115                 120                 125

Phe Asp Tyr Trp Gly Gln Gly Thr Leu Val Thr Val Ser Ala Gly Ser
    130                 135                 140

Ala Ser Ala Pro Thr Leu Phe Pro Leu Val Ser Cys Glu Asn Ser Pro
145                 150                 155                 160

Ser Asp Thr Ser Ser Val Ala Val Gly Cys Leu Ala Gln Asp Phe Leu
                165                 170                 175

Pro Asp Ser Ile Thr Phe Ser Trp Lys Tyr Lys Asn Asn Ser Asp Ile
            180                 185                 190

Ser Ser Thr Arg Gly Phe Pro Ser Val Leu Arg Gly Gly Lys Tyr Ala
        195                 200                 205

Ala Thr Ser Gln Val Leu Leu Pro Ser Lys Asp Val Met Gln Gly Thr
    210                 215                 220

Asp Glu His Val Val Cys Lys Val Gln His Pro Asn Gly Asn Lys Glu
225                 230                 235                 240

Lys Asn Val Pro Leu Pro Val Ile Ala Glu Leu Pro Pro Lys Val Ser
                245                 250                 255

Val Phe Val Pro Pro Arg Asp Gly Phe Phe Gly Asn Pro Arg Lys Ser
            260                 265                 270
```

Lys Leu Ile Cys Gln Ala Thr Gly Phe Ser Pro Arg Gln Ile Gln Val
            275                 280                 285

Ser Trp Leu Arg Glu Gly Lys Gln Val Gly Ser Gly Val Thr Thr Asp
    290                 295                 300

Gln Val Gln Ala Glu Ala Lys Glu Ser Gly Pro Thr Thr Tyr Lys Val
305                 310                 315                 320

Thr Ser Thr Leu Thr Ile Lys Glu Ser Asp Trp Leu Ser Gln Ser Met
                325                 330                 335

Phe Thr Cys Arg Val Asp His Arg Gly Leu Thr Phe Gln Gln Asn Ala
            340                 345                 350

Ser Ser Met Cys Val Pro Asp Gln Asp Thr Ala Ile Arg Val Phe Ala
        355                 360                 365

Ile Pro Pro Ser Phe Ala Ser Ile Phe Leu Thr Lys Ser Thr Lys Leu
    370                 375                 380

Thr Cys Leu Val Thr Asp Leu Thr Thr Tyr Asp Ser Val Thr Ile Ser
385                 390                 395                 400

Trp Thr Arg Gln Asn Gly Glu Ala Val Lys Thr His Thr Asn Ile Ser
                405                 410                 415

Glu Ser His Pro Asn Ala Thr Phe Ser Ala Val Gly Glu Ala Ser Ile
            420                 425                 430

Cys Glu Asp Asp Trp Asn Ser Gly Glu Arg Phe Thr Cys Thr Val Thr
        435                 440                 445

His Thr Asp Leu Pro Ser Pro Leu Lys Gln Thr Ile Ser Arg Pro Lys
    450                 455                 460

Gly Val Ala Leu His Arg Pro Asp Val Tyr Leu Leu Pro Pro Ala Arg
465                 470                 475                 480

Glu Gln Leu Asn Leu Arg Glu Ser Ala Thr Ile Thr Cys Leu Val Thr
                485                 490                 495

Gly Phe Ser Pro Ala Asp Val Phe Val Gln Trp Met Gln Arg Gly Gln
            500                 505                 510

Pro Leu Ser Pro Glu Lys Tyr Val Thr Ser Ala Pro Met Pro Glu Pro
        515                 520                 525

Gln Ala Pro Gly Arg Tyr Phe Ala His Ser Ile Leu Thr Val Ser Glu
    530                 535                 540

Glu Glu Trp Asn Thr Gly Glu Thr Tyr Thr Cys Val Val Ala His Glu
545                 550                 555                 560

Ala Leu Pro Asn Arg Val Thr Glu Arg Thr Val Asp Lys Ser Thr Gly
                565                 570                 575

Lys Pro Thr Leu Tyr Asn Val Ser Leu Val Met Ser Asp Thr Ala Gly
            580                 585                 590

Thr Cys Tyr
        595

<210> SEQ ID NO 105
<211> LENGTH: 705
<212> TYPE: DNA
<213> ORGANISM: Artificial Sequence
<220> FEATURE:
<223> OTHER INFORMATION: S70 IgM LC DNA

<400> SEQUENCE: 105
atggagaccg acaccctgct gctctgggtg ctgctgctct gggtgcccgg ctccaccgga        60
gacatccaga tgacccagtc ccctccagc ctgtctgcct ctgtgggcga cagagtgacc        120
atcacctgtc gggcctctca ggacgtgtcc accgccgtgg cttggtatca gcagaagcct       180

```
ggcaaggccc ccaagctgct gatctactcc gcctccttcc tgtactccgg cgtgccctcc    240
agattctccg gctctggctc tggcaccgac tttaccctga ccatcagctc cctgcagccc    300
gaggacttcg ccacctacta ctgccagcag tacctgtacc accccgccac ctttggccag    360
ggcaccaagg tggaaatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
gagagcgtga ccgagcagga ctccaaggac agcacctaca gcctgagcag caccctgacc    600
ctgagcaagg ccgactacga aaagcacaag gtgtacgcct gcgaggtgac ccaccaggga    660
ctgtctagcc ccgtgaccaa gagcttcaac cggggcgagt gctaa                    705
```

<210> SEQ ID NO 106
<211> LENGTH: 234
<212> TYPE: PRT
<213> ORGANISM: Artificial Sequence
<220> FEATURE:
<223> OTHER INFORMATION: S70 IgM LC AA

<400> SEQUENCE: 106

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Leu
            100                 105                 110

Tyr His Pro Ala Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 107
<211> LENGTH: 393
<212> TYPE: PRT
<213> ORGANISM: Artificial Sequence

<220> FEATURE:
<223> OTHER INFORMATION: Y15J DNA

<400> SEQUENCE: 107

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Gly Ser Ser Tyr Leu Ala Trp Tyr Gln Gln Lys Pro Gly Gln
                165                 170                 175

Ala Pro Arg Leu Leu Ile Tyr Gly Ala Phe Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Gly Ser Ser Pro Trp Thr Phe Gly Gln Gly Thr Lys Val Glu Ile
225                 230                 235                 240

Lys Gly Gly Gly Gly Ser Gly Gly Gly Gly Ser Gly Gly Gly Gly Ser
                245                 250                 255

Gln Glu Asp Glu Arg Ile Val Leu Val Asp Asn Lys Cys Lys Cys Ala
            260                 265                 270

Arg Ile Thr Ser Arg Ile Ile Arg Ser Ser Glu Asp Pro Asn Glu Asp
        275                 280                 285

Ile Val Glu Arg Asn Ile Arg Ile Ile Val Pro Leu Asn Asn Arg Glu
    290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
            340                 345                 350

Ala Thr Glu Thr Cys Tyr Thr Tyr Asp Arg Asn Lys Cys Tyr Thr Ala
        355                 360                 365

Val Val Pro Leu Val Tyr Gly Gly Glu Thr Lys Met Val Glu Thr Ala
    370                 375                 380

Leu Thr Pro Asp Ala Cys Tyr Pro Asp
385                 390

<210> SEQ ID NO 108
<211> LENGTH: 412
<212> TYPE: PRT
<213> ORGANISM: Artificial Sequence
<220> FEATURE:
<223> OTHER INFORMATION: Y15J AA

<400> SEQUENCE: 108

```
Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Ser Tyr Thr Met His Trp Val Arg Gln Ala Pro Gly Gln Gly Leu
    50                  55                  60

Glu Trp Met Gly Tyr Ile Asn Pro Arg Ser Gly Tyr Thr His Tyr Asn
65                  70                  75                  80

Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Leu Glu Ile Lys Gly Gly Gly Gly Ser Gly Gly Gly Gly Ser Gly Gly
            260                 265                 270

Gly Gly Ser Gln Glu Asp Glu Arg Ile Val Leu Val Asp Asn Lys Cys
        275                 280                 285

Lys Cys Ala Arg Ile Thr Ser Arg Ile Ile Arg Ser Ser Glu Asp Pro
    290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
            340                 345                 350

Glu Leu Asp Asn Gln Ile Val Thr Ala Thr Gln Ser Asn Ile Cys Asp
        355                 360                 365
```

Glu Asp Ser Ala Thr Glu Thr Cys Tyr Thr Tyr Asp Arg Asn Lys Cys
    370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp
                405                 410

<210> SEQ ID NO 109
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 109

Met Asp Met Arg Val Pro Ala Gln Leu Leu Gly Leu Leu Leu Leu Trp
1               5                   10                  15

Leu Arg Gly Ala Arg Cys Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 110
<211> LENGTH: 2378
<212> TYPE: DNA
<213> ORGANISM: Homo sapiens

<400> SEQUENCE: 110
cccagcagcc cagcagcctt ggacaaagac ctgaggcctc accacgcccc gccacccctg    60
atagccatga cagtctgggc tttggaggcc tgcaggtggg ctcggccttg gtggggcagc   120
cacagcggga cgcaagtagt gagggcactc agaacgccac tcagcccga caggcagggc   180

| | |
|---|---|
| acgaggaggc agctcctcac cctcccttc tcttttgtct gcgggtcctc agggagtgca | 240 |
| tccgccccaa cccttttccc cctcgtctcc tgtgagaatt ccccgtcgga tacgagcagc | 300 |
| gtggccgttg gctgcctcgc acaggacttc cttcccgact ccatcacttt gtcctggaaa | 360 |
| tacaagaaca actctgacat cagcagtacc cggggcttcc catcagtcct gagagggggc | 420 |
| aagtacgcag ccacctcaca ggtgctgctg ccttccaagg acgtcatgca gggcacagac | 480 |
| gaacacgtgg tgtgcaaagt ccagcacccc aacggcaaca agaaaagaa cgtgcctctt | 540 |
| ccaggtgagg gccgggcagc caccgggaca gagagggagc cgaaggggcg ggagtggcgg | 600 |
| gcaccgggct gacacgtgtc ctcactgcag tgattgccga gctgcctccc aaagtgagcg | 660 |
| tcttcgtccc accccgcgac ggcttcttcg gcaaccccg caagtccaag ctcatctgcc | 720 |
| aggccacggg tttcagtccc cggcagattc aggtgtcctg gctgcgcgag gggaagcagg | 780 |
| tggggtctgg cgtcaccacg gaccaggtgc aggctgaggc caaagagtct gggcccacga | 840 |
| cctacaaggt gaccagcaca ctgaccatca agagagcga ctggctcggc cagagcatgt | 900 |
| tcacctgccg cgtggatcac aggggcctga ccttccagca gaatgcgtcc tccatgtgtg | 960 |
| tccccggtga gtgacctgtc cctcaggggc agcacccacc gacacacagg gtccactcg | 1020 |
| ggtctcgatt cgccaccccg gatgcagcca tctactccct gagccttggc ttcccagagc | 1080 |
| ggccaagggc aggggctcgg gcggcaggac ccctgggctc ggcagaggca gttgctactc | 1140 |
| tttgggtggg aaccatgcct ccgcccacat ccacacctgc cccacctctg actcccttct | 1200 |
| cttgactcca gatcaagaca cagccatccg ggtcttcgcc atcccccat cctttgccag | 1260 |
| catcttcctc accaagtcca ccaagttgac ctgcctggtc acagacctga ccacctatga | 1320 |
| cagcgtgacc atctcctgga cccgccagaa tggcgaagct gtgaaaaccc acaccaacat | 1380 |
| ctccgagagc caccccaatg ccactttcag cgccgtgggt gaggccagca tctgcgagga | 1440 |
| tgactggaat tccggggaga ggttcacgtg caccgtgacc cacacagacc tgccctcgcc | 1500 |
| actgaagcag accatctccc ggcccaaggg taggccccac tcttgcccct cttcctgcac | 1560 |
| tccctgggac ctcccttggc ctctggggca tggtggaaag cacccctcac tccccgttg | 1620 |
| tctgggcaac tggggaaaag gggactcaac cccagcccac aggctgtccc cccactgccc | 1680 |
| cgccctcacc accatctctg ttcacagggg tggccctgca caggcccgat gtctacttgc | 1740 |
| tgccaccagc ccggggagcag ctgaacctgc gggagtcggc caccatcacg tgcctggtga | 1800 |
| cgggcttctc tcccgcggac gtcttcgtgc agtggatgca gaggggggcag cccttgtccc | 1860 |
| cggagaagta tgtgaccagc gccccaatgc ctgagcccca ggcccaggc cggtacttcg | 1920 |
| cccacagcat cctgaccgtg tccgaagagg aatggaacac gggggagacc tacacctgcg | 1980 |
| tggcccatga ggcctgccc aacagggtca ccgagaggac cgtggacaag tccaccggta | 2040 |
| aacccaccct gtacaacgtg tccctggtca tgtccgacac agctggcacc tgctactgac | 2100 |
| cctgctggcc tgcccacagg ctcggggcgg ctggccgctc tgtgtgtgca tgcaaactaa | 2160 |
| cccgtgtcaa cggggtgaga tgttgcatct tataaaatta gaaataaaaa gatccattca | 2220 |
| aaagatactg gtcctgagtg cacgatgctc tggcctactg gggcggcggc tgtgctgcac | 2280 |
| ccaccctgcg cctcccctgc agaacaccctt cctccacagc ccccaccct gcctcaccca | 2340 |
| cctgcgtgcc tcagtggctt ctagaaaccc ctgaattc | 2378 |

<210> SEQ ID NO 111
<211> LENGTH: 453
<212> TYPE: PRT
<213> ORGANISM: Homo sapiens

<400> SEQUENCE: 111

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Ile Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
```

-continued

```
                  405                 410                 415
His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
            435                 440                 445

Ala Gly Thr Cys Tyr
        450

<210> SEQ ID NO 112
<211> LENGTH: 453
<212> TYPE: PRT
<213> ORGANISM: Homo sapiens

<400> SEQUENCE: 112

Gly Ser Leu Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

His Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Thr Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Gly Pro Asp Gln Asp Thr Ala Ile Arg Val
    210                 215                 220

Phe Ser Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320
```

```
Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
        340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 113
<211> LENGTH: 604
<212> TYPE: PRT
<213> ORGANISM: Homo sapiens

<400> SEQUENCE: 113

Val Leu Leu Val Gly Ile Leu Lys Gly Val Gln Cys Glu Val Asn Leu
1               5                   10                  15

Val Glu Ser Gly Gly Asp Leu Val Gln Pro Gly Gly Ser Leu Arg Leu
                20                  25                  30

Ser Cys Glu Ala Ser Gly Phe Thr Ile Thr Ser Tyr Gly Met His Trp
        35                  40                  45

Val Arg Gln Ala Pro Gly Lys Gly Leu Val Trp Val Ser Glu Ile Asp
    50                  55                  60

Asn Asp Gly Arg Asp Ala Thr Tyr Ala Asp Ser Val Lys Gly Arg Phe
65              70                  75                  80

Thr Ser Leu Pro Asp Arg Ala Asn Asn Thr Leu Tyr Leu Gln Met Asn
                85                  90                  95

Ser Leu Arg Val Asp Asp Thr Ala Val Tyr Tyr Cys Val Arg Gly Asn
                100                 105                 110

Gly Gln Lys Cys Phe Asp Tyr Trp Gly Gln Gly Thr Leu Val Thr Val
            115                 120                 125

Ser Ser Gly Ser Ala Ser Ala Pro Thr Leu Phe Pro Leu Val Ser Cys
130             135                 140

Glu Asn Ser Pro Ser Asp Thr Ser Ser Val Ala Val Gly Cys Leu Ala
145                 150                 155                 160

Gln Asp Phe Leu Pro Asp Ser Ile Thr Phe Ser Trp Lys Tyr Lys Asn
                165                 170                 175

Asn Ser Asp Ile Ser Ser Thr Arg Gly Phe Pro Ser Val Leu Arg Gly
            180                 185                 190

Gly Lys Tyr Ala Ala Thr Ser Gln Val Leu Leu Pro Ser Lys Asp Val
        195                 200                 205

Met Gln Gly Thr Asp Glu His Val Val Cys Lys Val Gln His Pro Asn
    210                 215                 220

Gly Asn Lys Glu Lys Asn Val Pro Leu Pro Val Ile Ala Glu Leu Pro
225                 230                 235                 240
```

```
Pro Lys Val Ser Val Phe Val Pro Pro Arg Asp Gly Phe Phe Gly Asn
                245                 250                 255

Pro Arg Lys Ser Lys Leu Ile Cys Gln Ala Thr Gly Phe Ser Pro Arg
            260                 265                 270

Gln Ile Gln Val Ser Trp Leu Arg Glu Gly Lys Gln Val Gly Ser Gly
        275                 280                 285

Val Thr Thr Asp Gln Val Gln Ala Glu Ala Lys Glu Ser Gly Pro Thr
    290                 295                 300

Thr Tyr Lys Val Thr Ser Thr Leu Thr Ile Lys Glu Ser Asp Trp Leu
305                 310                 315                 320

Gly Gln Ser Met Phe Thr Cys Arg Val Asp His Arg Gly Leu Thr Phe
                325                 330                 335

Gln Gln Asn Ala Ser Ser Met Cys Gly Pro Asp Gln Asp Thr Ala Ile
            340                 345                 350

Arg Val Phe Ala Ile Pro Pro Ser Phe Ala Ser Ile Phe Leu Thr Lys
        355                 360                 365

Ser Thr Lys Leu Thr Cys Leu Val Thr Asp Leu Thr Thr Tyr Asp Ser
    370                 375                 380

Val Thr Ile Ser Trp Thr Arg Gln Asn Gly Glu Ala Val Lys Thr His
385                 390                 395                 400

Thr Asn Ile Ser Glu Ser His Pro Asn Ala Thr Phe Ser Ala Val Gly
                405                 410                 415

Glu Ala Ser Ile Cys Glu Asp Asp Trp Asn Ser Gly Glu Arg Phe Thr
            420                 425                 430

Cys Thr Val Thr His Thr Asp Leu Pro Ser Pro Leu Lys Gln Thr Ile
        435                 440                 445

Ser Arg Pro Lys Gly Val Ala Leu His Arg Pro Asp Val Tyr Leu Leu
    450                 455                 460

Pro Pro Ala Arg Glu Gln Leu Asn Leu Arg Glu Ser Ala Thr Ile Thr
465                 470                 475                 480

Cys Leu Val Thr Gly Phe Ser Pro Ala Asp Val Phe Val Gln Trp Met
                485                 490                 495

Gln Arg Gly Gln Pro Leu Ser Pro Glu Lys Tyr Val Thr Ser Ala Pro
            500                 505                 510

Met Pro Glu Pro Gln Ala Pro Gly Arg Tyr Phe Ala His Ser Ile Leu
        515                 520                 525

Thr Val Ser Glu Glu Glu Trp Asn Thr Gly Glu Thr Tyr Thr Cys Val
    530                 535                 540

Val Ala His Glu Ala Leu Pro Asn Arg Val Thr Glu Arg Thr Val Asp
545                 550                 555                 560

Lys Ser Thr Glu Gly Glu Val Ser Ala Asp Glu Glu Gly Phe Glu Asn
                565                 570                 575

Leu Trp Ala Thr Ala Ser Thr Phe Ile Val Leu Phe Leu Leu Ser Leu
            580                 585                 590

Phe Tyr Ser Thr Thr Val Thr Leu Phe Lys Val Lys
        595                 600
```

<210> SEQ ID NO 114
<211> LENGTH: 19795
<212> TYPE: DNA
<213> ORGANISM: Homo sapiens

<400> SEQUENCE: 114
ctgcaggtgg gctcggcctt ggtggggcag ccacagcggg acgcaagtag tgagggcact    60

```
cagaacgcca ctcagccctg acaggcaggg cacgaggagg cagctcctca ccctcccttt     120
ctcttttgtc ctgcgggtcc tcagggagtg catccgcccc aaccctttt c ccctcgtct     180 cctgtgagaa ttccccgtcg gatacgagca gcgtggccgt tggctgcctc gcacaggact     240
tccttcccga ctccatcact ttctcctgga aatacaagaa caactctgac atcagcagca     300
cccgggcctt cccatcagtc ctgagagggg gcaagtacgc agccacctca caggtgctgc     360
tgccttccaa ggacgtcatg cagggcacag acgaacacgt ggtgtgcaaa gtccagcacc     420
ccaacggcaa caaagaaaag aacgtgcctc ttccaggtga gggccgggcc cagccaccgg     480
gacagagagg gagccgaagg gggcgggagt ggcgggcacc gggctgacac gtgtccctca     540
ctgcagtgat tgctgagctg cctcccaaag tgagcgtctt cgtcccaccc cgcgacggct     600
tcttcggcaa ccccccgcaag tccaagctca tctgccaggc cacgggtttc agtcccggc     660 agattcaggt gtcctggctg cgcgagggga agcaggtggg gtctggcgtc accacggacc     720
aggtgcaggc tgaggccaaa gagtctgggc ccacgaccta caaggtgacc agcacactga     780
ccatcaaaga gagcgactgg ctcagccaga gcatgttcac ctgccgcgtg gatcacaggg     840
gcctgacctt ccagcagaat gcgtcctcca tgtgtgtccc cggtgagtga cctgtcccca     900
ggggcagcac ccaccgacac acaggggtcc actcgggtct ggcattcgcc accccggatg     960
cagccatcta ctccctgagc cttggcttcc cagagcggcc aagggcaggg gctcgggcgg    1020
caggacccct gggctcggca gaggcagttg ctactctttg ggtgggaacc atgcctccgc    1080
ccacatccac acctgcccca cctctgactc ccttctcttg actccagatc aagacacagc    1140
catccgggtc ttcgccatcc ccccatcctt tgccagcatc ttcctcacca agtccaccaa    1200
gttgacctgc ctggtcacag acctgaccac ctatgacagc gtgaccatct cctggaccg    1260 ccagaatggc gaagctgtga aaacccacac caacatctcc gagagccacc ccaatgccac    1320
tttcagcgcc gtgggtgagg ccagcatctg cgaggatgac tggaattccg gggagaggtt    1380
cacgtgcacc gtgacccaca cagacctgcc ctcgccactg aagcagacca tctcccggcc    1440
caagggtagg ccccactctt gcccctcttc ctgcactccc tgggacctcc cttggcctct    1500
ggggcatggt ggaaagcacc cctcactccc ccgttgtctg ggcaactggg gaaaagggga    1560 ctcaaccca gccacaggc tggcccccca ctgccccgcc ctcaccacca tctctgttca    1620
caggggtggc cctgcacagg cccgatgtct acttgctgcc accagcccgg gagcagctga    1680
acctgcggga gtcggccacc atcacgtgcc tggtgacggg cttctctccc gcggacgtct    1740
tcgtgcagtg gatgcagagg gggcagccct tgtccccgga aagtatgtg accagcgccc    1800 caatgcctga gccccaggcc ccaggccggt acttcgccca cagcatcctg accgtgtccg    1860
aagaggaatg gaacacgggg gagacctaca ctgcgtggt ggcccatgag gccctgccca    1920
acagggtcac cgagaggacc gtggacaagt ccaccggtaa acccacctg tacaacgtgt    1980 ccctggtcat gtccgacaca gctggcacct gctactgacc ctgctggcct gcccacaggc    2040
tcggggcggc tggccgctct gtgtgtgcat gcaaactaac cgtgtcaacg gggtgagatg    2100
ttgcatctta taaaattaga aataaaaaga tccattcaaa agatactggt cctgagtgca    2160
cgatgctctg gcctactggg gcggcggctg tgctgcaccc accctgcgcc tcccctgcag    2220
aacaccttcc tccacagccc ccacccctgc ctcacccacc tgcgtgcctc agtggcttct    2280
agaaacccct gaattccctg cagctgctca cagcaggctg acctcagact tgccattcct    2340
cctactgctt ccagaaagaa agctgaaagc aagaccacac gtatacaggc agcacacagg    2400
```

```
catgtgtgga tacacatgga cagacacgga cacacacaaa cacatggaca cacagagacg    2460
tgctaaccca tgggcacaca catacacaga catggaccca cacacaaaca tatgtggaca    2520
cacatgtaca aacatgcaca ggcacacaaa gagaacactg actacaggca cacacacaca    2580
cgggcacaca catggatatg tgcacacatg gacacataca tgtgcaggac atgcacacac    2640
acagacacac tagcacagag gcatacacac acagacacac acattcacaa acacacatgt    2700
gcatgcaaac acacacacat gtacagacac aagtacatgg acacatgcac acccagagac    2760
acactgacac agacacacag gagcatgtga tacactaaca cgtggacaca cacgtctacc    2820
cacaggcaca aacagatgg acacgcgtac acagacatgc acacacccac aggcacaaca    2880
cgtgcgcatg ccggccggcc cccgcccaca ttctcccagg gccctgccgg atactctgtc    2940
cctgcagcag tttgctccct gcgctgtgct ggccccgggg ctttgggccc aggctctgct    3000
tgtccttctg tctctgcttg gaggtgctgc catggcaccc agcttgggct ctgcctgggg    3060
agcggaggcc ccaggatag catgtgaccc ctgctgaggc caggctcctg atgaaggcag    3120
cagatagccc ccacacccac cggtgagcag aaccagagcc tgtgccatgt gctgagagca    3180
ggcagtgact aagcatatgg cccagagggc agagtggctg ccctgggcag ctgctcctct    3240
tagcaggagg cctcaggaga tgagctagag caagtctgcc cctgcaaata ccacctgctc    3300
cccaacccac agcagggagc aggcgaggtc agacagcagc agcccgggaa ggaccgagcc    3360
ccagcaggga aggcagggcc cgagtgaggt ctccacaccc aacgcacagt gctgtctcta    3420
actggggcca cctccgagtc cccgccacac tcttggccct ttggagtcct gggctccagg    3480
tgtctcccaa gggcccatct gtgcagggga tgcaaccccc cgaatgtcct catcccactg    3540
tggagctcag gtctctgtct gctccctggg tcctggcagg gtaggacaag tccgccagga    3600
tgtccccatg cagactctgc tccaagaggg agctggagag tcagggcctt ggtgagggag    3660
tcaggatcgg gttcccccca gctcagtcct cccacctgcc agcccccaca gcacagggca    3720
gggccacacc ccctgcttcc ccctccagga gagtcaggac atgctggccg ctgctccgct    3780 ggggcccgc cctccagccc ccaccttggt ctgtgtgctg catcccccac gctctctctg    3840
ccaccccagg actctgagga aaagacctca gagtcccagc cctgcccagc ctcggcctgt    3900 gccccgctg catcaggctt tcaggggccc agcccatgcc ctgggcagtg cccgagcccc    3960
cctgcacttg ctctccccac ccctgggtgc agcacagcct aggggccaag ggtgggccta    4020
gaggatgggc ccgggggggg cttgctggg tgccacccca gcctgaccct attccccgt    4080 gctgtgtctc ctgcagaggg ggaggtgagc gccgacgagg agggctttga gaacctgtgg    4140
gccaccgcct ccaccttcat cgtcctcttc ctcctgagcc tcttctacag taccaccgtc    4200
accttgttca aggtagcacg gctgtggcac agggaggagg gtgcagggcg agtgtggggc    4260
ccagggagca gcctgggctg gacgtctagc ccggaggccc ccacaccacc ccactgggtc    4320
atctctgccc cggctccctt cccgaccacg gggaaagcat ttcacactgt ctctgttgcc    4380
tgtaggtgaa atgatcccaa cagaagaaca tcggagacca gagagaggaa ctcaaagggg    4440
cgctgcctcc gggtctgggg tcctggcctg cgtgcctgtt ggcacgtgtt tctcttcccc    4500
gcccggcctc cagttgtgtg ctctcacaca ggcttccttc tcgaccggca ggggctggct    4560
ggcttgcagg ccacgaggtg ggctctaccc cacactgctt tgctgtgtat acgcttgttg    4620
ccctgaaata aatatgcaca ttttatccat gaaactgctt tctggtgagg gttttgttt    4680 ctttttcaaa actttcctgc tacatgggca tctcaagggg gaccccagtt ccaaaggag    4740 ctgtggaaaa ggcgctgggt cagccagcgc aaggggtttc gaggaaagcc acgtgcccag    4800
```

```
gaaaggggcc gcagaagcag gtgggccaga ctcagactcg gggcatgccc cagcctgatg   4860
gaaggaaggg gactgagcag gagagggttc caggcctggt cctccaagca cagcctgaat   4920
tgggagactg gggctcaggc ctcggggggcc tctgtgtgtg ctccacatgc ctacaactgc   4980
ccgggtcacc ttgccaccct tcccagcaag cccagacagt tcttggcctt gccccaaacc   5040
ttcatgatgt gtggtgcacg ccaccgggat ccaggaggtg caggctgagc cctcgagagc   5100
atgtgggcct caccgggatc caggaggtgc aggctgagcc ctcgagagca tgtgggcctg   5160
tctgcacagt gtgggggcct tgcactccac aggagcacag gggtggggta gcagtcgcgc   5220
ccgtggcagg ggagtggaag ttggagcaaa agtttcaggt gaacgagtgt cttagtctaa   5280
ttgggcagct atcacaaaac actatcggct gcaaagcttg agcaacagac atttgcctcc   5340
cacagcgctg gaggctgaaa gtctaagatc aaggcgccgg caacttcaac gtctggcgag   5400
ggccaattcc cagctcagag acgcgcctcc tcactgcatc ctcgcgcagc cgaagatggt   5460
gaaggagctc tcaggggtctc tgtcatacag gcactaagcc cgtcacgagg gtctctctca   5520
tacaggcact aagcccgtca cgagggtctc tctcatacag gcactaagcc cgtcacgagg   5580
gtctctctca tacaggcact aagcccgtca cgagggtctc tctcatacag gcactaagcc   5640
cgtcacgagg gtctctctca tacaggcact aagcccgtca cgagggtctc tctcatacag   5700
gcactaagcc cgtcacgagg gtctctctca tacaggcact aagcccgtca cgagggtctc   5760
tctcatacag gcactaagcc cgtcacgagg gtctctctca tacaggcact aagcccgtca   5820
cgagggtctc tctcatacag gcactaagcc cgtcacgagg gtctctctca tacaggcact   5880
aagcccatca cgaggtcctc atcattgccc agatgctagg gctcccagtg ccatcccctt   5940
gtggatgagg atgggggggcg tgaccatgtc gtccttagaa gccgttaggg aatgcatagt   6000
ggggaggaca agtctctgcc atcaccctga agatgggcag gtggtggcca ggcttgggggc   6060 agtgccgaaa aatgactccc caggtaggtg ggagcaggat caaagagcag gggattttttt   6120 cagagatggc agccaagcca aagttggggg ctcatgccag gaggctcact tggccatggt   6180
gcagtcaccc aggggtgacc cacagtccat ggcaaagtca aggacagcag tggctgtgag   6240
accagggtgg aggcaggtgg ctgggggggag aggaccaggc tggaaggact gggcagaccc   6300
caaggccata gaagtgtcct agaggaagca tccaggatgg cgtcttggga gggctcataa   6360
gctgggggcc cagaaggagg acatttcagg ttctgaggag cagcctggca cttgctctga   6420
gccagctgtc atgggtatct gggggctgct gggtacaagt tgtgtccctc ccactaaatg   6480
tgctctccac atggacccgg cccgcccttc tgtccctgct ggatccctga gctggcacca   6540
gccctgccct cagagacaat gtccaggaga caggtggagg tgcacgtgtg ggtccctggg   6600
gaaatccatc ctccaaccgt gggctccgag tcgcctccca gcctctcgct ccagcttcac   6660
cccatgtagc tcatcacagg ctcaacctcc cagcctgggg gaggatggag tgaggagccc   6720
cacactgccc agggcacacc caggggggctg gggagtctgc actgggctgg ggcagggagg   6780
cctcgtgcag cctgtggggc tggcagctca ggacaacact cgtatccggt taactgtggc   6840
cctggcaaca ctgcacccca gactgcgtgg cttaaacaac agacgtttat tccgtcctgg   6900
ttctggaggc cgggcatctg ggatggaggc cttgcgggg ctggctcctc tgtgtcacgg   6960
gagactctgt tccaggctct ctccctgctg ctgggctttg ccggccgtct ctggtgctct   7020
tggcttatgg aagcagcacc atcttccacag ggcgttctcc ccacgtgctg tctgtgccca   7080
gattccccct tttcatgagg acagcagtca tattggatca gaggcttgcc ctactccagg   7140
```

```
gtgacctcat ctgaacttga ttgcagctgc aaagactgtt tccagacaag gtcacattct   7200
gtggtcctgg gggttaggac ttcgacacat taatttacag gggacacatt ttaacccatg   7260
acagtttgcc ctccgttccc cccataatca tgtccttctc acatgcaaaa tccctgcatc   7320
ccatagcaac atctccagaa cggctgaccc cttccagcac caactcttag tccacaatct   7380
cagcgaaata tcacctgcat caagtgtggg agaaacccag ggtgagattc attctgggtg   7440
aaattcctct ccatctgtgg acctttgtaa cttgacaaga agttatctgc ttccaaagta   7500
caatgatggg gcaggcatag gatggacatt cctattctaa aagggataca tagaaaggga   7560
gagaggagcc atgggtccca agcaagccca aacccagcag ggaaagctgc attagattta   7620
aggctcaagg ctcatcctcc tgggtccgtg ctccatcttc caggcccact ggggtgaccc   7680
catgctcttc gcccatggtg gccagagccc ccacagcctc ctcatctttg gctctgatct   7740
caaagtcacc cttccttcat ttttttctggt cttctttccc ttccatccaa ttggcattgt   7800
ttcttctgtt ttacaattca caaaatcctt gtcagcttcc catgaaattc ctgggggttt   7860
gagtcatcag acaagagagc cctgcacagt tatatcctca ataaccttat ctctactcct   7920
ggtttctgct gagatggttg attggatccc cataagtcat gattccaatc tctttaacaa   7980
atggttgccc agacacatcc ttggccttgt ttccagagca tgctattgga caggctgaga   8040
attttccagc tgttcaagtt gtgggtcctg tttactgaac actttctctc acttttttact  8100 ataagcagtc aggagaaatc aggttgtgcc ttcaacactt tccttagaaa tatcctcagc   8160
taaaatccag gttcatcact tgtaagtcct acttaccata aatagaatgc aattcagcca   8220
agtgctttgc cactttctaa caaaggtcac ctttcctcca attttcaata acatcttcct   8280
catttctgtc tggggcctca ccagaggcat ctttaacatt cacatttcta gcaacattct   8340
gtttgtgaca atttatgtat tctctaagat gacaggagtt ttctctatag ctctcctctt   8400
tctttctgag cccccaccag gatcaccttc aatgtccaaa tttctaccat agtcttcaag   8460
gaaatctagg ctttttctaa catgcacctg aaaatctctt ctctacctca cacattaccc   8520
tatccgaaat tcatttccac agtttaggta tcaattaaat cagataaata aatcattacc   8580
ctgaattatt tcagttaagc atgttagttg gtggcataag agaaaactca gtcagatagt   8640
gctgaagaca ggactgtgga gacaccttag aaggacagat tctgttcaga atcactgatg   8700
cggcgtcagc aggactggcc tagtggaggc tctgggaggg tggccagccc ggcctgggct   8760
ttgggtctcc ccggactacc cggagctggg atgcgtggct tctgccgccg ggccgactgg   8820
ctgctcaggc cccagccctt gttaatggac ttggaggaat gattccatgc caaagctttt   8880
gcaaggttcg cagtgaccag gcacccgaca tggtaagaga caggcagccg ccgctgctgc   8940
attcacttct cttaaaactt tgtatttgat gtcttatttc cactagaagg cgaattggtc   9000
ttaattgctt ctcttaagcc accacttcta aagccaaaat ctgttttagt ttcttatgag   9060
ctattgtaac aaagtaccac aactgcatgg ctgaaacaac agaagtgtat tctgtctcat   9120
ttctggaggc caggtgtctg agatcaagct gtgggcaggg ttggctcccc tgggttggca   9180
gggagaatct gttccaggtg tctgtcctgg cttttgttgg tttgctggaa agctttggtg   9240
ttccttggct tttggaaaca gctcctccgc ctccatcttt accttacat ggcattctgc    9300 ctgcgtgcat gtctgtgtct aaatttccac tttgcataag gacaccagcc atattgggtc   9360
agaggctcac ctgcctccag cgtgacctca tcttaacttg attgcatctg caaaactctg   9420
cttccaaaga agggcacatt ctgaggccct acgggtcaga gcttcaacac gtccatttat   9480
ttggagacac aactcaaccc ataacaagac ccatccctag tgtctcacca gtggtgctgt   9540
```

```
agagggaggc ctggcagggc tgacatccca gaacctcagg gaaaaatgaa aacagcccag   9600
aggggtccaa gaggtggctc gaggaaggga attaggaaca cactgttcag gtggaagatt   9660
ctgagatggg ccgtgaatac tgcctaggat gtggagggtt gacaatgggt tgacaatcct   9720
gctcagaaaa tcccaggata aaggatgtaa atggggagaa gaggagggtc atccagaatt   9780
tgggaaagca gggcgacagt ttctgcccca agggagaagg gaaggaggat ggggccaccg   9840
ccacaccaga tgaccttgcg taccaggcca agaacggga acacctggcc ccacctgagc   9900
agcaatagtc agtgtggtgg tgggcagaca tgggtggagg cagggggtga gtagaaggtt   9960
agactaaaag acggagcacc tggggcctcc agggacccag gcaagaaccc tgcacttgct  10020
cagctgccct gggtacccag gtctccagga aagtgaggct gagagccaag cccagcaggc  10080
agccacacat tctgggacct gccaccctac agcctgctgt ccatgagtaa cacccccttac  10140 aaggggccag gtcagctcat gggtttatcc caggcagcag agccctggg gccaggaatc  10200 agggagagga gcatccaatc ccaccagctc ctccggagcc actcagaggg ccagacgcat  10260
ggccctccac agggacccca tggcccctgc agggcagctg aggacccgtg gctgggagcc  10320
tgggcaggag ggtcatacag ccctaggccc gttgctccca ggcttgagtg cccctcctcc  10380
cctcaggggc ccaagggaag tgggttccag agaggttggg ggcagcaggg aaggtggagg  10440
tcccaggaat gcccagaggg gcaccgaaac ctctggaggg aagaccccct cttcaggagc  10500
tctcggcaac aagagcccag ggtccacaaa gccacaggtc ccactcggtt attctgactc  10560
acaacacagg agcggcagag gggcattcgt gttcacgggc cacttggtca gccccgctca  10620
ccctgggcac tcctcctggg ccccttttcc ctgcctcccg tcaccctgcc gccagggcct  10680 ctgcccctgcc ctgccccttg tcctcagagt ttccagcctc agactcccac tgtgtctgtc  10740
ttccagcacc caccaaggct ccggatgtgt tccccatcat atcagggtgc agacacccaa  10800
aggataacag ccctgtggtc ctggcatgct tgataactgg gtaccaccca acgtccgtga  10860
ctgtcacctg gtacatgggg acacagagcc agccccagag aaccttccct gagatacaaa  10920
gacgggacag ctactacatg acaagcagcc agctctccac ccccctccag cagtggcgcc  10980
aaggcgagta caaatgcgtg gtccagcaca ccgccagcaa gagtaagaag gagatcttcc  11040
gctggccagg taggtcgcac cggagatcac ccagaagggc cccccaggac ccccagcacc  11100
ttccactcag ggcctgacca caaagacaga agcaagggct gggctgtgag gcaacccca  11160 cctcccccctc agagcacgtt cctcccccttt caccctgtat ccaccctcc ggaccctccc  11220 catctcagtc cctccgctcc ctctctctga ggcccatctc ccaataccca gatcactttc  11280
cttccagacc cttccctcag tgtgcacgga ggcagcttgc ccagcaaagg tgactgtcta  11340
gtgggcttcc cacagccaag ctcccacccc acgctgcggc cctcccttc ctcctgcttg  11400 gctgcctgtg ccccccacct gcctgtccac aacccagcct ctggtacatc catgccctct  11460
gccctcagcc tcacctgcac ttttccttgg atttcagagt ctccaaaggc acaggcctcc  11520
tcagtgccca ctgcacaacc ccaagcagag ggcagcctcg ccaaggcaac cacagcccca  11580
gccaccaccc gtaacacagg tgagaagccc cttccctgca cactccaccc ccacccacct  11640
gctcattcct cagccgcctc ctccaggcag cccttcataa ctccttgtct gagtctccaa  11700
gtcacacttt ggtaaggaga gggacactga acggacctct aacaaacacc tactgccagc  11760
cagccccagt ctgggggcca gcagatgcca aacagccagc agactcccag agcagacctg  11820
ggccggctcc ctggcccatg gacccagctc tgcctcgctg agctgaggca tgggctctca  11880
```

```
gcgcagcccc acatagagcc accctgccga ggcagtccgg cttgcagact cacaggtcac   11940
ttgggccgca gcagcccctc cccgtgaccc tcgcctcccg cccgcccag cctggctctc   12000 tccaagtgtt ggatcttggt ggccagcctg cttctcaccc tcaccctgcc tgccacctca   12060
gaatggcagg ggaaagaggg ccctcaccaa gaactttatc tgagaagtct gaggcttgtg   12120
actctgacct gcctgagatg tccatgtggc cggggggacg ggttcagtgt tcgggagaac   12180
tcgggtacgt gcctgacttt ctctgagtag ggcaggaagc tgtcaggaga agcagcagtg   12240
aggcgggctg gaccaacagg cagaatgact gtccctcagc caccctctgg gatgtgggtc   12300
aagctctgac aaaggcacgg cacagccatg gtggcccctg cttggatgag tggccacggt   12360
gccctcaccc tgggccagaa tctgcctcca ctctgcaggt gcagaaacac gacattcccg   12420
tctctaaaca cacctagctc ctaggcttgg ggtgggccta tcaaatgcag ggagatggac   12480
acagcacaag ggccagagct tcccatgaga aaggtgaggg cagctgctcc ctgacccggg   12540
catctgcact tgtccctctc caccctcctc atgggcagtg gagactcagc aacaaaacaa   12600
gttgagtgca ttagcagcca gctctggagc caagtcactc accccacggc cttggcgctg   12660
gtggaggggc cttcccctgg gcagcctcca agaagacagc caagtgctct tactcagacc   12720
acggcgctgc ttcctggcac ctcgatttcc cacaacaaca tggggtgcag acaggctagg   12780
gtcccctgcc ctagggccta gacggcatcc agttaaagat gacccttcac gggcggtgcc   12840
tgaggtgtgc tgacctcagc agctaagccc tcaggtctgg tctgcactgc cccacctgga   12900
ggacccaact gacccagaca cagccagggt tatggcatga ccccatggac ggtgacccac   12960
aggccagatg cagccagggg ctgttttgtg tggcctagaa atgtctttac agttgtagtg   13020
ggatggagga ggaagaggaa gagaggaggg gagagaaaag cagggaaggg gaaaaagagg   13080
agttcaatgc aaccccaaaa gccagaacag ttttgagctg aaagacaagg caggaaacat   13140
cccagtacct gacttcaaaa catactataa agcagttgta atcaaaacgg gatcataaaa   13200
acagcacaca aacccatgga acagaaaagc gagcccagaa ataaatctac atgcttgcag   13260
tccattgatt ttcaacaaag gcaccaggaa aacacaatgg ggagaggaca gtttcctcaa   13320
taaatagtgc tggggaaact ggatatccat gtgcagacta atgaaactac acaaaaatca   13380
attgaaaaca gtctaggcca ggcgcggtgg ctcatgccgg taatcccagc actttgggag   13440
gccgagacag gcggatcacc tgaggtcagg agttcgagac cagcttggcc aacatggcga   13500
aacccggtct ccactaaaaa tacaaaaatt agcacatggt ggcctacgtc tgttatccca   13560
gcttttcagg aggctgaggc aggagaatcg cttgaatccg ggaggtgaag gttgcaggga   13620
gccaagattg cgccactgca ttccagcctg ggcaatggag cgagactgtc tcaaaaaaaa   13680
aaaaaaaaag aaaagaaaac agtctaaagg tttaactgaa cagataaagc tactagaaga   13740
aaacataggg ggaaaactcc atgacattag tctgagcaac gattttttgga tatgatccca   13800 aaagctcagg cagcactagt ctacaaaagc caagatacag aaccaaccta agcacccctc   13860
agcagatgca caggtaaaga aaatgtggta cgtatggggc acaatggaat acgattcagc   13920
ctttaaaaac agtgaaattc tgtcattggc aacaatgtag atgaacctga aggacactta   13980
tgctaagtga aataagccag gcacagaagg agcaatactg catgattgca cttacatctg   14040
gcaggttaaa aaggcaaact cttagaggca gacagtagag aggtggtgcc agggagcggg   14100
cactggtggc tggggagatg ttggtcaaag ggcacaaaac tgcagttggg aggaattagt   14160
tcaggacatc ccttgtacat ggggacagtg gttagtaaca acggattgta tccttgaaaa   14220
ccgctaagaa aatagttttt aagtgttctt gacacaaaaa gtgacacgta tgtgagatac   14280
```

```
tgcatggtca ttagctggat ttagccattc cacaatgtac acatatttca aacattgtgt  14340
tgtatatgat aaacatgtat aattttttgtc aattaaaaat ttttaggaag aggaggagaa  14400
gagaagaaga aggagaagga gaaagaggaa caagaagaga gagagacaaa gacaccaggt  14460
tttttctgac ccctgggcta tcaaaacacc tattgcccaa taactagttg gccgttggtg  14520
ccctaaacta ttgaagcgat tgctgttatg tggatgggcc ccggacactt agaaactcgt  14580
gaccoctgag gaccoccacg aggacagtcg ggtcccoccg aactcaggga gcactgagga  14640
aggagctctt agaggcgtgg ggcccctcag gcccctcaga gggctctgcc acatgggtca  14700
ggggcaggct gaggggagt cccaggctcc atgcccagcc tctgtgcctc tgaccagggt  14760
gtcccccaca ccgcctcctc cccagtgccc tccactggcc acacctggcc agaagctggg  14820
gagaggagag cacagtggtt aagtcagtcc ctgcagggag acggaccag aaaaacctgg  14880
cctgtggatg agtcccggcc tggcagccac agagcagaga gctctggaag caacgaaggc  14940
ccgagtctgc tcagggaaga gcgggcagca gccccagggc cggacagtga ccaagagtgg  15000
caccgcccat ggctcaacgg gtcttttgccc acagatcccc cagcccctgg agacagggtc  15060
tgtgtgcctg gccgtgcagg caggcaccac actcagggg aggccactgt ggagctctgt  15120
gcagagcccc gggcgggagc ctactgctcc cgaaggtccg gccacagctg ctctcgtttg  15180
ctctcccctg cagagtgtcc gagccacacc cagcctcttg gcgtctacct gctaacccct  15240
gcagtgcagg acctgtggct ccgggacaaa gccaccttca cctgcttcgt ggtgggcagt  15300
gacctgaagg atgctcacct gacctgggag gtggctggga aggtccccac aggggcgtg  15360
gaggaagggc tgctggagcg gcacagcaac ggctcccaga gccagcacag ccgtctgacc  15420
ctgcccaggt ccttgtggaa cgcggggacc tccgtcacct gcacactgaa ccatcccagc  15480
ctcccacccc agaggttgat ggcgctgaga gaacccggtg agcctggctc ccaggtgggg  15540
agacgagggt gcccacagcc tgctgacccc tacgcccgcc caggccat gaccccgctg  15600
ggccccagca gcaccggtca tcctccacag gaaaggagaa gggaggcacc agcgccctgg  15660
ccggccccac ttctctccca gtgccccgt ggcagagcc tgacagcctc ccccacctcc  15720
ccgcagctgc gcaggcaccc gtcaagcttt ccctgaacct gctggcctcg tctgaccctc  15780
ccgaggcggc ctcgtggctc ctgtgtgagg tgtctggctt ctcgccccc aacatcctcc  15840
tgatgtggct ggaggaccag cgtgaggtga acacttctgg gtttgccccc gcacgccccc  15900
ctccacagcc caggagcacc acgttctggg cctggagtgt gctgcgtgtc ccagcccgc  15960
ccagcctca gccagccacc tacacgtgtg tggtcagcca cgaggactcc cggactctgc  16020
tcaacgccag ccggagccta gaagtcagct gtgagtcacc cccaggccca gggttgggac  16080
ggggactctg aggggggcca taaggagctg gaatccatac taggcagggg tgggcactgg  16140
gcagggcgg ggctaggctg tcctgggcac acaggcccct tctcggtgtc cggcaggagc  16200
acagacttcc cagtactcct gggccatgga tgtcccagcg tccatccttg ctgtccacac  16260
cacgtgctgg cccaggctgg ctggcacagt gtaagaggtg gatacaaccc ctcgccgtgc  16320
cctgaggagt ggcggtttcc tcccaagaca ttccccacag ctgggtgctg ggcacaggcc  16380
ttccctggtg tgaccgtgaa tgtggtcacc ctgaacagct gccctctctg gggacatctg  16440
actgtccaag accacagtca gcacctctgg gagccagagg ggtctccaga gaccccaga  16500
tgtcaggctt gggctcagtg cccagcgaaa ggtcagcccc acacatgccc ataatgggcg  16560
cccaccoaga gtgacagccc ccagcctcct gccaggccca cccttttccg cccccttgag  16620
```

```
gcatggcaca cagaccagtg cgcccactgc ccgagcatgg ccccagtggg atgtggtggc    16680
cacgaggggc tgtacacaca gcaggaggct gtccgccctg ctcagggcct gctgcctatg    16740
ccccagctgt ccagccaagg gaggcatgga agggcccctg gtgtaagctg gagccaggca    16800
cccaggcccc cggccaccct gcagagccaa ggaaaggaag cacccaagt caacaagggg     16860 cagggctgag ggctgtccca ggctcttttg gcccgagggg cgtcagcagc cctggacccg    16920
gcatgggcct tccccagaag cgaccctgtg aggtggcctc acagagaacc ccctctgagg    16980
acagtgtctg accctgcctg cctcacacag atgggcccca cagcagtggg caacctgggg    17040
ggcagcagcc caacctgacc ctgcaggac tgcccctgc agcagcagct gcttctcagt      17100
cccccaacct ccctgtcccc gccagagggt cttccccgaa gctgcagccc caacccatgg    17160
ctgcccacct ggaaccggga ctccctgtcc actgccccct cccctcgggg ccccatctg     17220 tgctggggcc taggttcggc ctacagattc ccatcattgc catggcctcc tgaccttgcc    17280
tatccacccc caaccaccgg ctccatgctg accctccccc aggctcccac gcccagctgg    17340
ccggccatcc ccaggcacag acagtctggg atctcacagg ttagcctgga ccatccacct    17400
ggccagacct gggagaggct ggaagctgcc ctgccaccat gctccagggc ccaggttgc     17460 agtactatgg ggtgagggtg tgtgtgcaca cccgtgtgta cctaggatat ccgagtgtac    17520
ccttgtgccc ccaagcacaa gtctccctcc caggcagtga ggcccagatg gtgcagtggt    17580
tagagctgag gcttatccca cagagaaccc tggcgccttg gtcaaggaag ccctatgcc    17640 tttcttgcct cgatttcccc tcttgtctgc tgagccagca ggggccacgt cctgggctgc    17700
tgtgaggagg aagcaagttg gtgctaggag gggctcctgt gtgtgcatgg gcgggagggg    17760
tgcaggtatc tgagcacccc ggtctccact tgagagagca gggcaggagc tccctgaccc    17820
acccagacta cacacgctgt gtccacgtgt ctcccattat ctgtggcaga ggatccggct    17880
tctttctcaa tttccagttc ttcacaaagc aatgcctttg taaaatgcaa taagaaatac    17940
tagaaaaatg atatgaacag aaagacacgc cgatttttg ttattagatg taacagacca     18000
tggccccatg aaatgatccc ggaccagatc cgtccacacc cgccactcag cagctctggc    18060
cgagctcaca gtacaaccac aataaactct tgttgaatga actctaggaa gtctgtgacg    18120
tggctggttc ttgtcaatgc ttcctgcctg cccacaggct cttcctcgtg gatggggctg    18180
tgcttgccac ggaagcgcgt ttttcccggc ctaggcttgc cttgggcccc actgccgtct    18240
ccagctggag atgaccttct atacacacat ttgctcatga cagacccttg cttagccccc    18300
ttccatggtc ctgctgctgg gataaaatca ccttgcctgg atatcccctc ctgggcccct    18360 ttccacccctc cttagtcagc accccagtt cagggcacct gctttcccg ctgcggagaa     18420 gccactctct ccttgctgcc cggctgtgtc ttgccttcca caccttgtca cagtggccac    18480
ttcctaagga aggcctccct gtgtgcaggt gtgcagaagt gccccagcct cccgtcacct    18540
ttgtcacggg agcccaatcc atgagagtct atggttctgt ctgtctgccc cactcagggc    18600
agcgacaagt ccaggcgggg aggacacagt aggcagagat ttgtcgaggg gacatatgag    18660
caagagggtg aggctgggag ctccctggag ataaccacgc ctcctgggaa gactcgccgt    18720
catttcagct ccacgctgtg cggggtggg tggagggta gcctggccct catgaccagg      18780
gagcttctca ctcagcccc gttcctcccc agacctggcc atgacccccc tgatccctca    18840
gagcaaggat gagaacagcg atgactacac gaccttttgat gatgtgggca gcctgtggac   18900 cacccctgtcc acgtttgtgg ccctcttcat cctcacccctc ctctacagcg gcattgtcac   18960
tttcatcaag gtcaggggag cggccaggct ctcagtgacc ctcggggtgg gtgtggggca    19020
```

```
aggtgccctt ccaggggaca tgccagagct ggtccaggga tcctggacag gcagaggcag    19080
ggctgaggga gcctggagga catgcaggcc ctctgtggcc tgtggacact gtcgaaggcc    19140
ctcttgaccc tgtggataaa ggacaacacc ccctcccctg ctcctctgtc tccctgccc    19200 ctccacccct caggcttcta gcccctgtc tgacccagg ggctgtcttt caggtgaagt    19260
agccccagaa gagcaggacg ccctgtacct gcagagaagg gaagcagcct ctgtacctca    19320
tctgtggcta ccagagagca gaaaggaccc accctggact cttctgtgtg caggaagatg    19380
cgccagcccc tgccccggc tccctctgt ccgccacaga atccagtctt ctagaccagg    19440
gggacgggcg acccatcact ccgcaggcga atcagagccc ccctgccccg gccctaaccc    19500
ctgtgcctcc ttcccgtgct tcccccagag ccagctacac ccctgccccg gccctaaccc    19560
ccatgcctcc ttcctgtgct tcccccagag ccagctagtc ccacctgcag cccgctggcc    19620
tccccataaa cacgctttgg ttcatttcac ctgcctcctg ttctttgtcc cagtggtctg    19680
gattcacctc aagttaaagg acacaggag ccaacggcaa cggggaggga gtttgggtg    19740 tcagcagcaa cagggaacgc aatagccaaa gctgtcacag caagaactga gcgga        19795

<210> SEQ ID NO 115
<211> LENGTH: 625
<212> TYPE: DNA
<213> ORGANISM: Homo sapiens

<400> SEQUENCE: 115
gagcagctga acctgcggga gtcggccacc atcacgtgcc tggtgacggg cttctctccc     60
gcggacgtct tcgtgcagtg gatgcagagg gggcagccct gtcccggga gaagtatgtg    120 accagcgccc caatgcctga gccccaggcc ccaggccggt acttcgccca gcatcctg    180 accgtgtccg aggaggaatg gaacacgggg gagacctaca cctgcgtggc ccatgacgcc    240
ctgcccaaca gggtcaccga gaggaccgtg gacaagtcca ccgtaaaacc caccctgtac    300
aacgtgtccc tggtcatgtc cgacacagct ggcacctgct actgaccctg ctggcctgcc    360
cacaggctcg gggcggctgg ccgctctgtg tgtgcatgca aactaaccgt gtcaacgggg    420
tcgagatgtt gcatcttata aaattagaaa taaaagatc cattcaaaag atactggtcc    480
tgagtgcacg atgctctggc ctactgggc ggcggctgtg ctgcacccac cctgcgcctc    540
ccctgcagaa caccttcctc cacagccccc acccctgcct cacccacctg cgtgcctcag    600
tggcttctag aaaccctga attcc                                           625

<210> SEQ ID NO 116
<211> LENGTH: 255
<212> TYPE: PRT
<213> ORGANISM: Homo sapiens

<400> SEQUENCE: 116

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80
```

```
Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 117
<211> LENGTH: 277
<212> TYPE: PRT
<213> ORGANISM: Homo sapiens

<400> SEQUENCE: 117

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
```

```
                195                 200                 205
Val Pro Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 118
<211> LENGTH: 277
<212> TYPE: PRT
<213> ORGANISM: Homo sapiens

<400> SEQUENCE: 118

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

<210> SEQ ID NO 119
<211> LENGTH: 241
<212> TYPE: PRT
<213> ORGANISM: Homo sapiens

<400> SEQUENCE: 119

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

<210> SEQ ID NO 120
<211> LENGTH: 260
<212> TYPE: PRT
<213> ORGANISM: Homo sapiens

<400> SEQUENCE: 120

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
```

```
                85                  90                  95
Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 121
<211> LENGTH: 283
<212> TYPE: PRT
<213> ORGANISM: Homo sapiens

<400> SEQUENCE: 121

Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
        130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190
```

```
Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
        210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Val Ala Val Glu Glu Thr
            260                 265                 270

Ile Pro Ser Phe Thr Gly Arg Ser Pro Asn His
        275                 280

<210> SEQ ID NO 122
<211> LENGTH: 455
<212> TYPE: PRT
<213> ORGANISM: Homo sapiens

<400> SEQUENCE: 122

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285
```

```
Pro Ser Ser Thr Phe Thr Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 123
<211> LENGTH: 461
<212> TYPE: PRT
<213> ORGANISM: Homo sapiens

<400> SEQUENCE: 123

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
```

```
            195                 200                 205
Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
450                 455                 460

<210> SEQ ID NO 124
<211> LENGTH: 335
<212> TYPE: PRT
<213> ORGANISM: Homo sapiens

<400> SEQUENCE: 124

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110
```

```
Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
            290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 125
<211> LENGTH: 595
<212> TYPE: PRT
<213> ORGANISM: Homo sapiens

<400> SEQUENCE: 125

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe His His Phe His
            115                 120                 125

Ser Val Cys Pro Ala Gly Met Ile Val Lys Phe Pro Gly Thr Ala Gln
        130                 135                 140

Lys Asn Thr Val Cys Glu Pro Ala Ser Pro Gly Val Ser Pro Ala Cys
145                 150                 155                 160
```

```
Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575
```

Leu Ser Val Glu Glu Gly Lys Glu Asp Pro Leu Pro Thr Ala Ala
            580                 585                 590

Ser Gly Lys
        595

<210> SEQ ID NO 126
<211> LENGTH: 468
<212> TYPE: PRT
<213> ORGANISM: Homo sapiens

<400> SEQUENCE: 126

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
            20                  25                  30

Thr Pro Ser Lys Val Trp Gly Ser Ala Gly Arg Ile Glu Pro Arg
        35                  40                  45

Gly Gly Gly Arg Gly Ala Leu Pro Thr Ser Met Gly Gln His Gly Pro
50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu His Pro Gly Ala
130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Arg Gly Cys Pro Arg Gly Met Val Lys Val Lys Asp Cys Thr Pro Trp
210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

-continued

```
Val Pro Ala Asn Gly Ala Asp Pro Thr Glu Thr Leu Met Leu Phe Phe
            355                 360                 365

Asp Lys Phe Ala Asn Ile Val Pro Phe Asp Ser Trp Asp Gln Leu Met
        370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Arg Glu Lys Ile Gln Asp Leu Leu
        435                 440                 445

Val Asp Ser Gly Lys Phe Ile Tyr Leu Glu Asp Gly Thr Gly Ser Ala
    450                 455                 460

Val Ser Leu Glu
465

<210> SEQ ID NO 127
<211> LENGTH: 440
<212> TYPE: PRT
<213> ORGANISM: Homo sapiens

<400> SEQUENCE: 127

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
```

```
                245                 250                 255
Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
        290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
            325                 330                 335

Thr Leu Arg Gln Cys Phe Asp Asp Phe Ala Asp Leu Val Pro Phe Asp
        340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
        370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
            405                 410                 415

Lys Ile Glu Asp His Leu Leu Ser Ser Gly Lys Phe Met Tyr Leu Glu
            420                 425                 430

Gly Asn Ala Asp Ser Ala Met Ser
            435                 440

<210> SEQ ID NO 128
<211> LENGTH: 259
<212> TYPE: PRT
<213> ORGANISM: Homo sapiens

<400> SEQUENCE: 128

Met Ala Arg Ile Pro Lys Thr Leu Lys Phe Val Val Ile Val Ala
1               5                   10                  15

Val Leu Leu Pro Val Leu Ala Tyr Ser Ala Thr Thr Ala Arg Gln Glu
            20                  25                  30

Glu Val Pro Gln Gln Thr Val Ala Pro Gln Gln Arg His Ser Phe
        35                  40                  45

Lys Gly Glu Glu Cys Pro Ala Gly Ser His Arg Ser Glu His Thr Gly
    50                  55                  60

Ala Cys Asn Pro Cys Thr Glu Gly Val Asp Tyr Thr Asn Ala Ser Asn
65                  70                  75                  80

Asn Glu Pro Ser Cys Phe Pro Cys Thr Val Cys Lys Ser Asp Gln Lys
            85                  90                  95

His Lys Ser Ser Cys Thr Met Thr Arg Asp Thr Val Cys Gln Cys Lys
            100                 105                 110

Glu Gly Thr Phe Arg Asn Glu Asn Ser Pro Glu Met Cys Arg Lys Cys
            115                 120                 125

Ser Arg Cys Pro Ser Gly Glu Val Gln Val Ser Asn Cys Thr Ser Trp
        130                 135                 140

Asp Asp Ile Gln Cys Val Glu Glu Phe Gly Ala Asn Ala Thr Val Glu
145                 150                 155                 160

Thr Pro Ala Ala Glu Glu Thr Met Asn Thr Ser Pro Gly Thr Pro Ala
            165                 170                 175
```

```
Pro Ala Ala Glu Glu Thr Met Asn Thr Ser Pro Gly Thr Pro Ala Pro
                180                 185                 190

Ala Ala Glu Glu Thr Met Thr Thr Ser Pro Gly Thr Pro Ala Pro Ala
            195                 200                 205

Ala Glu Glu Thr Met Thr Thr Ser Pro Gly Thr Pro Ala Pro Ala Ala
        210                 215                 220

Glu Glu Thr Met Ile Thr Ser Pro Gly Thr Pro Ala Ser Ser His Tyr
225                 230                 235                 240

Leu Ser Cys Thr Ile Val Gly Ile Ile Val Leu Ile Val Leu Leu Ile
                245                 250                 255

Val Phe Val

<210> SEQ ID NO 129
<211> LENGTH: 386
<212> TYPE: PRT
<213> ORGANISM: Homo sapiens

<400> SEQUENCE: 129

Met Gly Leu Trp Gly Gln Ser Val Pro Thr Ala Ser Ser Ala Arg Ala
1               5                   10                  15

Gly Arg Tyr Pro Gly Ala Arg Thr Ala Ser Gly Thr Arg Pro Trp Leu
            20                  25                  30

Leu Asp Pro Lys Ile Leu Lys Phe Val Val Phe Ile Val Ala Val Leu
        35                  40                  45

Leu Pro Val Arg Val Asp Ser Ala Thr Ile Pro Arg Gln Asp Glu Val
    50                  55                  60

Pro Gln Gln Thr Val Ala Pro Gln Gln Gln Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
        115                 120                 125

Ser Ser Cys Thr Thr Thr Arg Asp Thr Val Cys Gln Cys Glu Lys Gly
130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
            180                 185                 190

Pro Ala Ala Glu Glu Thr Val Thr Thr Ile Leu Gly Met Leu Ala Ser
        195                 200                 205

Pro Tyr His Tyr Leu Ile Ile Ile Val Val Leu Val Ile Ile Leu Ala
    210                 215                 220

Val Val Val Val Gly Phe Ser Cys Arg Lys Lys Phe Ile Ser Tyr Leu
225                 230                 235                 240

Lys Gly Ile Cys Ser Gly Gly Gly Gly Pro Glu Arg Val His Arg
                245                 250                 255

Val Leu Phe Arg Arg Arg Ser Cys Pro Ser Arg Val Pro Gly Ala Glu
            260                 265                 270

Asp Asn Ala Arg Asn Glu Thr Leu Ser Asn Arg Tyr Leu Gln Pro Thr
        275                 280                 285
```

```
Gln Val Ser Glu Gln Glu Ile Gln Gly Gln Leu Ala Glu Leu Thr
        290                 295                 300

Gly Val Thr Val Glu Ser Pro Glu Glu Pro Gln Arg Leu Leu Glu Gln
305                 310                 315                 320

Ala Glu Ala Glu Gly Cys Gln Arg Arg Leu Leu Val Pro Val Asn
                325                 330                 335

Asp Ala Asp Ser Ala Asp Ile Ser Thr Leu Leu Asp Ala Ser Ala Thr
                340                 345                 350

Leu Glu Glu Gly His Ala Lys Glu Thr Ile Gln Asp Gln Leu Val Gly
        355                 360                 365

Ser Glu Lys Leu Phe Tyr Glu Glu Asp Glu Ala Gly Ser Ala Thr Ser
370                 375                 380

Cys Leu
385

<210> SEQ ID NO 130
<211> LENGTH: 401
<212> TYPE: PRT
<213> ORGANISM: Homo sapiens

<400> SEQUENCE: 130

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
                20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270
```

Asp Ile Asp Leu Cys Glu Asn Ser Val Gln Arg His Ile Gly His Ala
            275                 280                 285

Asn Leu Thr Phe Glu Gln Leu Arg Ser Leu Met Glu Ser Leu Pro Gly
            290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
                340                 345                 350

Lys Thr Tyr His Phe Pro Lys Thr Val Thr Gln Ser Leu Lys Lys Thr
                355                 360                 365

Ile Arg Phe Leu His Ser Phe Thr Met Tyr Lys Leu Tyr Gln Lys Leu
            370                 375                 380

Phe Leu Glu Met Ile Gly Asn Gln Val Gln Ser Val Lys Ile Ser Cys
385                 390                 395                 400

Leu

<210> SEQ ID NO 131
<211> LENGTH: 129
<212> TYPE: PRT
<213> ORGANISM: Homo sapiens

<400> SEQUENCE: 131

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln

<210> SEQ ID NO 132
<211> LENGTH: 300
<212> TYPE: PRT
<213> ORGANISM: Homo sapiens

<400> SEQUENCE: 132

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
            35                  40                  45

Cys Ala Gln Cys Pro Pro Gly Thr Phe Val Gln Arg Pro Cys Arg Arg

```
            50                  55                  60
Asp Ser Pro Thr Thr Cys Gly Pro Cys Pro Arg His Tyr Thr Gln
 65                  70                  75                  80

Phe Trp Asn Tyr Leu Glu Arg Cys Arg Tyr Cys Asn Val Leu Cys Gly
                     85                  90                  95

Glu Arg Glu Glu Glu Ala Arg Ala Cys His Ala Thr His Asn Arg Ala
                    100                 105                 110

Cys Arg Cys Arg Thr Gly Phe Phe Ala His Ala Gly Phe Cys Leu Glu
                    115                 120                 125

His Ala Ser Cys Pro Pro Gly Ala Gly Val Ile Ala Pro Gly Thr Pro
                130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                    165                 170                 175

Leu Gly Leu Ala Leu Asn Val Pro Gly Ser Ser Ser His Asp Thr Leu
                    180                 185                 190

Cys Thr Ser Cys Thr Gly Phe Pro Leu Ser Thr Arg Val Pro Gly Ala
                    195                 200                 205

Glu Glu Cys Glu Arg Ala Val Ile Asp Phe Val Ala Phe Gln Asp Ile
                    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                    245                 250                 255

Leu Arg Arg Arg Leu Thr Glu Leu Leu Gly Ala Gln Asp Gly Ala Leu
                    260                 265                 270

Leu Val Arg Leu Leu Gln Ala Leu Arg Val Ala Arg Met Pro Gly Leu
                    275                 280                 285

Glu Arg Ser Val Arg Glu Arg Phe Leu Pro Val His
                    290                 295                 300

<210> SEQ ID NO 133
<211> LENGTH: 417
<212> TYPE: PRT
<213> ORGANISM: Homo sapiens

<400> SEQUENCE: 133

Met Glu Gln Arg Pro Arg Gly Cys Ala Ala Val Ala Ala Ala Leu Leu
 1                   5                  10                  15

Leu Val Leu Leu Gly Ala Arg Ala Gln Gly Gly Thr Arg Ser Pro Arg
                    20                  25                  30

Cys Asp Cys Ala Gly Asp Phe His Lys Lys Ile Gly Leu Phe Cys Cys
                    35                  40                  45

Arg Gly Cys Pro Ala Gly His Tyr Leu Lys Ala Pro Cys Thr Glu Pro
                50                  55                  60

Cys Gly Asn Ser Thr Cys Leu Val Cys Pro Gln Asp Thr Phe Leu Ala
 65                  70                  75                  80

Trp Glu Asn His His Asn Ser Glu Cys Ala Arg Cys Gln Ala Cys Asp
                    85                  90                  95

Glu Gln Ala Ser Gln Val Ala Leu Glu Asn Cys Ser Ala Val Ala Asp
                    100                 105                 110

Thr Arg Cys Gly Cys Lys Pro Gly Trp Phe Val Glu Cys Gln Val Ser
                    115                 120                 125
```

```
Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
                260                 265                 270

Thr Val Gln Leu Val Gly Asn Ser Trp Thr Pro Gly Tyr Pro Glu Thr
            275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
    370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 134
<211> LENGTH: 448
<212> TYPE: PRT
<213> ORGANISM: Homo sapiens

<400> SEQUENCE: 134

Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
                20                  25                  30

Glu Asn Glu Tyr Tyr Asn Gln Thr Thr Gly Leu Cys Gln Glu Cys Pro
            35                  40                  45

Pro Cys Gly Pro Gly Glu Glu Pro Tyr Leu Ser Cys Gly Tyr Gly Thr
        50                  55                  60

Lys Asp Glu Asp Tyr Gly Cys Val Pro Cys Pro Ala Glu Lys Phe Ser
65                  70                  75                  80
```

-continued

```
Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Lys Lys
225                 230                 235                 240

Glu Ala Pro Asp Asn Val Val Met Phe Ser Glu Lys Asp Glu Phe Glu
                245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
    290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
        355                 360                 365

Ala Val Val Lys Thr Trp Arg His Leu Ala Glu Ser Phe Gly Leu Lys
    370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
        435                 440                 445

<210> SEQ ID NO 135
<211> LENGTH: 299
<212> TYPE: PRT
<213> ORGANISM: Homo sapiens

<400> SEQUENCE: 135

Met Asp Cys Gln Glu Asn Glu Tyr Trp Asp Gln Trp Gly Arg Cys Val
1               5                   10                  15
```

```
Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Arg Arg
        35                  40                  45

Tyr Lys Ser Ser Trp Gly His His Arg Cys Gln Ser Cys Ile Thr Cys
 50                  55                  60

Ala Val Ile Asn Arg Val Gln Lys Val Asn Cys Thr Ala Thr Ser Asn
 65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
                100                 105                 110

Thr Ser Glu Val Gln Cys Ala Phe Gln Leu Ser Leu Val Glu Ala Asp
            115                 120                 125

Ala Pro Thr Val Pro Pro Gln Glu Ala Thr Leu Val Ala Leu Val Ser
130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Val Thr Gly Gly
                165                 170                 175

Leu Leu Gln Phe Glu Ala Asp Lys Thr Ala Lys Glu Glu Ser Leu Phe
                180                 185                 190

Pro Val Pro Pro Ser Lys Glu Thr Ser Ala Glu Ser Gln Val Ser Glu
                195                 200                 205

Asn Ile Phe Gln Thr Gln Pro Leu Asn Pro Ile Leu Glu Asp Asp Cys
                210                 215                 220

Ser Ser Thr Ser Gly Phe Pro Thr Gln Glu Ser Phe Thr Met Ala Ser
225                 230                 235                 240

Cys Thr Ser Glu Ser His Ser His Trp Val His Ser Pro Ile Glu Cys
                245                 250                 255

Thr Glu Leu Asp Leu Gln Lys Phe Ser Ser Ser Ala Ser Tyr Thr Gly
                260                 265                 270

Ala Glu Thr Leu Gly Gly Asn Thr Val Glu Ser Thr Gly Asp Arg Leu
                275                 280                 285

Glu Leu Asn Val Pro Phe Glu Val Pro Ser Pro
                290                 295

<210> SEQ ID NO 136
<211> LENGTH: 464
<212> TYPE: PRT
<213> ORGANISM: Homo sapiens

<400> SEQUENCE: 136

Met Ala Ala Glu Asp Val Ile Ile Cys Ala Gln Gln Cys Ser Gly Arg
1               5                   10                  15

Cys Arg Gly Lys Ser Pro Ser Asp Cys Cys His Asn Gln Cys Ala Ala
                20                  25                  30

Gly Cys Thr Gly Pro Arg Glu Ser Asp Cys Leu Val Cys Arg Lys Phe
            35                  40                  45

Arg Asp Glu Ala Thr Cys Lys Asp Thr Cys Pro Pro Leu Met Leu Tyr
 50                  55                  60

Asn Pro Thr Thr Tyr Gln Met Asp Val Asn Pro Glu Gly Lys Tyr Ser
 65                  70                  75                  80

Phe Gly Ala Thr Cys Val Lys Lys Cys Pro Arg Asn Tyr Val Val Thr
```

```
                    85                  90                  95
Asp His Gly Ser Cys Val Arg Ala Cys Gly Ala Asp Ser Tyr Glu Met
                100                 105                 110
Glu Glu Asp Gly Val Arg Lys Cys Lys Lys Cys Glu Gly Pro Cys Arg
                115                 120                 125
Lys Val Cys Asn Gly Ile Gly Ile Gly Glu Phe Lys Asp Ser Leu Ser
            130                 135                 140
Ile Asn Ala Thr Asn Ile Lys His Phe Lys Asn Cys Thr Ser Ile Ser
145                 150                 155                 160
Gly Asp Leu His Ile Leu Pro Val Ala Phe Arg Gly Asp Ser Phe Thr
                165                 170                 175
His Thr Pro Pro Leu Asp Pro Gln Glu Leu Asp Ile Leu Lys Thr Val
            180                 185                 190
Lys Glu Ile Thr Gly Phe Leu Leu Ile Gln Ala Trp Pro Glu Asn Arg
            195                 200                 205
Thr Asp Leu His Ala Phe Glu Asn Leu Glu Ile Ile Arg Gly Arg Thr
        210                 215                 220
Lys Gln His Gly Gln Phe Ser Leu Ala Val Val Ser Leu Asn Ile Thr
225                 230                 235                 240
Ser Leu Gly Leu Arg Ser Leu Lys Glu Ile Ser Asp Gly Asp Val Ile
                245                 250                 255
Ile Ser Gly Asn Lys Asn Leu Cys Tyr Ala Asn Thr Ile Asn Trp Lys
            260                 265                 270
Lys Leu Phe Gly Thr Ser Gly Gln Lys Thr Lys Ile Ile Ser Asn Arg
        275                 280                 285
Gly Glu Asn Ser Cys Lys Ala Thr Gly Gln Val Cys His Ala Leu Cys
    290                 295                 300
Ser Pro Glu Gly Cys Trp Gly Pro Glu Pro Arg Asp Cys Val Ser Cys
305                 310                 315                 320
Arg Asn Val Ser Arg Gly Arg Glu Cys Val Asp Lys Cys Asn Leu Leu
                325                 330                 335
Glu Gly Glu Pro Arg Glu Phe Val Glu Asn Ser Glu Cys Ile Gln Cys
            340                 345                 350
His Pro Glu Cys Leu Pro Gln Ala Met Asn Ile Thr Cys Thr Gly Arg
        355                 360                 365
Gly Pro Asp Asn Cys Ile Gln Cys Ala His Tyr Ile Asp Gly Pro His
    370                 375                 380
Cys Val Lys Thr Cys Pro Ala Gly Val Met Gly Glu Asn Asn Thr Leu
385                 390                 395                 400
Val Trp Lys Tyr Ala Asp Ala Gly His Val Cys His Leu Cys His Pro
                405                 410                 415
Asn Cys Thr Tyr Gly Cys Thr Gly Pro Gly Leu Glu Gly Cys Pro Thr
            420                 425                 430
Asn Gly Pro Lys Ile Pro Ser Ile Ala Thr Gly Met Val Gly Ala Leu
        435                 440                 445
Leu Leu Leu Leu Val Val Ala Leu Gly Ile Gly Pro Leu His Gly Arg
    450                 455                 460
```

<210> SEQ ID NO 137
<211> LENGTH: 1255
<212> TYPE: PRT
<213> ORGANISM: Homo sapiens

<400> SEQUENCE: 137

-continued

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
```

```
                420             425             430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
            450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
            530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
            610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
            675                 680                 685
Arg Leu Leu Gln Glu Thr Glu Leu Val Glu Pro Leu Thr Pro Ser Gly
            690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
            755                 760                 765
Asp Glu Ala Tyr Val Met Ala Gly Val Gly Ser Pro Tyr Val Ser Arg
            770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
            835                 840                 845
```

```
Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245
```

Leu Gly Leu Asp Val Pro Val
    1250            1255

<210> SEQ ID NO 138
<211> LENGTH: 1342
<212> TYPE: PRT
<213> ORGANISM: Homo sapiens

<400> SEQUENCE: 138

Met Arg Ala Asn Asp Ala Leu Gln Val Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

```
Asn Gly Asp Pro Trp His Lys Ile Pro Ala Leu Asp Pro Glu Lys Leu
        370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Cys Trp Gly Pro
                500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780
```

-continued

```
Leu Val Thr Gln Tyr Leu Pro Leu Gly Ser Leu Leu Asp His Val Arg
785                 790                 795                 800

Gln His Arg Gly Ala Leu Gly Pro Gln Leu Leu Asn Trp Gly Val
            805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
            930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Glu Ser Cys Gln Glu
    1055                1060                1065

Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
```

-continued

```
                 1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 139
<211> LENGTH: 314
<212> TYPE: PRT
<213> ORGANISM: Homo sapiens

<400> SEQUENCE: 139

Met Ala Pro Pro Gln Val Leu Ala Phe Gly Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
                100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
        130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205
```

```
Ile Ala Asp Val Ala Tyr Tyr Phe Glu Lys Asp Val Lys Gly Glu Ser
210                 215                 220
Leu Phe His Ser Lys Lys Met Asp Leu Thr Val Asn Gly Glu Gln Leu
225                 230                 235                 240
Asp Leu Asp Pro Gly Gln Thr Leu Ile Tyr Tyr Val Asp Glu Lys Ala
            245                 250                 255
Pro Glu Phe Ser Met Gln Gly Leu Lys Ala Gly Val Ile Ala Val Ile
            260                 265                 270
Val Val Val Val Ile Ala Val Val Ala Gly Ile Val Val Leu Val Ile
            275                 280                 285
Ser Arg Lys Lys Arg Met Ala Lys Tyr Glu Lys Ala Glu Ile Lys Glu
290                 295                 300
Met Gly Glu Met His Arg Glu Leu Asn Ala
305                 310

<210> SEQ ID NO 140
<211> LENGTH: 702
<212> TYPE: PRT
<213> ORGANISM: Homo sapiens

<400> SEQUENCE: 140

Met Glu Ser Pro Ser Ala Pro Pro His Arg Trp Cys Ile Pro Trp Gln
1               5                   10                  15
Arg Leu Leu Leu Thr Ala Ser Leu Leu Thr Phe Trp Asn Pro Pro Thr
            20                  25                  30
Thr Ala Lys Leu Thr Ile Glu Ser Thr Pro Phe Asn Val Ala Glu Gly
        35                  40                  45
Lys Glu Val Leu Leu Leu Val His Asn Leu Pro Gln His Leu Phe Gly
    50                  55                  60
Tyr Ser Trp Tyr Lys Gly Glu Arg Val Asp Gly Asn Arg Gln Ile Ile
65                  70                  75                  80
Gly Tyr Val Ile Gly Thr Gln Gln Ala Thr Pro Gly Pro Ala Tyr Ser
                85                  90                  95
Gly Arg Glu Ile Ile Tyr Pro Asn Ala Ser Leu Leu Ile Gln Asn Ile
            100                 105                 110
Ile Gln Asn Asp Thr Gly Phe Tyr Thr Leu His Val Ile Lys Ser Asp
        115                 120                 125
Leu Val Asn Glu Glu Ala Thr Gly Gln Phe Arg Val Tyr Pro Glu Leu
    130                 135                 140
Pro Lys Pro Ser Ile Ser Ser Asn Asn Ser Lys Pro Val Glu Asp Lys
145                 150                 155                 160
Asp Ala Val Ala Phe Thr Cys Glu Pro Glu Thr Gln Asp Ala Thr Tyr
                165                 170                 175
Leu Trp Trp Val Asn Asn Gln Ser Leu Pro Val Ser Pro Arg Leu Gln
            180                 185                 190
Leu Ser Asn Gly Asn Arg Thr Leu Thr Leu Phe Asn Val Thr Arg Asn
        195                 200                 205
Asp Thr Ala Ser Tyr Lys Cys Glu Thr Gln Asn Pro Val Ser Ala Arg
    210                 215                 220
Arg Ser Asp Ser Val Ile Leu Asn Val Leu Tyr Gly Pro Asp Ala Pro
225                 230                 235                 240
Thr Ile Ser Pro Leu Asn Thr Ser Tyr Arg Ser Gly Glu Asn Leu Asn
                245                 250                 255
Leu Ser Cys His Ala Ala Ser Asn Pro Pro Ala Gln Tyr Ser Trp Phe
            260                 265                 270
```

```
Val Asn Gly Thr Phe Gln Gln Ser Thr Gln Glu Leu Phe Ile Pro Asn
            275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
            355                 360                 365

Leu Gln Leu Ser Asn Asp Asn Arg Thr Leu Thr Leu Leu Ser Val Thr
            370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
            450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
            530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
                580                 585                 590

Pro Asp Thr Pro Ile Ile Ser Pro Pro Asp Ser Ser Tyr Leu Ser Gly
            595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
            675                 680                 685
```

```
Val Gly Ile Met Ile Gly Val Leu Val Gly Val Ala Leu Ile
    690                 695                 700
```

<210> SEQ ID NO 141
<211> LENGTH: 661
<212> TYPE: PRT
<213> ORGANISM: Homo sapiens

<400> SEQUENCE: 141

```
Met Asp Leu Val Leu Lys Arg Cys Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
            115                 120                 125

Ala Cys Ile Phe Pro Asp Gly Gly Pro Cys Pro Ser Gly Ser Trp Ser
            130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
            195                 200                 205

Ile Thr Asp Gln Val Pro Phe Ser Val Ser Val Ser Gln Leu Arg Ala
            210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
            290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365
```

```
Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
        420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Gly Asp Ala Phe Glu Leu
            500                 505                 510

Thr Val Ser Cys Gln Gly Gly Leu Pro Lys Glu Ala Cys Met Glu Ile
                515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
    595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 142
<211> LENGTH: 309
<212> TYPE: PRT
<213> ORGANISM: Homo sapiens

<400> SEQUENCE: 142

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
```

```
            65                  70                  75                  80
        Ser Ser Arg Glu Glu Glu Gly Pro Ser Thr Ser Cys Ile Leu Glu Ser
                            85                  90                  95

Leu Phe Arg Ala Val Ile Thr Lys Lys Val Ala Asp Leu Val Gly Phe
                        100                 105                 110

Leu Leu Leu Lys Tyr Arg Ala Arg Glu Pro Val Thr Lys Ala Glu Met
                    115                 120                 125

Leu Glu Ser Val Ile Lys Asn Tyr Lys His Cys Phe Pro Glu Ile Phe
                130                 135                 140

Gly Lys Ala Ser Glu Ser Leu Gln Leu Val Phe Gly Ile Asp Val Lys
        145                 150                 155                 160

Glu Ala Asp Pro Thr Gly His Ser Tyr Val Leu Val Thr Cys Leu Gly
                        165                 170                 175

Leu Ser Tyr Asp Gly Leu Leu Gly Asp Asn Gln Ile Met Pro Lys Thr
                    180                 185                 190

Gly Phe Leu Ile Ile Val Leu Val Met Ile Ala Met Glu Gly Gly His
                195                 200                 205

Ala Pro Glu Glu Glu Ile Trp Glu Glu Leu Ser Val Met Glu Val Tyr
            210                 215                 220

Asp Gly Arg Glu His Ser Ala Tyr Gly Glu Pro Arg Lys Leu Leu Thr
        225                 230                 235                 240

Gln Asp Leu Val Gln Glu Lys Tyr Leu Glu Tyr Arg Gln Val Pro Asp
                        245                 250                 255

Ser Asp Pro Ala Arg Tyr Glu Phe Leu Trp Gly Pro Arg Ala Leu Ala
                    260                 265                 270

Glu Thr Ser Tyr Val Lys Val Leu Glu Tyr Val Ile Lys Val Ser Ala
                275                 280                 285

Arg Val Arg Phe Phe Phe Pro Ser Leu Arg Glu Ala Ala Leu Arg Glu
                290                 295                 300

Glu Glu Glu Gly Val
        305

<210> SEQ ID NO 143
<211> LENGTH: 290
<212> TYPE: PRT
<213> ORGANISM: Homo sapiens

<400> SEQUENCE: 143

Met Arg Ile Phe Ala Val Phe Ile Phe Met Thr Tyr Trp His Leu Leu
        1                   5                   10                  15

Asn Ala Phe Thr Val Thr Val Pro Lys Asp Leu Tyr Val Val Glu Tyr
                        20                  25                  30

Gly Ser Asn Met Thr Ile Glu Cys Lys Phe Pro Val Glu Lys Gln Leu
                    35                  40                  45

Asp Leu Ala Ala Leu Ile Val Tyr Trp Glu Met Glu Asp Lys Asn Ile
                50                  55                  60

Ile Gln Phe Val His Gly Glu Glu Asp Leu Lys Val Gln His Ser Ser
        65                  70                  75                  80

Tyr Arg Gln Arg Ala Arg Leu Leu Lys Asp Gln Leu Ser Leu Gly Asn
                        85                  90                  95

Ala Ala Leu Gln Ile Thr Asp Val Lys Leu Gln Asp Ala Gly Val Tyr
                    100                 105                 110

Arg Cys Met Ile Ser Tyr Gly Gly Ala Asp Tyr Lys Arg Ile Thr Val
                115                 120                 125
```

```
Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 144
<211> LENGTH: 180
<212> TYPE: PRT
<213> ORGANISM: Homo sapiens

<400> SEQUENCE: 144

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
                35                  40                  45

Gly Ala Ala Arg Ala Ser Gly Pro Gly Gly Gly Ala Pro Arg Gly Pro
50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
                115                 120                 125

Ser Gly Asn Ile Leu Thr Ile Arg Leu Thr Ala Ala Asp His Arg Gln
                130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
    180

<210> SEQ ID NO 145
```

-continued

```
<211> LENGTH: 332
<212> TYPE: PRT
<213> ORGANISM: Homo sapiens

<400> SEQUENCE: 145

Met Cys Pro Ala Gly Trp Lys Leu Leu Ala Met Leu Ala Leu Val Leu
1               5                   10                  15

Val Val Met Val Trp Tyr Ser Ile Ser Arg Glu Asp Arg Tyr Ile Glu
            20                  25                  30

Leu Phe Tyr Phe Pro Ile Pro Glu Lys Lys Glu Pro Cys Leu Gln Gly
        35                  40                  45

Glu Ala Glu Ser Lys Ala Ser Lys Leu Phe Gly Asn Tyr Ser Arg Asp
    50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
                85                  90                  95

Leu Arg Val Leu Ala Ile Thr Ser Ser Ile Pro Lys Asn Ile Gln
            100                 105                 110

Ser Leu Arg Cys Arg Arg Cys Val Val Gly Asn Gly His Arg Leu
        115                 120                 125

Arg Asn Ser Ser Leu Gly Asp Ala Ile Asn Lys Tyr Asp Val Val Ile
    130                 135                 140

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
            180                 185                 190

Ala Met Asp Phe His Trp Ile Glu Thr Ile Leu Ser Asp Lys Lys Arg
        195                 200                 205

Val Arg Lys Gly Phe Trp Lys Gln Pro Pro Leu Ile Trp Asp Val Asn
    210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
            260                 265                 270

Asp Leu Val His Ile Ala Gly Phe Gly Tyr Pro Asp Ala Tyr Asn Lys
        275                 280                 285

Lys Gln Thr Ile His Tyr Tyr Glu Gln Ile Thr Leu Lys Ser Met Ala
    290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330

<210> SEQ ID NO 146
<211> LENGTH: 556
<212> TYPE: PRT
<213> ORGANISM: Homo sapiens

<400> SEQUENCE: 146

Met Pro Pro Pro Arg Leu Leu Phe Phe Leu Leu Phe Leu Thr Pro Met
1               5                   10                  15
```

Glu Val Arg Pro Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
 50                  55                  60

Ser Leu Gly Leu Pro Gly Leu Gly Ile His Met Arg Pro Leu Ala Ser
65                   70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

```
Ser Gln Asp Gly Ser Gly Tyr Glu Asn Pro Glu Asp Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
530                 535                 540

Gly Gly Gly Gly Arg Met Gly Thr Trp Ser Thr Arg
545                 550                 555

<210> SEQ ID NO 147
<211> LENGTH: 297
<212> TYPE: PRT
<213> ORGANISM: Homo sapiens

<400> SEQUENCE: 147

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
        50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255
```

-continued

Lys Asn Glu Glu Asp Ile Glu Ile Pro Ile Gln Glu Glu Glu
            260                 265                 270

Glu Glu Thr Glu Thr Asn Phe Pro Glu Pro Gln Asp Gln Glu Ser
    275                 280                 285

Ser Pro Ile Glu Asn Asp Ser Ser Pro
    290                 295

<210> SEQ ID NO 148
<211> LENGTH: 847
<212> TYPE: PRT
<213> ORGANISM: Homo sapiens

<400> SEQUENCE: 148

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val

-continued

```
                325                 330                 335
Gln Ile Leu His Ser Pro Ala Val Glu Gly Ser Gln Val Glu Phe Leu
            340                 345                 350
Cys Met Ser Leu Ala Asn Pro Leu Pro Thr Asn Tyr Thr Trp Tyr His
        355                 360                 365
Asn Gly Lys Glu Met Gln Gly Arg Thr Glu Glu Lys Val His Ile Pro
    370                 375                 380
Lys Ile Leu Pro Trp His Ala Gly Thr Tyr Ser Cys Val Ala Glu Asn
385                 390                 395                 400
Ile Leu Gly Thr Gly Gln Arg Gly Pro Gly Ala Glu Leu Asp Val Gln
            405                 410                 415
Tyr Pro Pro Lys Lys Val Thr Thr Val Ile Gln Asn Pro Met Pro Ile
        420                 425                 430
Arg Glu Gly Asp Thr Val Thr Leu Ser Cys Asn Tyr Asn Ser Ser Asn
    435                 440                 445
Pro Ser Val Thr Arg Tyr Glu Trp Lys Pro His Gly Ala Trp Glu Glu
450                 455                 460
Pro Ser Leu Gly Val Leu Lys Ile Gln Asn Val Gly Trp Asp Asn Thr
465                 470                 475                 480
Thr Ile Ala Cys Ala Ala Cys Asn Ser Trp Cys Ser Trp Ala Ser Pro
            485                 490                 495
Val Ala Leu Asn Val Gln Tyr Ala Pro Arg Asp Val Arg Val Arg Lys
        500                 505                 510
Ile Lys Pro Leu Ser Glu Ile His Ser Gly Asn Ser Val Ser Leu Gln
    515                 520                 525
Cys Asp Phe Ser Ser Ser His Pro Lys Glu Val Gln Phe Phe Trp Glu
530                 535                 540
Lys Asn Gly Arg Leu Leu Gly Lys Glu Ser Gln Leu Asn Phe Asp Ser
545                 550                 555                 560
Ile Ser Pro Glu Asp Ala Gly Ser Tyr Ser Cys Trp Val Asn Asn Ser
            565                 570                 575
Ile Gly Gln Thr Ala Ser Lys Ala Trp Thr Leu Glu Val Leu Tyr Ala
        580                 585                 590
Pro Arg Arg Leu Arg Val Ser Met Ser Pro Gly Asp Gln Val Met Glu
    595                 600                 605
Gly Lys Ser Ala Thr Leu Thr Cys Glu Ser Asp Ala Asn Pro Pro Val
610                 615                 620
Ser His Tyr Thr Trp Phe Asp Trp Asn Asn Gln Ser Leu Pro Tyr His
625                 630                 635                 640
Ser Gln Lys Leu Arg Leu Glu Pro Val Lys Val Gln His Ser Gly Ala
            645                 650                 655
Tyr Trp Cys Gln Gly Thr Asn Ser Val Gly Lys Gly Arg Ser Pro Leu
        660                 665                 670
Ser Thr Leu Thr Val Tyr Tyr Ser Pro Glu Thr Ile Gly Arg Arg Val
    675                 680                 685
Ala Val Gly Leu Gly Ser Cys Leu Ala Ile Leu Ile Leu Ala Ile Cys
690                 695                 700
Gly Leu Lys Leu Gln Arg Arg Trp Lys Arg Thr Gln Ser Gln Gln Gly
705                 710                 715                 720
Leu Gln Glu Asn Ser Ser Gly Gln Ser Phe Phe Val Arg Asn Lys Lys
            725                 730                 735
Val Arg Arg Ala Pro Leu Ser Glu Gly Pro His Ser Leu Gly Cys Tyr
        740                 745                 750
```

```
Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
        770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
            835                 840                 845

<210> SEQ ID NO 149
<211> LENGTH: 364
<212> TYPE: PRT
<213> ORGANISM: Homo sapiens

<400> SEQUENCE: 149

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
```

```
            275                 280                 285
Ala Ala Arg Thr Ala Val Gly Arg Asn Asp Thr His Pro Thr Thr Gly
    290                 295                 300
Ser Ala Ser Pro Lys His Gln Lys Lys Ser Lys Leu His Gly Pro Thr
305                 310                 315                 320
Glu Thr Ser Ser Cys Ser Gly Ala Ala Pro Thr Val Glu Met Asp Glu
                325                 330                 335
Glu Leu His Tyr Ala Ser Leu Asn Phe His Gly Met Asn Pro Ser Lys
            340                 345                 350
Asp Thr Ser Thr Glu Tyr Ser Glu Val Arg Thr Gln
            355                 360

<210> SEQ ID NO 150
<211> LENGTH: 300
<212> TYPE: PRT
<213> ORGANISM: Homo sapiens

<400> SEQUENCE: 150

Met Ala Asn Cys Glu Phe Ser Pro Val Ser Gly Asp Lys Pro Cys Cys
1               5                   10                  15
Arg Leu Ser Arg Arg Ala Gln Leu Cys Leu Gly Val Ser Ile Leu Val
            20                  25                  30
Leu Ile Leu Val Val Val Leu Ala Val Val Pro Arg Trp Arg Gln
            35                  40                  45
Gln Trp Ser Gly Pro Gly Thr Thr Lys Arg Phe Pro Glu Thr Val Leu
    50                  55                  60
Ala Arg Cys Val Lys Tyr Thr Glu Ile His Pro Glu Met Arg His Val
65                  70                  75                  80
Asp Cys Gln Ser Val Trp Asp Ala Phe Lys Gly Ala Phe Ile Ser Lys
                85                  90                  95
His Pro Cys Asn Ile Thr Glu Glu Asp Tyr Gln Pro Leu Met Lys Leu
            100                 105                 110
Gly Thr Gln Thr Val Pro Cys Asn Lys Ile Leu Leu Trp Ser Arg Ile
            115                 120                 125
Lys Asp Leu Ala His Gln Phe Thr Gln Val Gln Arg Asp Met Phe Thr
    130                 135                 140
Leu Glu Asp Thr Leu Leu Gly Tyr Leu Ala Asp Asp Leu Thr Trp Cys
145                 150                 155                 160
Gly Glu Phe Asn Thr Ser Lys Ile Asn Tyr Gln Ser Cys Pro Asp Trp
                165                 170                 175
Arg Lys Asp Cys Ser Asn Asn Pro Val Ser Val Phe Trp Lys Thr Val
            180                 185                 190
Ser Arg Arg Phe Ala Glu Ala Ala Cys Asp Val Val His Val Met Leu
            195                 200                 205
Asn Gly Ser Arg Ser Lys Ile Phe Asp Lys Asn Ser Thr Phe Gly Ser
    210                 215                 220
Val Glu Val His Asn Leu Gln Pro Glu Lys Val Gln Thr Leu Glu Ala
225                 230                 235                 240
Trp Val Ile His Gly Gly Arg Glu Asp Ser Arg Asp Leu Cys Gln Asp
                245                 250                 255
Pro Thr Ile Lys Glu Leu Glu Ser Ile Ile Ser Lys Arg Asn Ile Gln
            260                 265                 270
Phe Ser Cys Lys Asn Ile Tyr Arg Pro Asp Lys Phe Leu Gln Cys Val
            275                 280                 285
```

```
Lys Asn Pro Glu Asp Ser Ser Cys Thr Ser Glu Ile
    290                 295                 300
```

```
<210> SEQ ID NO 151
<211> LENGTH: 61
<212> TYPE: PRT
<213> ORGANISM: Homo sapiens

<400> SEQUENCE: 151

Met Lys Arg Phe Leu Phe Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
            35                  40                  45

Phe Val Ala Asn Ala Ile Ile His Leu Phe Cys Phe Ser
        50                  55                  60
```

```
<210> SEQ ID NO 152
<211> LENGTH: 193
<212> TYPE: PRT
<213> ORGANISM: Homo sapiens

<400> SEQUENCE: 152

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

BINDING MOLECULES WITH MODIFIED J-CHAIN

CROSS REFERENCE TO RELATED APPLICATIONS

This application is a US National Stage Entry of PCT Application No. PCT/US2016/055053, filed Sep. 30, 2016, which claims priority benefit of the filing date of U.S. Provisional Patent Application Ser. No. 62/235,486, filed on Sep. 30, 2015, which are each hereby incorporated by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. The ASCII file, named Sequence-Listing.TXT, is 399 Kb in size and was created on 4 Jun. 2022.

FIELD OF THE INVENTION

The present invention concerns binding molecules that comprise an IgM, IgA, IgG/IgM or IgG/IgA antibody with a J-chain modified to include a binding moiety that affects a T-cell signaling pathway, and their uses.

BACKGROUND OF THE INVENTION

J-chain is an acidic 15-kDa polypeptide, which is associated with pentameric IgM and dimeric IgA via disulfide bonds involving the penultimate cysteine residue in the 18-amino acid secretory tail-piece (tp) at the C-terminus of the IgM μ or IgA α heavy chain. The three disulfide bridges are formed between Cys 12 and 100, Cys 71 and 91, and Cys 108 and 133, respectively. See, e.g., Frutiger et al. 1992, *Biochemistry* 31, 12643-12647. Structural requirements for incorporation of the J-chain into human IgM and IgA and for polymeric immunoglobulin assembly and association with the J-chain are reported by Sorensen et al. 2000, *Int. Immunol.* 12(1): 19-27 and Yoo et al. 1999, *J. Biol. Chem.* 274(47):33771-33777, respectively. Recombinant production of soluble J-chain in *E coli* is reported by Redwan et al. 2006, *Human Antibodies* 15:95-102.

Methods for making hybrid IgA/IgG and IgM/IgG antibodies are known in the art. Thus, recombinant production of hybrid IgA2/IgG1 antibodies is reported in Chintalacharuvu et al. 2001, *Clin Immunol* 101(1):21-31. It has been reported that addition of αtp or μtp at the end of IgG γ heavy chain facilitates polymerization and enhances effector function such as complement activation (Smith et al., *J Immunol* 1995, 154:2226-2236). The IgA/IgG hybrid antibodies possess properties of both IgA and IgG. Methods for recombinant production of IgM antibodies are also known in the art. E.g., Tchoudakova A, et al., High level expression of functional human IgMs in human PER.C6 cells. *mAbs.* 2009; 1(2):163-171.

Despite the advances made in the design of antibodies, there remains a need for modified antibodies with improved properties, such as improved affinity, specificity and/or avidity, as well as the ability to bind to multiple binding targets.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g., antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumomab" (MT103 or AMG103) which binds the CD3 and CD19 receptors, on T- and B-cells, respectively. This tethering of a cytotoxic T-cell to a cancerous B-cell, allows for effective treatment of B-cell leukemia.

The blockade of immune checkpoints has emerged as a promising area for the advancement of cancer treatment. Immune checkpoints refer to inhibitory signaling pathways that are encoded into the immune system, and which play a vital role in maintaining self-tolerance, as well as modulating the duration and amplitude of immune responses. See, e.g., Pardoll, Drew M. "The blockade of immune checkpoints in cancer immunotherapy." *Nature Reviews Cancer* 12.4 (2012): 252-264; Postow, Michael A. et al., "Immune Checkpoint Blockade in Cancer Therapy," *J Clin Oncol.* 2015 Jun. 10; 33(17):1974-82. doi: 10.1200/JCO.2014.59.4358.

Despite positive proof of concept results in preclinical models, investigators have reported that monoclonal IgG blocking antibodies directed against T-cell inhibitory signaling pathway components (for example, ipilimumab (Bristol-Myers Squibb) and tremelimumab (MedImmune/AstraZenica), both directed against CTLA4) have only achieved minimal efficacy results in a clinical setting. E.g., Postow et al., pp. 1-2. In addition, treatments involving monoclonal IgG antibodies have resulted in immune-related adverse events, such as dermatologic, GI, hepatic, endocrine and other inflammatory events. E.g., Id. at p. 4. As such, the use of monoclonal IgG antibodies in immune checkpoint blockade may be limited by the therapeutic index of such molecules, in that the dose of a monoclonal IgG antibody required to elicit the desired therapeutic effect also causes immune-related adverse events.

Accordingly, there is a need for binding molecules with increased avidity that will provide increased potency so that lower dosage levels can be used, thereby preventing the occurrence of immune-related adverse events, while still achieving effective blockade of T-cell inhibitory signaling pathways.

SUMMARY OF THE INVENTION

The present invention is based, at least in part, on the recognition that the J-chain of an IgM or IgA antibody can be modified by introducing one or more binding moieties into a native J-chain sequence, and the modified J-chain can be introduced into IgM, IgA, IgG/IgM or IgG/IgA antibodies without compromising the functionality of the recipient antibody or the binding of the modified J-chain to its target. This allows the modified J-chain with binding moiety to interact with one set of target antigens, while the IgM, IgA, IgG/IgM or IgG/IgA antibody can interact with a different set of target antigens.

The invention is further based on the recognition that due to their multivalent nature, IgM, IgA, IgG/IgM or IgG/IgA antibodies can provide increased avidity between the antibody and a target antigen, thereby facilitating binding of antigens with low level expression and/or low binding affinity. Furthermore, the optional multi-specific nature of the IgM, IgA, IgG/IgM or IgG/IgA portion of the subject binding molecules allows binding between specific numbers and/or specific types of binding targets, thereby facilitating binding between specific combinations of antigen targets. The modified J-chain portion of the subject binding molecules provides additional opportunities for target binding, allowing the subject binding molecules to bind one or more targets via the IgM, IgA, IgG/IgM or IgG/IgA portion of the molecule, while simultaneously binding to one or more targets via a binding moiety on the J-chain.

Aspects of the invention include binding molecules comprising an IgM, IgA, IgG/IgM or IgG/IgA antibody with a modified J-chain, or an antigen binding fragment thereof, wherein the modified J-chain comprises a binding moiety that affects a T-cell signaling pathway. In some embodiments, a binding molecule according to claim 1, wherein the binding moiety antagonizes a T-cell inhibitory signaling pathway. In some embodiments, a binding moiety on the modified J-chain binds to a cell surface protein selected from the group consisting of: CTLA4, PD-1, TIM3, LAG3, BTLA, VISTA and TIGIT. In some embodiments, the IgM, IgA, IgG/IgM or IgG/IgA antibody antagonizes a T-cell inhibitory signaling pathway. In some embodiments, the antibody binds to a target selected from the group consisting of: PD-1, PD-L1, TIM3 and LAG3.

In some embodiments, an IgM, IgA, IgG/IgM or IgG/IgA antibody agonizes a T-cell stimulatory signaling pathway. In some embodiments, the antibody binds to a target selected from the group consisting of: CD137, OX40, CD40, GITR, CD27 and HVEM. In some embodiments, the IgM, IgA, IgG/IgM or IgG/IgA antibody binds to a low level expression target. In some embodiments, the low level expression target is selected from the group consisting of: EGFR, HER2, HER3, EpCAM, CEACAM, Gp100, MAGE1 and PD-L1. In some embodiments, the low level expression target is a cell surface protein on an epithelial cancer cell.

In some embodiments, an IgM, IgA, IgG/IgM or IgG/IgA antibody binds to a low affinity target. In some embodiments, the low affinity target is selected from the group consisting of: NY-ESO-1, Sialyl Lewis X antigen and Tn antigen. In some embodiments, the low affinity target is a cell surface protein on an epithelial cancer cell. In some embodiments, the antibody target is a cell surface protein on a hematologic cancer cell. In some embodiments, the antibody target is selected from the group consisting of: CD19, CD20, CD22, CD33, CD38, CD52 and CD70.

In some embodiments, a modified J-chain comprises a modified human J-chain sequence, or a functional fragment thereof. In some embodiments, the modified human J-chain sequence comprises the native human J-chain sequence of SEQ ID NO: 1. In some embodiments, the J-chain binding moiety is introduced into the native human J-chain sequence of SEQ ID NO: 1 by direct or indirect fusion. In some embodiments, the binding moiety is introduced by indirect fusion through a peptide linker. In some embodiments, the indirect fusion is through a peptide linker at or around a C- and/or an N-terminus of the binding moiety. In some embodiments, the binding moiety is introduced into the native human J-chain sequence of SEQ ID NO: 1 at or around the C-terminus. In some embodiments, the binding moiety is introduced into the native human J-chain sequence of SEQ ID NO: 1 within about 10 residues from the C-terminus. In some embodiments, the binding moiety is introduced into the native human J-chain sequence of SEQ ID NO: 1 at or around the N-terminus. In some embodiments, the binding moiety is introduced into the native human J-chain sequence of SEQ ID NO: 1 within about 10 amino acid residues from the N-terminus. In some embodiments, the binding moiety is introduced into the native human J-chain sequence in between cysteine residues 92 and 101 of SEQ ID NO: 1. In some embodiments, the binding moiety is introduced into the native human J-chain sequence of SEQ ID NO: 1 at or near a glycosylation site. In some embodiments, the peptide linker is about 10 to 20 amino acids long. In some embodiments, the peptide linker is about 15 to 20 amino acids long. In some embodiments, the peptide linker is 15 amino acids long.

In some embodiments, the binding moiety is introduced into the native human J-chain sequence of SEQ ID NO: 1 by chemical or chemo-enzymatic derivatization. In some embodiments, the binding moiety is introduced into the native human J-chain sequence of SEQ ID NO: 1 by a chemical linker. In some embodiments, the chemical linker is a cleavable or non-cleavable linker. In some embodiments, the cleavable linker is a chemically labile linker or an enzyme-labile linker. In some embodiments, the linker is selected from the group consisting of N-succinimidyl-3-(2-pyridyldithio) propionate (SPDP), succinimidyl-4-(N-maleimidomethyl) cyclohexane-1-carboxylate (SMCC), N-succinimidyl-4-(2-pyridylthio) pentanoate (SPP), iminothiolane (IT), bifunctional derivatives of imidoesters, active esters, aldehydes, bis-azido compounds, bis-diazonium derivatives, diisocyanates, and bis-active fluorine compounds. In some embodiments, the modified J-chain is modified by insertion of an enzyme recognition site, and by post-translationally attaching a binding moiety at the enzyme recognition site through a peptide or non-peptide linker.

In some embodiments, a binding moiety is selected from the group consisting of: antibodies, antigen-binding fragments of antibodies, antibody-drug conjugates, antibody-like molecules, antigen-binding fragments of antibody-like molecules, ligands and receptors. In some embodiments, the binding moiety is an antigen-binding fragment and is selected from the group consisting of: F(ab')$_2$, F(ab)$_2$, Fab', Fab, Fv, scFv, and single domain antibody. In some embodiments, the antigen-binding fragment is an scFv.

In some embodiments, the modified J-chain is in a V-linker-J orientation. In some embodiments, the modified J-chain is in a J-linker-V orientation. In some embodiments, the IgM, IgA, IgG/IgM or IgG/IgA antibody is a bispecific antibody. In some embodiments, the IgM, IgA, IgG/IgM or IgG/IgA antibody is a multispecific antibody.

Aspects of the invention include pharmaceutical compositions for the treatment of cancer, wherein the pharmaceutical composition comprises an effective amount of a binding molecule and a pharmaceutically acceptable carrier. Aspects of the invention include sse of a binding molecule in the preparation of a medicament for treating cancer. In some embodiments, the cancer is a hematologic cancer or an epithelial cancer. In some embodiments, the hematologic cancer is a leukemia, lymphoma, myeloma, or myelodysplastic syndrome. In some embodiments, the leukemia is an acute myeloid leukemia, acute lymphoblastic leukemia, chronic myelogenous leukemia, or chronic lymphocytic leukemia. In some embodiments, the lymphoma is Hodgkin's lymphoma or non-Hodgkin's lymphoma. In some embodiments, the epithelial cancer is a melanoma, nonsmall-cell lung, nasopharyngeal, colorectal, liver, urinary bladder, ovarian, gastric, esophageal, pancreatic, renal, thyroid or breast cancer. In some embodiments, the breast cancer is hormone receptor negative or triple negative breast cancer.

In some embodiments, the medicament further comprises an effective amount of a second therapeutic agent.

BRIEF DESCRIPTION OF THE DRAWINGS

FIG. 3 shows the amino acid sequence of mature human J-chain (SEQ ID NO: 1).

FIG. 5 is a schematic illustration of two different orientations of J-chain constructs comprising a modified J-chain with a binding moiety that binds to CTLA4.

FIG. 7 lists IgM, IgA, IgG/IgM or IgG/IgA antibody targets and targets for a binding moiety on a J-chain. Any of the antibody targets listed in the left column can be combined with any of the targets for a binding moiety on a J-chain listed in the right column.

FIG. 12, Panel A shows an SDS PAGE hybrid gel of S70 IgM with the wild type or CD3-binding scFv fused J-chain. Panel B is a graph showing results from a PD-1:PD-L1 interaction blockade assay showing that the CD3-binding J chain does not disrupt PD-L1 binding and resultant blockade of activity.

DETAILED DESCRIPTION OF THE INVENTION

I. Definitions

Figure 1:
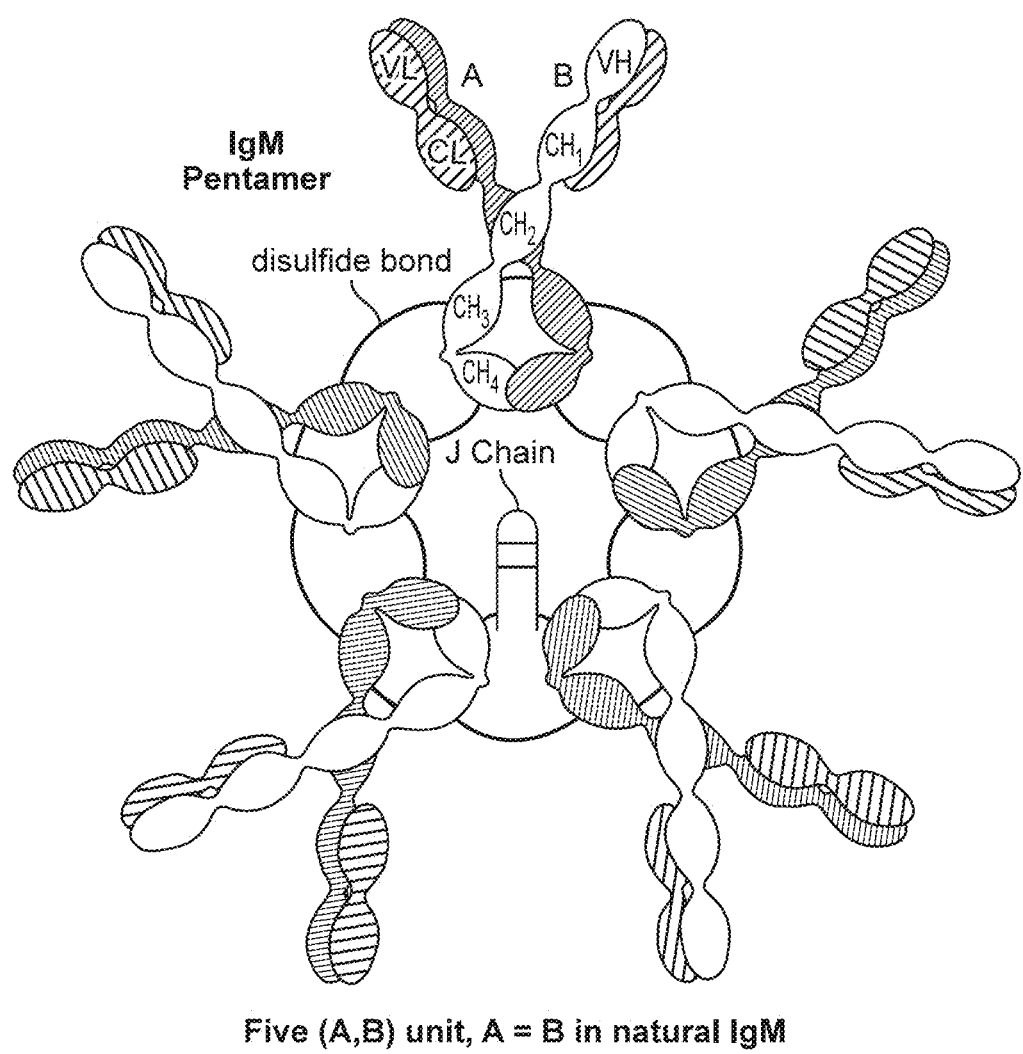
FIG. 1 illustrates the structure of an IgM pentamer, comprising a J-chain, wherein chains A and B are identical in native IgM.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

All publications mentioned herein are expressly incorporated herein by reference to disclose and describe the methods and/or materials in connection with which the publications are cited.

The term "antibody" includes monoclonal antibodies (including full length antibodies which have an immunoglobulin Fc region), single-chain molecules, as well as antibody fragments (e.g., Fab, F(ab')$_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments. Preferred antibodies herein include IgM and IgA antibodies and their antigen-binding fragments, which may be modified to include sequences from other isotypes, such as IgG to produce chimeric antibodies.

In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

IgM is a glycoprotein which forms polymers where multiple immunoglobulins are covalently linked together with disulfide bonds. IgM mostly exists as a pentamer but also as a hexamer and therefore contains 10 or 12 antigen binding sites. The pentameric form typically contains an additional polypeptide, called the J-chain, but can also be made in the absence of J-chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or Cμ1, CM2 or Cμ2, CM3 or Cμ3, and CM4 or Cμ4, wherein the "CM" and "Cμ." designations are used interchangeably. The structure of an IgM pentamer is illustrated in FIG. 1.

The term "IgM" is used herein in the broadest sense and specifically includes mono-, and multi-specific (including bispecific) IgM molecules, such as, for example, the multi-specific IgM binding molecules disclosed in PCT Application No. PCT/US2014/054079, the entire disclosure of which is expressly incorporated by reference herein.

The term "IgM binding unit" or "IgM antibody binding unit" is used in the broadest sense and specifically covers an IgM antibody heavy chain constant region polypeptide, comprising at least a CM4 constant domain, fused to a variable domain sequence ($V_H$) binding to a target (e.g., antigen), with or without an associated antibody light chain variable domain ($V_L$) sequence.

The term "bispecific IgM binding unit" or "bispecific IgM antibody binding unit" is used in the broadest sense and specifically covers a pair of IgM antibody heavy chain constant region polypeptides, comprising at least a CM4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_H V_L$ antigen binding regions, each capable of binding to a different epitope on one antigen or epitopes on two different antigens. The bispecific IgM antibody binding units can be full length from a single species, or be chimerized or humanized. The bispecific IgM antibodies of the present invention have a penta- or hexameric ring structure comprising five or six bispecific IgM binding units.

The term "multi-specific IgM" is used herein in the broadest sense to refer to IgM antibodies with two or more binding specificities. Thus, the term "multi-specific" includes "bispecific", e.g., bispecific antibodies or bispecific binding units, including IgM pentamers comprising at least two monospecific subunits, each binding to a different antigen (AA, BB), or five or six bispecific subunits, each binding to two different antigens (AB, AB). Thus, the bispecific and multi-specific IgM pentamers may include five identical bispecific binding units, monospecific IgM binding units, at least two of them have different binding specificities, or any combination thereof.

A "full length IgM antibody heavy chain" is a polypeptide consisting in N-terminal to C-terminal direction of an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full length IgM antibodies as defined herein comprise five or six monomers (binding units), each with two antigen binding sites, which specifically bind to two different binding targets (epitopes). The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

Figure 2:
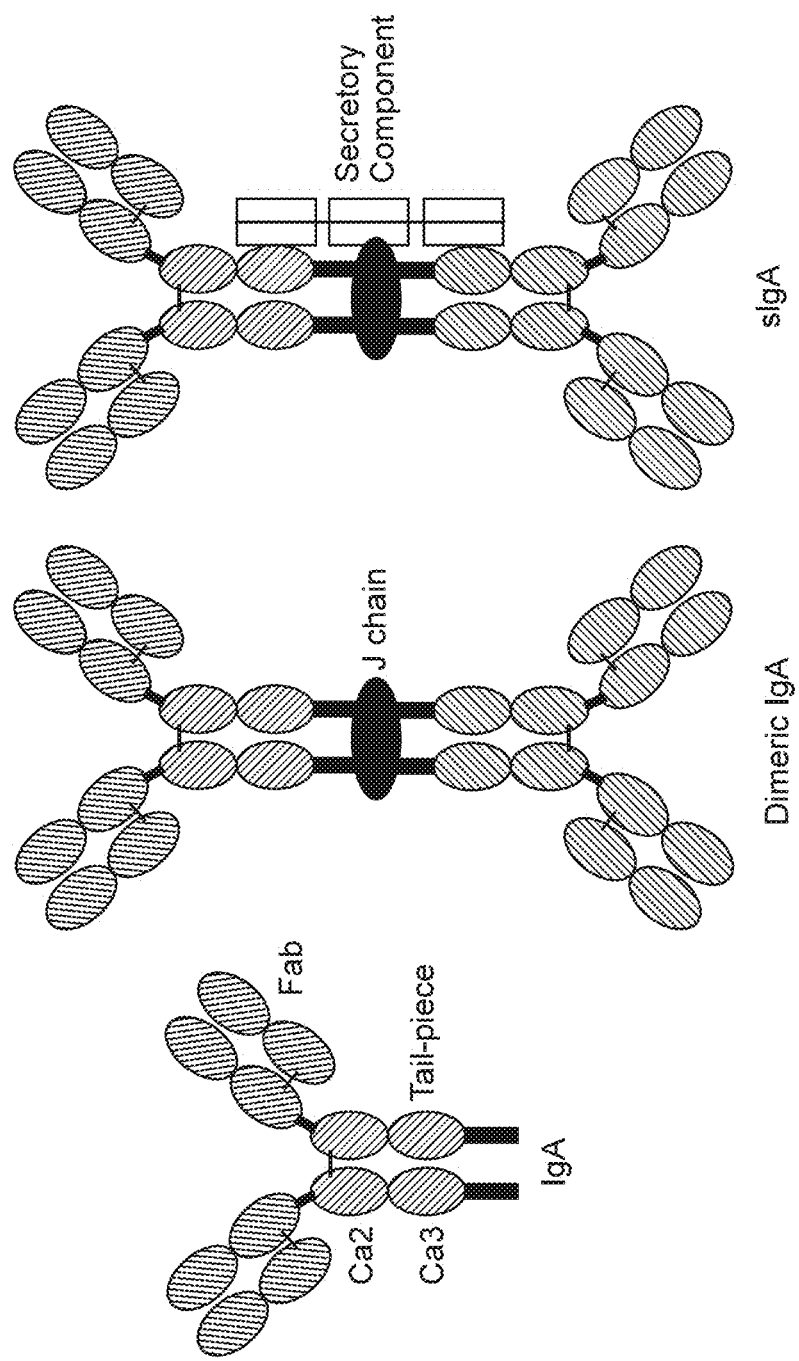
FIG. 2 shows the schematic structures of IgA, dimeric IgA, and secretory IgA (sIgA).

Native IgA is a tetrameric protein comprising two identical light chains (κ or λ) and two identical heavy chains (α). In the human, there are two IgA isotypes, IgA1 and IgA2. IgA, similarly to IgG, contains three constant domains (CA1-CA3 or Cα1-Cα3), with a hinge region between the Cα1 and Cα2 domains, wherein the "CA" and "Cα" designations are used interchangeably. All IgA isotypes have an 18 amino acid "tailpiece", which is located C-terminal to the Cα3 domain, which enables polymeric Ig formation (see, e.g., Garcia-Pardo et al., 1981, *J Biol. Chem.* 256, 11734-11738 and Davis et al., 1988, *Eur. J Immunol.* 18, 1001-1008). Serum IgA is a monomer but can also polymerize. In its secretory form IgA comprises from 2-5 of the basic 4-chain units, linked by a J-chain, which may include a tail-piece, and may be associated by a secretory component. The structures of tail-piece, dimeric IgA and secretory IgA, associated with a secretory component (sIgA) are illustrated in FIG. 2. IgA antibodies can be further divided into IgA1 and IgA2 sub-classes. The term "IgA" antibody is used herein to specifically include all sub-classes, i.e., IgA1 and IgA2 antibodies, including dimeric and multimeric forms, with and without a secretory component, as well as fragments, preferably antigen-binding fragments, of such antibodies. For the purposes of the present invention, the IgA antibody preferably is a dimer, where two tail-pieces are connected by a J-chain (see, FIG. 2).

The term "IgA" is used herein in the broadest sense and specifically includes mono-, and multi-specific IgA molecules, such as, for example, the multi-specific IgA binding molecules disclosed in PCT Application No. PCT/US2015/015268, the entire disclosure of which is expressly incorporated by reference herein.

The term "multi-specific IgA" is used herein in the broadest sense to refer to IgA antibodies with two or more binding specificities. Thus, the term "multi-specific" includes "bispecific", e.g., bispecific antibodies or bispecific binding units, including IgA dimers comprising two monospecific subunits, each binding to a different antigen (AA, BB), or two bispecific subunits, each binding to two different antigens (AB, AB).

In one embodiment, the dimeric multi-specific IgA molecules consist of two monospecific binding units, each binding unit having binding specificity to a different binding target (AA, BB). In another embodiment, in the dimeric IgA molecules at least one of the two binding units has two different binding specificities (i.e., is a bispecific, e.g., AA, A, B or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_H V_L$ antigen binding regions, each capable of binding to a different epitope on one antigen or epitopes on two different antigens. The bispecific IgA antibody binding units can be full length from a single species, or be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). The bi- or multi-specific full length IgA antibodies according to the invention comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

The term "interface", as used herein, is used to refer to a region, which comprises those "contact" amino acid residues (or other non-amino acid groups such as, for example, carbohydrate groups) in a first IgM heavy chain constant region which interact with one or more "contact" amino acid residues (or other non-amino acid groups) in a second IgM heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling a µ heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g., by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e., genetically engineered or mutated) to encode a protuberance or cavity. The original or starting nucleic acid may be a naturally occurring nucleic acid or may comprise a nucleic acid which has been subjected to prior alteration (e.g., a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g., by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g., a humanized monoclonal antibody).

Preferably the import amino acid residue for forming the protuberance has a relatively small number of "rotamers" (e.g., about 3-6). A "rotamer" is an energetically favorable conformation of an amino acid side chain. The number of rotamers for the various amino acid residues are reviewed in Ponders and Richards, J. Mol. Biol. 193: 775-791 (1987).

Unless stated otherwise, the term "antibody" specifically includes native human and non-human IgG1, IgG2, IgG3, IgG4, IgE, IgA, IgD and IgM antibodies, including naturally occurring variants. Thus, for example, the human IgM sequence is given as SEQ ID NO: 110, while variants have been reported as SEQ ID NOs: 111-115.

The term "native" with reference to a polypeptide (e.g., an antibody or a J-chain) is used herein to refer to a polypeptide having a sequence that occurs in nature, regardless of its mode of preparation. Thus, the terms "native" and "native sequence" are used herein interchangeably, and expressly encompass recombinant polypeptides with a sequence that is found in nature.

The term "native sequence J-chain" or "native J-chain" as used herein refers to J-chain of native sequence IgM or IgA antibodies of any animal species, including mature human J-chain, the amino acid sequence of which is shown in FIG. 3 (SEQ ID NO: 1).

The term "modified J-chain" is used herein to refer to variants of native sequence J-chain polypeptides comprising an extraneous binding moiety introduced into the native sequence. The introduction can be achieved by any means, including direct or indirect fusion of an extraneous binding moiety or by attachment through a chemical linker. The term "modified human J-chain" specifically encompasses, without limitation, a native sequence human J-chain of the amino acid sequence of SEQ ID NO: 1 modified by the introduction of a binding moiety. The term specifically encompasses, without limitation, a native sequence human J-chain of the amino acid sequence of SEQ ID NO: 1 modified by the introduction of an extraneous binding moiety which does not interfere with efficient polymerization (dimerization) of IgM or IgA and binding of such polymers (dimers) to a target The term "binding moiety" is used herein in the broadest sense to encompass any chemical entity capable of specific binding to a target, such as an antigen. Examples of binding moieties include, without limitation, antibodies, antigen-binding fragments of antibodies, antibody-drug conjugates, antibody-like molecules, antigen-binding fragments of antibody-like molecules, ligands and receptors. Preferred binding moieties are polypeptides (including peptides), preferably with a biological function. An example of a biological function is the ability of a binding moiety to bind to and activate or block the activity of a signaling pathway.

The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "extraneous" with reference to a "binding moiety" is used herein to refer to a binding moiety not present in a reference native polypeptide sequence at the same location. Thus, an extraneous polypeptide sequence (including peptide sequences), might be comprised within the corresponding native sequence but at a different location. In a preferred embodiment, the "extraneous" sequence is not present in the corresponding native sequence in any location.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352:624-628 and Marks et al. (1991) J. Mol. Biol. 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding nonhuman residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) Nature 321:522-525; Riechmann et al. (1988) Nature 332:323-329; and Presta (1992) Curr. Op. Struct. Biol. 2:593-596.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or non-proteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of a amino acid sequencer, or (3) to homogeneity by SDS-PAGE under reducing or non-reducing conditions using Coomassie blue or, preferably, silver stain. Ordinarily, an isolated antibody will be prepare by at least one purification step.

The term "specific binding" or "specifically binds to" or is "specific for" refers to the binding of a binding moiety to a binding target, such as the binding of an antibody to a target antigen, e.g., an epitope on a particular polypeptide, peptide, or other target (e.g., a glycoprotein target), and means binding that is measurably different from a non-specific interaction (e.g., a non-specific interaction may be binding to bovine serum albumin or casein). Specific binding can be measured, for example, by determining binding of a binding moiety, or an antibody, or an antibody modified by introduction of a binding moiety, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$ M, or $10^{-8}$ M or better.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances, which elicit the production of antibodies, and/or activate T-cells and/or other reactive immune cells directed against an antigen of the immunogen.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a VH or a VL domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "antagonist" as used herein refers to a molecule that causes a decrease in a function or activity as compared to the same function or activity in the absence of the molecule. An "antagonist" of a signaling pathway is therefore a molecule whose presence causes a decrease in a function or activity of the signaling pathway. The term "antagonize" as used herein refers to causing a decrease in a function or activity.

The term "agonist" as used herein refers to a molecule that causes an increase in a function or activity as compared to the same function or activity in the absence of the molecule. An "agonist" of a signaling pathway is therefore a molecule whose presence causes an increase in a function or activity of the signaling pathway. The term "agonize" as used herein refers to causing an increase in a function or activity.

The term "T-cell inhibitory signaling pathway" as used herein refers to a T-cell signaling pathway that leads to a qualitative or quantitative decrease in, blocking or, or halting of a T-cell immune response.

The term "T-cell stimulatory signaling pathway" as used herein refers to a T-cell signaling pathway that leads to a qualitative or quantitative increase in or maintenance of a T-cell immune response.

The term "low level expression target" as used herein refers to a target whose expression level on a target cell ranges from 0 to 1+, as determined by immunohistochemistry (IHC) tissue analysis, preferably performed on frozen, formalin-fixed, paraffin-embedded tissue sections. Guidelines for determining expression level via IHC are provided, for example, by the College of American Pathologists (CAP), and are exemplified by the ASCO-CAP HER2 Test Guideline Recommendations, available on the World Wide Web at cap.org/apps/docs/committees/immunohistochemistry/summary_of_recommendations.pdf.

The term "low affinity target" as used herein refers to a target whose binding interaction with an antibody has a dissociation constant $K_d$ that is greater than or equal to a value ranging from about 10 to 100 nM, such as about 25 to about 75 nM, as measured by ELISA.

Design and Production of Binding Molecules with Modified J-Chain

IgM is the first immunoglobulin produced by B cells in response to stimulation by antigen, and is present at around 1.5 mg/ml in serum with a half-life of 5 days. IgM is a pentameric or hexameric molecule. Just as IgG, IgM monomers consist of two light and two heavy chains. However, while IgG contains three heavy chain constant domains ($C_H1$, $C_H2$ and $C_H3$), the heavy (μ) chain of IgM additionally contains a fourth constant domain ($C_H4$), similarly to the ε heavy chains in IgE. This extra constant domain is located in place of the IgG and IgA proline-rich hinge region that is responsible for the rotational flexibility of the antigen-binding Fab domains relative to the Fc domain of IgG and IgA antibodies.

Five IgM monomers form a complex with an additional small polypeptide chain (the J-chain) to form a native IgM molecule. The J-chain is considered to facilitate polymerization of μ chains before IgM is secreted from antibody-producing cells. While crystallization of IgM has proved to be notoriously challenging, Czajkowsky and Shao (PNAS 106(35):14960-14965, 2009) recently published a homology-based structural model of IgM, based on the structure of the IgE Fc domain and the known disulfide pairings. The authors report that the human IgM pentamer is a mushroom-shaped molecule with a flexural bias. The IgM heavy (μ) chain contains five N-linked glycosylation sites: Asn-171, Asn-332, Asn-395, Asn-402 and Asn-563.

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcαR, are key mediators of IgA effector function. Human IgA may have two different IgA heavy constant region (Cα) genes which give rise to the two subclasses, IgA1 and IgA2. The main difference between IgA1 and IgA2 resides in the hinge region that lies between the two Fab arms and the Fc region. IgA1 has an extended hinge region due to the insertion of a duplicated stretch of amino acids, which is absent in IgA2. IgA has the capacity to form dimers, in which two monomer units, each comprising two heavy chains and light chains, are postulated to be arranged in an end-to-end configuration stabilized by disulfide bridges and incorporation of a J-chain. Dimeric IgA, produced locally at mucosal sites, is transported across the epithelial cell boundary and out into the secretions by interaction with the polymeric immunoglobulin receptor (pIgR). During this process the pIgR is cleaved and the major fragment, termed secretory component (SC), becomes covalently attached to the IgA dimer.

Both IgA and IgM possess an 18-amino acid extension in the C terminus called the "tail-piece" (tp). The IgM (μtp) and IgA (αtp) tail-pieces differ at seven amino acid positions. The IgM and IgA tail-piece is highly conserved among various animal species. The conserved penultimate cysteine residue in the IgA and IgM tail-pieces has been demonstrated to be involved in polymerization. Both tail-pieces contain an N-linked carbohydrate addition site, the presence of which is required for dimer formation in IgA and J-chain incorporation and pentamer formation in IgM. However, the structure and composition of the N-linked carbohydrates in the tail-pieces differ, suggesting differences in the accessibility of the glycans to processing by glycosyltransferases.

The nucleotide and/or protein sequences of J-chains of human, and various vertebrate animal species, such as cow, mouse, avian, amphibian, and rabbit, have been reported. The human J-chain contains eight cysteine residues, two (Cys13 and Cys69) are involved in disulfide bridges with the α or μ-chains (in IgA and IgM, respectively), and six are involved in intrachain disulfide bridges (Cys13: Cys101, Cys72: Cys92, Cys109: Cys134). The three-dimensional crystal structure of the J-chain has not been reported.

Figure 6:
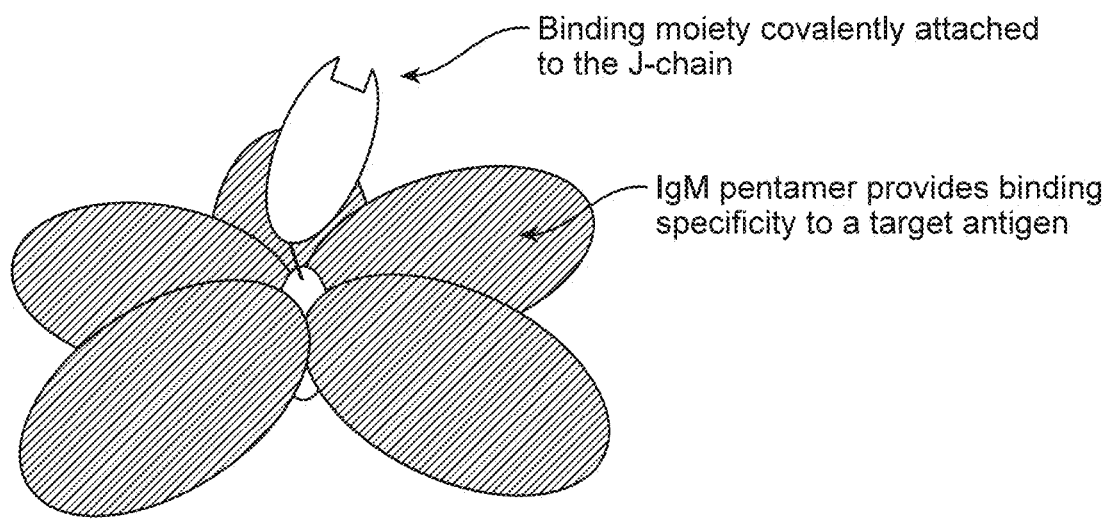
FIG. 6 is a schematic illustration of an asymmetric IgM pentamer with binding specificity for a target antigen and comprising a binding moiety attached to the J-chain.

The binding molecules of the present invention include a J-chain that comprises a binding moiety that antagonizes a T-cell inhibitory signaling pathway, without interfering with the ability of the IgM, IgA, IgG/IgM or IgG/IgA antibody to bind to its binding target(s). A binding molecule can, for example, be an IgM antibody, an IgA antibody, or an IgG/IgM or IgG/IgA hybrid antibody, which may contain an IgM or IgA tail-piece at the IgG heavy chain and thus combine the properties of IgG and IgA or IgA, including the ability to incorporate and form polymers with a modified J-chain whose binding moiety antagonizes a T-cell inhibitory signaling pathway. For further details on IgG/IgM and IgG/IgA hybrid antibodies see, e.g., Koteswara et al., Clinical Immunology 2001, 101(1):21-31. An illustration of an example binding molecule in accordance with aspects of the invention is depicted in FIG. 6. The depicted binding molecule comprises an IgM pentamer with binding specificity for a target antigen, and comprises a binding moiety attached to the J-chain.

T-cell inhibitory signaling pathways are known in the art, and include, without limitation, those described in Pardoll, Drew M. "The blockade of immune checkpoints in cancer immunotherapy." *Nature Reviews Cancer* 12.4 (2012): 252-264, the disclosure of which is herein incorporated by reference in its entirety. Non-limiting examples of T-cell inhibitory signaling pathways and components thereof are described in further detail below.

Cytotoxic T-lymphocyte-associated protein 4 (CTLA4) is a member of the immunoglobulin superfamily and has been shown to transmit an inhibitory signal to T-cells. The membrane-bound isoform of CTLA4 functions as a homodimer interconnected by a disulfide bond, while the soluble isoform functions as a monomer. E.g., Pardoll at 255.

In addition to CTLA4, other T-cell inhibitory signaling pathways include, for example, those involving programmed cell death-1 (PD-1) and its ligand, programmed cell death ligand-1 (PD-L1). PD-1 is an inhibitory cell surface receptor protein of the immunoglobulin superfamily, and is involved in the regulation of T-cell function in immunity and self-tolerance. PD-L1 interacts with PD-1 on the surface of T-cells, and inhibits proliferation of T-cells by blocking cell cycle progression and cytokine production. Id.

Another example of a T-cell inhibitory signaling pathway is the signaling pathway involving T-cell immunoglobulin and mucin domain 3 (TIM3). TIM3 is a cell surface glycoprotein that is expressed on the surface of T-cells, and functions as an inhibitory molecule that is involved in the termination of Th1 cells. Id.

Another example of a T-cell inhibitory signaling pathway is the signaling pathway involving lymphocyte-activation gene 3 (LAG3). LAG3 belongs to the immunoglobulin superfamily, and functions as an inhibitor of cellular proliferation, activation and homeostasis of T-cells. Id.

Another example of a T-cell inhibitory signaling pathway is the signaling pathway involving B- and T-lymphocyte attenuator protein (BTLA). BTLA is a cell surface protein that functions by inhibiting T-cells via interaction with members of the tumor necrosis factor receptor superfamily. BTLA is known to negatively regulate T-cell immune responses. Id.

Another example of a T-cell inhibitory signaling pathway is the signaling pathway involving V-domain Ig suppressor of T-cell activation (VISTA). VISTA is a regulator of T-cell function that is expressed on hematopoietic cells and leukocytes, and functions by suppressing T-cell activation. E.g., Lines J L, et al., Cancer research. 2014; 74(7):1924-1932.

Another example of a T-cell inhibitory signaling pathway is the signaling pathway involving the protein T-cell immunoreceptor with Ig and ITIM Domains (TIGIT). TIGIT is expressed in several classes of T-cells, and binds with high affinity to the poliovirus receptor. TIGIT suppresses T-cell activation by promoting generation of mature immunoregulatory dendritic cells. E.g., Yu X et al., Nat Immunol. 2009 January; 10(1):48-57.

As reviewed above, the subject binding molecules comprise a binding moiety on the J-chain that antagonizes a T-cell inhibitory signaling pathway. In some embodiments, a binding moiety on the J-chain binds to a target in a T-cell inhibitory signaling pathway, and thereby blocks or diminishes inhibitory signals that are received by a T-cell via the pathway. As a result, the T-cell's immune response is not blocked, halted or diminished, or, at least, the inhibition of the T-cell's immune response is reduced or diminished. The binding moiety on the J-chain of a subject binding molecule can be used to antagonize any T-cell inhibitory signaling pathway, including but not limited to the inhibitory signaling pathways that involve the proteins listed in Table 1, below. The GenBank Accession Numbers corresponding to the human protein sequences of these T-cell inhibitory signaling pathway targets are provided in Table 1, below.

TABLE 1

Sequence information
for T-cell inhibitory signaling pathway targets

| T-cell inhibitory signaling pathway member: | SEQ ID NO. |
|---|---|
| CTLA4 | 16 |
| PD-1 | 17 |
| TIM3 | 18 |
| LAG3 | 19 |
| BTLA | 20 |
| VISTA | 21 |
| TIGIT | 22 |

A binding moiety on the J-chain of a subject binding molecule can include, without limitation, antibodies, antigen-binding fragments of antibodies, antibody-drug conjugates, antigen-binding fragments of antibody-drug conjugate, antibody-like molecules, antigen-binding fragments of antibody-like molecules, soluble and membrane-bound proteins, ligands and receptors. It is emphasized that any type of binding moiety can be introduced into a J-chain, following the teaching of the present disclosure, by appropriately selecting the location and type of addition (e.g., direct or indirect fusion, chemical tethering, etc.).

In a preferred embodiment, a binding moiety on a J-chain is an antibody or an antigen-binding fragment of an antibody (also referred to as an "antibody fragment"), including monospecific, bispecific, and multi-specific antibodies and antibody fragments, that functions as an antagonist of a T-cell inhibitory signaling pathway. The term "antibody fragment" is used in the broadest sense and includes, without limitation, Fab, Fab', F(ab')$_2$, scFv, and (scFv)$_2$ fragments, complementarity determining region (CDR) fragments, linear antibodies, single-chain antibody molecules, minibodies, and multi-specific antibodies formed from antibody fragments. In a preferred embodiment, the antibody fragment is a single chain Fv (scFv).

In another preferred embodiment, a binding moiety on a J-chain is an antibody-like molecule, such as, for example, a human domain antibody (dAb), Dual-Affinity Re-Targeting (DART) molecule, a diabody, a di-diabody, dual-variable domain antibody, a Stacked Variable Domain antibody, a Small Modular ImmunoPharmaceutical (SMIP), a Surrobody, a strand-exchange engineered domain (SEED)-body, or TandAb that functions as an antagonist of a T-cell inhibitory signaling pathway.

A binding moiety on a J-chain can be introduced into a native J-chain sequence at any location that allows the binding of the binding moiety to its binding target without interfering with the binding of the recipient IgM, IgA, IgG/IgM or IgG/IgA molecule to its binding target or binding targets. Preferred locations include at or near the C-terminus, at or near the N-terminus or at an internal location that, based on the three-dimensional structure of the J-chain is accessible. In preferred embodiments, the binding moiety is introduced into the native sequence J-chain without about 10 residues from the C-terminus or without about 10 amino acid residues from the N-terminus, where the native sequence J-chain preferably is human J-chain of SEQ ID NO: 1. In another embodiment, the binding moiety is introduced into the native sequence human J-chain of SEQ ID NO: 1 in between cysteine residues 92 and 101 of SEQ ID NO: 1, or at an equivalent location of another native sequence J-chain. In a further embodiment, the binding moiety is introduced in a native sequence J-chain, such as a J-chain of SEQ ID NO: 1, at or near a glycosylation site.

Most preferably, the binding moiety is introduced into the native sequence human J-chain of SEQ ID NO: 1 within about 10 amino acid residues from the C-terminus.

Introduction can be accomplished by direct or indirect fusion, i.e., by the combination of the J-chain and binding moiety amino acid sequences in one polypeptide chain by in-frame combination of their coding nucleotide sequences, with or without a peptide linker. The peptide linker (indirect fusion), if used, may, for example, be about 1 to 50, or about 1 to 40, or about 1 to 30, or about 1 to 20, or about 1 to 10, or about 10 to 20 amino acid residues, and may be present at one or both ends of the binding moiety to be introduced into the J-chain sequence. In a preferred embodiment, the peptide linker is about 10 to 20, or 10 to 15 amino acids long. In another preferred embodiment, the peptide linker is 15 amino acids long.

A J-chain binding moiety can also be appended to a native J-chain sequence by chemical linkage using heterobifunctional protein crosslinkers containing two different functional groups, which have their own reactivity and selectivity. These crosslinkers can be used in a one step process or can be used to create activated proteins, which can often be preserved and reacted with the second biomolecule in a separate step. Thus, for example, a heterobifunctional cross-linking reagent can be used to form conjugates between a J-chain and a binding moiety. The reactive groups include, without limitation imine reactive groups (such as NHS or Sulfo-NHS), maleimide groups, and the like. Such cross-linkers, which can be cleavable or non-cleavable, have been used, for example, in the formation of hapten carrier proteins and in preparing enzyme-antibody conjugates. Chemically, the cleavable crosslinkers specifically include, without limitation, disulfide-based, hydrazone, and peptide linkers. A well-known and much studied enzyme-labile linker is a valine-citrulline linker but other peptide linkers are also known and suitable. Typical representatives of non-cleavable linkers include thioethers, such as SMCC (N-succinimidyl-4-(N-maleimidomethyl)-cyclohexane-1-carboxylate). For further details see, e.g., Ducry L and Stump B, Bioconjugate Chem. 2010, 21:5-13, the entire disclosure of which is expressly incorporated by reference herein. For listing of further suitable linkers see, e.g., Klein et al., Protein Engineering, Design & Selection; 2014, 27(10): 325-330, the entire disclosure of which is expressly incorporated by reference herein.

In some embodiments, a binding molecule comprises an amino acid sequence listed in Table 7. In some embodiments, a binding molecule comprises an amino acid sequence that is substantially similar to an amino acid sequence listed in Table 7, for example, has at least about 80% amino acid sequence identity, alternatively, has about 81%, 82%, 83%, 84%, 85%, 86%, 87%, 88%, 89%, 90%, 91%, 92%, 93%, 94%, 95%, 96%, 97%, 98%, 99%. 99.5%, or about 99.9% amino acid sequence identity to an amino acid sequence that is listed in Table 7.

While the modified J-chain usually contains one extraneous binding moiety, it is also possible to introduce more than one binding moiety into a J-chain. In some embodiments, a modified J-chain comprises one extraneous binding moiety. In some embodiments, a modified J-chain comprises more than one extraneous binding moiety. For example, in some embodiments, one binding moiety is introduced into a modified J-chain at either the N-terminus or the C-terminus. In some embodiments, a first binding moiety is introduced into a modified J-chain at the N-terminus, and a second binding moiety is introduced into the same modified J-chain at the C-terminus. For examples, in some embodiments, a first binding moiety is introduced into a modified J-chain at the N-terminus, and a second binding moiety is introduced into the same modified J-chain at the C-terminus. A binding molecule that comprises a binding moiety at both the N-terminus and the C-terminus of the J-chain is referred to herein as a binding molecule that comprises a "bidentate" J-chain.

The modified J-chain may be produced by well-known techniques of recombinant DNA technology, by expressing nucleic acid encoding the modified J-chain in a suitable prokaryotic or eukaryotic host organism, such as CHO cells or *E. coli*. Thus, the modified J-chain may, for example, be expressed in *E. coli*, as described by Symersky et al., Mol Immunol 2000, 37:133-140.

In one embodiment, the J-chain can be initially modified by insertion of an enzyme recognition site, and post-translationally modified by a peptide or non-peptide linker, which can tether any extraneous binding moiety to the J-chain, such as, for example, cytotoxic small molecule to make an antibody-drug conjugate (ADC).

The modified J-chain can also be co-expressed with the heavy and light chains of the recipient IgM, IgA, IgG/IgM or IgG/IgA antibody. Although due to its complex structure, the large scale production of recombinant IgM has been difficult, several recombinant production systems for IgM using non-lymphoid cells have been reported, including co-expression of the IgM heavy (H) and light (L) chains in C6 glioma cells, CHO cells, and HeLa cells (see, e.g. WO89/01975 and Wood et al., J. Immunol. 145, 3011-3016 (1990) for expression in CHO cells). Expression of an IgM monoclonal antibody in *E. coli*, with or without a J-chain, is described, e.g., in Azuma et al., Clin Cancer Res 2007, 13(9):2745-2750. Production of IgM in an immortalized human retina cell line expressing E1A and E1B proteins of an adenovirus is described in U. S. Application Publication No. 20060063234.

The recipient IgM, IgA, IgG/IgM or IgG/IgA antibody may be monospecific, bispecific or multi-specific. Bispecific and multi-specific IgM and IgA binding molecules, including antibodies, are described, for example, in PCT Application No. PCT/US2014/054079 and PCT/US2015/015268, the entire disclosures of which are expressly incorporated by reference herein.

A subject binding molecule can bind to any binding target via the IgM, IgA, IgG/IgM or IgG/IgA antibody, while the J-chain binding moiety antagonizes a T-cell inhibitory signaling pathway. As such, the subject binding molecules can be used to localize the functionality of the J-chain binding moiety to the location of a binding target that is targeted by the IgM, IgA, IgG/IgM or IgG/IgA antibody. Classes of antibody targets are described in further detail below.

Antagonist Targets

Aspects of the invention include binding molecules having an IgM, IgA, IgG/IgM or IgG/IgA antibody that antagonizes a T-cell inhibitory signaling pathway. T-cell inhibitory signaling pathways are known in the art, and include, without limitation, those described in Pardoll et al. Non-limiting examples of T-cell inhibitory signaling pathways and components thereof are described in further detail below.

One example of a T-cell inhibitory signaling pathway is the signaling pathway involving programmed cell death-1 (PD-1) and its ligand, programmed cell death ligand-1 (PD-L1). PD-1 is an inhibitory cell surface receptor protein of the immunoglobulin superfamily, and is involved in the regulation of T-cell function in immunity and self-tolerance. PD-L1 interacts with PD-1 on the surface of T-cells, and inhibits proliferation of T-cells by blocking cell cycle progression and cytokine production. Id.

Another example of a T-cell inhibitory signaling pathway is the signaling pathway involving T-cell immunoglobulin and mucin domain 3 (TIM3). TIM3 is a cell surface glycoprotein that is expressed on the surface of T-cells, and functions as an inhibitory molecule that is involved in the termination of Th1 cells. Id.

Another example of a T-cell inhibitory signaling pathway is the signaling pathway involving lymphocyte-activation gene 3 (LAG3). LAG3 belongs to the immunoglobulin superfamily, and functions as an inhibitor of cellular proliferation, activation and homeostasis of T-cells. Id.

As reviewed above, the subject binding molecules comprise a J-chain binding moiety that antagonizes a T-cell inhibitory signaling pathway. In some embodiments, an IgM, IgA, IgG/IgM or IgG/IgA antibody binds to a target that is involved in a T-cell inhibitory signaling pathway and antagonizes the inhibitory signaling pathway, thereby blocking or diminishing inhibitory signals that are received by a T-cell via the pathway, while the J-chain binding moiety also antagonizes a T-cell inhibitory signaling pathway. Due to their higher avidity, the subject IgM, IgA, IgG/IgM or IgG/IgA antibodies act more effectively as antagonists when directed against T-cell inhibitory signaling pathway targets, as compared to IgG antibodies, which only have two binding sites. As a result, the T-cell's immune response is not blocked, halted or diminished, or, at least, the inhibition of the T-cell's immune response is reduced or diminished. The antibody of a subject binding molecule can be used to antagonize any T-cell inhibitory signaling pathway, including but not limited to the inhibitory signaling pathways that involve the proteins listed in Table 2, below. The GenBank Accession Numbers corresponding to the human protein sequences of these T-cell inhibitory signaling pathway targets are provided in Table 2, below.

TABLE 2

| Sequence information for T-cell stimulatory signaling pathway targets | |
|---|---|
| T-cell stimulatory signaling pathway member: | SEQ ID NO. |
| PD-1 | 23 |
| PD-L1 | 24 |
| TIM3 | 25 |
| LAG3 | 26 |

Agonist Targets

Aspects of the invention include binding molecules having an IgM, IgA, IgG/IgM or IgG/IgA antibody that agonizes a T-cell stimulatory signaling pathway. T-cell stimulatory signaling pathways are known in the art, and include, without limitation, those described in Pardoll et al. Non-limiting examples of T-cell stimulatory signaling pathways and components thereof are described in further detail below.

CD137 is a member of the tumor necrosis factor receptor (TNF-R) superfamily, and is expressed on the surface of T-cells. Its function is to stimulate T-cell proliferation and cytokine secretion. E.g., Pardoll at 254. OX40 is another member of the tumor necrosis factor receptor superfamily that is expressed on T-cells, and it functions by delivering a stimulatory signal to T-cells that helps to maintain the immune response over time. Id.

Another T-cell stimulatory signaling pathway involves CD40. CD40 is a member of the tumor necrosis factor receptor superfamily, and is expressed on antigen presenting cells. Engagement of CD40 with its ligand CD40L results in various T-cell stimulatory signals. Id.

Another T-cell stimulatory signaling pathway involves gluococorticoid-induced TNFR-related protein (GITR). GITR is a member of the tumor necrosis factor receptor superfamily, and is expressed on T-cells. It functions by increasing T-cell proliferation, activation and cytokine production. E.g., Nocentini, G. et al., Proc Natl Acad Sci USA. 1997 Jun. 10; 94(12): 6216-21.

CD27 is another protein that is involved in a T-cell stimulatory signaling pathway. Another member of the tumor necrosis factor receptor superfamily, CD27 is expressed on the surface of T-cells and functions by delivering a stimulatory signal to T-cells when it interacts with CD70. E.g., Pardoll at 254.

Another T-cell stimulatory signaling pathway involves herpesvirus entry mediator (HVEM). HVEM is a member of the tumor necrosis factor receptor superfamily, and is expressed on the surface of antigen presenting cells. When HVEM interacts with certain ligands, such as CD258, it delivers a stimulatory signal to T-cells. Id.

As reviewed above, the subject binding molecules comprise a binding moiety on the J-chain that antagonizes a T-cell inhibitory signaling pathway. In some embodiments, an IgM, IgA, IgG/IgM or IgG/IgA antibody binds to a target that is involved in a T-cell stimulatory signaling pathway and agonizes the stimulatory signaling pathway, thereby maintaining or increasing stimulatory signals that are received by a T-cell via the pathway, while the binding moiety on the J-chain antagonizes a T-cell inhibitory signaling pathway. Due to their higher avidity, the subject IgM, IgA, IgG/IgM or IgG/IgA antibodies act more effectively as agonists when directed against T-cell stimulatory signaling pathway targets, as compared to IgG antibodies, which only have two binding sites. As a result, a T-cell's immune response is maintained or increased. An antibody of a subject binding molecule can be used to agonize any T-cell stimulatory signaling pathway, including but not limited to the stimulatory signaling pathways that involve the proteins listed in Table 3, below. The GenBank Accession Numbers corresponding to the human protein sequences of these T-cell stimulatory signaling pathway targets are provided in Table 3, below.

TABLE 3

| Sequence information for T-cell stimulatory signaling pathway targets | |
|---|---|
| T-cell stimulatory signaling pathway member: | SEQ ID NO. |
| CD137 (4-1BB) | 116 |
| OX40 | 117 |
| CD40 | 118 |
| GITR | 119 |
| CD27 | 120 |
| HVEM | 121 |

Other non-limiting examples of T-cell stimulatory signaling pathways include those mediated by: TNFR1 (DR1) (SEQ ID NO: 122); TNFR2 (SEQ ID NO: 123); Fas (CD95, Apo1, DR2) (SEQ ID NO: 124); CD30 (SEQ ID NO: 125); TRAILR1 (DR4, Apo2) (SEQ ID NO: 126); DR5 (TRAILR2) (SEQ ID NO: 127); TRAILR3 (DcR1) (SEQ ID NO: 128); TRAILR4 (DcR2) (SEQ ID NO: 129); OPG (OCIF) (SEQ ID NO: 130); TWEAKR (FN14) (SEQ ID NO: 131); DcR3 (SEQ ID NO: 132); DR3 (SEQ ID NO: 133); EDAR (SEQ ID NO: 134); and XEDAR (SEQ ID NO: 135). See, e.g., Aggarwal et al., Blood, 119:651-665, 2012, the disclosure of which is herein incorporated by reference in its entirety. In some embodiments, an IgM, IgA, IgG/IgM or IgG/IgA antibody binds to any one of these targets and agonizes a T-cell stimulatory signaling pathway, thereby maintaining or increasing stimulatory signals that are received by a T-cell via the pathway, while the binding moiety on the J-chain antagonizes a T-cell inhibitory signaling pathway.

Low Level Expression Targets

Aspects of the invention include binding molecules having an IgM, IgA, IgG/IgM or IgG/IgA antibody that binds to a low level expression target. Due to their higher avidity, the subject binding molecules are more potent than IgG antibodies. As such, the subject binding molecules can be employed in settings where a particular binding target is expressed at a low level, and where higher avidity is beneficial in facilitating binding between an antibody and a target. An antibody of a subject binding molecule can be used to target any low level expression target. Specific examples of low level expression targets that may be targeted by an IgM, IgA, IgG/IgM or IgG/IgA antibody of the subject binding molecules include, without limitation, EGFR, HER2, HER3, EpCAM, CEACAM, Gp100, MAGE1 and PD-L1. The GenBank Accession Numbers corresponding to the human protein sequences of these targets are provided in Table 4, below.

TABLE 4

| Sequence information for low level expression targets | |
|---|---|
| Target Name | SEQ ID NO. |
| EGFR | 136 |
| HER2 | 137 |
| HER3 | 138 |
| EpCAM | 139 |
| CEACAM | 140 |
| Gp100 | 141 |
| MAGE1 | 142 |
| PD-L1 | 143 |

Low Affinity Targets

Figure 4:
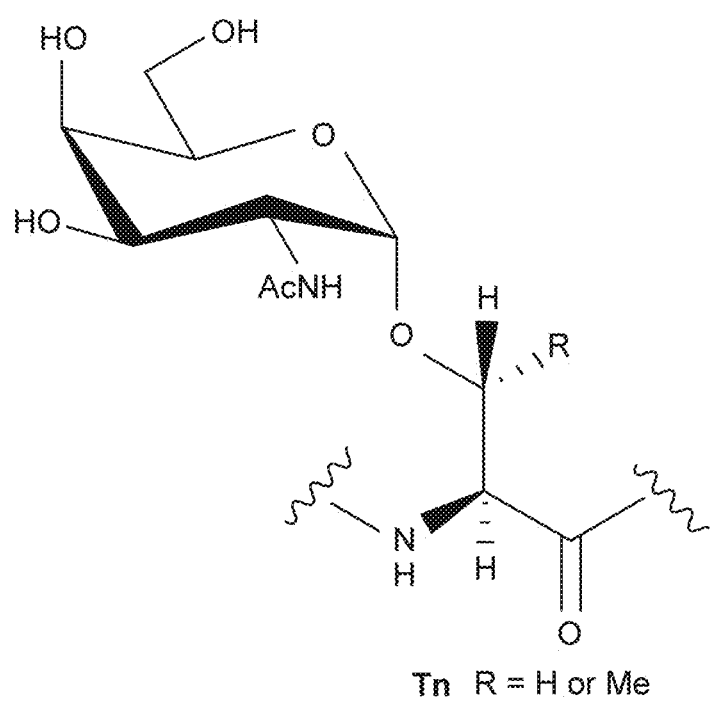
FIG. 4 is an illustration of the structure of Tn antigen.

Aspects of the invention include binding molecules having an IgM, IgA, IgG/IgM or IgG/IgA antibody that binds to a low affinity target. Due to their higher avidity, the subject binding molecules are more potent than IgG antibodies. As such, the subject binding molecules can be employed in settings where a particular binding target has a low binding affinity, and where higher avidity is beneficial in facilitating binding between an antibody and a target. An antibody of a subject binding molecule can be used to target any low affinity target. Specific examples of low affinity targets that may be targeted by an IgM, IgA, IgG/IgM or IgG/IgA antibody of the subject binding molecules include, without limitation, NY-ESO-1, Sialyl Lewis X antigen, and Tn antigen. The GenBank Accession Numbers corresponding to the human protein sequences of NY-ESO-1 and Sialyl Lewis X antigen are provided in Table 5, below. The structure of Tn antigen is provided in FIG. 4.

TABLE 5

Sequence information for low affinity targets

| Target Name | SEQ ID NO. |
| --- | --- |
| NY-ESO-1 | 144 |
| Sialyl Lewis X antigen | 145 |

Hematologic Cancer Targets

Aspects of the invention include binding molecules having an IgM, IgA, IgG/IgM or IgG/IgA antibody that binds to a hematologic cancer target. Due to their higher avidity, the subject binding molecules are more potent than IgG antibodies. As such, the subject binding molecules can be employed in settings where a particular binding target is expressed at a low level, as is the case in certain hematologic cancers. The higher avidity of the subject binding molecules facilitates binding between an antibody and a target. An antibody of a subject binding molecule can be used to target any binding target, such as a low level expression target on a hematologic cancer cell. Specific examples of hematologic cancer targets that can be targeted by an IgM, IgA, IgG/IgM or IgG/IgA antibody of the subject binding molecules include, without limitation, CD19, CD20, CD22, CD33, CD38, CD52 and CD70. The GenBank Accession Numbers corresponding to the human protein sequences of these targets are provided in Table 6, below.

TABLE 6

Sequence information for hematologic cancer targets

| Target Name | SEQ ID NO. |
| --- | --- |
| CD19 | 146 |
| CD20 | 147 |
| CD22 | 148 |
| CD33 | 149 |
| CD38 | 150 |
| CD52 | 151 |
| CD70 | 152 |

Applications of Binding Molecules with Modified J-Chain

Binding molecules comprising a modified J-chain of the present invention have widespread therapeutic and diagnostic applications, including but not limited to the treatment of various cancers and immune diseases by modulating, among other things, the activity of a T-cell immune response. The subject binding molecules comprising a modified J-chain may broadly be used for the treatment of any of a variety of cancers. It is anticipated that any type of tumor and any type of tumor-associated antigen may be targeted by the subject binding molecules. Examples of cancer types include, without limitation, acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer. However, the skilled artisan will realize that tumor-associated antigens are known in the art for virtually any type of cancer.

In some embodiments, a J-chain of a subject binding molecule includes a binding moiety that antagonizes a T-cell inhibitory signaling pathway, and the antibody also antagonizes a T-cell inhibitory signaling pathway. Without being held to theory, the purpose of such a binding molecule is to block or decrease T-cell inhibitory signaling via both the antibody and the binding moiety on the J-chain. Such binding molecules provide a blockade or decrease of T-cell inhibitory signaling, thereby maintaining or increasing a T-cell immune response at a specific location, such as, e.g., the surface of a cancer cell. Due to their increased avidity, the subject IgM, IgA, IgG/IgM and IgG/IgA antibodies act more effectively as antagonists when directed to certain binding targets, such as members of a T-cell inhibitory signaling pathway, as described above. Such binding molecules find utility, for example, in the treatment of diseases wherein maintenance or activation of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an antagonist antibody and an antagonist binding moiety on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an antagonist antibody and an antagonist binding moiety on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, a J-chain of a subject binding molecule includes a binding moiety that antagonizes a T-cell inhibitory signaling pathway, while the antibody agonizes a T-cell stimulatory signaling pathway. Without being held to theory, the purpose of such a binding molecule is to block or decrease T-cell inhibitory signaling via the J-chain moiety, while simultaneously maintaining or increasing T-cell stimulatory signaling via the antibody. Such binding molecules localize a blockade or decrease of T-cell inhibitory signaling (facilitated by the binding moiety on the J-chain) to the same site as the maintenance or activation of T-cell stimulatory signaling (facilitated by the antibody), thereby maintaining or increasing a T-cell immune response at a specific location, such as, e.g., the surface of a cancer cell. Due to their increased avidity, the subject IgM, IgA, IgG/IgM and IgG/IgA antibodies act more effectively as agonists when directed to certain binding targets, such as members of a T-cell stimulatory signaling pathway, as described above. Such binding molecules find utility, for example, in the treatment of diseases wherein maintenance or activation of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an agonist antibody and an antagonist binding moiety on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an agonist antibody and an antagonist binding moiety on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, a J-chain of a subject binding molecule includes a binding moiety that antagonizes a T-cell inhibitory signaling pathway, while the antibody binds to a low level expression target. Without being held to theory, the purpose of such a binding molecule is to block or decrease T-cell inhibitory signaling via the binding moiety on the J-chain, while simultaneously binding to a low level expression target using the higher avidity of the IgM, IgA, IgG/IgM or IgG/IgA antibody. Such binding molecules provide localization of the blockade or decrease of T-cell inhibitory signaling at the site of a low level expression target, and find utility in the treatment of diseases wherein maintenance or activation of a T-cell immune response is desirable at the location of a low level expression target, such as, for example, certain cancers and immune disorders. For example, certain epithelial cancers are known to express tumor antigens that have a low level of expression, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, a J-chain of a subject binding molecule includes a binding moiety that antagonizes a T-cell inhibitory signaling pathway, while the antibody binds to a low affinity target. Without being held to theory, the purpose of such a binding molecule is to block or decrease T-cell inhibitory signaling via the binding moiety on the J-chain, while simultaneously binding to a low affinity target using the higher avidity of the IgM, IgA, IgG/IgM or IgG/IgA antibody. Such binding molecules provide localization of the blockade or decrease of T-cell inhibitory signaling at the site of a low affinity target. As reviewed above, due to their increased avidity, the subject IgM, IgA, IgG/IgM and IgG/IgA antibodies, comprising a modified J-chain, are especially advantageous in situations where IgG antibodies bind to their target with low affinity. Thus, in some embodiments, the IgM, IgA, IgG/IgM and IgG/IgA antibodies described herein can comprise the binding domain of a therapeutic IgG antibody. Such binding molecules find utility in the treatment of diseases wherein maintenance or activation of a T-cell immune response is desirable at the location of a low affinity target, such as, for example, certain cancers and immune disorders. For example, certain epithelial cancers are known to express tumor antigens that have a low binding affinity, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, a J-chain of a subject binding molecule includes a binding moiety that antagonizes a T-cell inhibitory signaling pathway, while the antibody binds to a target on a hematologic cancer cell. Without being held to theory, the purpose of such a binding molecule is to block or decrease T-cell inhibitory signaling via the binding moiety on the J-chain, while simultaneously binding to a hematologic cancer target using the higher avidity of the IgM, IgA, IgG/IgM or IgG/IgA antibody. Such binding molecules provide localization of the blockade or decrease of T-cell inhibitory signaling at the site of a hematologic cancer target, such as, e.g., on the surface of a hematologic cancer cell. Such binding molecules find utility in the treatment of hematologic cancers. For example, certain hematologic cancers are known to express tumor antigens at a low level, as described above. Such hematologic cancers include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

Examples of IgM, IgA, IgG/IgM, or IgG/IgA antibodies including a modified J-chain that antagonizes a T-cell inhibitory signaling pathway may include the binding regions of known IgG antibodies to tumor-associated antigens, such as, for example, blinatumomab (also known as MT103) (anti-CD19), CD19hA19 (anti-CD19, U.S. Pat. No. 7,109,304), hPAM4 (anti-mucin, U.S. Pat. No. 7,282,567), hA20 (anti-CD20, U.S. Pat. No. 7,251,164), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the disclosures of which are expressly incorporated by reference herein.

Other antibodies that can provide binding regions for use in combination with a modified J-chain that antagonizes a T-cell inhibitory signaling pathway include, for example, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), tositumomab (anti-CD20), trastuzumab (anti-ErbB2), lambrolizumab (anti-PD-1 receptor), nivolumab (anti-PD-1 receptor), ipilimumab (anti-CTLA4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-.alpha.4 integrin), omalizumab (anti-IgE); anti-TNF-.alpha. antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA.® (Human Genome Sciences); antibodies for therapy of Alzheimer's disease such as Alz 50 (Ksiezak-Reding et al., 1987, J Biol Chem 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson); trastuzumab (anti-HER2); tremelimumab (anti-CTLA4); urelumab (anti-CD137 (4-1BB)); vorsetuzumab (anti-CD70); duligotumab (anti-HER3); dacetuzumab (anti-CD40); varlilumab (anti-CD27); atezolizumab (anti-PD-L1); anti-MAGE1 antibodies such as MA454 (Thermo Scientific, Rockford, Ill.); anti-OX-40 antibodies such as ACT35 (Affymetrix eBioscience, San Diego, Calif.); anti-GITR antibodies such as 621 (BioLegend, San Diego, Calif.); anti-HVEM antibodies such as 122 (BioLegend, San Diego, Calif.); anti-TIM3 antibodies such as F38-2E2 (BioLegend, San Diego, Calif.); anti-LAG3 antibodies such as 3DS223H (Affymetrix eBioscience, San Diego, Calif.); anti-BTLA antibodies such as MIH26 (BioLegend, San Diego, Calif.); anti-VISTA antibodies such as MAB71261 (R&D Systems, Minneapolis, Minn.); anti-TIGIT antibodies such as MBSA43 (Affymetrix eBioscience, San Diego, Calif.); anti-CEACAM antibodies such as D14HD11 (abcam, Cambridge, Mass.); anti-Gp100 antibodies such as ab52058 (abcam, Cambridge, Mass.); anti-NY-ESO-1 antibodies such as E978 (Thermo Scientific, Rockford, Ill.); anti-Sialyl Lewis X antigen antibodies such as MAB2096 (EMD Millipore, Billerica, Mass.); anti-Tn antigen antibodies such as MA1-90544 (Thermo Scientific, Rockford, Ill.); anti-HIV antibodies such as P4/D10 (U.S. Pat. No. 8,333,971), Ab 75, Ab 76, Ab 77 (Paulik et al., 1999, Biochem Pharmacol 58:1781-90), as well as the anti-HIV antibodies described in U.S. Pat. Nos. 5,831,034, 5,911,989, and Vcelar et al., AIDS 2007; 21(16):2161-2170 and Joos et al., Antimicrob. Agents Chemother. 2006; 50(5): 1773-9.

In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to PD-1 and antagonizes a PD-1-mediated T-cell inhibitory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to PD-L1 and antagonizes a PD-L1-mediated T-cell inhibitory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to TIM3 and antagonizes a TIM3-mediated T-cell inhibitory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to LAG3 and antagonizes a LAG3-mediated T-cell inhibitory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to CD137 and agonizes a CD137-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to OX40 and agonizes an OX40-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to CD40 and agonizes a CD40-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to GITR and agonizes a GITR-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to CD27 and agonizes a CD27-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to CTLA4 and antagonizes a CTLA4-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to PD-1 and antagonizes a PD-1-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to TIM3 and antagonizes a TIM3-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to LAG3 and antagonizes a LGA3-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to BTLA and antagonizes a BTLA-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to VISTA and antagonizes a VISTA-mediated T-cell inhibitory signaling pathway. In a specific embodiment, a binding molecule whose IgM, IgA, IgG/IgM, or IgG/IgA antibody binds to HVEM and agonizes an HVEM-mediated T-cell stimulatory signaling pathway has a binding moiety on the J-chain that binds to TIGIT and antagonizes a TIGIT-mediated T-cell inhibitory signaling pathway. Such binding molecules find use in the treatment of cancers, including but not limited to epithelial cancers and hematologic cancers.

In one specific embodiment, a binding molecule whose IgM, IgA, IgG/IgM, or IgG/IgA antibody binds to EGFR has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to EGFR has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to EGFR has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to EGFR has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to EGFR has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to EGFR has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to EGFR has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to HER2 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to HER2 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to HER2 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to HER2 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to HER2 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to HER2 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to HER2 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to HER3 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to HER3 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to HER3 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to HER3 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to HER3 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to HER3 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to HER3 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to EPCAM has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to EPCAM has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to EPCAM has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to EPCAM has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to EPCAM has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to EPCAM has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to EPCAM has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to CEACAM has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CEACAM has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CEACAM has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CEACAM has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CEACAM has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CEACAM has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CEACAM has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to GP100 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to GP100 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to GP100 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to GP100 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to GP100 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to GP100 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to GP100 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to MAGE1 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to MAGE1 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to PD-L1 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to PD-L1 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to NY-ESO-1 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to NY-ESO-1 has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to Sialyl Lewis X antigen has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to Sialyl Lewis X antigen has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to Tn antigen has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to Tn antigen has a binding moiety on the J-chain that binds to TIGIT and antagonizes a TIGIT-mediated T-cell inhibitory signaling pathway. Such binding molecules find use in the treatment of cancers, including but not limited to epithelial cancers.

In one specific embodiment, a binding molecule whose IgM, IgA, IgG/IgM, or IgG/IgA antibody binds to CD19 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD19 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD19 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD19 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD19 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD19 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD19 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD20 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD20 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD20 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD20 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD20 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD20 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD20 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD22 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD22 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD22 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD22 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD22 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD22 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD22 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD33 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD33 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD33 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD33 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD33 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD33 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD33 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD38 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD38 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD38 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD38 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD38 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD38 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD38 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD52 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD52 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD52 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD52 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD52 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD52 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD52 has a binding moiety on the J-chain that binds to TIGIT and antagonizes a TIGIT-mediated T-cell inhibitory signaling pathway. Such binding molecules find use in the treatment of cancers, including but not limited to hematologic cancers.

In one specific embodiment, a binding molecule whose IgM, IgA, IgG/IgM, or IgG/IgA antibody binds to CD70 has a binding moiety on the J-chain that binds to CTLA4 and antagonizes a CTLA4-mediated T-cell inhibitory signaling pathway. In one specific embodiment, a binding molecule whose IgM, IgA, IgG/IgM, or IgG/IgA antibody binds to CD70 has a binding moiety on the J-chain that binds to PD-1 and antagonizes a PD-1-mediated T-cell inhibitory signaling pathway. In one specific embodiment, a binding molecule whose IgM, IgA, IgG/IgM, or IgG/IgA antibody binds to CD70 has a binding moiety on the J-chain that binds to TIM3 and antagonizes a TIM3-mediated T-cell inhibitory signaling pathway. In one specific embodiment, a binding molecule whose IgM, IgA, IgG/IgM, or IgG/IgA antibody binds to CD70 has a binding moiety on the J-chain that binds to LAG3 and antagonizes a LAG3-mediated T-cell inhibitory signaling pathway. In one specific embodiment, a binding molecule whose IgM, IgA, IgG/IgM, or IgG/IgA antibody binds to CD70 has a binding moiety on the J-chain that binds to BTLA and antagonizes a BTLA-mediated T-cell inhibitory signaling pathway. In one specific embodiment, a binding molecule whose IgM, IgA, IgG/IgM, or IgG/IgA antibody binds to CD70 has a binding moiety on the J-chain that binds to VISTA and antagonizes a VISTA-mediated T-cell inhibitory signaling pathway. In one specific embodiment, a binding molecule whose IgM, IgA, IgG/IgM, or IgG/IgA antibody binds to CD70 has a binding moiety on the J-chain that binds to TIGIT and antagonizes a TIGIT-mediated T-cell inhibitory signaling pathway. Such binding molecules find use in the treatment of cancers, including but not limited to hematologic cancers.

It is to be understood that an IgM, IgA, IgG/IgM or IgG/IgA antibody that binds to any of the listed tumor antigens can be combined with a modified J-chain with any of the binding specificities listed herein to create a binding molecule. Thus, any antibody target listed herein can be combined with any modified J-chain target listed herein.

While certain preferred embodiments are specifically referred to herein, it is to be understood that IgM, IgA, IgG/IgM and IgG/IgA antibodies with binding specificity to any target, such as any tumor antigen, comprising a modified J-chain with a binding moiety that binds to any target that antagonizes a T-cell inhibitory signaling pathway are contemplated and are within the scope of the present invention. FIG. 7 provide a list of antibody targets and targets for the binding moiety of a J-chain. Any of the antibody targets listed in the left column of FIG. 7 can be combined with any of the binding moiety targets for the J-chain listed in the right column of FIG. 7.

In a preferred embodiment, an IgM, IgA, IgG/IgM or IgG/IgA antibody binds to one or more of the tumor targets listed herein, while the J-chain comprises a binding moiety that antagonizes a T-cell inhibitory signaling pathway.

In one preferred embodiment, a J-chain of a subject binding molecule includes a binding moiety that is an scFv, and that antagonizes a T-cell inhibitory signaling pathway by binding to a target in the pathway.

In one preferred embodiment, the binding moiety on the J-chain is an scFv that binds to CTLA4 (i.e., is an anti-CTLA4$_{scFv}$) and antagonizes a CTLA4-mediated T-cell inhibitory signaling pathway.

In one preferred embodiment, a binding molecule includes an IgM antibody that binds to PD-L1, and the binding moiety on the J-chain is an anti-CTLA4$_{scFv}$ that antagonizes a CTLA4-mediated T-cell inhibitory signaling pathway.

In one preferred embodiment, a binding molecule includes an IgM antibody that binds to PD-1, and the binding moiety on the J-chain is an anti-CTLA4$_{scFv}$ that antagonizes a CTLA4-mediated T-cell inhibitory signaling pathway.

In one preferred embodiment, a binding molecule includes an IgM antibody that binds to TIM3, and the binding moiety on the J-chain is an anti-CTLA4$_{scFv}$ that antagonizes a CTLA4-mediated T-cell inhibitory signaling pathway.

In one preferred embodiment, a binding molecule includes an IgM antibody that binds to LAG3, and the binding moiety on the J-chain is an anti-CTLA4$_{scFv}$ that antagonizes a CTLA4-mediated T-cell inhibitory signaling pathway.

In all embodiments, a binding moiety on a modified J-chain may be introduced before or after the J-chain. Thus, for example, a modified J-chain with an scFv binding moiety that antagonizes a T-cell inhibitory signaling pathway by binding to CTLA4 may have an anti-CTLA4$_{scFv}$-J or a J-anti-CTLA4$_{scFv}$ configuration. A schematic illustration of both of these configurations is shown in FIG. 5.

Due to their increased avidity, the subject binding molecules are superior relative to bispecific IgG antibodies. For example, as a result, they are suitable for targeting low level expression targets, such as Rituxan-resistant Burkitt lymphoma cells characterized by a low level of CD20 expression. In addition, the IgM, IgA, IgG/IgM and IgG/IgA antibodies herein comprising a modified J-chain have greatly enhanced potency relative to bispecific IgG antibodies.

Pharmaceutical Compositions of Antibodies with Modified J-Chain

For therapeutic uses, a subject binding molecule can be formulated into pharmaceutical compositions. A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

The following examples, sequence listing and figures are provided to aid the understanding of the present invention, the true scope of which is set forth in the appended claims. It is understood that modifications can be made in the procedures set forth without departing from the spirit of the invention.

Further details of the invention are illustrated by the following, non-limiting Examples.

Example 1: Preparation of a Bispecific Anti-PD-L1 Antibody Comprising a Modified J-Chain with a Binding Moiety that Binds to CTLA4

1. Generation of DNA constructs with designed mutations:
   a. DNA construct synthesis. All the DNA constructs with designed mutations are synthesized by commercial vendors (Genescript), with compatible restriction sites at both ends for subcloning into respective expression vectors.
   b. Constructing expression vectors. The synthesized DNA constructs are re-suspended in Tris-EDTA buffer at 1 µg/ml. DNA (1 µg) is subjected to enzyme digestion and the synthesized gene is separated from the carrier plasmid DNA by electrophoresis. The digested DNA is ligated to pre-digested plasmid DNA (pCAGGS for J-chain, Gene 108 (1991) 193-200) by standard molecular biology techniques. The ligated DNA is transformed into competent bacteria and plated on LB plates with multiple selective antibiotics, Several bacterial colonies are picked and DNA preparations are made by standard molecular biology techniques. The prepared DNA are verified by sequencing. Only the bacterial clones with 100% match of DNA sequence with the designed DNA sequence are used for plasmid DNA preparation and subsequently for cell transfection.
      i. The first construct is composed of a scFv version of anti-CTLA4 fused with N-terminus of human J-chain (CTLA4 scFv-15 aa Linker-J). The amino acid sequence of this construct (Y15J) is:

```
                                              (SEQ ID NO: 2)
QVQLVESGGGVVQPGRSLRLSCAASGFTFSSYTMHWVRQAPGKGLEWVTF

ISYDGNNKYYADSVKGRFTISRDNSKNTLYLQMNSLRAEDTAIYYCARTG

WLGPFDYWGQGTLVTVSSGGGGSGGGGSGGGGSEIVLTQSPGTLSLSPGE

RATLSCRASQSVGSSYLAWYQQKPGQAPRLLIYGAFSRATGIPDRFSGSG

SGTDFTLTISRLEPEDFAVYYCQQYGSSPWTFGQGTKVEIKGGGGSGGGG

SGGGGSQEDERIVLVDNKCKCARITSRIIRSSEDPNEDIVERNIRIIVPL

NNRENISDPTSPLRTRFVYHLSDLCKKCDPTEVELDNQIVTATQSNICDE

DSATETCYTYDRNKCYTAVVPLVYGGETKMVETALTPDACYPD
``` ii. The second construct is composed of a scFv of anti-CTLA4 fused with C-terminus of human J-chain (J-15 aa Linker-CTLA4 scFv). The amino acid sequence of this construct (J15Y) is:

```
                                              (SEQ ID NO: 3)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPDGGGGSGGGGSGGG

GSQVQLVESGGGVVQPGRSLRLSCAASGFTFSSYTMHWVRQAPGKGLEWV

TFISYDGNNKYYADSVKGRFTISRDNSKNTLYLQMNSLRAEDTAIYYCAR

TGWLGPFDYWGQGTLVTVSSGGGGSGGGGSGGGGSEIVLTQSPGTLSLSP

GERATLSCRASQSVGSSYLAWYQQKPGQAPRLLIYGAFSRATGIPDRFSG

SGSGTDFTLTISRLEPEDFAVYYCQQYGSSPWTFGQGTKVEIK
```

Both of these constructs are designed to enable integration of the J-chain into an IgM that is specific for PD-L1.

IgM heavy chain: This heavy chain construct has a full length µ chain with a Vh region derived from an anti-PD-L1 antibody:

```
                                              (SEQ ID NO: 4)
MDPKGSLSWRILLFLSLAFELSYGEVQLVESGGGLVQPGGSLRLSCAASG

HTSDSWIHWVRQAPGKGLEWVAWISPYGGSTYYADSVKGRFTISADTSKN

TAYIQMNSLRAEDTAVYYCARRHWPGGFDYWGQGTLVTVSAGSASAPTLF

PLVSCENSPSDTSSVAVGCLAQDFLPDSITFSWKYKNNSDISSTRGFPSV

LRGGKYAATSQVLLPSKDVMQGTDEHVVCKVQHPNGNKEKNVPLPVIAEL

PPKVSVFVPPRDGFFGNPRKSKLICQATGESPRQIQVSWLREGKQVGSGV

TTDQVQAEAKESGPTTYKVTSTLTIKESDWLSQSMFTCRVDHRGLTFQQN

ASSMCVPDQDTAIRVFAIPPSFASIFLTKSTKLTCLVTDLTTYDSVTISW

TRQNGEAVKTHTNISESHPNATFSAVGEASICEDDWNSGERFTCTVTHTD

LPSPLKQTISRPKGVALHRPDVYLLPPAREQLNLRESATITCLVTGFSPA

DVFVQWMQRGQPLSPEKYVTSAPMPEPQAPGRYFAHSILTVSEEEWNTGE

TYTCVVAHEALPNRVTERTVDKSTGKPTLYNVSLVMSDTAGTCY
```

This heavy chain construct has a molecular weight about 64 kD and when co-expressed with light chain, the resultant IgM is designed to bind to PD-L1 over-expressed on tumor cells.

d. Light chain for this bispecific IgM is derived from an anti-PD-L1 antibody:

```
                                           (SEQ ID NO: 5)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPITFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

The light chain construct has a molecular weight about 24 kD and when co-expressed with the appropriate heavy chain (SEQ ID NO: 4) is designed to bind to PD-L1 on tumor cells.

2. Protein expression, purification and characterization
   a. Transfection. Heavy, Light and Modified J-chain DNA is transfected into CHO cells. DNA for expression vectors are mixed typically in 1:1:1 ratio with PEI and then added to CHO-S cells. PEI transfection with CHO-S cells is conducted according to established techniques (see "Biotechnology and Bioengineering, Vol 87, 553-545").
   b. Immunoprecipitation
      i. CAPTURESELECT® IgM (BAC, Thermo Fisher). IgM proteins from transfected CHO cell supernatants are partially purified by immunoprecipitation with CAPTURESELECT® IgM affinity matrix according to manufacturers' protocol (GE Life Sciences). After incubation at room temperature for 2 hours, the affinity matrix is separated from the supernatant by centrifugation. The matrix is further washed with PBS for 3 times before the PBS is carefully removed. The captured protein is eluted from the matrix by incubating with NuPage LDS protein buffer (Life Technology) for 5 minutes.
   c. Gel electrophoresis
      i. Non-reducing SDS PAGE separates native IgM and its mutant forms according to size. Pentameric IgM, composed of homodimeric heavy and light chains, produces a protein band of approximately 1,000.000 molecular weight. NuPage LDS Sample Buffer (Life Technologies) is added to IgM protein samples at 25 C for 30 minutes before loading onto the gel. Native-Page Novex 3-12% Bis-Tris Gel (Life Technologies) is used with Novex Tris-Acetate SDS Running Buffer (Life Technologies) Run gel until the dye front reaches the bottom of the gel. (FIG. 8)
      ii. Reducing SDS-PAGE. NuPage LDS sample buffer (Life Technologies) and NuPage reducing agent dithiothreitol (Life Technologies) are added to IgM protein samples and heated to 80° C. for 10 minutes before loading on NuPage Novex 4-12% Bis-Tris Gel (Life Technologies). NuPage MES SDS Running Buffer (Life Technologies) is used for gel electrophoresis. Gels are run until the dye front reaches the bottom of the gel. After electrophoresis is complete, remove gel from apparatus and stain the gel using Colloidal Blue Staining (Life Technologies).
      iii. Western Blot Detection. After electrophoresis is complete, remove gel from XCELL SURELOCK® Mini-Cell. Transfer to PVDF membrane at 30 volts for 1 hour (refer to Life Technologies' manual). Block with 20 ml 3% BSA in PBST at 25 C for 1 hour.

Figure 8:
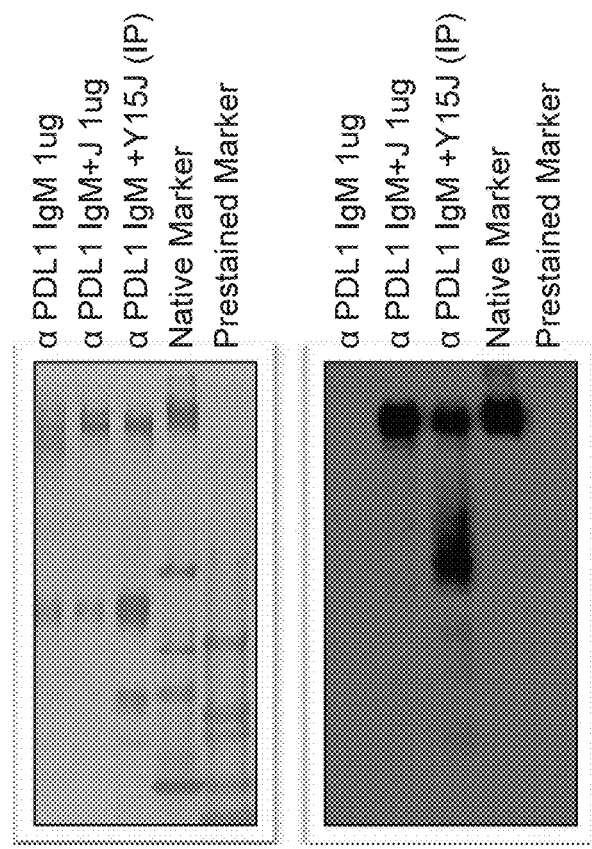
FIG. 8 shows hybrid SDS PAGE and western blot analyses of various anti-PD-L1 IgM antibodies with an anti-CTLA4 binding moiety attached to the J-chain. Proper assembly of the pentameric PD-L1 binding IgM in the presence of a J-chain with or without anti-CTLA-4 scFv results in an increased amount of assembled product and a gel mobility shift.

For anti-J-chain Western blot, add anti-J (SP105, Thermo Fisher) at 1:500 in 3% BSA in PBST overnight at 4 C. Wash with PBST four times at room temperature. Add HRP-Goat anti rabbit IgG (Jackson Immunology) at 1:5,000 in 3% BSA in PBST for 1 hour at room temperature. Wash with PBST 4 times at room temperature. Add 10 ml of HRP chemiluminescent substrate (Thermo Fisher) for 10 minutes before exposing the blot to film. Anti-J-chain antibody only reacts with IgM which is co-expressed with either unmodified J-chain or modified J-chain. As shown in FIG. 8, the anti-PD-L1 IgM with either the wild type J-chain or the modified J-chain carrying the anti-CTLA4 scFv (Y15J) is clearly assembled correctly.

Example 2: Anti-CD20 IgMs Carrying Anti-CD3 scFv Binding Moiety on their J-Chains can Activate T-Cells Only in the Presence of CD20 Positive B-Cells This example illustrates the preparation and characterization of an IgM molecule comprising a modified J-chain. Specifically, this example describes the preparation of the molecular cloning, expression and purification of an IgM antibody targeting a B-cell antigen (CD20) and a modified J-chain that comprises a binding moiety that binds to CD3, to demonstrate production of a bispecific IgM and measurement of the functional activity in a relevant system. The DNA corresponding to the heavy, light and J-chain sequences below was prepared using the methods as described in Example 1.

Amino acid sequence of IgM Light chain sequence of an anti-CD20 antibody:

```
                                           (SEQ ID NO: 6)
MDMRVPAQLLGLLLLWLRGARCQIVLSQSPAILSASPGEKVTMTCRASSS

VSYIHWFQQKPGSSPKPWIYATSNLASGVPVRFSGSGSGTSYSLTISRVE

AEDAATVYCQQWTSNPPTFGGGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVIKSFNRGEC
```

Amino acid sequence of IgM Heavy chain sequence of an anti-CD20 antibody:

```
                                           (SEQ ID NO: 7)
MGWSYIILFLVATATGVHSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSSGSASAPTLFP

LVSCENSPSDTSSVAVGCLAQDFLPDSITFSWKYKNNSDISSTRGFPSVL

RGGKYAATSQVLLPSKDVMQGTDEHVVCKVQHPNGNKEKNVPLPVIAELP

PKVSVFVPPRDGFFGNPRKSKLICQATGFSPRQIQVSWLREGKQVGSGVT

TDQVQAEAKESGPTTYKVTSTLTIKESDWLSQSMFTCRVDHRGLTFQQNA

SSMCVPDQDTAIRVFAIPPSFASIFLTKSTKLTCVTDLTTYDSVTISWTR

QNGEAVKTHTNISESHPNATFSAVGEASICEDDWNSGERFTCTVTHTDLP

SPLKQTISRPKGVALHRPDVYLLPPAREQLNLRESATITCLVTGFSPADV

FVQWMQRGQPLSPEKYVTSAPMPEPQAPGRYFAHSILTVSEEEWNTGETY

TCVVAHEALPNRVTERTVDKSTGKPTLYNVSLVMSDTAGTCY
```

Amino acid sequence of J chain sequence for V15J:

(SEQ ID NO: 8)
MGWSYIILFLVATATGVHSQVQLVQSGAEVKKPGASVKVSCKASGYTFIS

YTMHWVRQAPGQGLEWMGYINPRSGYTHYNQKLKDKATLTADKSASTAYM

ELSSLRSEDTAVYYCARSAYYDYDGFAYWGQGTLVTVSSGGGGSGGGGSG

GGGSDIQMTQSPSSLSASVGDRVTITCSASSSVSYMNWYQQKPGKAPKRL

IYDTSKLASGVPSRFSGSGSGTDFTLTISSLQPEDFATYYCQQWSSNPPT

FGGGTKLEIKGGGGSGGGGSGGGGSQEDERIVLVDNKCKCARITSRIIRS

SEDPNEDIVERNIRIIVPLNNRENISDPTSPLRTRFVYHLSDLCKKCDPT

EVELDNQTVTATQSNICDEDSATETCYTYDRNKCYTAVVPLVYGGETKMV

ETALTPDACYPD

Amino acid sequence of J-chain sequence for J15V:

(SEQ ID NO: 9)
MKNHLLFWGVLAVFIKAVHVKAQEDERIVINDNKCKCARITSRIIRSSED

PNEDIVERNIRIIVPLNNRENISDPTSPLRTRFVYHLSDLCKKCDPTEVE

LDNQIVTATQSNICDEDSATETCYTYDRNKCYTAVVPLVYGGETKMVETA

LTPDACYPDGGGGSGGGGSGGGGSQVQLVQSGAEVKKPGASVKVSCKASG

YTFISYTMHWVRQAPGQGLEWMGYINPRSGYTHYNQKLKDKATLTADKSA

STAYMELSSLRSEDTAVYYCARSAYYDYDGFAYWGQGTLVTVSSGGGGSG

GGGSGGGGSDIQMTQSPSSLSASVGDRVTITCSASSSVSYMNWYQQKPGK

APKRLIYDTSKLASGVPSRFSGSGSGTDFTLTISSLQPEDFATYYCQQWS

SNPPTFGGGTKLEIK

Amino acid sequence of J-chain sequence for O15J:

(SEQ ID NO: 10)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYSLDYWGQGTTLTVSSGGGGSGGGGSGGGGSQIVLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTFGSGTKLEIKGGGGSGGGGS

GGGGSQEDERIVLVDNKCKCARITSRIIRSSEDPNEDIVERNIRIIVPLN

NRENISDPTSPLRTRFVYHLSDLCKKCDPTEVELDNQIVTATQSNICDED

SATETCYTYDRNKCYTAVVPLVYGGETKMVETALTPDACYPDGGGSEQKL

ISEEDLNSAVDHHHHHH

Amino acid sequence of J-chain sequence for J15O:

(SEQ ID NO: 11)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPDGGGSGGGGSGGG

GSQVQLQQSGAELARPGASVKMSCKASGYTFTRYTMHWVKQRPGQGLEWI

GYINPSRGYTNYNQKFKDKATLTTDKSSSTAYMQLSSLTSEDSAVYYCAR

YYDDHYSLDYWGQGTTLTVSSGGGGSGGGGSGGGGSQIVLTQSPAIMSAS

PGEKVTMTCSASSSVSYMNWYQQKSGTSPKRWIYDTSKLASGVPAHFRGS

GSGTSYSLTISGMEAEDAATYYCQQWSSNPFTFGSGTKLEIKEQKLISEE

DLNSAVDHHHHHH

Figure 9:
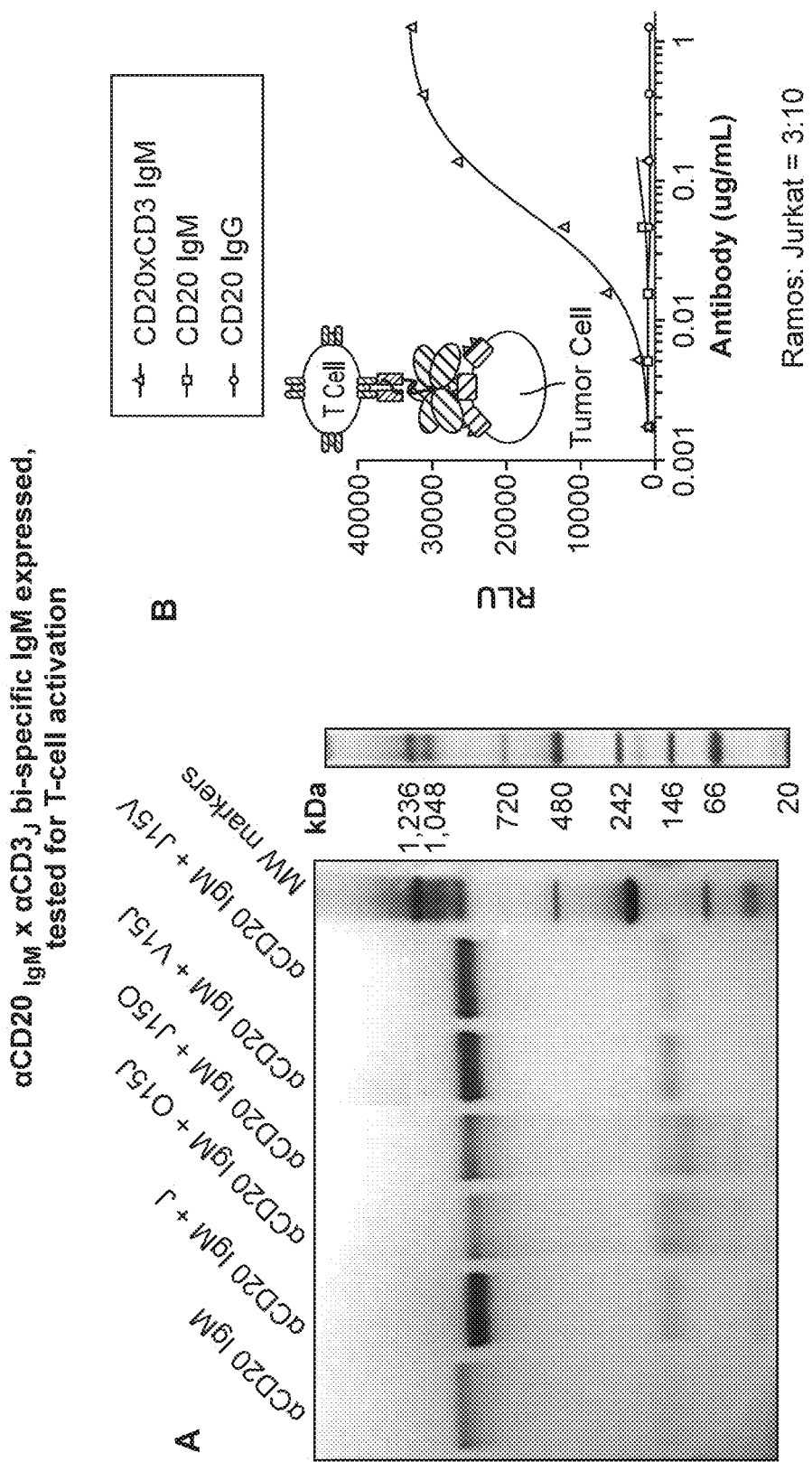
FIG. 9, Panel A shows an SDS PAGE analysis of anti-CD20 IgM antibodies with or without various anti-CD3 binding moieties on the J-chain. Panel B is a graph showing results of a T-cell activation assay comparing the ability of an anti-CD20 IgM with a CD3-binding moiety on the J-chain to activate T-cells, as compared to anti-CD20 IgM antibodies without a CD3-binding moiety on the J-chain, as well as anti-CD20 IgG antibodies.

The DNA corresponding to these heavy and light chains as well as that corresponding to either the wild-type (wt) J-chain (FIG. 3), V15J or J15V J-chain sequences shown above were co-transfected into HEK293 cells and proteins expressed and purified using the camelid resin as described before. As shown in FIG. 9, Panel A, all four proteins express well. The anti-CD20 IgM hexamer without J-chain is clearly resolved from the J-chain containing pentamers for the IgM pentamer with the wild type J-chain as well as for the bispecific IgM's where the anti-CD3 scFv is linked to the J-chain in either orientation (FIG. 9, Panel A).

Purified proteins were analyzed for T-cell activation using a commercially available Luciferase reporter gene based kit (Promega). Briefly, purified protein was added to 7500 Ramos and 25000 engineered Jurkat cells (Promega CS176403) in 40 uL RPMI with 10% FBS. Mixture was incubated for 5 h 37 C with 5% $CO_2$. Cells were mixed with lysis buffer containing luciferin to measure luciferase reporter activity. Light output was measured by EnVision plate reader and analyzed by Prism software. As shown in FIG. 9, Panel B, only the antibodies that carried the CD3 specific scFv binding moiety on the J-chain are able to show dose dependent activation, whereas the IgM antibody lacking the modified J-chain or the IgG are unable to show any signal in this assay.

Example 3: IgM Binds Better to Low Abundance Targets than IgG

Figure 10:
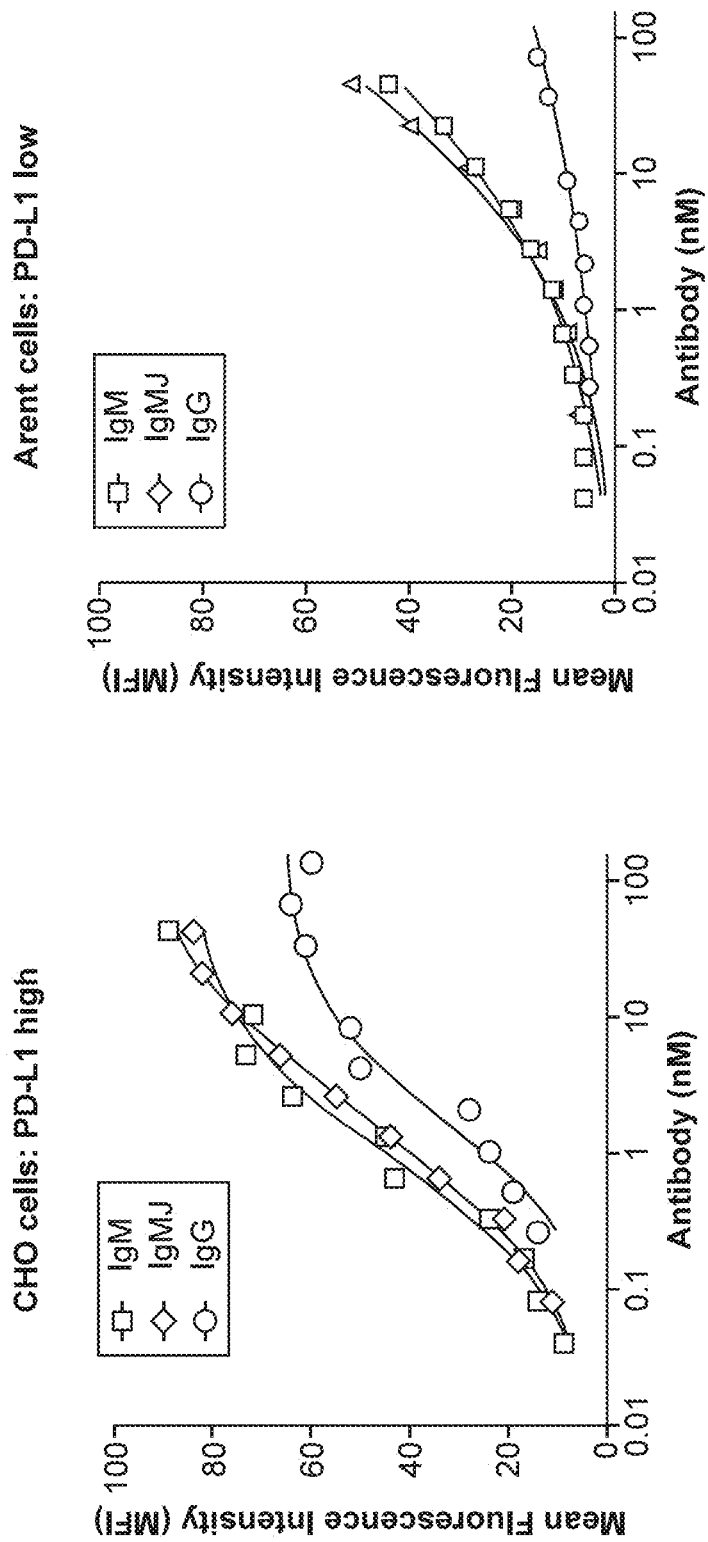
FIG. 10 shows two graphs that compare binding of anti-PD-L1 IgM and anti-PD-L1 IgG molecules in two different cell types having high and low levels of PD-L1 expression.

Roughly 30×10^3 cells per well were loaded in FACS buffer (2% FBS/PBS) in a V-bottom plate. The plates were spun and supernatant aspirated. Serially diluted antibodies in FACS buffer were added in a volume of 50 μL to the cells and incubated for 30 minutes on ice. The cells were then washed with 150 μL of FACS buffer and then pelleted at 1200 rpm for 5 minutes at room temperature. The supernatant was aspirated and 50 μL of relevant secondary at 1 μg/mL was added to each well. The plate was further incubated for 30 minutes on ice. The cells were then washed with 150 μL of FACS buffer, pelleted at 1200 rpm for 5 minutes at room temperature, supernatant aspirated and 60 μL of 7-AAD FACS buffer (1:100) added. After a brief incubation (5 min), data were acquired, gating for AAD negative cells, on a FACS calibur. Binding data was analyzed using GraphPad Prism software. As shown in FIG. 10, the anti-PD-L1 IgM and IgG bind comparably to the high PD-L1 expressing cells (Promega transfected CHO cell line). On a low PD-L1 expressing cell line (Arent), the anti-PD-L1 IgM is seen to bind significantly better than the anti-PD-L1 IgG (more than 10× better on a molar basis).

Example 4: Anti-PD-L1 IgM has Functional Effect on T-Cell Activation Better than IgG Anti-PD-L1 IgG and IgM antibodies were characterized for B cell dependent activation of T cells using a reporter cell line (Promega). T cell activation increases the NFAT dependent luciferase expression, engineered into Jurkat cells. The enhanced expression can be measured after lysis using a luminescence readout.

Briefly, purified protein was added to 7500 Ramos and 25000 engineered Jurkat cells (Promega CS176403) in 40 μL RPMI with 10% FBS. Mixture was incubated for 5 h 37 C with 5% $CO_2$. Cells were mixed with lysis buffer containing luciferin to measure luciferase reporter activity. Light output was measured by EnVision plate reader and analyzed by Prism software.

Figure 11:
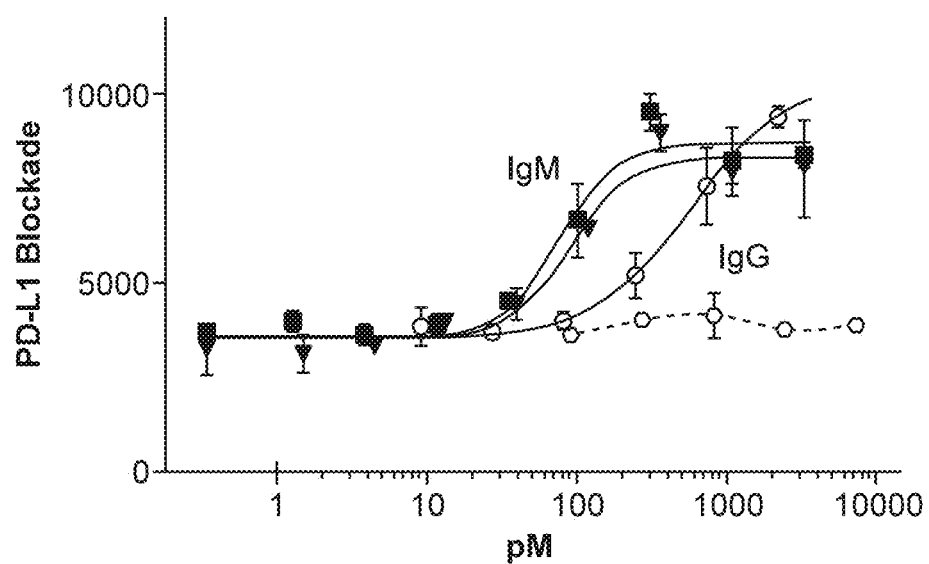
FIG. 11 shows a graph that compares inhibition of PD-1: PD-L1 interaction by IgM and IgG molecules made with VH sequences from anti-PD-L1 S70 antibody.

As shown in FIG. 11, the anti-PD-L1 IgM with or without a J-chain can inhibit PD-L1:PD-1, interaction leading to activation of the reporter cell and increased luminescence. It is also clear that on a molar basis the anti-PD-L1 IgM is able to activate T-cells better than the corresponding IgG.

Example 5: Bispecific Anti-PD-L1 IgM with Anti-CD3 scFv Fused to J-Chain can can Activate T-Cells in the Presence of PD-L1 Expressing Cells This example illustrates the preparation and characterization of an IgM molecule comprising a modified J-chain. Specifically, this example describes the preparation of the molecular cloning, expression and purification of an IgM antibody targeting a PD-L1 and a modified J-chain that comprises a binding moiety that binds to CD3, to demonstrate production of a bispecific IgM and measurement of the functional activity in a relevant system. The DNA corresponding to the heavy, light and J-chain sequences below was prepared using the methods as described in Example 1.

Amino acid sequence of IgM Light chain sequence of an anti-PD-L1 antibody:

(SEQ ID NO: 106)
MDMRVPAQLLGLLLLWLRGARCQIVLSQSPAILSASPGEKVTMTCRASSS

VSYIHWFQQKPGSSPKPWIYATSNLASGVPVRFSGSGSGTSYSLTISRVE

AEDAATYYCQQWTSNPPTFGGGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

Amino acid sequence of IgM Heavy chain sequence of an anti-PD-L1 antibody:

(SEQ ID NO: 104)
MDPKGSLSWRILLFLSLAFELSYGEVQLVESGGGLVQPGGSLRLSCAASG

FTFSDSWIHWVRQAPGKGLEWVAWISPYGGSTYYADSVKGRFTISADTSK

NTAYLQMNSLRAEDTAVYYCARRHWPGGFDYWGQGTLVTVSAGSASAPTL

FPLVSCENSPSDTSSVAVGCLAQDFLPDSITFSWKYKNNSDISSTRGFPS

VLRGGKYAATSQVLLPSKDVMQGTDEHVVCKVQHPNGNKEKNVPLPVIAE

LPPKVSVFVPPRDGFFGNPRKSKLICQATGFSPRQIQVSWLREGKQVGSG

VTTDQVQAEAKESGPTTYKVTSTLTIKESDWLSQSMFTCRVDHRGLTFQQ

NASSMCVPDQDTAIRVFAIPPSFASIFLTKSTKLTCLVTDLTTYDSVTIS

WTRQNGEAVKTHTNISESHPNATFSAVGEASICEDDWNSGERFTCTVTHT

DLPSPLKQTISRPKGVALHRPDVYLLPPAREQLNLRESATITCLVTGFSP

ADVFVQWMQRGQPLSPEKYVTSAPMPEPQAPGRYFAHSILTVSEEEWNTG

ETYTCVVAHEALPNRVTERTVDKSTGKPTLYNVSLVMSDTAGTCY

Amino acid sequence of J chain sequence for V15J:

(SEQ ID NO: 108)
MGWSYIILFLVATATGVHSQVQLVQSGAEVKKPGASVKVSCKASGYTFIS

YTMHWVRQAPGQGLEWMGYINPRSGYTHYNQKLKDKATLTADKSASTAYM

ELSSLRSEDTAVYYCARSAYYDYDGFAYWGQGTLVTVSSGGGGSGGGGSG

GGGSDIQMTQSPSSLSASVGDRVTITCSASSSVSYMNWYQQKPGKAPKRL

IYDTSKLASGVPSRFSGSGSGTDFTLTISSLQPEDFATYYCQQWSSNPPT

FGGGTKLEIKGGGGSGGGGSGGGGSQEDERIVLVDNKCKCARITSRIIRS

SEDPNEDIVERNIRIIVPLNNRENISDPTSPLRTRFVYHLSDLCKKCDPT

EVELDNQIVTATQSNICDEDSATETCYTYDRNKCYTAVVPLVYGGETKMV

ETALTPDACYPD

The DNA corresponding to these heavy and light chains as well as that corresponding to either the wild-type (wt) J-chain (FIG. 12), V15J sequences shown above were co-transfected into HEK293 cells and proteins expressed and purified using the camelid resin as described before. As shown in FIG. 9, Panel A, all four proteins express well. The anti-PD-L1 hexamer without J-chain is clearly resolved from the J-chain containing pentamers for the IgM pentamer with the wild type J-chain as well as for the bispecific IgM's where the anti-CD3 scFv is linked to the J-chain (FIG. 12, Panel A).

Anti-PD-L1 IgM antibodies with or without the J-chains described above were characterized for release of PD-L1 expressing tumor cell dependent inactivation of T cells using a reporter cell line (Promega). T cell activation increases the NFAT dependent luciferase expression, engineered into Jurkat cells. The enhanced expression can be measured after lysis using a luminescence readout.

Briefly, purified protein was added to 7500 Ramos and 25000 engineered Jurkat cells (Promega CS176403) in 40 μL RPMI with 10% FBS. Mixture was incubated for 5 h 37 C with 5% $CO_2$. Cells were mixed with lysis buffer containing luciferin to measure luciferase reporter activity. Light output was measured by EnVision plate reader and analyzed by Prism software.

As shown in FIG. 12 Panel B, the anti-PD-L1 IgM with or without a J-chain can inhibit PD-L1:PD-1, interaction leading to activation of the reporter cell and increased luminescence. It is also clear that addition of the CD3 binding J-chain fusion does not interfere with the ability of this IgM to block PD-1:PD-L1 interaction.

Figure 14:
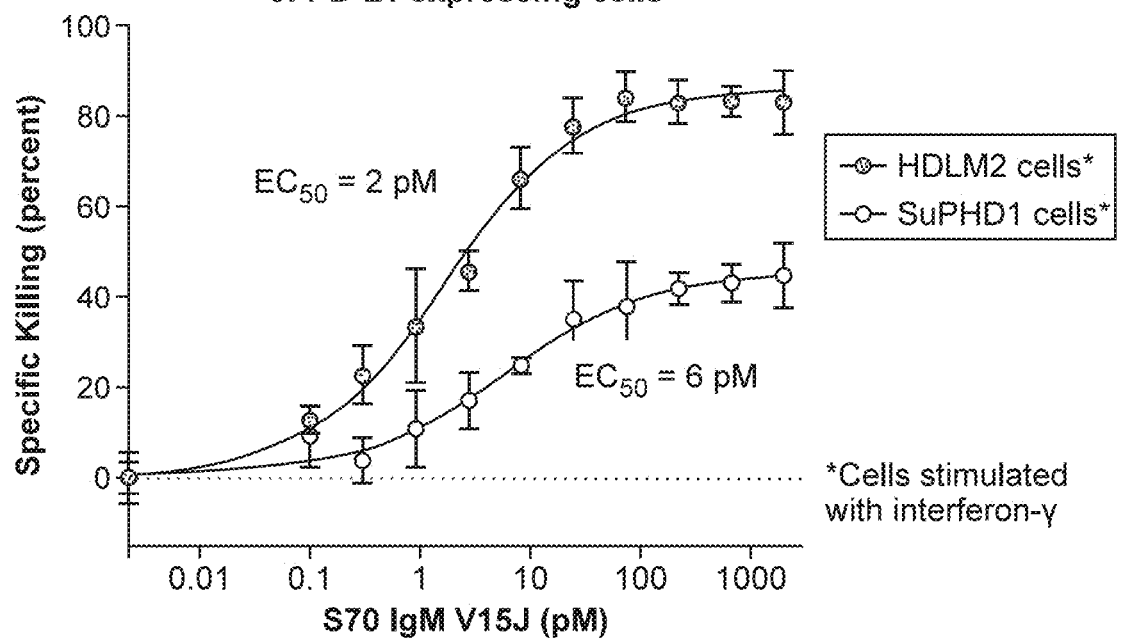
FIG. 14 is a graph showing T-cell-dependent target cell killing with low (HDML2) and high (SUPHD) PD-L1 expressing cells.

Example 6: Bispecific Anti PD-L1 IgM with Anti-CD3 scFv Fused to J-Chain can Use T-Cells to Kill PD-L1 Expressing Cells Engagement of effector T-cells by bispecific IgM antibodies with a modified J-chain is expected to greatly enhance killing of the target B-cell populations compared to the IgM carrying no J-chain or the wild type J-chain. To test cell killing in co-culture, we performed a cell killing assay. Antibody doses were incubated with Oregon Green 488 labeled PD-L1+ cells (either high expressing HDML2 or low expressing SUPHD1) and purified CD8+ effector cells. As shown in FIG. 14, the bispecific IgM carrying a CD3 binding scFv on its J-chain is able to cause complete killing of PD-L1 expressing cells. Complete killing of target cells by bispecific IgM is observed at concentrations as low as 2 pM.

Example 7: Half-Life Extended Anti-PD-L1 IgM with Albumin or Albumin Binding scFv Fused to J-Chain can be Made and Still Block PD-1:PD-L1 Interaction The half-life of IgMs in human plasma is estimated to be around 2-3 days and shorter still in mice. This is significantly shorter than for IgGs, which interact with the neonatal Fc receptor (FcRn) and are recycled after endocytosis enabling a much longer half-life of roughly 21 days. In order to increase the half-life of our anti-PD-L1 IgMs, we took advantage of the fact that we can tether scFvs to either terminus of the J-chain without significantly altering the effector functions of IgMs such as CDC.

There are several approaches that have been described in the art to enable half-life extension of biologics. These include tethering of mutants of human serum albumin (Andersen et al, JBC VOL. 289, NO. 19, pp. 13492-13502, 2014), peptides (Dennis et al, *J. Biol. Chem.* 2002, 277: 35035-35043) or scFvs that can bind human serum albumin (Muller et al mAbs 4:6, 673-685; 2012), Modified J-Chain Sequences are Provided Herein.

Figure 15A:
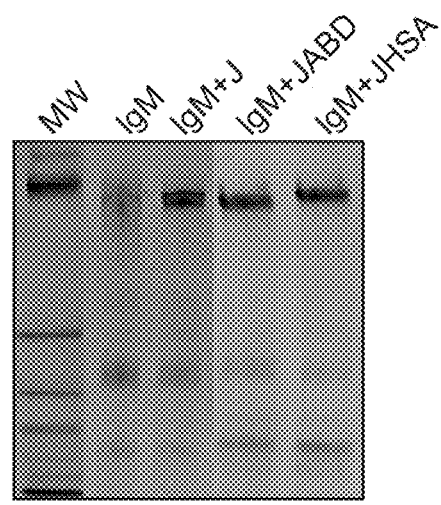
FIG. 15, Panel A shows an SDS PAGE hybrid gel demonstrating expression and assembly of S70 IgM in the presence of wild type, CD3-binding (V) or anti-CTLA-4 (Y) scFv. Panel B is a graph that demonstrates blockade of PD-1:PD-L1 interaction with each of these antibodies.
Figure 15B:
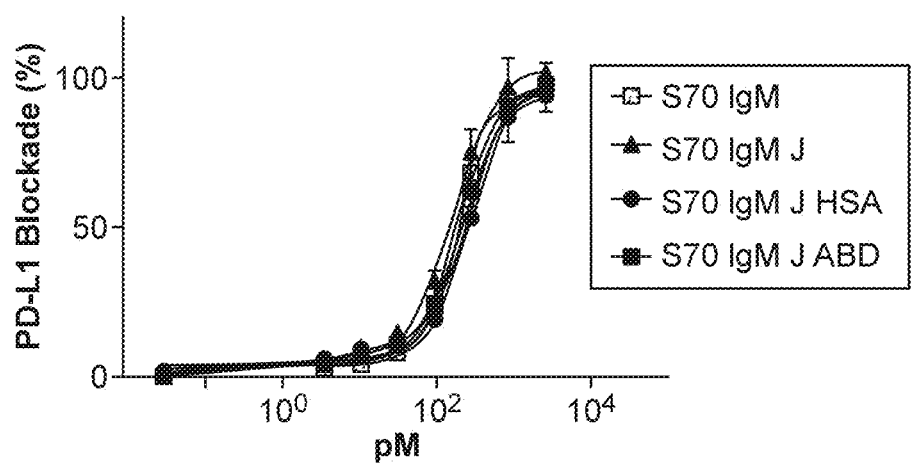

Expression and assembly of this ABD-J-chain fusion or HSA-J-chain fusion into IgMs was tested using the IgM sequence described in Example 1 (FIG. 15 Panel A). In addition, we verified that fusion of ABD or HSA to J-chain does not perturb the blockade activity on anti-PD-L1 IgM on target cell lines carrying PD-L1 on their surface as described in Example 5.

Figure 16B:
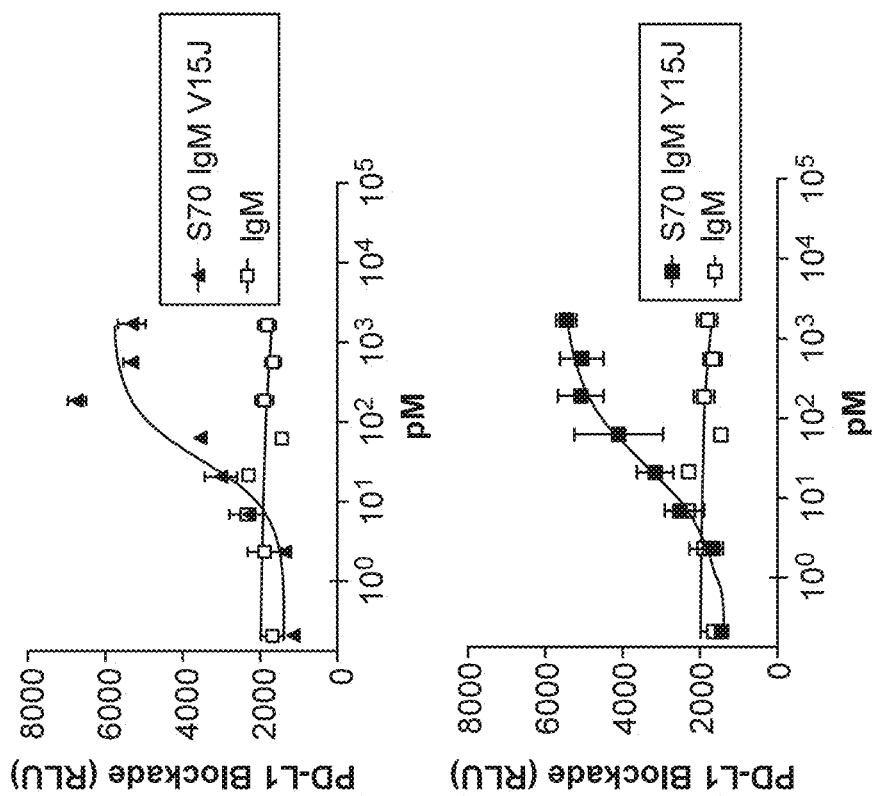
FIG. 16, Panel A shows a hybrid gel of anti-PD-L1IgM with and without wt J-chain as well as with two modified J-chains carrying either an anti-CTLA-4 scFv (Y) or and anti-CD3 scFv(V).
Figure 16A:
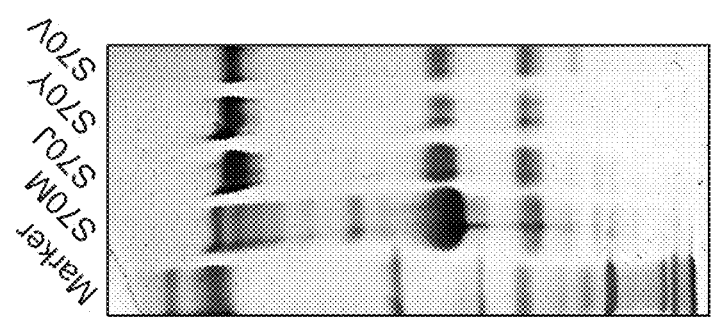

Example 8: Anti-PDL-1 IgM (S70) with Anti-CTLA-4 J-Chain (Y15J) can be Made and Retains Activity of Both Arms Expression and assembly of this anti-CTLA-4 scFv-J-chain fusion (Y15J) into S70 IgMs was tested using the IgM sequence described in Example 1 (FIG. 16 Panel A). In addition, we verified that fusion of this scFv to J-chain does not perturb the blockade activity on anti-PD-L1 IgM on target cell lines carrying PD-L1 on their surface (FIG. 16 Panel B) as described in Example 5.

Figure 17A:
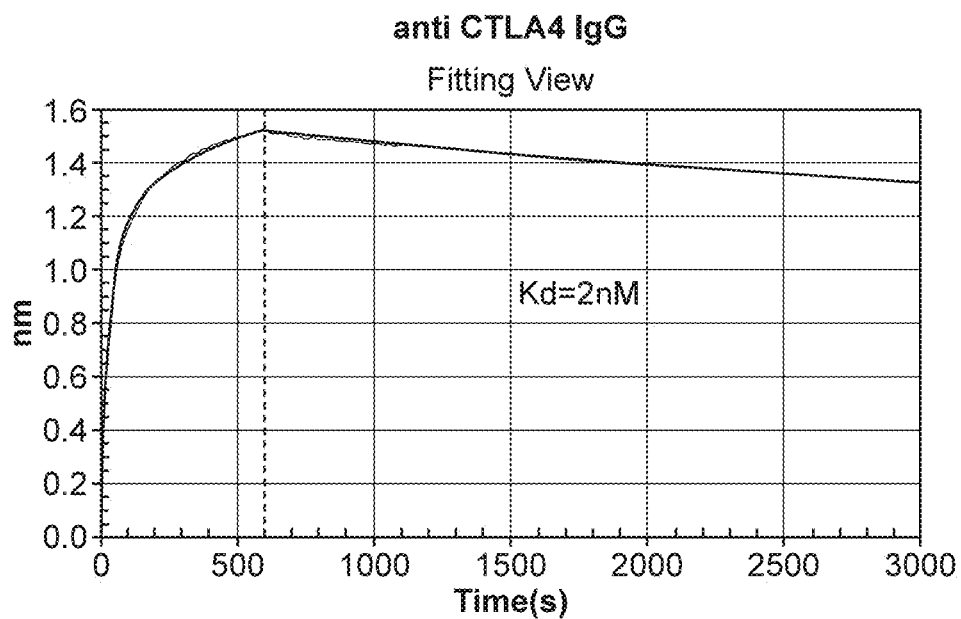
FIG. 17 shows two graphs that show binding kinetics of S70 IgM carrying the CTLA-4 binding J-chain or the parent anti-CTLA-4 binding IgG, using Forte Bio BLI readout. The parent CTLA-4 binding antibody (IgG) binds with a Kd of 2 nM versus the monovalent binding of the S70 Y15J.
Figure 17B:
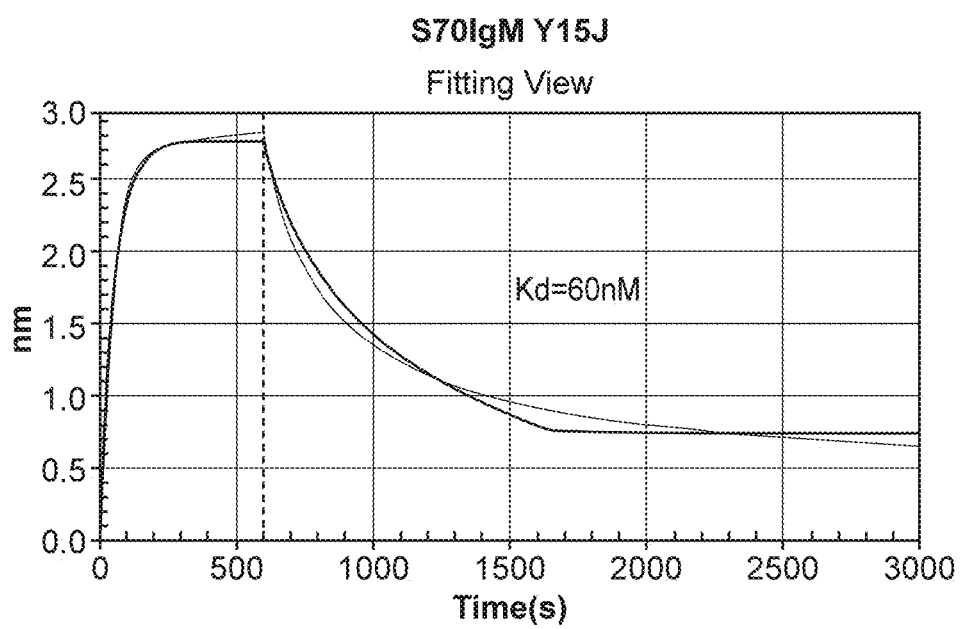
Figure 18:
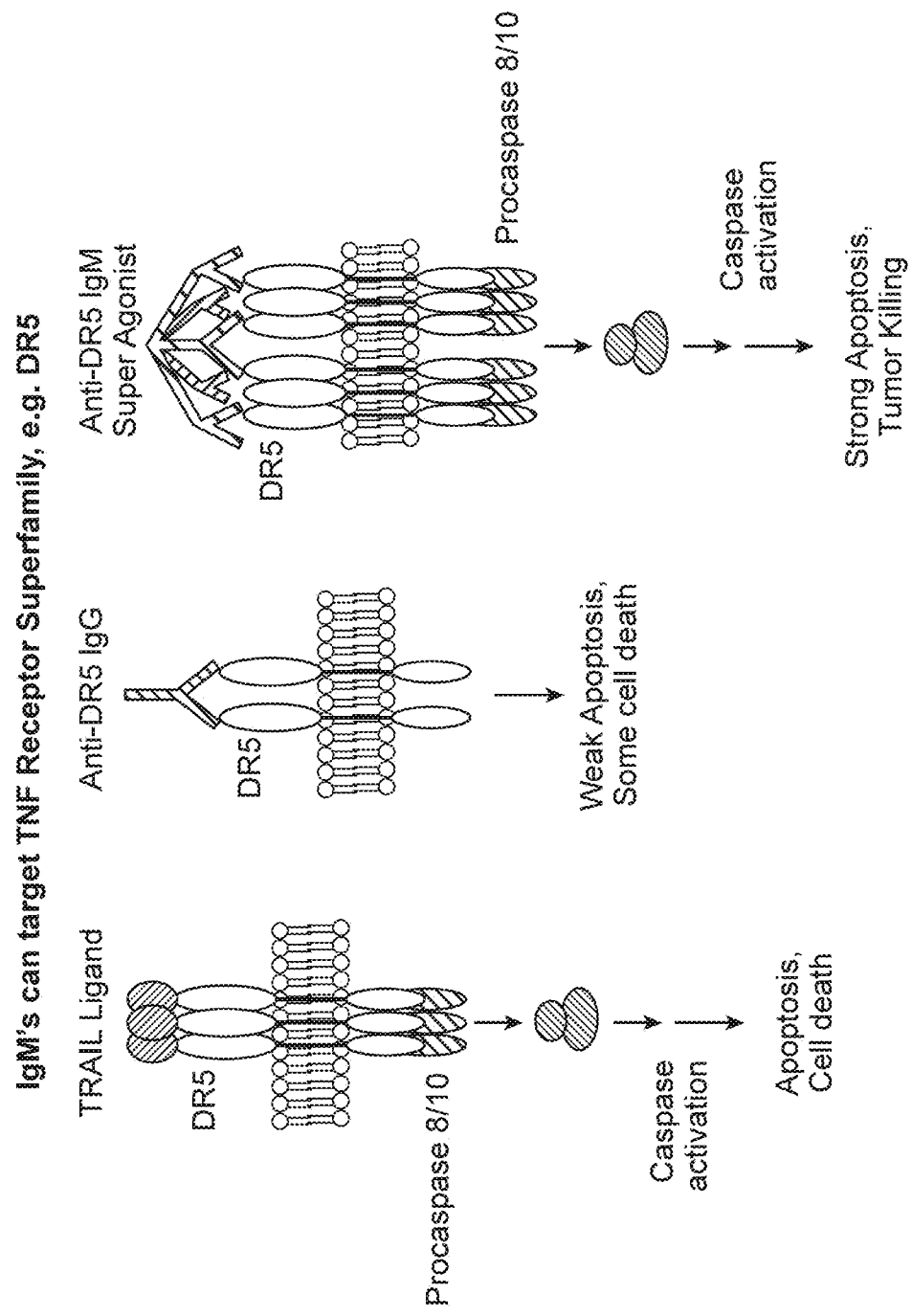
FIG. 18 is a schematic illustration comparing the ability of TRAIL ligand, IgG and IgM antibodies to target members of the tumor necrosis factor (TNF) superfamily.
Figure 19:
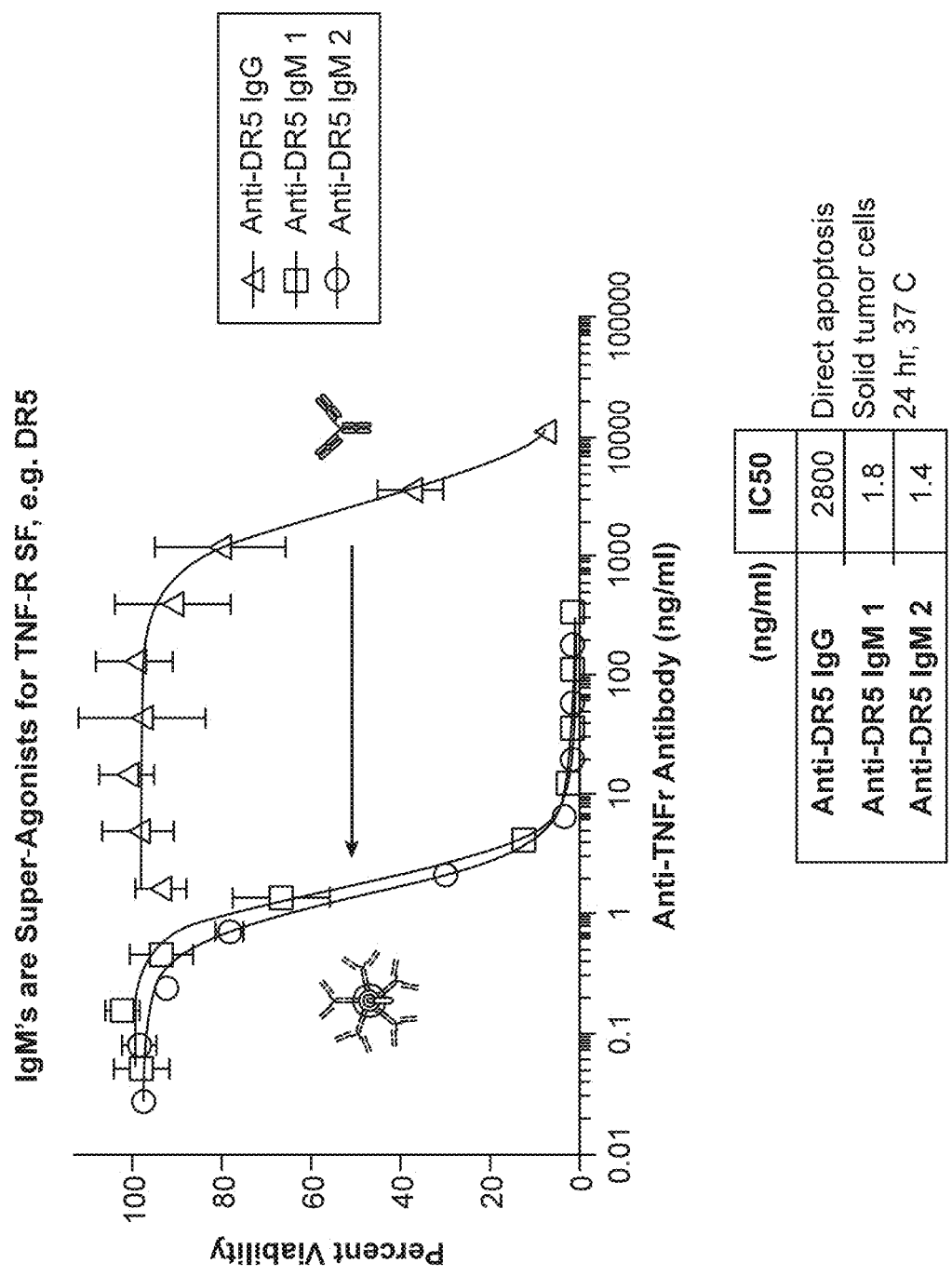
FIG. 19 is a graph that compares the agonistic activity of anti-DR5 IgM and IgG antibodies.

To verify that the CTLA-4 binding scFv on the J-chain retains binding to CTLA-4, bispecific anti PDL1 IgM with antiCTLA-4 linked to amino terminus of J chain was expressed in Expi293 and affinity purified by CAPTURE-SELECT® IgM as described in previous examples. Purified Fc fusion protein of Human CTLA4 was immobilized to Fortebio sensors using amine reactive chemistry in sodium Acetate at pH 6.0. Anti CTLA4 IgG (BioLegend A3.B10.G1) binds to immobilized CTLA4 sensor with KD of 2 nM. Binding rates of anti CTLA4 scFv are similar to that of IgG. As expected, the dissociating rate of the monovalent anti CTLA4 scfv is faster than that of the IgG (FIG. 17 Panels A and B).

Example 9: Demonstration that an Anti-TNF Receptor Superfamily (DR5) Antibody can have Super-Agonist Activity with Dramatic Improvement Over IgG The multivalent nature of IgA or IgM molecules presents a useful tool for application to specific biological systems in which multiple components necessarily must be bound simultaneously to transmit biological signals. For instance, many receptor proteins on the surface of eukaryotic cells require the simultaneous activation of multiple monomers or subunits to achieve activation and transmission of a biological signal across a cell membrane, to the cytoplasm of the cell.

One such system of cell surface protein receptors requiring multimerization prior to, or commensurate with, activation is found in the Tumor Necrosis Factor (TNF) superfamily of receptor proteins. Within this superfamily of receptor proteins are members which, upon activation, transmit a signal to the nucleus of the cell causing apoptosis. Other family members of this superfamily cause activation of NF-κB, apoptosis pathways, extracellular signal-regulated kinase (ERK), p38 mitogen-activated protein kinase (p38MAPK), and c-Jun N-terminal kinase (JNK). Non-limiting examples of TNF superfamily receptor members that regulate apoptosis of a cell when activated include the following: TNFR1 (DR1), TNFR2, CD40 (p50), Fas (CD95, Apo1, DR2), CD30, 4-1BB (CD137, ILA), TRAILR1 (DR4, Apo2), DR5 (TRAILR2), TRAILR3 (DcR1), TRAILR4 (DcR2), OPG (OCIF), TWEAKR (FN14), LIGHTR (HVEM), DcR3, DR3, EDAR, and XEDAR. (See, Aggarwal et al., Blood, 119:651-665, 2012).

More particularly, it is postulated that activation of the TNF superfamily receptor protein members mentioned above requires that at least three non-interacting receptor monomers be cross-linked, e.g., by a ligand, to form a stabilized receptor trimer, resulting in signal transduction across the cell membrane. Clustering of these TNF superfamily receptor protein trimers into "rafts" of trimers has been observed and has been postulated to lead to more effective activation of this TNF superfamily receptor protein-dependent signaling cascade. (See, Valley et al., *J. Biol. Chem.*, 287(25):21265-21278, 2012). Additional modes of activation have been discussed. (See, for instance, Lewis et al., *Biophys. J.*, 106(6):L21-L24, 2014) (FIG. 12).

Amino acid sequence of IgM Heavy chain sequence of an anti-DR5 antibody:

```
                                         (SEQ ID NO: 12)
EVQLVQSGGGVERPGGSLRL SCAASGFTFD DYGMSWVRQA

PGKGLEWVSG INWNGGSTGY ADSVKGRVTI SRDNAKNSLY

LQMNSLRAED TAVYYCAKIL GAGRGWYFDL WGKGTTVTVS

SASTKGPSVF PLAPSSKSTS GGFAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPELLG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRE

EMTKNQVSLT CLVKGFYPSD IAVEWESNGQ PENNYKTTPP

VLDSDGSFFL YSKLTVDKSR WQQGNVFSCS VMHEALHNHY

TQKSLSLSPG K
```

Amino acid sequence of IgM Light chain sequence of the anti-DR5 antibody:

```
                                         (SEQ ID NO: 13)
SSELTQDPAV SVALGQTVRI TCQGDSLRSY YASWYQQKPG

QAPVLVIYGK NNRPSGIPDR FSGSSSGNTA SLTITGAQAE
```

```
         -continued
DEADYYCNSR DSSGNHVVFG GGTKLTVLGQ PKAAPSVTLF

PPSSEELQAN KATLVCLISD FYPGAVTVAW KADSSPVKAG

VETTTPSKQS NNKYAASSYL SLTPEQWKSH RSYSCQVTHE

GSTVEKTVAP TECS
```

Amino acid sequence of wild-type J-chain sequence:

```
                                    (SEQ ID NO: 1)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPD
```

Figure 13:
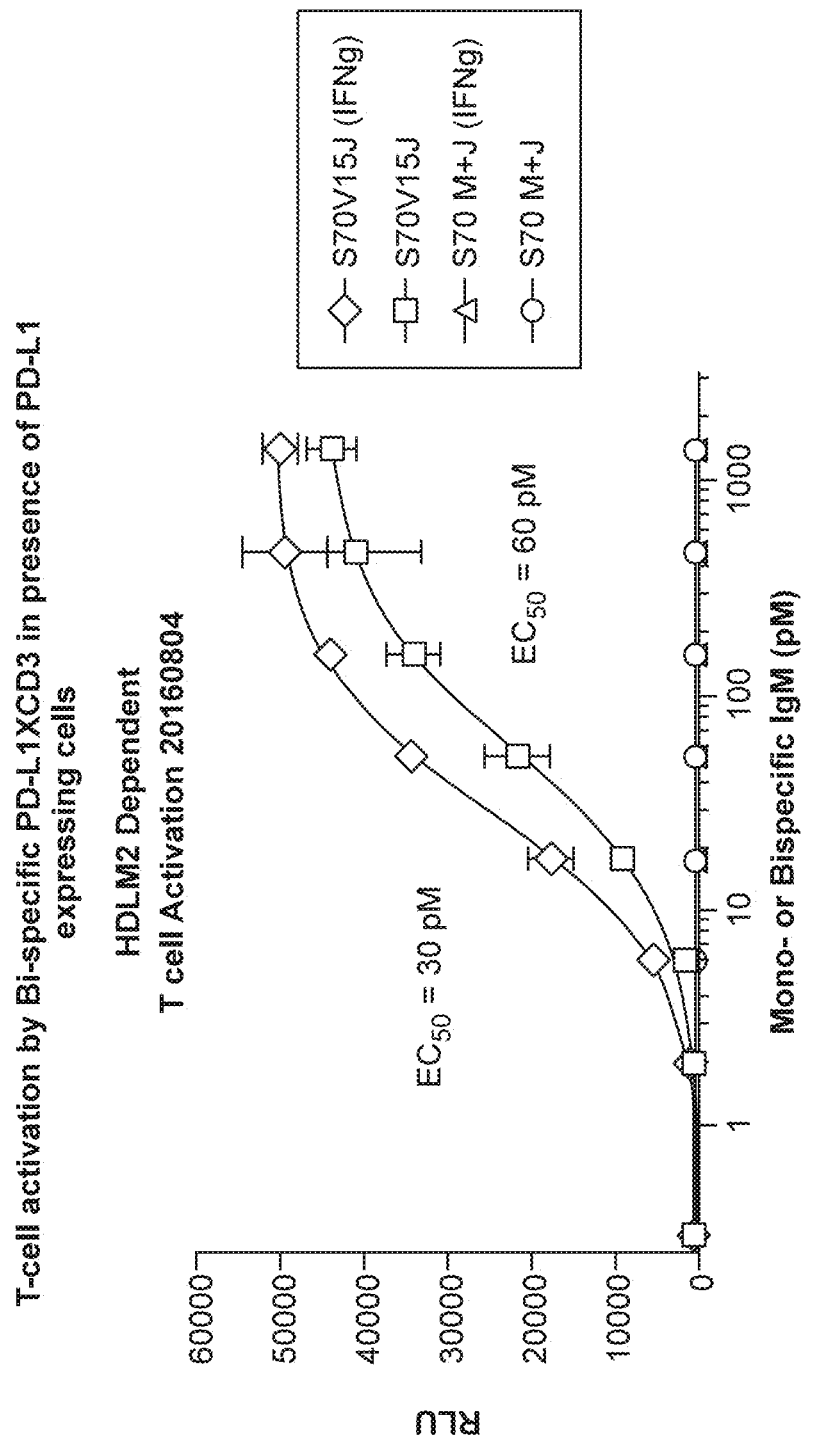
FIG. 13 is a graph showing T-cell activation by S70 IgM carrying the wt or CD3-binding J-chain on a PD-L1 expressing cell line, with and without additional interferon gamma stimulation to increase PD-L1 expression.

The DNA corresponding to these heavy and light chains as well as that corresponding to the wild-type (wt) J-chain sequence were co-transfected into HEK293 cells, and proteins were expressed and purified using the camelid resin as described above. To test cytotoxicity of the purified proteins, a cell viability assay was carried out using COLO205 cells. Briefly, 5000 cells per well were seeded into a 96 well white plate in 25 μL. Antibodies were diluted in phenol-red free medium in a volume of 25 μL and the dilution added to the plate containing the cells. After incubating at 37 C for 24 hours, cell viability was measured using Cell-Titer Glo reagent (Promega). As shown in FIG. 13, the anti-DR5 IgM and IgM+wt J-chain antibodies show dramatically improved cytotoxic effect (greater than 1,000 fold) compared to the corresponding IgG. This underscores the ability of IgM pentamers/hexamers to carry out super-agonist activity on TNF receptor superfamily targets.

Example 10: Anti-CDIM Antibody (IGM-55.5)

IGM-55.5 is a recombinant monoclonal human IgM antibody derived from a natural monoclonal antibody 216 isolated at Stanford University from the splenocytes of a patient with Non-Hodgkin's lymphoma. HuMab 216 was previously used in a B-cell acute lymphoblastic leukemia phase I trial and was demonstrated to be well tolerated with significant decrease in peripheral blasts observed (Liedtke et al, Haematologica, 2012). IGM-55.5 has been re-engineered to be more specific to a carbohydrate determinant as an epitope on normal human B cells as well as B-cell lymphoma and B-progenitor lymphoblasts and therefore to be a potential therapeutic for advanced B cell malignancies, especially indicated for rituximab resistant or refractory patients. The amino acid sequences of the IGM-55.5 light chain and heavy chain are provided below.

IGM-55.5 heavy chain. This heavy chain construct has a full length μ chain for IGM-55.5 which binds CDIM on the surface of B-cells:

```
                                    (SEQ ID NO: 14)
QVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARGRM

AWGASVNFDYWGQGTLVTVSSGSASAPTLFPLVSCENSPSDTSSVAVGCL

AQDFLPDSITFSWKYKNNSDISSTRGFPSVLRGGKYAATSQVLLPSKDVM

QGTDEHVVCKVQHPNGNKEKNVPLPVIAELPPKVSVFVPPRDGFFGNPRK

SKLICQATGFSPRQIQVSWLREGKQVGSGVTTDQVQAEAKESGPTTYKVT

STLTIKESDWLSQSMFTCRVDHRGLTFQQNASSMCVPDQDTAIRVFAIPP

SFASIFLTKSTKLTCLVTDLTTYDSVTISWTRQNGEAVKTHTNISESHPN

ATFSAVGEASICEDDWNSGERFTCTVTHTDLPSPLKQTISRPKGVALHRP

DVYLLPPAREQLNLRESATITCLVTGFSPADVFVQWMQRGQPLSPEKYVT

SAPMPEPQAPGRYFAHSILTVSEEEWNTGETYTCVVAHEALPNRVTERTV

DKSTGKPTLYNVSLVMSDTAGTCY
```

This heavy chain construct has a molecular weight about 64 kD and when co-expressed with light chain, the resultant IgM is able to bind to CDIM positive B cells.

Light chain for IGM-55.5 known as IGM-55.5, which binds CDIM (cell death inducing molecule) on the surface of B-cells:

```
                                    (SEQ ID NO: 15)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPITFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

The light chain construct has a molecular weight about 24 kD and when co-expressed with the appropriate heavy chain (SEQ ID NO: 14) is able to bind to CDIM positive B cells. IGM-55.5 can be made with a modified J-chain, as described herein, and any of the above-described binding moieties can be added to the J-chain.

TABLE 7

Sequence Summary

| SEQ ID NO: | Short Name | Sequence |
|---|---|---|
| 27 | Rituximab VH | QVQLQQPGAELVKPGASVKMSCKASGYTFTSYNMHWVKQTPGRGLEWIGAIYPGNGDT SYNQKFKGKATLTADKSSSTAYMQLSSLTSEDSAVYYCARSTYYGGDWYFNVWGAGTT VTVSA |
| 28 | Rituximab HCDR1 | SYNMH |
| 29 | Rituximab HCDR2 | AIYPGNGDTSYNQKFKG |

TABLE 7-continued

Sequence Summary

| SEQ ID NO: | Short Name | Sequence |
|---|---|---|
| 30 | Rituximab HCDR3 | STYYGGDWYFNV |
| 31 | Rituximab VL | QIVLSQSPAILSASPGEKVTMTCRASSSVSYTHWFQQKPGSSPKPWIYATSNLASGVPVRFSGSGSGTSYSLTISRVEAEDAATYYCQQWTSNPPTFGGGTKLEIKR |
| 32 | Rituximab LCDR1 | RASSSVSYIH |
| 33 | Rituximab LCDR2 | ATSNLAS |
| 34 | Rituximab LCDR3 | QQWTSNPPT |
| 35 | 900 VH | EVQLVESGGG LVQPGGSLRL SCAASGYTFT SYNMHWVRQA PGKGLEWVGA IYPGNGDTSY NQKFKGRFTI SVDKSKNTLY LQMNSLRAED TAVYYCARVV YYSNSYWYFD VWGQGTLVTV SSASTKGPSV FPLAPSSKST SGGTAALGCL VKDYFPEPVT VSWNSGALTS GVHTFPAVLQ SSGLYSLSSV VTVPSSSLGT |
| 36 | 900HCDR3 | VVYYSNSYWYFDV |
| 37 | 900VL | DIQMTQSPSS LSASVGDRVT ITCRASSSVS YMHWYQQKPG KAPKPLIYAP SNLASGVPSR FSGSGSGTDF TLTISSLQPE DFATYYCQQW SFNPPTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL |
| 38 | 900LCDR1 | RASSSVSYMH |
| 39 | 900LCDR2 | APSNLAS |
| 40 | 900LCDR3 | QQWSFNPPT |
| 41 | 125 VH | EVQLVQSGAEVKKPGESLKISCKGSGRTFTSYNMHWVRQMPGKGLEWMGAIYPLTGDTSYNQKSKLQVTISADKSISTAYLQWSSLKASDTAMYYCARSTYVGGDWQFDVWGKGTTVTVSS |
| 42 | 125HCDR2 | AIYPLTGDTSYNQKSKL |
| 43 | 125HCDR3 | STYVGGDWQFDV |
| 44 | 125 VL | EIVLTQSPGTLSLSPGERATLSCRASSSVPYIHWYQQKPGQAPRLLIYATSALASGIPDRFSGSGSGTDFTLTISRLEPEDFAVYYCQQWLSNPPTFGQGTKLEIK |
| 45 | 125LCDR1 | RASSSVPYIH |
| 46 | 125LCDR2 | ATSALAS |
| 47 | 125LCDR3 | QQWLSNPPT |
| 48 | 844 VH #2 | QVQLQQPGAELKKPGASVKVSCKASGYTFTSYNMHWVKQTPGRGLEWTGAIYPGNGDTSYNQKFKGKTTLTADKSSSTAYMELSSLRSEDTAVYYCARSTYYGGDWYFNVWGAGTTVTVSA |
| 49 | 844 VH #3 | QVQLQQPGAELKKPGASVKVSCKASGYTFTSYNMHWVKQTPGRGLEWIGAIYPGNGDTSYNQKFKGKTTLTADKSSSTAYMELSSLRSEDTAVYYCARSTYYGGDWYFNVWGAGTTVTVSA |
| 50 | 844 VL #5 | QIVLSQSPAIITASPGEKVTMTCRASTSASYIHWFQQKPTSSPKPWIYATSNLASGVPSRFSGSGSGTTYSMTISSLEAEDAATYYCQQWTSNPPTFGGGTKLEIK |
| 51 | 844 VL #5 LCDR1 | RASTSASYIH |
| 52 | 844 VL #6 | QIVLSQSPAIITASPGEKVTMTCRASTSVSYIHWFQQKPTSSPKPWIYATSNLASGVPSRFSGSGSGTTYSMTISSLEAEDAATYYCQQWTSNPPTFGGGTKLEIK |
| 53 | 844 VL #6, #7 LCDR1 | RASTSVSYIH |
| 54 | 844 VL #7 | QIVLSQSPAIITASPGEKVTMTCRASTSVSYIHWFQQKPGSSPKPWIYATSNLASGVPSRFSGSGSGTTYSMTISSLEAEDAATYYCQQWTSNPPTFGGGTKLEIK |

TABLE 7-continued

Sequence Summary

| SEQ ID NO: | Short Name | Sequence |
|---|---|---|
| 55 | 844 VL #8 | QIVLSQSPAIITASPGEKVTMTCRASSSVSYIHWFQQKPGSSPKPWIYATSNLASGVPSRFSGSGSGTTYSMTISSLEAEDAATYYCQQWTSNPPTFGGGTKLEIK |
| 56 | 844 VH #10 | EVQLQQSGAELKKPGASVKVSCKASGYTFTSYNMHWVKQTPGQGLEWIGAIYPGNGDTSYNQKFKGKTTLTADKSSSTAYMELSSLRSEDTAVYYCARSNYYGSSYWFFDVWGTGTTVTVSS |
| 57 | 844 VH #10 HCDR3 | SNYYGSSYWFFDV |
| 58 | 844 VL #12 | DIVLTQSPAIITASPGEKVTMTCRASSSVNYMDWYQKKPGSSPKPWIYATSNLASGVPSRFSGSGSGTTYSMTISSLEAEDAATYYCQQWSFNPPTFGGGTKLEIK |
| 59 | 844 VL #12 LCDR1 | RASSSVNYMD |
| 60 | 844 VL #12 LCDR3 | QQWSFNPPT |
| 61 | 164 VH | QVQLQQSGAEVKKPGSSVKVSCKASGYTFTSYNMHWVKQAPGQGLEWIGAIYPGNGDTSYNQKFKGKATLTADESTNTAYMELSSLRSEDTAFYYCARSTYYGGDWYFDVWGQGTTVTVSS |
| 62 | 164 VH HCDR3 | STYYGGDWYFDV |
| 63 | 164 VL | MGWSCIILFLVATATGVHSDIQLTQSPSSLSASVGDRVTMTCRASSSVSYIHWFQQKPGKAPKPWIYATSNLASGVPVRFSGSGSGTDYTFTISSLQPEDIATYYCQQWTSNPPTFGGGTKLEIK |
| 64 | 1.5.3 VH | EVQLVQSGAEVKKPGESLKISCKGSGYSFTSYWIGWVRQMPGKGLEWMGIIYPGDSDTRYSPSFQGQVTISADKSITTAYLQWSSLKASDTAMYYCARHPSYGSGSPNFDYWGQGTLVTVSS |
| 65 | 1.5.3 HCDR1 | GYSFTSYWIG |
| 66 | 1.5.3 HCDR2 | IIYPGDSDTRYSPSFQG |
| 67 | 1.5.3 HCDR3 | HPSYGSGSPNFDY |
| 68 | 1.5.3 VL | DIVMTQTPLSSPVTLGQPASISCRSSQSLVYSDGNTYLSWLQQRPGQPPRLLIYKSNRFSGVPDRFSGSGAGTDFTLKISRVEAEDVGVYYCVQATQFPLTFGGGTKVEIK |
| 69 | 1.5.3 LCDR1 | RSSQSLVYSDGNTYLS |
| 70 | 1.5.3 LCDR2 | KISNRFS |
| 71 | 1.5.3 LCDR3 | VQATQFPLT |
| 72 | human IgM constant region DNA | GCCCCAACCCTTTTCCCCCTCGTCTCCTGTGAGAATTCCCCGTCGGATACGAGCAGCGTGGCCGTTGGCTGCCTCGCACAGGACTTCCTTCCCGACTCCATCACTTTCTCCTGGAAATACAAGAACAACTCTGACATCAGCAGCACCCGGGGCTTCCCATCAGTCCTGAGAGGGGGCAAGCACGCAGCCACCTCACAGGTGCTGCTGCCTTCCAAGGACGTCATGCAGGGCACAGACGAACACGTGGTGTGCAAAGTCCAGCACCCCAACGGCAACAAAGAAAAGAACGTGCCTCTTCCAGTGATTGCTGAGCTGCCTCCCAAAGTGAGCGTCTTCGTCCCACCCCGCGACGGCTTCTTCGGCAACCCCCGCAAGTCCAAGCTCATCTGCCAGGCCACGGGTTTCAGTCCCCGGCAGATTCAGGTGTCCTGGCTGCGCGAGGGGAAGCAGGTGGGGTCTGGCGTCACCACGGACCAGGTGCAGGCTGAGGCAAAGGAGTCTGGGACCACGACCTACAAGGTGACCAGCACACTGACCATCAAAGAGAGCGACTGGCTCAGCCAGAGCATGTTCACCTGCCGCGTGGATCACAGGGGCCTGACCTTCCAGCAGAATGCGTCCTCCATGTGTGGCCCCGATCAAGACACAGCCATCCGGGTCTTCTCCATCCCCCCATCCTTTGCCAGCATCTTCCTCACCAAGTCCACCAAGTTGACCTGCCTGGTCACAGACCTGACCACCTATGACAGCGTGACCATCTCCTGGACCCGCCAGAATGGCGAAGCTGTGAAAACCCACACCAACATCTCCGAGAGCCACCCCAATGCCACTTTCAGCGCCGTGGGTGAGGCCAGCATCTGCGAGGATGACTGGAATTCCGGGGAGAGGTTCACGTGCACCGTGACCCACACAGACCTGCCCTCGCCACTGAAGCAGACCATCTCCCGGCCCAAGGGGGTGGCCCTGCACAGGCCCGATGTCTACTTGCTGCCACCAGCCCGGGAGCAGCTGAACCTGCGGGAGTCGGCCACCATCACGTGCCTGGTGACGGGCTTCTCTCCCGCGGACGTCTTCGTGCAGTGGATGCAGAGGGGGCAGCCCTTGTCCCCGGAGAAGTATGTGACCAGCGCCCCAATGCCTGAGCCCCAGGCCCCAGGCCGGTACTTCGCCCACAGCATCCTGACCGTGTCCGAAGAGGAATGGAACACGGGGGAGACCTACACCTGCGTGGTGGCCCATGAGGCCCTGCCCAACAGGGTCACCGAGAGGACCGTGGACAAGTCCACCGGTAAACCCACCCTGTACAACGTGTCCCTGGTCATGTCCGACACAGCTGGCACCTGCTAC |

TABLE 7-continued

Sequence Summary

| SEQ ID NO: | Short Name | Sequence |
|---|---|---|
| 73 | human IgM constant region AA | GSASAPTLFPLVSCENSPSDTSSVAVGCLAQDFLPDSITFSWKYKNNSDISSTRGFPS VLRGGKYAATSQVLLPSKDVMQGTDEHVVCKVQHPNGNKEKNVPLPVIAELPPKVSVF VPPRDGFFGNPRKSKLICQATGFSPRQIQVSWLREGKQVGSGVTTDQVQAEAKESGPT TYKVTSTLTIKESDWLSQSMFTCRVDHRGLTFQQNASSMCVPDQDTAIRVFAIPPSFA SIFLTKSTKLTCLVTDLTTYDSVTISWTRQNGEAVKTHTNISESHPNATFSAVGEASI CEDDWNSGERFTCTVTHTDLPSPLKQTISRPKGVALHRPDVYLLPPAREQLNLRESAT ITCLVTGFSPADVFVQWMQRGQPLSPEKYVTSAPMPEPQAPGRYFAHSILTVSEEEWN TGETYTCVVAHEALPNRVTERTVDKSTGKPTLYNVSLVMSDTAGTCY |
| 74 | J Chain DNA | ATGAAGAACCATTTGCTTTTCTGGGGAGTCCTGGCGGTTTTTATTAAGGCTGTTCATG TGAAAGCCCAAGAAGATGAAAGGATTGTTCTTGTTGACAACAAATGTAAGTGTCCCG GATTACTTCCAGGATCATCCGTTCTTCCGAAGATCCTAATGAGGACATTGTGGAGAGA AACATCCGAATTATTGTTCCTCTGAACAACAGGGAGAATATCTCTGATCCCACCTCAC CATTGAGAACCAGATTTGTGTACCATTTGTCTGACCTCTGTAAAAAATGTGATCCTAC AGAAGTGGAGCTGGATAATCAGATAGTTACTGCTACCCAGAGCAATATCTGTGATGAA GACAGTGCTACAGAGACCTGCTACACTTATGACAGAAACAAGTGCTACACAGCTGTGG TCCCACTCGTATATGGTGGTGAGACCAAAATGGTGGAAACAGCCTTAACCCCAGATGC CTGCTATCCTGACTAA |
| 75 | J Chain AA | MKNHLLFWGVLAVFIKAVHVKAQEDERIVLVDNKCKCARITSRIIRSSEDPNEDIVER NIIIVPLNNRENISDPTSPLRTRFVYHLSDLCKKCDPTEVELDNQIVTATQSNICDED SATETCYTYDRNKCYTAVVPLVYGGETKMVETALTPDACYPD |
| 76 | human CD20 amino acid | MTTPRNSVNGTFPAEPMKGPIAMQSGPKPLFRRMSSLVGPTQSFFMRESKTLGAVQIM NGLFHIALGGLLMIPAGIYAPICVTVWYPLWGGIMYIISGSLLAATEKNSRKCLVKGK MIMNSLSLFAAISGMILSIMDILNIKISHFLKMESLNFIRAHTPYINIYNCEPANPSE KNSPSTQYCYSIQSLFLGILSVMLIFAFFQELVIAGIVENEWKRTCSRPKSNIVLLSA EEKKEQTIEIKEEVVGLTETSSQPKNEEDIEIIPIQEEEEEETETNFPEPPQDQESSP IENDSSP |
| 77 | Ritux-IgM heavy chain DNA | CAGGTTCAGCTGCAGCAGCCCGGAGCCGAGCTGGTCAAACCTGGCGCTAGTGTGAAAA TGTCATGCAAGGCATCCGGATACACATTCACTAGCTATAACATGCACTGGGTGAAGCA GACCCCCGGCAGGGGTCTGGAGTGGATCGGAGCTATCTACCCCGGCAACGGAGACACA TCTTATAATCAGAAGTTTAAAGGCAAGGCCACCCTGACAGCTGATAAGTCCAGCTCTA CCGCATACATGCAGCTGAGTTCACTGACAAGCGAGGACTCCGCCGTGTACTATTGCGC CCGGTCCACTTACTATGGCGGAGATTGGTATTTCAATGTGTGGGGAGCAGGCACCACA GTCACCGTCTCGAGCGGCAGTGCTAGCGCCCCAACCCTTTTCCCCCTCGTCTCCTGTG AGAATTCCCCGTCGGATACGAGCAGCGTGGCCGTTGGCTGCCTCGCACAGGACTTCCT TCCCGACTCCATCACTTTCTCCTGGAAATACAAGAACAACTCTGACATCAGCAGCACC CGGGGCTTCCCATCAGTCCTGAGGGGGGCAAGTACGGCAGCCACCTCACAGGTGCTGC TGCCTTCCAAGGACGTCATGCAGGGCACAGACGAACACGTGGTGTGCAAAGTCCAGCA CCCCAACGGCAACAAAGAAAAGAACGTGCCTCTTCCAGTGATTGCTGAGCTGCCTCCC AAAGTGAGCGTCTTCGTCCCACCCCGCGACGGCTTCTTCGGCAACCCCCGCAAGTCCA AGCTGCATCTGCCAGGCCACGGGTTTCAGTCCCCGGCAGATTCAGGTGTCCTGGCTGCG CGAGGGGAAGCAGGTGGGGTCTGGCGTCACCACGGACCAGGTGCAGGCTGAGGCCAAA GAGTCTGGGCCCACGACCTACAAGGTGACCAGCACACTGACCATCAAAGAGAGCGACT GGCTCAGCCAGAGCATGTTCACCTGCCGCGTGGATCACAGGGGCCTGACCTTCCAGCA GAATGCGTCCTCCATGTGTGTCCCCGATCAAGACACAGCCATCCGGGTCTTCGCCATC CCCCCATCCTTTGCCAGCATCTTCCTCACCAAGTCCACCAAGTTGACCTGCCTGGTCA CAGACCTGACCACCTATGACAGCGTGACCATCTCCTGGACCCGCCAGAATGGCGAAGC TGTGAAAACCCACACCAACATCTCCGAGAGCCACCCCAATGCCACTTTCAGCGCCGTG GGTGAGGCCAGCATCTGCGAGGATGACTGGAATTCCGGGGAGAGGTTCACGTGCACCG TGACCCACACAGACCTGCCCTCGCCACTGAAGCAGACCATCTCCCGGCCCAAGGGGGT GGCCCTGCACAGGCCCGATGTCTACTTGCTGCCACCAGCCCGGGAGCAGCTGAACCTG CGGGAGTCGGCCACCATCACGTGCCTGGTGACGGGCTTCTCTCCCGCGGACGTCTTCG TGCAGTGGATGCAGAGGGGGCAGCCCTTGTCCCCGGAGAAGTATGTGACCAGCGCCCC AATGCCTGAGCCCCAGGCCCCAGGCCGGTACTTCGCCCACAGCATCCTGACCGTGTCC GAAGAGGAATGGAACACGGGGGAGACCTACACCTGCGTGGTGGCCCATGAGGCCCTGC CCAACAGGGTCACCGAGAGGACCGTGGACAAGTCCACCGGTAAACCCACCCTGTACAA CGTGTCCCTGGTCATGTCCGACACAGCTGGCACCTGCTACTGA |
| 78 | Ritux-IgM heavy chain AA | QVQLQQPGAELVKPGASVKMSCKASGYTFTSYNMHWVKQTPGRGLEWIGAIYPGNGDT SYNQKFKGKATLTADKSSSTAYMQLSSLTSEDSAVYYCARSTYYGGDWYFNVWGAGTT VTVSSGSASAPTLFPLVSCENSPSDTSSVAVGCLAQDFLPDSITFSWKYKNNSDISST RGFPSVLRGGKYAATSQVLLPSKDVMQGTDEHVVCKVQHPNGNKEKNVPLPVIAELPP KVSVFVPPRDGFFGNPRKSKLICQATGFSPRQIQVSWLREGKQVGSGVTTDQVQAEAK ESGPTTYKVTSTLTIKESDWLSQSMFTCRVDHRGLTFQQNASSMCVPDQDTAIRVFAI PPSFASIFLTKSTKLTCLVTDLTTYDSVTISWTRQNGEAVKTHTNISESHPNATFSAV GEASICEDDWNSGERFTCTVTHTDLPSPLKQTISRPKGVALHRPDVYLLPPAREQLNL RESATITCLVTGFSPADVFVQWMQRGQPLSPEKYVTSAPMPEPQAPGRYFAHSILTVS EEEWNTGETYTCVVAHEALPNRVTERTVDKSTGKPTLYNVSLVMSDTAGTCY- |
| 79 | Ritux-light chain DNA | CAAATTGTGCTGTCTCAGAGTCCAGCTATCCTGAGCGCATCTCCCGGAGAGAAGGTGA CCATGACATGCAGAGCCTCCAGCTCTGTCTCCTACATCCACTGGTTCCAGCAGAAGCC |

TABLE 7-continued

Sequence Summary

| SEQ ID NO: | Short Name | Sequence |
|---|---|---|
| | | CGGCTCCTCCCCAAAACCCTGGATCTACGCCACCTCTAACCTGGCTAGTGGTGTGCCT<br>GTCAGGTTTAGTGGATCAGGGTCCGGCACCAGCTACTCTCTGACAATCAGCCGGGTGG<br>AGGCTGAAGACGCCGCTACATACTATTGCCAGCAGTGGACTTCTAATCCCCCTACCTT<br>CGGCGGAGGGACAAAGCTGGAGATCAAG<u>CGTA</u>CGGTGGCTGCACCATCTGTCTTCATC<br>TTCCCGCCATCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGCCCTCCAATC<br>GGGTAACTCCCAGGAGAGTGTCACAGAGCAGGACAGCAAGGACACCTACAGCCTC<br>AGCAGCACCCTGACGCTGAGCAAAGCAGACTACGAGAAACACAAAGTCTACGCCTGCG<br>AAGTCACCCATCAGGGCCTGAGCTCGCCCGTCACAAAGAGCTTCAACAGGGGAGAGTG<br>TT<u>AG</u> |
| 80 | Ritux-light chain AA | QIVLSQSPAILSASPGEKVTMTCRASSSVSYIHWFQQKPGSSPKPWIYATSNLASGVP<br>VRFSGSGSGTSYSLTISRVEAEDAATYYCQQWTSNPPTFGGGTKLEIKRTVAAPSVFI<br>FPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC- |
| 81 | 1.5.3 -IgM heavy chain DNA | GAGGTGCAGCTGGTGCAGTCCGGCGCCGAGGTGAAGAAGCCCGGCGAGTCCCTGAAGA<br>TCTCCTGCAAGGGCTCCGGCTACTCCTTCACCTCCTACTGGATCGGCTGGGTGAGGCA<br>GATGCCCGGCAAGGGCCTGGAGTGGATGGGCATCATCTACCCCGGCGACTCCGACACC<br>AGGTACTCCCCCTCCTTCCAGGGCCAGGTGACCATCTCCGCCGACAAGTCCATCACCA<br>CCGCCTACCTGCAGTGGTCCTCCCTGAAGGCCTCCGACACCGCCATGTACTACTGCGC<br>CAGGCACCCCTCCTACGGCTCCGGCTCCCCCAACTTCGACTACTGGGGCCAGGGCACC<br>CTGGTGACCGTGTCCTCCGGCAGTGCTAGCGCCCCAACCCTTTTCCCCCTCGTCTCCT<br>GTGAGAATTCCCCGTCGGATACGAGCAGCGTGGCCGTTGGCTGCCTCGCACAGGACTT<br>CCTTCCCGACTCCATCACTTTCTCCTGGAAATACAAGAACAACTCTGACATCAGCAGC<br>ACCCGGGGCTTCCCATCAGTCCTGAGAGGGGGCAAGTACGCAGCCACCTCACAGGTGC<br>TGCTGCCTTCCAAGGACGTCATGCAGGGCACAGACGAACACGTGGTGTGCAAAGTCCA<br>GCACCCCAACGGCAACAAAGAAAAGAACGTGCCTCTTCCAGTGATTGCTGAGCTGCCT<br>CCCAAAGTGAGCGTCTTCGTCCCACCCCGCGACGGCTTCTTCGGCAACCCCCGCAAGT<br>CCAAGCTCATCTGCCAGGCCACGGGTTTCAGTCCCGGCAGATTCAGGTGTCCTGGCT<br>GCGCGAGGGGAAGCAGGTGGGGTCTGGCGTCACCACGGACCAGGTGCAGGCTGAGGCC<br>AAAGAGTCTGGGCCCACGACCTACAAGGTGACCAGCACACTGACCATCAAAGAGAGCG<br>ACTGGCTCAGCCAGAGCATGTTCACCTGCCGCGTGGATCACAGGGGCCTGACCTTCCA<br>GCAGAATGCGTCCTCCATGTGTGTCCCCGATCAAGACACAGCCATCCGGGTCTTCGCC<br>ATCCCCCCATCCTTTGCCAGCATCTTCCTCACCAAGTCCACCAAGTTGACCTGCCTGG<br>TCACAGACCTGACCACCTATGACAGCGTGACCATCTCCTGGACCCGCCAGAATGGCGA<br>AGCTGTGAAAACCCACACCAACATCTCCGAGAGCCACCCCAATGCCACTTTCAGCGCC<br>GTGGGTGAGGCCAGCATCTGCGAGGATGACTGGAATTCCGGGGAGAGGTTCACGTGCA<br>CCGTGACCCACACAGACCTGCCCTCGCCACTGAAGCAGACCATCTCCCGGCCCAAGGG<br>GGTGGCCCTGCACAGGCCCGATGTCTACTTGCTGCCACCAGCCCGGGAGCAGCTGAAC<br>CTGCGGGAGTCGGCCACCATCACGTGCCTGGTGACGGGCTTCTCTCCCGCGGACGTCT<br>TCGTGCAGTGGATGCAGAGGGGGCAGCCCTTGTCCCCGGAGAAGTATGTGACCAGCGC<br>CCCCATGCCTGAGCCCCAGGCCCCAGGCCGGTACTTCGCCCACAGCATCCTGACCGTG<br>TCCGAAGAGGAATGGAACACGGGGGAGACCTACACCTGCGTGGTGGCCCATGAGGCCC<br>TGCCCAACAGGGTCACCGAGAGGACCGTGGACAAGTCCACCGGTAAACCCACCCTGTA<br>CAACGTGTCCCTGGTCATGTCCGACACAGCTGGCACCTGCTACTGA |
| 82 | 1.5.3 -IgM heavy chain AA | EVQLVQSGAEVKKPGESLKISCKGSGYSFTSYWIGWVRQMPGKGLEWMGIIYPGDSDT<br>RYSPSFQGQVTISADKSITTAYLQWSSLKASDTAMYYCARHPSYGSGSPNFDYWGQGT<br>LVTVSSGSASAPTLFPLVSCENSPSDTSSVAVGCLAQDFLPDSITFSWKYKNNSDISS<br>TRGFPSVLRGGKYAATSQVLLPSKDVMQGTDEHVVCKVQHPNGNKEKNVPLPVIAELP<br>PKVSVFVPPRDGFFGNPRKSKLICQATGFSPRQIQVSWLREGKQVGSGVTTDQVQAEA<br>KESGPTTYKVTSTLTIKESDWLSQSMFTCRVDHRGLTFQQNASSMCVPDQDTAIRVFA<br>IPPSFASIFLTKSTKLTCLVTDLTTYDSVTISWTRQNGEAVKTHTNISESHPNATFSA<br>VGEASICEDDWNSGERFTCTVTHTDLPSPLKQTISRPKGVALHRPDVYLLPPAREQLN<br>LRESATITCLVTGFSPADVFVQWMQRGQPLSPEKYVTSAPMPEPQAPGRYFAHSILTV<br>SEEEWNTGETYTCVVAHEALPNRVTERTVDKSTGKPTLYNVSLVMSDTAGTCY- |
| 83 | 1.5.3 light chain DNA | GACATCGTGATGACCCAGACCCCCCTGTCCTCCCCCGTGACCCTGGGCCAGCCCGCCT<br>CCATCTCCTGCAGGTCCTCCCAGTCCCTGGTGTACTCCGACGGCAACACCTACCTGTC<br>CTGGCTGCAGCAGAGGCCCGGCCAGCCCCCCAGGCTGCTGATCTACAAGATCTCCAAC<br>AGGTTCTCCGGCGTGCCCGACAGGTTCTCCGGCTCCGGCGCCGGCACCGACTTCACCC<br>TGAAGATCTCCAGGGTGGAGGCCGAGGACGTGGGCGTGTACTACTGCGTGCAGGCCAC<br>CCAGTTCCCCCTGACCTTCGGCGGCGGCACCAAGGTGGAGATCAAGCGTACGGTGGCT<br>GCACCATCTGTCTTCATCTTCCCGCCATCTGATGAGCAGTTGAAATCTGGAACTGCCT<br>CTGTTGTGTGCCTGCTGAATAACTTCTATCCCAGAGAGGCCAAAGTACAGTGGAAGGT<br>GGATAACGCCCTCCAATCGGGTAACTCCCAGGAGAGTGTCACAGAGCAGGACAGCAAG<br>GACAGCACCTACAGCCTCAGCAGCACCCTGACGCTGAGCAAAGCAGACTACGAGAAAC<br>ACAAAGTCTACGCCTGCGAAGTCACCCATCAGGGCCTGAGCTCGCCCGTCACAAAGAG<br>CTTCAACAGGGGAGAGTGTTAG |

TABLE 7-continued

Sequence Summary

| SEQ ID NO: | Short Name | Sequence |
|---|---|---|
| 84 | 1.5.3 light chain AA | DIVMTQTPLSSPVTLGQPASISCRSSQSLVYSDGNTYLSWLQQRPGQPPRLLIYKISN<br>RFSGVPDRFSGSGAGTDFTLKISRVEAEDVGVYYCVQATQFPLTFGGGTKVEIKRTVA<br>APSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC- |
| 85 | human IgA1 constant region aa P01876 | ASPTSPKVFPLSLCSTQPDGNVVIACLVQGFFPQEPLSVTWSESGQGVTARNFPPSQD<br>ASGDLYTTSSQLTLPATQCLAGKSVTCHVKHYTNPSQDVTVPCPVPSTPPTPSPSTPP<br>TPSPSCCHPRLSLHRPALEDLLLGSEANLTCTLTGLRDASGVTFTWTPSSGKSAVQGP<br>PERDLCGCYSVSSVLPGCAEPWNHGKTFTCTAAYPESKTPLTATLSKSGNTFRPEVHL<br>LPPPSEELALNELVTLTCLARGFSPKDVLVRWLQGSQELPREKYLTWASRQEPSQGTT<br>TFAVTSILRVAAEDWKKGDTFSCMVGHEALPLAFTQKTIDRLAGKPTHVNVSVVMAEV<br>DGTCY |
| 86 | human IgA2 constant region aa P01877 | ASPTSPKVFPLSLDSTPQDGNVVVACLVQGFFPQEPLSVTWSESGQNVTARNFPPSQD<br>ASGDLYTTSSQLTLPATQCPDGKSVTCHVKHYTNPSQDVTVPCPVPPPPPCCHPRLSL<br>HRPALEDLLLGSEANLTCTLTGLRDASGATFTWTPSSGKSAVQGPPERDLCGCYSVSS<br>VLPGCAQPWNHGETFTCTAAHPELKTPLTANITKSGNTFRPEVHLLPPPSEELALNEL<br>VTLTCLARGFSPKDVLVRWLQGSQELPREKYLTWASRQEPSQGTTTFAVTSILRVAAE<br>DWKKGDTFSCMVGHEALPLAFTQKTIDRMAGKPTHVNVSVVMAEVDGTCY |
| 87 | Human Secretory Component Precursor | MLLFVLTCLLAVFPAISTKSPIFGPEEVNSVEGNSVSITCYYPPTSVNRHTRKYWCRQ<br>GARGGCITLISSEGYVSSKYAGRANLTNFPENGTFVVNIAQLSQDDSGRYKCGLGINS<br>RGLSFDVSLEVSQGPGLLNDTKVYTVDLGRTVTINCPFKTENAQKRKSLYKQIGLYPV<br>LVIDSSGYVNPNYTGRIRLDIQGTGQLLFSVVINQLRLSDAGQYLCQAGDDSNSNKKN<br>ADLQVLKPEPELVYEDLRGSVTFHCALGPEVANVAKFLCRQSSGENCDVVVNTLGKRA<br>PAFEGRILLNPQDKDGSFSVVITGLRKEDAGRYLCGAHSDGQLQEGSPIQAWQLFVNE<br>ESTIPRSPTVVKGVAGGSVAVLCPYNRKESKSIKYWCLWEGAQNGRCPLLVDSEGWVK<br>AQYEGRLSLLEEPGNGTFTVILNQLTSRDAGFYWCLTNGDTLWRTTVEIKIIEGEPNL<br>KVPGNVTAVLGETLKVPCHFPCKFSSYEKYWCKWNNTGCQALPSQDEGPSKAFVNCDE<br>NSRLVSLTLNLVTRADEGWYWCGVKQGHFYGETAAVYVAVEERKAAGSRDVSLAKADA<br>APDEKVLDSGFREIENKAIQDPRLFAEEKAVADTRDQADGSRASVDSGSSEEQGGSSR<br>ALVSTLVPLGLVLAVGAVAVGVARARHRKNVDRVSIRSYRTDISMSDFENSREFGAND<br>NMGASSITQETSLGGKEEFVATTESTTETKEPKKAKRSSKEEAEMAYKDFLLQSSTVA<br>AEAQDGPQEA |
| 88 | human secretory component mature | KSPIFGPEEVNSVEGNSVSITCYYPPTSVNRHTRKYWCRQGARGGCITLISSEGYVSS<br>KYAGRANLTNFPENGTFVVNIAQLSQDDSGRYKCGLGINSRGLSFDVSLEVSQGPGLL<br>NDTKVYTVDLGRTVTINCPFKTENAQKRKSLYKQIGLYPVLVIDSSGYVNPNYTGRIR<br>LDIQGTGQLLFSVVINQLRLSDAGQYLCQAGDDSNSNKKNADLQVLKPEPELVYEDLR<br>GSVTFHCALGPEVANVAKFLCRQSSGENCDVVVNTLGKRAPAFEGRILLNPQDKDGSF<br>SVVITGLRKEDAGRYLCGAHSDGQLQEGSPIQAWQLFVNEESTIPRSPTVVKGVAGGS<br>VAVLCPYNRKESKSIKYWCLWEGAQNGRCPLLVDSEGWVKAQYEGRLSLLEEPGNGTF<br>TVILNQLTSRDAGFYWCLTNGDTLWRTTVEIKIIEGEPNLKVPGNVTAVLGETLKVPC<br>HFPCKFSSYEKYWCKWNNTGCQALPSQDEGPSKAFVNCDENSRLVSLTLNLVTRADEG<br>WYWCGVKQGHFYGETAAVYVAVEERKAAGSRDVSLAKADAAPDEKVLDSGFREIENKA<br>IQDPR |
| 89 | J15ABD DNA | ATGGAATGGAGCTGGGTCTTTCTCTTCTTCCTGTCAGTAACGACTGGTGTCCACTCCC<br>AGGAAGATGAGCGGATCGTGCTGGTGGACAACAAGTGCAAGTGCGCCCGGATCACCTC<br>CCGGATCATCCGGTCCTCCGAGGATCCCAACGAGGACATCGTGGAACGGAACATCAGA<br>ATCATCGTGCCCCTGAACAACCGCGAGAACATCTCCGACCCCACCAGCCCTCTGCGGA<br>CCAGATTCGTGTACCACCTGTCCGACCTGTGCAAGAAGTGCGACCCTACCGAGGTGGA<br>ACTGGACAACCAGATCGTGACCGCCACCCAGTCCAACATCTGCGACGAGGACTCCGCC<br>ACCGAGACATGCTACACCTACGACCGGAACAAGTGCTACACCGCCGTGGTGCCTCTGG<br>TGTACGGCGGCGAGACAAAGATGGTGGAAACCGCCCTGACCCCCGACGCCTGCTATCC<br>TGATGAGGCGGAGGATCTGGTGGCGGTGGTTCTGGCGGAGGGGGCTCTCAGCACGAT<br>GAGGCCGTGGACGCCAATTCTCTGGCCGAGGCTAAGGTGCTGGCCAACAGAGAGCTGG<br>ATAAGTACGGCGTGTCCGACTACTACAAGAACCTGATCAACAACGCCAAGACCGTGGA<br>AGGCGTGAAGGCCCTGATCGACGAGATCCTGGCTGCCCTGCCTTGA |
| 90 | J15ABD AA | MEWSWVFLFFLSVTTGVHSQEDERIVLVDNKCKCARITSRIIRSSEDPNEDIVERNIR<br>IIVPLNNRENISDPTSPLRTRFVYHLSDLCKKCDPTEVELDNQIVTATQSNICDEDSA<br>TETCYTYDRNKCYTAVVPLVYGGETKMVETALTPDACYPDGGGSGGGGSGGGGSQHD<br>EAVDANSLAEAKVLANRELDKYGVSDYYKNLINNAKTVEGVKALIDEILAALP |
| 91 | ABD15J DNA | ATGGAATGGAGCTGGGTCTTTCTCTTCTTCCTGTCAGTAACGACTGGTGTCCACTCCC<br>AGCACGATGAGGCCGTGGACGCCAATTCTCTGGCCGAGGCTAAGGTGCTGGCCAACAG<br>AGAGCTGGATAAGTACGGCGTGTCCGACTACTACAAGAACCTGATCAACAACGCCAAG<br>ACCGTGGAAGGCGTGAAGGCCCTGATCGACGAGATCCTGGCTGCCCTGCCTGGAGGCG<br>GAGGATCTGGTGCCGTGGTTCTGGCGGAGGGGGCTCTCAGGAAGATGAGCGGATCGT<br>GCTGGTGGACAACAAGTGCAAGTGCGCCCGGATCACCTCCCGGATCATCCGGTCCTCC<br>GAGGATCCCAACGAGGACATCGTGGAACGGAACATCAGAATCATCGTGCCCCTGAACA<br>ACCGCGAGAACATCTCCGACCCCACCAGCCCTCTGCGGACCAGATTCGTGTACCACCT |

TABLE 7-continued

Sequence Summary

| SEQ ID NO: | Short Name | Sequence |
|---|---|---|
| | | GTCCGACCTGTGCAAGAAGTGCGACCCTACCGAGGTGGAACTGGACAACCAGATCGTG<br>ACCGCCACCCAGTCCAACATCTGCGACGAGGACTCCGCCACCGAGACATGCTACACCT<br>ACGACCGGAACAAGTGCTACACCGCCGTGGTGCCTCTGGTGTACGGCGGCGAGACAAA<br>GATGGTGGAAACCGCCCTGACCCCCGACGCCTGCTATCCTGATTGA |
| 92 | ABD15J AA | MEWSWVFLFFLSVTTGVHSQHDEAVDANSLAEAKVLANRELDKYGVSDYYKNLINNAK<br>TVEGVKALIDEILAALPGGGSGGGGSGGGGSQEDERIVLVDNKCKCARITSRIIRSS<br>EDPNEDIVERNIRIIVPLNNRENISDPTSPLRTRFVYHLSDLCKKCDPTEVELDNQIV<br>TATQSNICDEDSATETCYTYDRNKCYTAVVPLVYGGETKMVETALTPDACYPD |
| 93 | HSA15J DNA | ATGAAATGGGTCACCTTTATCTCCCTGCTGTTCCTGTTCTCCTCCGCCTACTCTCGGG<br>GCGTGTTCAGAAGAGACGCCCACAAATCGGAGGTAGCGCACCGGTTCAAAGACTTGGG<br>AGAAGAAAACTTTAAGGCCCTTGTACTCATTGCGTTTGCGCAGTATTTGCAGCAGTGC<br>CCATTCGAGGACCATGTCAAACTTGTCAACGAAGTGACAGAGTTTGCGAAAACTTGCG<br>TCGCCGACGAATCCGCGGAGAACTGTGACAAGTCGCTGCATACGTTGTTCGGGGATAA<br>GCTCTGTACCGTAGCGACCTTGAGGGAAACTTACGGGGAAATGGCGGACTGTTGCGCT<br>AAGCAGGAGCCGGAACGGAACGAGTGTTTCCTTCAGCATAAGGATGACAACCCCAACC<br>TCCCTAGATTGGTCAGACCCGAAGTGGATGTGATGTGCACAGCATTCCATGACAATGA<br>GGAAACCTTTCTCAAAAAGTATTTGTACGAGATTGCCCGACGACACCCCTATTTCTAC<br>GCTCCCGAGTTGCTCTTCTTCGCGAAACGGTATAAAGCTGCCTTTACTGAATGCTGTC<br>AAGCAGCGGACAAGGCCGCATGCCTCCTTCCCAAATTGGATGAACTCCGCGATGAAGG<br>GAAGGCGTCATCGGCCAAACAGCGGCTTAAGTGCGCATCGCTTCAGAAATTCGGAGAG<br>AGGGCGTTCAAAGCGTGGGCCGTCGCGAGACTGTCGCAGAGATTCCCTAAGGCGGAAT<br>TTGCAGAGGTATCGAAGCTCGTGACAGACCTCACAAAGGTCCACACCGAATGTTGCCA<br>TGGAGACCTGCTTGAGTGCGCCGATGATAGGGCAGACCTCGCAAAGTACATTTGTGAG<br>AATCAGGACAGCATTAGCTCCAAGCTGAAAGAGTGCTGTGAGAAGCCTTTGCTGGAAA<br>ATCCCACTGTATCGCCGAGGTAGAAAACGATGAAATGCCCGCTGATCTTCCCTCGCT<br>GGCGGCAGACTTCGTCGAGTCGAAGGACGTCTGCAAGAATTACGCAGAGGCAAAAGAT<br>GTGTTTCTTGGAATGTTCCTTTATGAGTATGCGAGAAGGCACCCGGATTATTCCGTGG<br>TACTGCTCTTGCGATTGGCGAAAACGTACGAAACAACGCTTGAGAAGTGTTGTGCGGC<br>TGCCGACCCGCATGAGTGCTACGCCAAGGTATTTGATGAGTTTAAACCTCTTGTCGAG<br>GAACCCCAGAATCTTATCAAGCAGAACTGCGAGCTTTTCAAGCAGTTGGGTGAATACA<br>AATTCCAGAACGCGCTTCTGGTGAGGTATACCAAGAAAGTACCTCAAGTCTCAACACC<br>CACACTCGTCGAGGTGTCACGGAACCTCGGGAAAGTAGGGTCGAAGTGCTGTAAACAC<br>CCAGAGGCCAAGCGCATGCCCTGTGCGGAGGACTACCTCTCGGTAGTGTTGAATCAAC<br>TGTGTGTCCTCCACGAAAAGACGCCGGTGTCAGACCGCGTCACAAAGTGCTGCACGGA<br>GAGCCTGGTCAATAGACGCCCCTGCTTCTCAGCGCTGGAGGTGGATGAGACATACGTC<br>CCGAAAGAGTTTAACGCCGAAACGTTTACTTTTCATGCTGATATCTGTACGTTGTCAG<br>AGAAGGAAAGGCAAATCAAGAAACAAACTGCGCTTGTGGAACTGGTGAAGCACAAACC<br>GAAGGCGACTAAGGAACAGCTGAAGGCGGTGATGGATGACTTTGCCGCGTTCGTAGAG<br>AAATGCTGTAAAGCAGACGATAAGGAGACTTGTTTTGCGAAGAGGGACCTAAACTTG<br>TTGCTGCAAGTCAAGCTGCCTTAGGCTTAGGAGGCGGAGGATCTGGTGGCGGTGGTTC<br>TGGCGGAGGGGGCTCTCAGGAAGATGAGCGGATCGTGCTGGTGGACAACAAGTGCAAG<br>TGCGCCCGGATCACCTCCCGGATCATCCGGTCCTCCGAGGATCCCAACGAGGACATCG<br>TGGAACGGAACATCAGAATCATCGTGCCCCTGAACAACCGCGAGAACATCTCCGACCC<br>CACCAGCCCTCTGCGGACCAGATTCGTGTACCACCTGTCCGACCTGTGCAAGAAGTGC<br>GACCCTACCGAGGTGGAACTGGACAACCAGATCGTGACCGCCACCCAGTCCAACATCT<br>GCGACGAGGACTCCGCCACCGAGACATGCTACACCTACGACCGGAACAAGTGCTACAC<br>CGCCGTGGTGCCTCTGGTGTACGGCGGCGAGACAAAGATGGTGGAAACCGCCCTGACC<br>CCCGACGCCTGCTATCCTGATTAG |
| 94 | HSA15J AA | MKWVTFISLLFLFSSAYSRGVFRRDAHKSEVAHRFKDLGEENFKALVLIAFAQYLQQC<br>PFEDHVKLVNEVTEFAKTCVADESAENCDKSLHTLFGDKLCTVATLRETYGEMADCCA<br>KQEPERNECFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKCASLQKFGE<br>RAFKAWAVARLSQRFPKAEFAEVSKLVTDLTKVHTECCHGDLLECADDRADLAKYICE<br>NQDSISSKLKECCEKPLLEKSHCIAEVENDEMPADLPSLAADFVESKDVCKNYAEAKD<br>VFLGMFLYEYARRHPDYSVVLLRLAKTYETTLEKCCAAADPHECYAKVFDEFKPLVE<br>EPQNLIKQNCELFKQLGEYKFQNALLVRYTKKVPQVSTPTLVEVSRNLGKVGSKCCKH<br>PEAKRMPCAEDYLSVVLNQLCVLHEKTPVSDRVTKCCTESLVNRRPCFSALEVDETYV<br>PKEFNAETFTFHADICTLSEKERQIKKQTALVELVKHKPKATKEQLKAVMDDFAAFVE<br>KCCCKADDKETCFAEEGPKLVAASQAALGLGGGGSGGGGSGGGGSQEDERIVLVDNKCK<br>CARTTSRIIRSSEDPNEDIVERNIRIIVPLNNRENISDPTSPLRTRFVYHLSDLCKKC<br>DPTEVELDNQIVTATQSNICDEDSATETCYTYDRNKCYTAVVPLVYGGETKMVETALT<br>PDACYPD |
| 95 | J15HSA DNA | ATGAAGAACCATCTGCTGTTCTGGGGCGTGCTGGCCGTGTTCATCAAGGCCGTGCACG<br>TGAAGGCCCAGGAAGATGAGCGGATCGTGCTGGTGGACAACAAGTGCAAGTGCGCCCG<br>GATCACCTCCCGGATCATCCGGTCCTCCGAGGATCCCAACGAGGACATCGTGGAACGG<br>AACATCAGAATCATCGTGCCCCTGAACAACCGCGAGAACATCTCCGACCCCACCAGCC<br>CTCTGCGGACCAGATTCGTGTACCACCTGTCCGACCTGTGCAAGAAGTGCGACCCTAC<br>CGAGGTGGAACTGGACAACCAGATCGTGACCGCCACCCAGTCCAACATCTGCGACGAG<br>GACTCCGCCACCGAGACATGCTACACCTACGACCGGAACAAGTGCTACACCGCCGTGG<br>TGCCTCTGGTGTACGGCGGCGAGACAAAGATGGTGGAAACCGCCCTGACCCCCGACGC |

TABLE 7-continued

Sequence Summary

| SEQ ID NO: | Short Name | Sequence |
|---|---|---|
| | | CTGCTATCCTGATGGAGGCGGAGGATCTGGTGGCGGTGGTTCTGGCGGAGGGGCTCT<br>GACGCCCACAAATCGGAGGTAGCGCACCGGTTCAAAGACTTGGGAGAAGAAAACTTTA<br>AGGCCCTTGTACTCATTGCGTTTGCGCAGTATTTGCAGCAGTGCCCATTCGAGGACCA<br>TGTCAAACTTGTCAACGAAGTGACAGAGTTTGCGAAAACTTGCGTCGCCGACGAATCC<br>GCGGAGAACTGTGACAAGTCGCTGCATACGTTGTTCGGGGATAAGCTCTGTACCGTAG<br>CGACCTTGAGGGAAACTTACGGGGAAATGGCGACTGTTGCGCTAAGCAGGAGCCGGA<br>ACGGAACGAGTGTTTCCTTCAGCATAAGGATGACAACCCCAACCTCCCTAGATTGGTC<br>AGACCCGAAGTGGATGTGATGTGCACAGCATTCCATGACAATGAGGAAACCTTTCTCA<br>AAAAGTATTTGTACGAGATTGCCCGACGACACCCCTATTTCTACGCTCCCGAGTTGCT<br>CTTCTTCGCGAAACGGTATAAAGCTGCCTTTACTGAATGCTGTCAAGCAGCGGACAAG<br>GCCGCATGCCTCCTTCCCAAATTGGATGAACTCCGCGATGAAGGGAAGGCGTCATCGG<br>CCAAACAGCGGCTTAAGTGCGCATCGCTTCAGAAATTCGGAGAGAGGGCGTTCAAAGC<br>GTGGGCCGTCGCGAGACTGTCGCAGAGATTCCCTAAGGCGGAATTTGCAGAGGTATCG<br>AAGCTCGTGACAGACCTCACAAAGGTCCACACCGAATGTTGCCATGGAGACCTGCTTG<br>AGTGCGCCGATGATAGGGCAGACCTCGCAAAGTACATTTGTGAGAATCAGGACAGCAT<br>TAGCTCCAAGCTGAAAGAGTGCTGTGAGAAGCCTTTGCTGGAAAAATCCCACTGTATC<br>GCCGAGGTAGAAAACGATGAAATGCCCGCTGATCTTCCCTCGCTGGCGGCAGACTTCG<br>TCGAGTCGAAGGACGTCTGCAAGAATTACGCAGAGGCAAAAGATGTGTTTCTTGGAAT<br>GTTCCTTTATGAGTATGCGAGAAGGCACCCGGATTATTCCGTGGTACTGCTCTTGCGA<br>TTGGCGAAAACGTACGAAACAACGCTTGAGAAGTGTTGTGCGGCTGCCGACCCGCATG<br>AGTGCTACGCCAAGGTATTTGATGAGTTTAAACCTCTTGTCGAGGAACCCCAGAATCT<br>TATCAAGCAGAACTGCGAGCTTTTCAAGCAGTTGGGTGAATACAAATTCCAGAACGCG<br>CTTCTGGTGAGGTATACCAAGAAAGTACCTCAAGTCTCAACACCCACACTCGTCGAGG<br>TGTCACGGAACCTCGGGAAAGTAGGGTCGAAGTGCTGTAAACACCCAGAGGCCAAGCG<br>CATGCCCTGTGCGGAGGACTACCTCTCGGTAGTGTTGAATCAACTGTGTGTCCTCCAC<br>GAAAAGACGCCGGTGTCAGACCGCGTCACAAAGTGCTGCACGGAGAGCCTGGTCAATA<br>GACGCCCCTGCTTCTCAGCGCTGGAGGTGGATGAGACATACGTCCCGAAAGAGTTTAA<br>CGCCGAAACGTTTACTTTTCATGCTGATATCTGTACGTTGTCAGAGAAGGAAAGGCAA<br>ATCAAGAAACAAACTGCGCTTGTGGAACTGGTGAAGCACAAACCGAAGGCGACTAAGG<br>AACAGCTGAAGGCGGTGATGGATGACTTTGCCGCGTTCGTAGAGAAATGCTGTAAAGC<br>AGACGATAAGGAGACTTGTTTTGCGGAAGAGGGACCTAAACTTGTTGCTGCAAGTCAA<br>GCTGCCTTAGGCTTATAG |
| 96 | J15HSA AA | MKNHLLFWGVLAVFIKAVHVKAQEDERIVLVDNKCKCARITSRIIRSSEDPNEDIVER<br>NIRIIVPLNNRENISDPTSPLRTRFVYHLSDLCKKCDPTEVELDNQIVTATQSNICDE<br>DSATETCYTYDRNKCYTAVVPLVYGGETKMVETALTPDACYPDGGGSGSGGGSGGGGS<br>DAHKSEVAHRFKDLGEENFKALVLIAFAQYLQQCPFEDHVKLVNEVTEFAKTCVADES<br>AENCDKSLHTLFGDKLCTVATLRETYGEMADCCAKQEPERNECFLQHKDDNPNLPRLV<br>RPEVDVMCTAFHDNEETFLKKYLYEIARRHPYFYAPELLFFAKRYKAAFTECCQAADK<br>AACLLPKLDELRDEGKASSAKQRLKCASLQKFGERAFKAWAVARLSQRFPKAEFAEVS<br>KLVTDLTKVHTECCHGDLLECADDRADLAKYICENQDSISSKLKECCEKPLLEKSHCI<br>AEVENDEMPADLPSLAADFVESKDVCKNYAEAKDVFLGMFLYEYARRHPDYSVVLLLR<br>LAKTYETTLEKCCAAADPHECYAKVFDEFKPLVEEPQNLIKQNCELFKQLGEYKFQNA<br>LLVRYTKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEKERQ<br>IKKQTALVELVKHKPKATKEQLKAVMDDFAAFVEKCCKADDKETCFAEEGPKLVAASQ<br>AALGL |
| 97 | V15J15ABD DNA | ATGGGGTGGTCCTACATTATCCTGTTCCTCGTGGCCACCGCCACTGGCGTGCACTCAC<br>AGGTGCAGCTGGTGCAGTCTGGCGCCGAAGTGAAGAAACCTGGCGCCTCCGTGAAGGT<br>GTCCTGCAAGGCCTCCGGCTACACCTTCATCAGCTACACCATGCACTGGGTGCGACAG<br>GCCCCTGGACAGGGCCTGGAATGGATGGGCTACATCAACCCTAGATCTGGCTACACCC<br>ACTACAACCAGAAGCTGAAGGACAAGGCCACCCTGACCGCCGACAAGTCTGCCTCCAC<br>CGCCTACATGGAACTGTCCTCCCTGCGGAGCGAGGACACCGCCGTGTACTACTGTGCC<br>AGATCCGCCTACTACGACTACGACGGCTTCGCCTATTGGGGCCAGGGCACCCTCGTGA<br>CAGTGTCTAGCGGTGGCGGAGGATCTGGCGGAGGCGGTAGTGGCGGTGGCGGATCTGA<br>TATCCAGATGACCCAGTCCCCCTCCAGCCTGTCTGCCTCTGTGGGCGACAGAGTGACA<br>ATTACCTGCTCCGCCAGCTCCTCCGTGTCTTACATGAACTGGTATCAGCAGAAGCCCG<br>GCAAGGCCCCCAAGCGGCTGATCTACGACACCTCCAAGCTGGCCTCTGGCGTGCCCTC<br>CAGATTCTCCGGCTCTGGCTCTGGCACCGACTTTACCCTGACCATCAGCTCCCTGCAG<br>CCCGAGGACTTCGCCACCTACTACTGCCAGCAGTGGTCCTCCAACCCTCCCACCTTTG<br>GCGGAGGCACCAAGGTGGAAATCAAAGGCGGCGGAGGAAGCGGGGGAGGCGGTTCTGG<br>GGGTGGTGGATCTCAGGAAGATGAGCGGATCGTGCTGGTGGACAACAAGTGCAAGTGC<br>GCCCGGATCACCTCCCGGATCATCCGGTCCTCCGAGGATCCCAACGAGGACATCGTGG<br>AACGGAACATCAGAATCATCGTGCCCCTGAACAACCGCGAGAACATCTCCGACCCCAC<br>CAGCCCTCTGCGGACCAGATTCGTGTACCACCTGTCCGACCTGTGCAAGAAGTGCGAC<br>CCTACCGAGGTGGAACTGGACAACCAGATCGTGACCGCCACCCAGTCCAACATCTGCG<br>ACGAGGACTCCGCCACCGAGACATGCTACACCTACGACCGGAACAAGTGCTACACCGC<br>CGTGGTGCCTCTGGTGTACGGCGGCGAGACAAAGATGGTGGAAACCGCCCTGACCCCC<br>GACGCCTGCTATCCTGATGGAGGCGGAGGATCTGGTGGCGGTGGTTCTGGCGGAGGGG<br>GCTCTCAGCACGATGAGGCCGTGGACGCCAATTCTCTGGCCGAGGCTAAGGTGCTGGC<br>CAACAGAGAGCTGGATAAGTACGGCGTGTCCGACTACTACAAGAACCTGATCAACAAC<br>GCCAAGACCGTGGAAGGCGTGAAGGCCCTGATCGACGAGATCCTGGCTGCCCTGCCTT<br>GA |

TABLE 7-continued

Sequence Summary

| SEQ ID NO: | Short Name | Sequence |
|---|---|---|
| 98 | V15J15ABD AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSQHDEAVDANSLAEAKVLANRELDKYGVSDYYKNLINN AKTVEGVKALIDEILAALP |
| 99 | V15J15HSA (K573P) DNA | ATGGGGTGGTCCTACATTATCCTGTTCCTCGTGGCCACCGCCACTGGCGTGCACTCAC AGGTGCAGCTGGTGCAGTCTGGCGCCGAAGTGAAGAAACCTGGCGCCTCCGTGAAGGT GTCCTGCAAGGCCTCCGGCTACACCTTCATCAGCTACACCATGCACTGGGTGCGACAG GCCCCTGGACAGGGCCTGGAATGGATGGGCTACATCAACCCTAGATCTGGCTACACCC ACTACAACCAGAAGCTGAAGGACAAGGCCACCCTGACCGCCGACAAGTCTGCCTCCAC CGCCTACATGGAACTGTCCTCCCTGCGGAGCGAGGACACCGCCGTGTACTACTGTGCC AGATCCGCCTACTACGACTACGACGGCTTCGCCTATTGGGGCCAGGGCACCCTCGTGA CAGTGTCTAGCGGTGGCGGAGGATCTGGCGGAGGCGGTAGTGGCGGTGGCGGATCTGA TATCCAGATGACCCAGTCCCCCTCCAGCCTGTCTGCCTCTGTGGGCGACAGAGTGACA ATTACCTGCTCCGCCAGCTCCTCCGTGTCTTACATGAACTGGTATCAGCAGAAGCCCG GCAAGGCCCCCAAGCGGCTGATCTACGACACCTCCAAGCTGGCCTCTGGCGTGCCCTC CAGATTCTCCGGCTCTGGCTCTGGCACCGACTTTACCCTGACCATCAGCTCCCTGCAG CCCGAGGACTTCGCCACCTACTACTGCCAGCAGTGGTCCTCCAACCCTCCCACCTTTG GCGGAGGCACCAAGGTGGAAATCAAAGGCGGCGGAGGAAGCGGGGGAGGCGGTTCTGG GGGTGGTGGATCTCAGGAAGATGAGCGGATCGTGCTGGTGGACAACAAGTGCAAGTGC GCCCGGATCACCTCCCGGATCATCCGGTCCTCCGAGGATCCCAACGAGGACATCGTGG AACGGAACATCAGAATCATCGTGCCCCTGAACAACCGCGAGAACATCTCCGACCCCAC CAGCCCTCTGCGGACCAGATTCGTGTACCACCTGTCCGACCTGTGCAAGAAGTGCGAC CCTACCGAGGTGGAACTGGACAACCAGATCGTGACCGCCACCCAGTCCAACATCTGCG ACGAGGACTCCGCCACCGAGACATGCTACACCTACGACCGGAACAAGTGCTACACCGC CGTGGTGCCTCTGGTGTACGGCGGCGAGACAAAGATGGTGGAAACCGCCCTGACCCCC GACGCCTGCTATCCTGATGGAGGCGGAGGATCTGGTGGCGGTGGTTCTGGCGGAGGGG GCTCTGACGCCCACAAATCGGAGGTAGCGCACCGGTTCAAAGACTTGGGAGAAGAAAA CTTTAAGGCCCTTGTACTCATTGCGTTTGCGCAGTATTTGCAGCAGTGCCCATTCGAG GACCATGTCAAACTTGTCAACGAAGTGACAGAGTTTGCGAAAACTTGCGTCGCCGACG AATCCGCGGAGAACTGTGACAAGTCGCTGCATACGTTGTTCGGGGATAAGCTCTGTAC CGTAGCGACCTTGAGGGAAACTTACGGGGAAATGGCGGACTGTTGCGCTAAGCAGGAG CCGGAACGGAACGAGTGTTTCCTTCAGCATAAGGATGACAACCCCAACCTCCCTAGAT TGGTCAGACCCGAAGTGGATGTGATGTGCACAGCATTCCATGACAATGAGGAAACCTT TCTCAAAAAGTATTTGTACGAGATTGCCCGACGACACCCCTATTTCTACGCTCCCGAG TTGCTCTTCTTCGCGAAACGGTATAAAGCTGCCTTTACTGAATGCTGTCAAGCAGCGG ACAAGGCCGCATGCCTCCTTCCCAAATTGGATGAACTCCGCGATGAAGGGAAGGCGTC ATCGGCCAAACAGCGGCTTAAGTGCGCATCGCTTCAGAAATTCGGAGAGAGGGCGTTC AAAGCGTGGGCCGTCGCGAGACTGTCGCAGAGATTCCCTAAGGCGGAATTTGCAGAGG TATCGAAGCTCGTGACAGACCTCACAAAGGTCCACACCGAATGTTGCCATGGAGACCT GCTTGAGTGCGCCGATGATAGGGCAGACCTCGCAAAGTACATTTGTGAGAATCAGGAC AGCATTAGCTCCAAGCTGAAAGAGTGCTGTGAGAAGCCTTTGCTGGAAAAATCCCACT GTATCGCCGAGGTAGAAAACGATGAAATGCCCGCTGATCTTCCCTCGCTGGCGGCAGA CTTCGTCGAGTCGAAGGACGTCTGCAAGAATTACGCAGAGGCAAAAGATGTGTTTCTT GGAATGTTCCTTTATGAGTATGCGAGAAGGCACCCGGATTATTCCGTGGTACTGCTCT TGCGATTGGCGAAAACGTACGAAACAACGCTTGAGAAGTGTTGTGCGGCTGCCGACCC GCATGAGTGCTACGCCAAGGTATTTGATGAGTTTAAACCTCTTGTCGAGGAACCCCAG AATCTTATCAAGCAGAACTGCGAGCTTTTCAAGCAGTTGGGTGAATACAAATTCCAGA ACGCGCTTCTGGTGAGGTATACCAAGAAAGTACCTCAAGTCTCAACACCCACACTCGT CGAGGTGTCACGGAACCTCGGGAAAGTAGGGTCGAAGTGCTGTAAACACCCAGAGGCC AAGCGCATGCCCTGTGCGGAGGACTACCTCTCGGTAGTGTTGAATCAACTGTGTGTCC TCCACGAAAAGACGCCGGTGTCAGACCGCGTCACAAAGTGCTGCACGGAGAGCCTGGT CAATAGACGCCCCTGCTTCTCAGCGCTGGAGGTGGATGAGACATACGTCCCGAAAGAG TTTAACGCCGAAACGTTTACTTTTCATGCTGATATCTGTACGTTGTCAGAGAAGGAAA GGCAAATCAAGAAACAAACTGCGCTTGTGGAACTGGTGAAGCACAAACCGAAGGCGAC TAAGGAACAGCTGAAGGCGGTGATGGATGACTTTGCCGCGTTCGTAGAGAAATGCTGT AAAGCAGACGATAAGGAGACTTGTTTTGCGGAAGAGGGACCTAAACTTGTTGCTGCAA GTCAAGCTGCCTTAGGCTTATAG |
| 100 | V15J15HSA (K573P) AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSDAHKSEVAHRFKDLGEENFKALVLIAFAQYLQQCPFE DHVKLVNEVTEFAKTCVADESAENCDKSLHTLFGDKLCTVATLRETYGEMADCCAKQE |

TABLE 7-continued

Sequence Summary

| SEQ ID NO: | Short Name | Sequence |
|---|---|---|
| | | PERNECFLQHKDDNPNLPRLVRPEVDVMCTAFHDNEETFLKKYLYEIARRHPYFYAPE LLFFAKRYKAAFTECCQAADKAACLLPKLDELRDEGKASSAKQRLKCASLQKFGERAF KAWAVARLSQRFPKAEFAEVSKLVTDLTKVHTECCHGDLLECADDRADLAKYICENQD SISSKLKECCEKPLLEKSHCIAEVENDEMPADLPSLAADFVESKDVCKNYAEAKDVFL GMFLYEYARRHPDYSVVLLLRLAKTYETTLEKCCAAADPHECYAKVFDEFKPLVEEPQ NLIKQNCELFKQLGEYKFQNALLVRYTKKVPQVSTPTLVEVSRNLGKVGSKCCKHPEA KRMPCAEDYLSVVLNQLCVLHEKTPVSDRVTKCCTESLVNRRPCFSALEVDETYVPKE FNAETFTFHADICTLSEKERQIKKQTALVELVKHKPKATKEQLKAVMDDFAAFVEKCC KADDKETCFAEEGPKLVAASQAALGL |
| 101 | V15J15HSA (wt) DNA | ATGGGGTGGTCCTACATTATCCTGTTCCTCGTGGCCACCGCCACTGGCGTGCACTCAC AGGTGCAGCTGGTGCAGTCTGGCGCCGAAGTGAAGAAACCTGGCGCCTCCGTGAAGGT GTCCTGCAAGGCCTCCGGCTACACCTTCATCAGCTACACCATGCACTGGGTGCGACAG GCCCCTGGACAGGGCCTGGAATGGATGGGCTACATCAACCCTAGATCTGGCTACACCC ACTACAACCAGAAGCTGAAGGACAAGGCCACCCTGACCGCCGACAAGTCTGCCTCCAC CGCCTACATGGAACTGTCCTCCCTGCGGAGCGAGGACACCGCCGTGTACTACTGTGCC AGATCCGCCTACTACGACTACGACGGCTTCGCCTATTGGGGCCAGGGCACCCTCGTGA CAGTGTCTAGCGGTGGCGGAGGATCTGGCGGAGGCGGTAGTGGCGGTGGCGGATCTGA TATCCAGATGACCCAGTCCCCCTCCAGCCTGTCTGCCTCTGTGGGCGACAGAGTGACA ATTACCTGCTCCGCCAGCTCCTCCGTGTCTTACATGAACTGGTATCAGCAGAAGCCCG GCAAGGCCCCCAAGCGGCTGATCTACGACACCTCCAAGCTGGCCTCTGGCGTGCCCTC CAGATTCTCCGGCTCTGGCTCTGGCACCGACTTTACCCTGACCATCAGCTCCCTGCAG CCCGAGGACTTCGCCACCTACTACTGCCAGCAGTGGTCCTCCAACCCTCCCACCTTTG GCGGAGGCACCAAGGTGGAAATCAAAGGCGGCGGAGGAAGCGGGGGAGGCGGTTCTGG GGGTGGTGGATCTCAGGAAGATGAGCGGATCGTGCTGGTGGACAACAAGTGCAAGTGC GCCCGGATCACCTCCCGGATCATCCGGTCCTCCGAGGATCCCAACGAGGACATCGTGG AACGGAACATCAGAATCATCGTGCCCCTGAACAACCGCGAGAACATCTCCGACCCCAC CAGCCCTCTGCGGACCAGATTCGTGTACCACCTGTCCGACCTGTGCAAGAAGTGCGAC CCTACCGAGGTGGAACTGGACAACCAGATCGTGACCGCCACCCAGTCCAACATCTGCG ACGAGGACTCCGCCACCGAGACATGCTACACCTACGACCGGAACAAGTGCTACACCGC CGTGGTGCCTCTGGTGTACGGCGGCGAGACAAAGATGGTGGAAACCGCCCTGACCCCC GACGCCTGCTATCCTGATGGAGGCGGAGGATCTGGTGGCGGTGGTTCTGGCGGAGGGG CTCTGACGCCCACAAATCGGAGGTAGCGCACCGGTTCAAAGACTTGGGAGAAGAAAA CTTTAAGGCCCTTGTACTCATTGCGTTTGCGCAGTATTTGCAGCAGTGCCCATTCGAG GACCATGTCAAACTTGTCAACGAAGTGACAGAGTTTGCGAAAACTTGCGTCGCCGACG AATCCGCGGAGAACTGTGACAAGTCGCTGCATACGTTGTTCGGGGATAAGCTCTGTAC CGTAGCGACCTTGAGGGAAACTTACGGGGAAATGGCGGACTGTTGCGCTAAGCAGGAG CCGGAACGGAACGAGTGTTTCCTTCAGCATAAGGATGACAACCCCAACCTCCCTAGAT TGGTCAGACCCGAAGTGGATGTGATGTGCACAGCATTCCATGACAATGAGGAAACCTT TCTCAAAAAGTATTTGTACGAGATTGCCCGACGACACCCCTATTTCTACGCTCCCGAG TTGCTCTTCTTCGCGAAACGGTATAAAGCTGCCTTTACTGAATGCTGTCAAGCAGCGG ACAAGGCCGCATGCCTCCTTCCCAAATTGGATGAACTCCGCGATGAAGGGAAGGCGTC ATCGGCCAAACAGCGGCTTAAGTGCGCATCGCTTCAGAAATTCGGAGAGAGGGCGTTC AAAGCGTGGGCCGTCGCGAGACTGTCGCAGAGATTCCCTAAGGCGGAATTTGCAGAGG TATCGAAGCTCGTGACAGACCTCACAAAGGTCCACACCGAATGTTGCCATGGAGACCT GCTTGAGTGCGCCGATGATAGGGCAGACCTCGCAAAGTACATTTGTGAGAATCAGGAC AGCATTAGCTCCAAGCTGAAAGAGTGCTGTGAGAAGCCTTTGCTGGAAAAATCCCACT GTATCGCCGAGGTAGAAAACGATGAAATGCCCGCTGATCTTCCCTCGCTGGCGGCAGA CTTCGTCGAGTCGAAGGACGTCTGCAAGAATTACGCAGAGGCAAAAGATGTGTTTCTT GGAATGTTCCTTTATGAGTATGCGAGAAGGCACCCGGATTATTCCGTGGTACTGCTCT TGCGATTGGCGAAAACGTACGAAACAACGCTTGAGAAGTGTTGTGCGGCTGCCGACCC GCATGAGTGCTACGCCAAGGTATTTGATGAGTTTAAACCTCTTGTCGAGGAACCCCAG AATCTTATCAAGCAGAACTGCGAGCTTTTCAAGCAGTTGGGTGAATACAAATTCCAGA ACGCGCTTCTGGTGAGGTATACCAAGAAAGTACCTCAAGTCTCAACACCCACACTCGT CGAGGTGTCACGGAACCTCGGGAAAGTAGGGTCGAAGTGCTGTAAACACCCAGAGGCC AAGCGCATGCCCTGTGCGGAGGACTACCTCTCGGTAGTGTTGAATCAACTGTGTGTCC TCCACGAAAAGACGCCGGTGTCAGACCGCGTCACAAAGTGCTGCACGGAGAGCCTGGT CAATAGACGCCCCTGCTTCTCAGCGCTGGAGGTGGATGAGACATACGTCCCGAAAGAG TTTAACGCCGAAACGTTTACTTTTCATGCTGATATCTGTACGTTGTCAGAGAAGGAAA GGCAAATCAAGAAACAAACTGCGCTTGTGGAACTGGTGAAGCACAAACCGAAGGCGAC TAAGGAACAGCTGAAGGCGGTGATGGATGACTTTGCCGCGTTCGTAGAGAAATGCTGT AAAGCAGACGATAAGGAGACTTGTTTTGCGGAAGAGGGAAAGAAACTTGTTGCTGCAA GTCAAGCTGCCTTAGGCTTATAG |
| 102 | V15J15HSA (wt) AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSDAHKSEVAHRFKDLGEENFKALVLIAFAQYLQQCPFE DHVKLVNEVTEFAKTCVADESAENCDKSLHTLFGDKLCTVATLRETYGEMADCCAKQE PERNECFLQHKDDNPNLPRLVRPEVDVMCTAFHDNEETFLKKYLYEIARRHPYFYAPE |

TABLE 7-continued

Sequence Summary

| SEQ ID NO: | Short Name | Sequence |
|---|---|---|
| | | LLFFAKRYKAAFTECCQAADKAACLLPKLDELRDEGKASSAKQRLKCASLQKFGERAF KAWAVARLSQRFPKAEFAEVSKLVTDLTKVHTECCHGDLLECADDRADLAKYICENQD SISSKLKECCEKPLLEKSHCIAEVENDEMPADLPSLAADFVESKDVCKNYAEAKDVFL GMFLYEYARRHPDYSVVLLLRLAKTYETTLEKCCAAADPHECYAKVFDEFKPLVEEPQ NLIKQNCELFKQLGEYKFQNALLVRYTKKVPQVSTPTLVEVSRNLGKVGSKCCKHPEA KRMPCAEDYLSVVLNQLCVLHEKTPVSDRVTKCCTESLVNRRPCFSALEVDETYVPKE FNAETFTFHADICTLSEKERQIKKQTALVELVKHKPKATKEQLKAVMDDFAAFVEKCC KADDKETCFAEEGKKLVAASQAALGL |
| 103 | S70 IgM HC DNA | ATGGACCCCAAGGGCAGCCTGAGCTGGAGAATCCTGCTGTTCCTGAGCCTGGCCTTC GAGCTGAGCTACGGCGAAGTGCAGCTGGTGGAATCTGGCGGCGGACTGGTGCAGC CTGGCGGATCTCTGAGACTGTCTTGTGCCGCCTCCGGCTTTACCTTCTCCGACTCCTG GATCCACTGGGTGCGACAGGCCCCTGGCAAGGGACTGGAATGGGTGGCCTGGATCT CTCCCTACGGCGGCTCTACCTACTACGCCGACTCCGTGAAGGGCCGGTTCACCATCTC TGCCGACACCTCCAAGAACACCGCCTACCTGCAGATGAACTCCCTGCGGGCCGAGGA CACCGCCGTGTACTACTGTGCTCGGAGACATTGGCCTGGCGGCTTCGACTATTGGGG CCAGGGCACACTCGTGACCGTGTCTGCTGGAAGTGCTAGCGCCCCAACCCTTTTCCCC CTCGTCTCCTGTGAGAATTCCCCGTCGGATACGAGCAGCGTGGCCGTTGGCTGCCTC GCACAGGACTTCCTTCCCGACTCCATCACTTTCTCCTGGAAATACAAGAACAACTCTG ACATCAGCAGCACCCGGGGCTTCCCATCAGTCCTGAGAGGGGGCAAGTACGCAGCC ACCTCACAGGTGCTGCTGCCTTCCAAGGACGTCATGCAGGGCACAGACGAACACGT GGTGTGCAAAGTCCAGCACCCCAACGGCAACAAAGAAAAGAACGTGCCTCTTCCAG TGATTGCTGAGCTGCCTCCCAAAGTGAGCGTCTTCGTCCCACCCCGCGACGGCTTCT CGGCAACCCCCGCAAGTCCAAGCTCATCTGCCAGGCCACGGGTTTCAGTCCCCGGCA GATTCAGGTGTCCTGGCTGCGCGAGGGGAAGCAGGTGGGGTCTGGCGTCACCACG GACCAGGTGCAGGCTGAGGCCAAAGAGTCTGGGCCCACGACCTACAAGGTGACCAG CACACTGACCATCAAAGAGAGCGACTGGCTCAGCCAGAGCATGTTCACCTGCCGCGT GGATCACAGGGGCCTGACCTTCCAGCAGAATGCGTCCTCCATGTGTGTCCCCGATCA AGACACAGCCATCCGGGTCTTCGCCATCCCCCCATCCTTTGCCAGCATCTTCCTCACCA AGTCCACCAAGTTGACCTGCCTGGTCACAGACCTGACCACCTATGACAGCGTGACCA TCTCCTGGACCCGCCAGAATGGCGAAGCTGTGAAAACCCACACCAACATCTCCGAGA GCCACCCCAATGCCACTTTCAGCGCCGTGGGTGAGGCCAGCATCTGCGAGGATGACT GGAATTCCGGGGAGAGGTTCACGTGCACCGTGACCCACACAGACCTGCCCTCGCCAC TGAAGCAGACCATCTCCCGGCCCAAGGGGGTGGCCCTGCACAGGCCCGATGTCTACT TGCTGCCACCAGCCCGGGAGCAGCTGAACCTGCGGGAGTCGGCCACCATCACGTGC CTGGTGACGGGCTTCTCTCCCGCGGACGTCTTCGTGCAGTGGATGCAGAGGGGGCA GCCCTTGTCCCCGGAGAAGTATGTGACCAGCGCCCCAATGCCTGAGCCCCAGGCCCC AGGCCGGTACTTCGCCCACAGCATCCTGACCGTGTCCGAAGAGGAATGGAACACGG GGGAGACCTACACCTGCGTGGTGGCCCATGAGGCCCTGCCCAACAGGGTCACCGAG AGGACCGTGGACAAGTCCACCGGTAAACCCACCCTGTACAACGTGTCCCTGGTCATG TCCGACACAGCTGGCACCTGCTACTAGTAA |
| 104 | S70 IgM HC AA | MDPKGSLSWRILLFLSLAFELSYGEVQLVESGGGLVQPGGSLRLSCAASGFTFSDSWIHW VRQAPGKGLEWVAWISPYGGSTYYADSVKGRFTISADTSKNTAYLQMNSLRAEDTAVYY CARRHWPGGFDYWGQGTLVTVSAGSASAPTLFPLVSCENSPSDTSSVAVGCLAQDFLP DSITFSWKYKNNSDISSTRGFPSVLRGGKYAATSQVLLPSKDVMQGTDEHVVCKVQHPN GNKEKNVPLPVIAELPPKVSVFVPPRDGFFGNPRKSKLICQATGFSPRQIQVSWLREGKQ VGSGVTTDQVQAEAKESGPTTYKVTSTLTIKESDWLSQSMFTCRVDHRGLTFQQNASS MCVPDQDTAIRVFAIPPSFASIFLTKSTKLTCLVTDLTTYDSVTISWTRQNGEAVKTHTNIS ESHPNATFSAVGEASICEDDWNSGERFTCTVTHTDLPSPLKQTISRPKGVALHRPDVYLLP PAREQLNLRESATITCLVTGFSPADVFVQWMQRGQPLSPEKYVTSAPMPEPQAPGRYF AHSILTVSEEEWNTGETYTCVVAHEALPNRVTERTVDKSTGKPTLYNVSLVMSDTAGTCY |
| 105 | S70 IgM LC DNA | ATGGAGACCGACACCCTGCTGCTCTGGGTGCTGCTGCTCTGGGTGCCCGGCTCCACC GGAGACATCCAGATGACCCAGTCCCCCTCCAGCCTGTCTGCCTCTGTGGGCGACAGA GTGACCATCACCTGTCGGGCCTCTCAGGACGTGTCCACCGCCGTGGCTTGGTATCAG CAGAAGCCTGGCAAGGCCCCCAAGCTGCTGATCTACTCCGCCTCCTTCCTGTACTCCG GCGTGCCCTCCAGATTCTCCGGCTCTGGCTCTGGCACCGACTTTACCCTGACCATCAG CTCCCTGCAGCCCGAGGACTTCGCCACCTACTACTGCCAGCAGTACCTGTACCACCCC GCCACCTTTGGCCAGGGCACCAAGGTGGAAATCAAGCGGACCGTGGCCGCTCCCAG CGTGTTCATCTTCCCTCCCAGCGACGAGCAGCTGAAGTCTGGCACCGCCAGCGTGGT GTGCCTGCTGAACAACTTCTACCCCCGCGAGGCCAAGGTGCAGTGGAAGGTGGACA ACGCCCTGCAGAGCGGCAACAGCCAGGAGAGCGTGACCGAGCAGGACTCCAAGGA CAGCACCTACAGCCTGAGCAGCACCCTGACCCTGAGCAAGGCCGACTACGAGAAGC ACAAGGTGTACGCCTGCGAGGTGACCCACCAGGGACTGTCTAGCCCCGTGACCAAG AGCTTCAACCGGGGCGAGTGCTAA |
| 106 | S70 IgM LC AA | METDTLLLWVLLLWVPGSTGDIQMTQSPSSLSASVGDRVTITCRASQDVSTAVAWYQQ KPGKAPKLLIYSASFLYSGVPSRFSGSGSGTDFTLTISSLQPEDFATYYCQQYLYHPATFGQ GTKVEIKRIVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGEC |
| 107 | Y15J AA | QVQLVESGGGVVQPGRSLRLSCAASGFTFSSYTMHWVRQAPGKGLEWVTFISYDGNN KYYADSVKGRFTISRDNSKNTLYLQMNSLRAEDTAIYYCARTGWLGPFDYWGQGTLVTV |

TABLE 7-continued

Sequence Summary

| SEQ ID NO: | Short Name | Sequence |
|---|---|---|
| | | SSGGGGSGGGGSGGGGSEIVLTQSPGTLSLSPGERATLSCRASQSVGSSYLAWYQQKPG QAPRLLIYGAFSRATGIPDRFSGSGSGTDFTLTISRLEPEDFAVYYCQQYGSSPWTFGQGT KVEIKGGGGSGGGGSGGGGSQEDERIVLVDNKCKCARITSRIIRSSEDPNEDIVERNIRIIV PLNNRENISDPTSPLRTRFVYHLSDLCKKCDPTEVELDNQIVTATQSNICDEDSATETCYTY DRNKCYTAVVPLVYGGETKMVETALTPDACYPD |
| 108 | V15J AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCAR SAYYDYDGFAYWGQGTLVTVSSGGGGSGGGGSGGGGSDIQMTQSPSSLSASVGDRVTI TCSASSSVSYMNWYQQKPGKAPKRLIYDTSKLASGVPSRFSGSGSGTDFTLTISSLQPEDF ATYYCQQWSSNPPTFGGGTKLEIKGGGGSGGGGSGGGGSQEDERIVLVDNKCKCARIT SRIIRSSEDPNEDIVERNIRIIVPLNNRENISDPTSPLRTRFVYHLSDLCKKCDPTEVELDNQI VTATQSNICDEDSATETCYTYDRNKCYTAVVPLVYGGETKMVETALTPDACYPD |

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

The invention claimed is:

1. An antibody comprising: five IgM antibody monomers or five IgG/IgM antibody monomers that form a pentamer; and a modified J-chain, wherein the modified J-chain comprises SEQ ID NO: 1 and a binding moiety that antagonizes a T-cell inhibitory signaling pathway, wherein the binding moiety is attached to SEQ ID NO: 1 at a C- or an N-terminus of the binding moiety, wherein the binding moiety is attached to SEQ ID NO: 1 at a C- or an N-terminus of SEQ ID NO:1 or between cysteine residues 92 and 101 of SEQ ID NO: 1, wherein the IgG/IgM antibody monomers are hybrid antibody monomers which contain an IgM tail-piece at the end of the IgG heavy chain and has the ability to incorporate and form polymers with the modified J-chain, and wherein the binding moiety on the modified J-chain binds to a cell surface protein selected from the group consisting of: CTLA4, PD-1, TIM3, LAG3, BTLA, VISTA and TIGIT.

2. The antibody according to claim 1, wherein the antibody monomers comprise antigen-binding sites that antagonize a T-cell inhibitory signaling pathway.

3. The antibody according to claim 2, wherein the antigen-binding sites bind to a target selected from the group consisting of: PD-1, PD-L1, TIM3 and LAG3.

4. The antibody according to claim 1, wherein the antibody monomers comprise antigen-binding sites that agonize a T-cell stimulatory signaling pathway.

5. The antibody according to claim 4, wherein the antigen-binding sites bind to a target selected from the group consisting of: CD137, OX40, CD40, GITR, CD27 and HVEM.

6. The antibody according to claim 1, wherein the antibody monomers comprise antigen-binding sites that bind to a target selected from the group consisting of: EGFR, HER2, HER3, EpCAM, CEACAM, Gp100, MAGE1 and PD-L1.

7. The antibody according to claim 1, wherein the antibody monomers comprise antigen-binding sites that bind to a target selected from the group consisting of: NY-ESO-1, Sialyl Lewis X antigen and Tn antigen.

8. The antibody according to claim 1, wherein the antibody monomers comprise antigen-binding sites that bind to a cell surface protein on a hematologic cancer cell selected from the group consisting of: CD19, CD20, CD22, CD33, CD38, CD52 and CD70.

9. The antibody according to claim 1, wherein the J-chain binding moiety is attached to SEQ ID NO: 1 by direct or indirect fusion, wherein indirect fusion is via a peptide linker.

10. The antibody according to claim 1, wherein the binding moiety was introduced into the native human J-chain sequence of SEQ ID NO: 1 by chemical or chemo-enzymatic derivatization.

11. The antibody according to claim 1, wherein the binding moiety was introduced into SEQ ID NO: 1 by a cleavable or non-cleavable chemical linker.

12. The antibody according to claim 1, wherein the binding moiety of the modified J-chain is selected from the group consisting of: antigen-binding fragments of antibodies, antibody-drug conjugates, antibody-like molecules, antigen-binding fragments of antibody-like molecules, ligands, and receptors.

13. The antibody according to claim 12, wherein the binding moiety is an antigen-binding fragment of an antibody and is selected from the group consisting of: F(ab')$_2$, Fab', Fab, Fv, scFv, and single domain antibody.

14. A pharmaceutical composition for the treatment of cancer, comprising an effective amount of the antibody according to claim 1 and a pharmaceutically acceptable carrier.

\* \* \* \* \*

UNITED STATES PATENT AND TRADEMARK OFFICE
CERTIFICATE OF CORRECTION

| | |
|---|---|
| PATENT NO. | : 11,639,389 B2 |
| APPLICATION NO. | : 15/764870 |
| DATED | : May 2, 2023 |
| INVENTOR(S) | : Bruce A. Keyt, Leonard G. Presta and Ramesh Baliga |

It is certified that error appears in the above-identified patent and that said Letters Patent is hereby corrected as shown below:

In the Claims

Column 344, Line 18, Claim 11, replace "according to claim 1," with --according to claim 10,--

Signed and Sealed this
Eighth Day of August, 2023

Katherine Kelly Vidal
*Director of the United States Patent and Trademark Office*